United States Patent
Yu et al.

(10) Patent No.: US 12,162,857 B2
(45) Date of Patent: Dec. 10, 2024

(54) ANTIVIRAL COMPOUNDS

(71) Applicant: ENANTA PHARMACEUTICALS, INC., Watertown, MA (US)

(72) Inventors: Jianming Yu, Plainsboro, NJ (US); Xiben Li, Lexington, MA (US); Robert Leon, Sharon, MA (US); Adam Szymaniak, Boston, MA (US); In Jong Kim, Lexington, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 18/139,405

(22) Filed: Apr. 26, 2023

(65) Prior Publication Data

US 2023/0365525 A1 Nov. 16, 2023

Related U.S. Application Data

(60) Provisional application No. 63/335,283, filed on Apr. 27, 2022.

(51) Int. Cl.
| | | |
|---|---|---|
| *C07D 401/12* | (2006.01) | |
| *A61K 45/06* | (2006.01) | |
| *A61P 31/14* | (2006.01) | |
| *C07D 401/14* | (2006.01) | |
| *C07D 405/14* | (2006.01) | |
| *C07D 409/14* | (2006.01) | |
| *C07D 413/14* | (2006.01) | |
| *C07D 417/12* | (2006.01) | |
| *C07D 417/14* | (2006.01) | |
| *C07D 471/04* | (2006.01) | |

(52) U.S. Cl.
CPC ............ *C07D 401/12* (2013.01); *A61K 45/06* (2013.01); *A61P 31/14* (2018.01); *C07D 401/14* (2013.01); *C07D 405/14* (2013.01); *C07D 409/14* (2013.01); *C07D 413/14* (2013.01); *C07D 417/12* (2013.01); *C07D 417/14* (2013.01); *C07D 471/04* (2013.01)

(58) Field of Classification Search
CPC ................ C07D 401/12; C07D 401/14; C07D 405/14; C07D 409/14; C07D 413/14; C07D 417/12; C07D 417/14; C07D 471/04; A61K 45/06; A61P 31/14
See application file for complete search history.

(56) References Cited

U.S. PATENT DOCUMENTS

| | | | |
|---|---|---|---|
| 4,010,153 A | 3/1977 | Kajfez et al. | |
| 4,511,510 A | 4/1985 | Mauri | |
| 4,835,168 A | 5/1989 | Paget et al. | |
| 4,988,692 A | 1/1991 | Gasc et al. | |
| 5,571,809 A | 11/1996 | Hargrave et al. | |
| 5,637,697 A | 6/1997 | Finch et al. | |
| 5,646,140 A | 7/1997 | Sugg et al. | |
| 5,681,833 A | 10/1997 | Castro et al. | |
| 7,041,662 B2 | 5/2006 | Sattlegger et al. | |
| 7,582,624 B2 | 9/2009 | Carter et al. | |
| 8,999,969 B2 | 4/2015 | Mackman et al. | |
| 9,617,289 B2 | 4/2017 | Tahri et al. | |
| 9,732,098 B2 | 8/2017 | Hunt et al. | |
| 9,957,281 B2 | 5/2018 | Shook et al. | |
| 10,358,441 B2 | 7/2019 | Kim et al. | |
| 10,398,706 B2 | 9/2019 | Shook et al. | |
| 10,865,215 B2 | 12/2020 | Shook et al. | |
| 11,254,664 B2 | 2/2022 | Zhu et al. | |
| 11,420,976 B2 | 8/2022 | He et al. | |

(Continued)

FOREIGN PATENT DOCUMENTS

| | | |
|---|---|---|
| EP | 0167919 A2 | 1/1986 |
| WO | 9308175 A1 | 4/1993 |

(Continued)

OTHER PUBLICATIONS

Pubchem, SID 311324621, Available Date: Feb. 23, 2016 [retrieved on Jul. 14, 2023]. Retrieved from the Internet: <URL: https://pubchem.ncbi.nlm.nih.gov/substance/311324621.
Pubchem, SID 74832 [retrieved on Jun. 12, 2023]. Retrieved from the Internet <URL: https://pubchem.ncbi.nlm.nih.gov/substance/74832>.
STN Registry database entry: CAS RN 1348594-72-8 (Entered STN: Dec. 4, 2011).
STN Registry database entry: CAS RN 1348849-53-5 (Entered STN: Dec. 5, 2011).

(Continued)

*Primary Examiner* — Jean P Cornet
*Assistant Examiner* — Chihyi Lee
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, esters, or prodrugs thereof:

which inhibit Human Respiratory Syncytial Virus (HRSV) or Human Metapneumovirus (HMPV) inhibitors. The present invention further relates to pharmaceutical compositions comprising the compounds of Formula (I) for administration to a subject suffering from HRSV or HMPV infection. The invention also relates to methods of treating an HRSV or HMPV infection in a subject by administering a pharmaceutical composition comprising the compounds of the present invention.

15 Claims, No Drawings

(56) References Cited

U.S. PATENT DOCUMENTS

| | | |
|---|---|---|
| 11,505,558 B1 | 11/2022 | Szymaniak et al. |
| 11,572,367 B2 | 2/2023 | Szymaniak et al. |
| 2005/0261339 A1 | 11/2005 | Ohi et al. |
| 2006/0040923 A1 | 2/2006 | Carter et al. |
| 2006/0083741 A1 | 4/2006 | Hoffman et al. |
| 2007/0142403 A1 | 6/2007 | Powell et al. |
| 2007/0185094 A1 | 8/2007 | Lattmann et al. |
| 2007/0185096 A1 | 8/2007 | Powell et al. |
| 2007/0293482 A1 | 12/2007 | Dowdell et al. |
| 2008/0139536 A1 | 6/2008 | Dowdell et al. |
| 2009/0274655 A1 | 11/2009 | Grimes et al. |
| 2010/0015063 A1 | 1/2010 | Carter et al. |
| 2010/0168384 A1 | 7/2010 | Mdcaniel et al. |
| 2011/0274654 A1 | 11/2011 | Bahadoor et al. |
| 2012/0196846 A1 | 8/2012 | Mackman et al. |
| 2012/0245151 A1 | 9/2012 | Gavai et al. |
| 2014/0038947 A1 | 2/2014 | Glick et al. |
| 2014/0100365 A1 | 4/2014 | Gavai et al. |
| 2014/0148573 A1 | 5/2014 | Ku et al. |
| 2014/0328796 A1 | 11/2014 | Phadke et al. |
| 2015/0038514 A1 | 2/2015 | Grunenberg et al. |
| 2015/0065504 A1 | 3/2015 | Wang et al. |
| 2015/0218111 A1 | 8/2015 | Gavai et al. |
| 2015/0231152 A1 | 8/2015 | Zhao et al. |
| 2015/0299210 A1 | 10/2015 | Bailey et al. |
| 2016/0244460 A1 | 8/2016 | Wang et al. |
| 2017/0022221 A1 | 1/2017 | Blaisdell et al. |
| 2017/0226127 A1 | 8/2017 | Estrada et al. |
| 2017/0226129 A1 | 8/2017 | Yu et al. |
| 2017/0305935 A1 | 10/2017 | Hunt et al. |
| 2017/0355717 A1 | 12/2017 | Hunt et al. |
| 2018/0065932 A1 | 3/2018 | Wang et al. |
| 2018/0193352 A1 | 7/2018 | Shook et al. |
| 2018/0237425 A1 | 8/2018 | Kim et al. |
| 2018/0258102 A1 | 9/2018 | Shook et al. |
| 2018/0354912 A1 | 12/2018 | Or et al. |
| 2019/0002478 A1 | 1/2019 | Kim et al. |
| 2019/0002479 A1 | 1/2019 | Kim et al. |
| 2019/0023692 A1 | 1/2019 | Tahri et al. |
| 2019/0040084 A1 | 2/2019 | Yu et al. |
| 2019/0092791 A1 | 3/2019 | Hunt et al. |
| 2019/0152968 A1 | 5/2019 | Blaisdell et al. |
| 2019/0177283 A1 | 6/2019 | Hague |
| 2019/0192535 A1 | 6/2019 | Shook et al. |
| 2019/0202841 A1 | 7/2019 | Hunt et al. |
| 2019/0315766 A1 | 10/2019 | Yu et al. |
| 2021/0238188 A1 | 8/2021 | He et al. |
| 2022/0119398 A1 | 4/2022 | Or et al. |
| 2022/0356189 A1 | 11/2022 | Szymaniak et al. |
| 2023/0108803 A1 | 4/2023 | Szymaniak et al. |
| 2023/0115580 A1 | 4/2023 | Szymaniak et al. |
| 2023/0125803 A1 | 4/2023 | Szymaniak et al. |
| 2023/0357258 A1 | 11/2023 | Szymaniak et al. |
| 2023/0365525 A1 | 11/2023 | Yu et al. |

FOREIGN PATENT DOCUMENTS

| | | | |
|---|---|---|---|
| WO | 9426718 A1 | 11/1994 | |
| WO | 2004026843 A1 | 4/2004 | |
| WO | 2004052348 A2 | 6/2004 | |
| WO | 2005042530 A1 | 5/2005 | |
| WO | 2005089769 A1 | 9/2005 | |
| WO | 2005090319 A1 | 9/2005 | |
| WO | 2006081389 A1 | 8/2006 | |
| WO | 2010103306 A1 | 9/2010 | |
| WO | 2011005842 A1 | 1/2011 | |
| WO | 2011112186 A1 | 9/2011 | |
| WO | 2011151651 A1 | 12/2011 | |
| WO | 2012012776 A1 | 1/2012 | |
| WO | 2012068622 A1 | 5/2012 | |
| WO | 2012080446 A1 | 6/2012 | |
| WO | 2012080447 A1 | 6/2012 | |
| WO | 2012080449 A1 | 6/2012 | |
| WO | 2012080450 A1 | 6/2012 | |
| WO | 2012080451 A1 | 6/2012 | |
| WO | 2013096681 A1 | 6/2013 | |
| WO | 2013186332 A1 | 12/2013 | |
| WO | 2013186334 A1 | 12/2013 | |
| WO | 2014031784 A1 | 2/2014 | |
| WO | 2014047369 A1 | 3/2014 | |
| WO | 2014047397 A1 | 3/2014 | |
| WO | 2014060411 A1 | 4/2014 | |
| WO | 2014125444 A1 | 8/2014 | |
| WO | 2014184350 A1 | 11/2014 | |
| WO | 2014186035 A1 | 11/2014 | |
| WO | 2014209983 A1 | 12/2014 | |
| WO | 2015026792 A1 | 2/2015 | |
| WO | 2015110446 A1 | 7/2015 | |
| WO | 2016018697 A1 | 2/2016 | |
| WO | 2016022464 A1 | 2/2016 | |
| WO | 2016055791 A1 | 4/2016 | |
| WO | 2016055792 A1 | 4/2016 | |
| WO | 2016097761 A1 | 6/2016 | |
| WO | 2016138158 A1 | 9/2016 | |
| WO | 2016166546 A1 | 10/2016 | |
| WO | 2017015449 A1 | 1/2017 | |
| WO | 2017123864 A1 | 7/2017 | |
| WO | 2017123884 A1 | 7/2017 | |
| WO | 2017175000 A1 | 10/2017 | |
| WO | 2019067864 A1 | 4/2019 | |
| WO | 2021066922 A1 | 4/2021 | |
| WO | 2021198981 A1 | 10/2021 | |
| WO | WO-2021214136 A1 * | 10/2021 | ......... A61K 31/4709 |

OTHER PUBLICATIONS

STN Registry database entry: CAS RN 1348924-24-2 (Entered STN: Dec. 5, 2011).

STN Registry database entry: CAS RN 1349463-13-3 (Entered STN: Dec. 6, 2011).

STN Registry database entry: CAS RN 1349533-81-8 (Entered STN: Dec. 6, 2011).

STN Registry database entry: CAS RN 1349749-23-0 (Entered STN: Dec. 6, 2011).

STN Registry database entry: CAS RN 1350148-32-1 (Entered STN: Dec. 7, 2011).

PUBCHEM-CID: 10595203p. 3, Fig, Oct. 25, 2006.

"4-(2-Hydroxyethoxy)-3-methoxy-N-[3,3,3-1-22 trifluoro-2-[7-(4-fluorophenyl)-3-[2-(methylamino)ethyl]-2,3-dihydrofuro[2,3-c]pyridin-5-yl]-2-methylpropyl]benzamide", Pubmed Compound Record for CID 139332032, U.S. National Library of Medicine, Nov. 2, 2019, https://pubchem.ncbi.nlm.nih.gov/compound/139332032).

"N-[(2R)-2-[(3S)-3-Amino-7-(3-chloro-4-A fluorophenyl)-3-methyl-2H-furo[2,3-c]pyridin-5-yl]-3,3,3-trifluoro-2-hydroxypropyl]-4-ethoxy-3-methoxybenzamide", Pubchem Compound Record for CID 117923975, U.S. National Library of Medicine, Feb. 23, 2016 (Feb. 23, 2016), 1 pg-9 (https://pubchem.ncbi.nlm.nih.gov/compound/117923975); p. 2.

"N-[(2R)-2-[3-(Aminomethyl)-7-(4-fluorophenyl)-1-22 3-methyl-2H-furo[2,3-c]pyridin-5-yl]-3,3,3-trifluoro-2-hydroxypropyl]-4-(2-hydroxyethoxy)-3-methoxybenzamide", Pubmed Compound Record for CID 117924934, U.S. National Library of Medicine, Feb. 23, 2016, https://pubchem.ncbi.nlm.nih.gov/compound/117924934.

"N-[2-[8-[4-Fluoro-3-(1-fluoroethyl)phenyl]-4-iodo-4-methyl-2,3-dihydropyrano[2,3-]pyridin-6-yl]-2-oxoethyl]-3-methoxy-4-[2-[(4-methoxyphenyl)methoxy]ethoxy]benzamide", Pubchem Compound Record for CID 117924454, U.S. National library of Medicine, Feb. 23, 2016 (Feb. 23, 2016), pp. 1-8 (https://pubchem.ncbi.nlm.nih.gov/compound/117924454); p. 2.

Albright, et al., " ", (Document No. 129:54301) retrieved from STN; entered in STN on Jun. 17, 1998.

Albright, et al., " ", (Document No. 130:153583) retrieved from STN; entered in STN on Feb. 16, 1999.

Andrzej, et al., " ", (Document No. 144:274313) retrieved from STN; entered in STN on Mar. 3, 2006.

Aquino, C. J., et al., "Discovery of 1,5-Benzodiazepines with Peripheral Cholecystokinin (CCK-A) Receptor Agonist Activity. 1. Optimization of the Agonist "Trigger"", J. Med. Chem., 39, 1996, 562-569.

(56) References Cited

OTHER PUBLICATIONS

Bond, S., et al., "1,2,3,9b-Tetrahydro-5H-imidazo[2,1-a]isoindol-5-ones as a new class of respiratory syncytial virus (RSV) fusion inhibitors. Part 2: Identification of BTA9881 as a preclinical candidate", Bioorg & Med Chem Lett, 25, 976-981.

Carter, M. C, et al., "1,4-Benzodiazepines as Inhibitors of Respiratory Syncytial Virus", J. Med. Chem., 49DOI: http://dx.doi.org/10.1021/jm051185t, Mar. 9, 2006, 2311-2319.

Chapman, J., et al., "RSV604, a Novel Inhibitor of Respiratory Syncytial Virus Replication", Antimicrobial Agents and Chemotherapy, 51(9), 3346-3353.

Fernandez, H., et al., "Ribavirin: A Clinical Overview", Euro J. Epidemiology, 2(1), 1-14.

Fordyce, et al., "Discovery of novel benzothienoazepine derivatives as potent inhibitors of respiratory syncytial virus", Bioorganic & Medicinal Chemistry Letters, 27, 2017, 2201-2206.

Heeney, et al., " ", (Document No. 153:359062) retrieved from STN; entered in STN on Sep. 2, 2010.

Henderson, E. A, et al., "1,4-Benzodiazepines as Inhibitors of Respiratory Syncytial Virus. The Identification of a Clinical Candidate", Journal of Medicinal Chemistry, 50(7)DOI: http://dx.doi.org/10.1021/jm0607471, Apr. 2007, 1685-1692.

Lee, et al., (Document No. 140:69941) retrieved from STN; entered in STN on Jul. 8, 2003.

Mackman, R. L., et al., "Discovery of an Oral Respiratory Syncytial Virus (RSV) Fusion Inhibitor (GS-5806) and Clinical Proof of Concept in a Human RSV Challenge Study", J. Med. Chem., 58, 2015, 1630-1643.

Mayo Clinic Staff, Respiratory syncytial virus (RSV) [online], retrieved from from internet on Jun. 25, 2017.; URLhttp://www.mayoclinic.org/diseases-condiitons/respiratory-syncytial-virus/basics/prevention.

Olszewska, W., et al., "Emerging drugs for respiratory syncytial virus infection", Expert Opin. Emerg. Drugs, 14(2), 207-217.

Peesapati, et al., (Document No. 120:244848) retrieved from STN; entered in STN on May 14, 1994.

Perron, M., et al., "GS-5806 Inhibits a Broad Range of Respiratory Syncytial Virus Clinical Isolates by Blocking the Virus-Cell Fusion Process", Antimicrobial Agents and Chemotherapy, 60(3)https://www.ncbi.nlm.nih.gov/pmc/articles/PMC4776015/, 1264-1273.

Stein, D. S, et al., "Oral ribavirin treatment of influenza A and B", Antimicrobial Agents and Chemotherapy, 31(8)URL:http://dx.doi.org/10.1128/AAC.31.8.1285>, Aug. 1987, 1285-1287.

Sudo, K., et al., "YM-53403, a unique anti-respiratory syncytial virus agent with a novel mechanism of action", Antiviral Research, 65, 125-131.

Wang, et al., (Document No. 160:385666) retreved from STN; entered in STN on Feb. 27, 2014.

Wang, G. et al., "Discovery of 4'-Chloromethyl-2'-deoxy-3',5'-di-O-isobutyryl-2'-fluorocytidine (ALS-8176), A First-in-Class RSV Polymerase Inhibitor for Treatment of Human Respiratory Syncytial Virus Infection", J. Med. Chem., 58, 1862-1878.

Xiong, et al., " ", (Document No. 160:101182) retreved from STN; entered in STN on Nov. 12, 2013.

Xiong, H. "Discovery of a Potent Respiratory Syncytial Virus RNA Polymerase Inhibitor", Bioorganic & Medicinal Chemistry Letters, 23, 6789-6793.

Zheng, et al., (Document No. 161 :399872) retrieved from STN; entered in STN on Jul. 23, 2014.

\* cited by examiner

ANTIVIRAL COMPOUNDS

RELATED APPLICATION

This application claims the benefit of U.S. Provisional Application No. 63/335,283, filed on Apr. 27, 2022. The entire teachings of the above application are incorporated herein by reference.

TECHNICAL FIELD

The present invention relates generally to compounds and pharmaceutical compositions useful as Respiratory Syncytial Virus (RSV) inhibitors and Human Metapneumovirus (HMPV) inhibitors.

BACKGROUND OF THE INVENTION

Human respiratory syncytial virus (HRSV) is a negative sense virus, containing a non-segmented, single-stranded linear RNA genome. As a Paramyxovirus of two serotypes in the genus Pneumoviridae, HRSV contains 10 genes that encode for 11 proteins. The nucleocapsid protein (N), the RNA polymerase protein (L), the phosphoprotein (P) and the transcription anti-termination factor (M2-1) along with the RNA genome make up the ribonucleoprotein (RNP) complex. Several small-molecule compounds have been shown to target the RNP complex. Additionally, the fusion protein (F), paramount for viral attachment to the host, has been extensively studied. High resolution structures of the F protein interacting with inhibitors have been attained, while structural studies with the N protein are earlier in development. A direct result of the HRSV protein studies and research, the F protein, L protein and N protein have been the major focus of drug discovery efforts.

The increased effort in HRSV drug discovery is a result of HRSV being the leading cause of acute lower respiratory infections (ALRI) in patients of all ages. In addition to respiratory infections, patient populations at high risk during HRSV infections include the elderly, immunocompromised, children up to the age of two and patients with chronic obstructive pulmonary disorder (COPD) or chronic heart failure (CHF). HRSV was found over four years to cause 177,500 hospital admissions and 14,000 deaths in the U.S. elderly population. It is well-known that almost all children will be infected with HRSV in the first 3 years after birth and HRSV infection is more severe in premature infants. In fact, HRSV is the most common cause of bronchiolitis and pneumonia in infants under the age of one in the U.S. It is estimated that approximately 3.2 million hospitalizations and 66,000 deaths worldwide in children less than 5 years old are due to HRSV. HRSV has been associated with more deaths of infants below one year old and more infant hospitalizations than influenza.

HRSV infection can also affect healthy individuals and repeated HRSV infections even over the course of two months can occur. Symptoms are similar to colds in healthy individuals, however fever, wheezing, rapid and difficult breathing, and cyanosis occur in more severe cases. Currently, the treatment options for HRSV infection are quite limited and there is no vaccine due to unsuccessful attempts to date. Palivizumab is a monoclonal antibody that is approved for prophylactic use, but its use is limited due to its high price. Palivizumab is generally only used for high risk infants, such as premature infants or those with cardiac/lung disease, but has been only 60% effective in reducing hospitalizations. Ribavirin is approved as an inhalation treatment option, but its effectiveness is limited and there are safety concerns associated with it. Taking into account the treatment options, and the consistent seasonality of the HRSV epidemic, the development of new therapeutic agents for the treatment of HRSV is desirable.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, WO 2015/110446, WO 2017/009316, WO 2021/214136, *J. Med Chem.* 2015, 58, 1630-1643, *Bioorg. Med Chem. Lett.*, 2015, 25, 976-981 and *Nat. Commun.*, 2017, 8, 167. Examples of other N-protein inhibitors for treatment of HRSV have been disclosed in the following publications: WO 2004/026843, *J. Med Chem.* 2006, 49, 2311-2319, and *J. Med Chem.* 2007, 50, 1685-1692. Examples of L-protein inhibitors for HRSV have been disclosed in the following publications: WO 2023/052593, WO 2021/214136, WO 2021/198981, WO 2021/150806, WO 2021/066922, WO 2011/005842, WO 2005/042530, *Antiviral Res.* 2005, 65, 125-131, and *Bioorg. Med Chem. Lett.* 2013, 23, 6789-6793. Examples of nucleosides/polymerase inhibitors have been disclosed in the following publications: WO 2011/005842, WO 2013/242525, WO 2014/031784, WO 2015/026792, WO 2016/0055791, WO 2016/138158, and *J. Med. Chem.* 2015, 58, 1862-1878.

Likewise, human metapneumovirus (HMPV), a negative-sense, single-stranded RNA enveloped virus, that belongs to the Pneumoviridae family and Metapneumovirus genus discovered by van Den Hoogen in 2001, is also a common cause of acute lower respiratory tract infections (ALRTIs). Although often mild, this virus can be serious and life-threatening in high-risk groups, such as children under the age of 5 years, elderly adults over the age of 65 years, and adults with underlying disease (e.g., Chronic Obstructive Pulmonary Disease (COPD), asthma, congestive heart failure, or diabetes). In healthy adults over the age of 65 years, the annual incidence rate of HMPV infection is 1.2/1,000, and 38% of disease (e.g., COPD), and individuals are twice as likely to have symptomatic disease and requirement for medical care. In immunocompromised individuals, HMPV is responsible for 6% of total respiratory infections in lung transplants and 3% of lower respiratory infections associated with stem cell transplant. HMPV infection is also thought to be associated with acute graft rejection.

Like HRSV, infection is thought to attach to the target cell via the glycoprotein (G) protein interactions and followed by fusion via the F protein. HMPV L protein sequence is homologous to HRSV L protein.

HMPV infection is the second most common cause of lower respiratory tract infection in children (behind HRSV) and is also problematic for the elderly population. There are 4 subtypes of HMPV found in clinical isolates (A1, A2, B1 and B2). Reinfection occurs throughout childhood following initial infection. No therapeutics are currently available for HMPV infection.

Taking into account the seasonality and predictability of the HRSV and HMPV epidemics, HRSV epidemics in elderly institutions, and the severity of infection in high risk infants, the need for a potent and effective treatment for HRSV and HMPV is clear. The present invention has identified compounds that are heterocyclic molecules that are potent against HRSV-A/B and HMPV. The invention includes methods to prepare these molecules, methods for the RSV cell-based assay, the HMPV-TN/94-49 A2 cell-based assay and small-molecules that have potential to treat HRSV/HEMPV infection.

SUMMARY OF THE INVENTION

The present invention provides compounds represented by Formula (I), and pharmaceutically acceptable salts, esters and prodrugs thereof that can be used to treat or prevent viral (particularly HRSV or HMPV) infection:

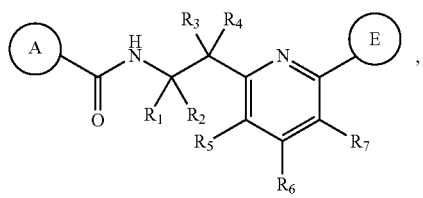

(I)

wherein:
A is selected from the group consisting of:
  1) optionally substituted aryl; and
  2) optionally substituted heteroaryl;
E is selected from the group consisting of:
  1) optionally substituted aryl; and
  2) optionally substituted heteroaryl;
$R_1$ and $R_2$ are each independently selected from the group consisting of:
  1) hydrogen; and
  2) fluorine;
$R_3$ is hydroxy or fluorine;
$R_4$ is selected from the group consisting of:
  1) optionally substituted —$C_1$-$C_6$ alkyl;
  2) optionally substituted —$C_3$-$C_8$ cycloalkyl;
  3) optionally substituted 3- to 8-membered heterocyclic;
  4) optionally substituted aryl;
  5) optionally substituted arylalkyl;
  6) optionally substituted heteroaryl; and
  7) optionally substituted heteroarylalkyl;
$R_5$ and $R_7$ are each independently selected from the group consisting of:
  1) hydrogen;
  2) halogen;
  3) optionally substituted —$C_1$-$C_6$ alkyl;
  4) optionally substituted —$C_1$-$C_6$ alkoxy; and
  5) optionally substituted —$C_3$-$C_6$ cycloalkyl;
$R_6$ is selected from the group consisting of:
  1) —$C(O)NH_2$;
  2) optionally substituted —$C_1$-$C_8$-alkyl;
  3) optionally substituted —$C_3$-$C_8$-cycloalkyl;
  4) hydrogen;
  5) optionally substituted 4- or 5-membered heterocyclic ring;
  6) —$C(O)NHR_{11}$; and
  7) —$C(O)NR_{11}R_{12}$;
and $R_{11}$ and $R_{12}$ are each independently selected from the group consisting of:
  1) optionally substituted —$C_1$-$C_8$ alkyl;
  2) optionally substituted —$C_2$-$C_8$ alkenyl;
  3) optionally substituted —$C_2$-$C_8$ alkynyl;
  4) optionally substituted —$C_3$-$C_8$ cycloalkyl;
  5) optionally substituted 3- to 8-membered heterocloalkyl;
  6) optionally substituted aryl;
  7) optionally substituted arylalkyl;
  8) optionally substituted heteroaryl; and
  9) optionally substituted heteroarylalkyl;
alternatively, $R_{11}$ and $R_{12}$ are taken together with the nitrogen atom to which they are attached to form an optionally substituted heterocyclic ring.

DETAILED DESCRIPTION OF THE INVENTION

In one embodiment of the present invention is a compound of Formula (I) as described above, or a pharmaceutically acceptable salt thereof.

In certain embodiments of the compounds of Formula (I), $R_1$ is hydrogen or F.

In certain embodiments of the compounds of Formula (I), $R_2$ is hydrogen or F.

In certain embodiments of the compounds of Formula (I), $R_1$ and $R_2$ are hydrogen.

In certain embodiments of the compounds of Formula (I), $R_3$ is OH.

In certain embodiments of the compounds of Formula (I), $R_4$ is optionally substituted methyl, optionally substituted cyclopropyl, or optionally substituted phenyl. Preferred substituents include fluorine.

In certain embodiments of the compounds of Formula (I), $R_4$ is selected from one of the following:

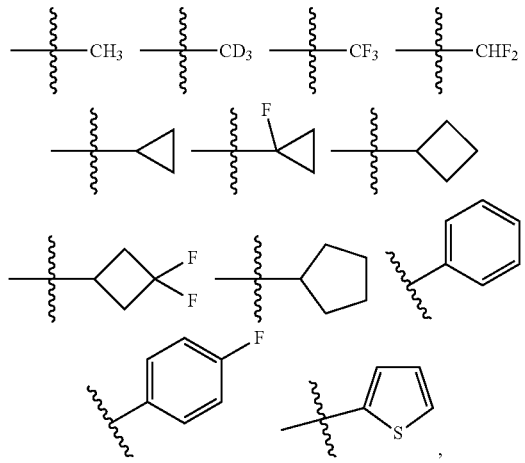

In certain embodiments of the compounds of Formula (I), $R_4$ is

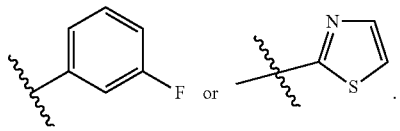 [SMILES: *c1cccc(F)c1 ; *c1nccs1]

In certain embodiments of the compounds of Formula (I), $R_3$ is OH, and $R_4$ is $CF_3$ or optionally substituted cyclopropyl.

In certain embodiments of the compounds of Formula (I), $R_1$ is hydrogen, $R_2$ is hydrogen, $R_3$ is OH, and $R_4$ is $CF_3$ or optionally substituted cyclopropyl.

In certain embodiments of the compounds of Formula (I), $R_5$ is hydrogen, $C_1$ or F.

In certain embodiments of the compounds of Formula (I), $R_7$ is hydrogen, $C_1$, F, optionally substituted methyl or optionally substituted methoxyl.

In certain embodiments of the compounds of Formula (I), $R_1$ is hydrogen, $R_2$ is hydrogen, and $R_5$ is hydrogen.

In certain embodiments of the compounds of Formula (I), $R_1$ is hydrogen, $R_2$ is hydrogen, $R_3$ is OH, $R_4$ is $CF_3$, optionally substituted cyclopropyl, or optionally substituted phenyl, $R_5$ is hydrogen, and $R_7$ is F.

In certain embodiments of the compounds of Formula (I), $R_6$ is —C(O)NH$_2$; optionally substituted —$C_1$-$C_8$-alkyl; or optionally substituted —$C_3$-$C_8$-cycloalkyl.

In certain embodiments of the compounds of Formula (I), $R_6$ is optionally substituted cyclopropyl or optionally substituted isopropyl.

In certain embodiments of the compounds of Formula (I), $R_6$ is selected from the following:

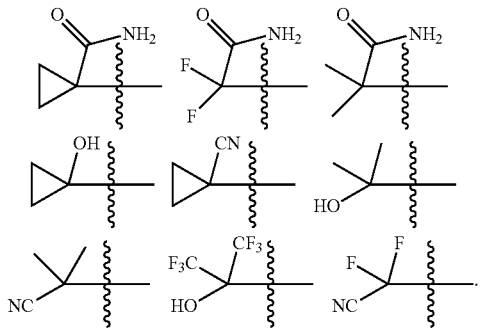

In certain embodiments of the compounds of Formula (I), $R_6$ is selected from the following:

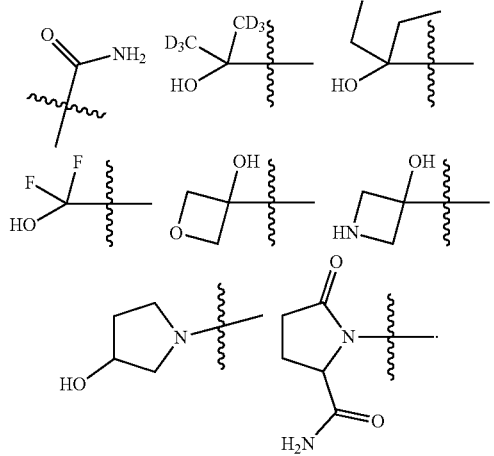

In certain embodiments of the compounds of Formula (I), A is selected from the following by removal of a hydrogen atom:

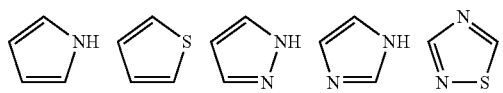

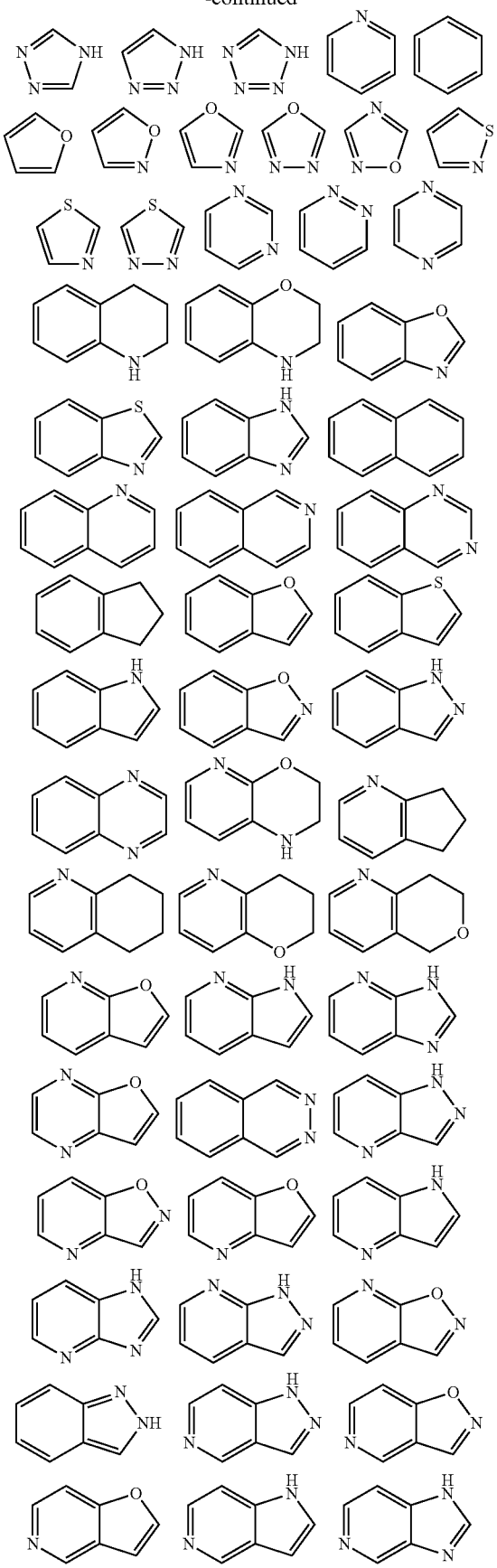

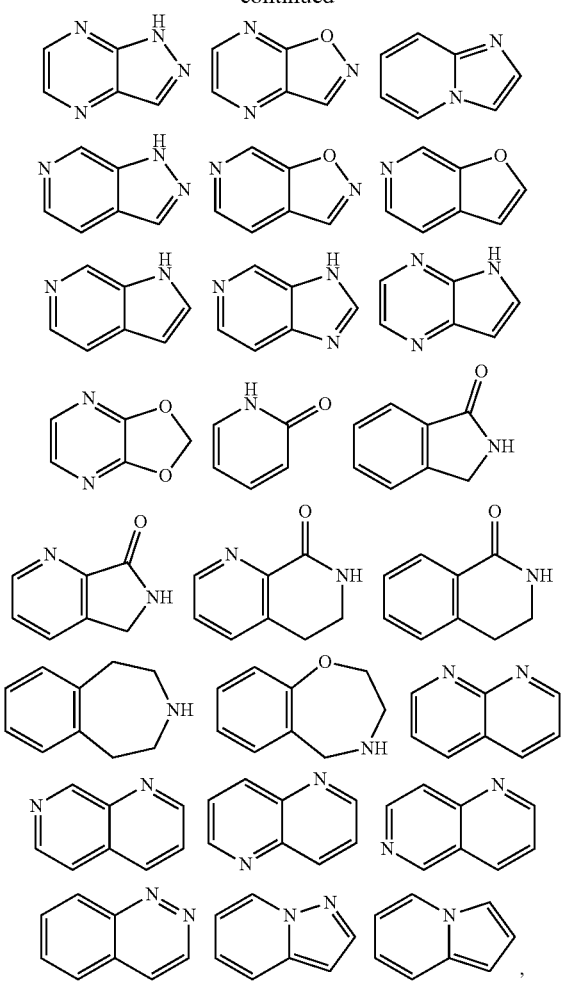
wherein each of these groups is optionally substituted.
In certain embodiments of the compounds of Formula (I), A is selected from the following by removal of a hydrogen atom:
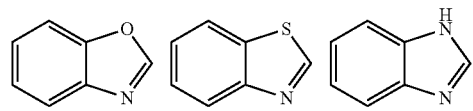
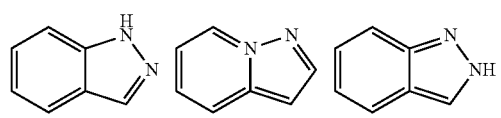
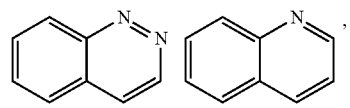
wherein each of these groups is optionally substituted.
In certain embodiments of the compounds of Formula (I), A is selected from the groups set forth below,
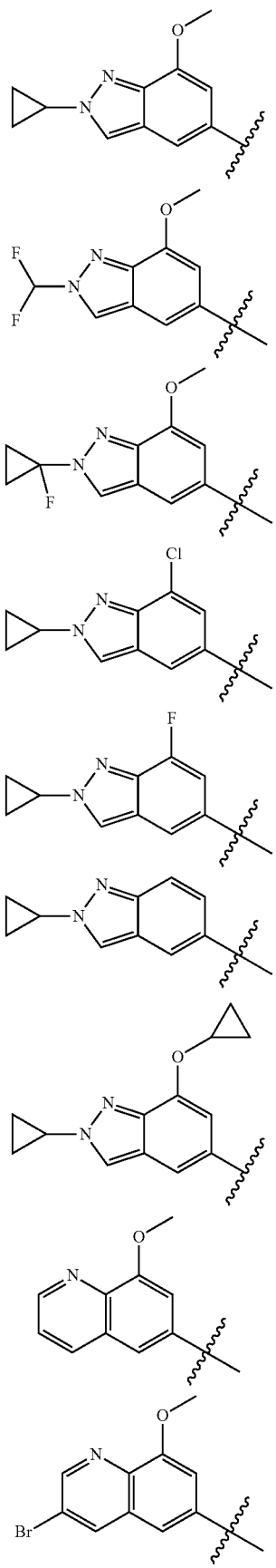

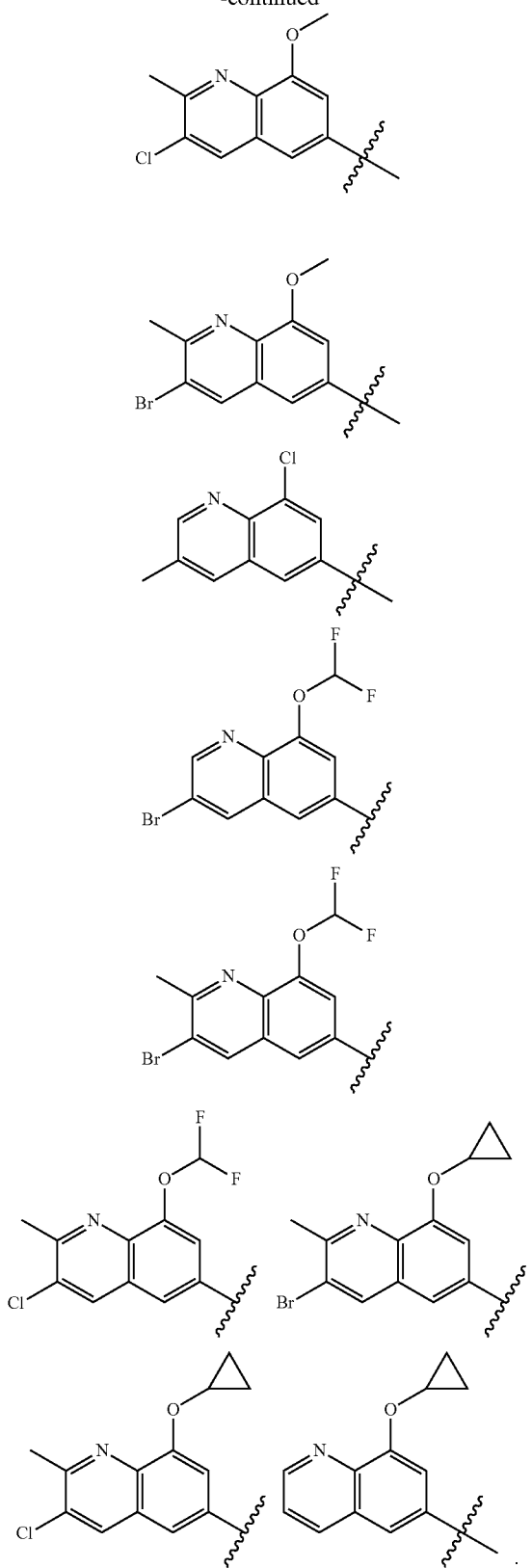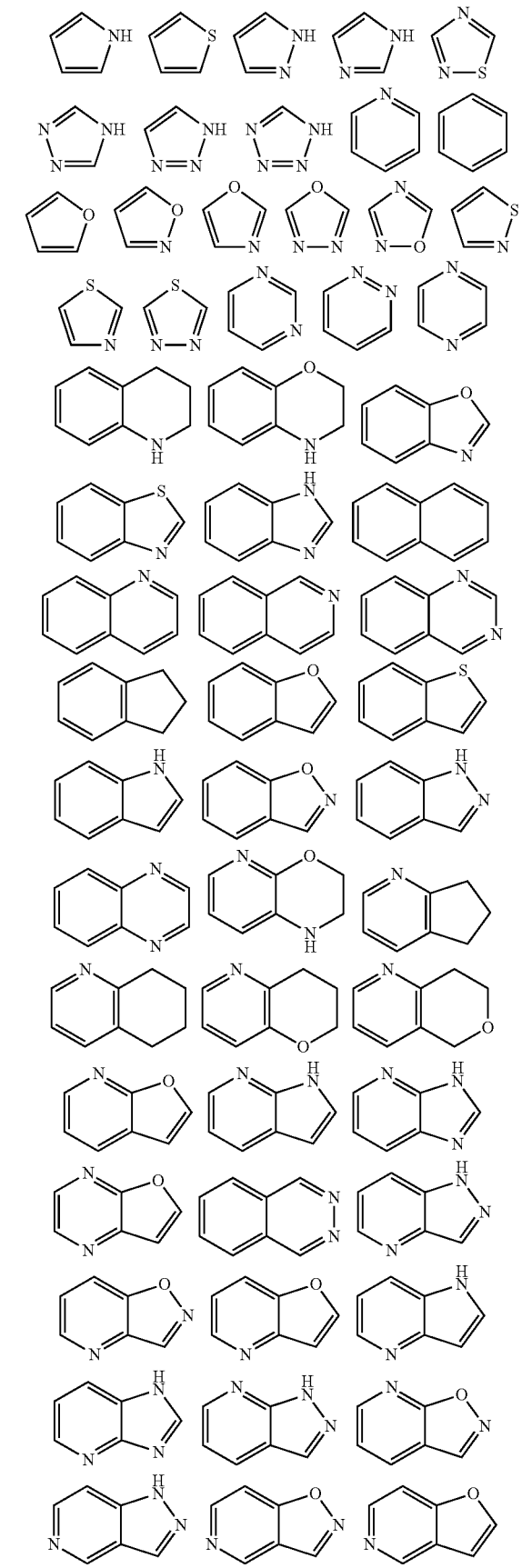
In certain embodiments of the compounds of Formula (I), E is selected from the following by removal of a hydrogen atom:

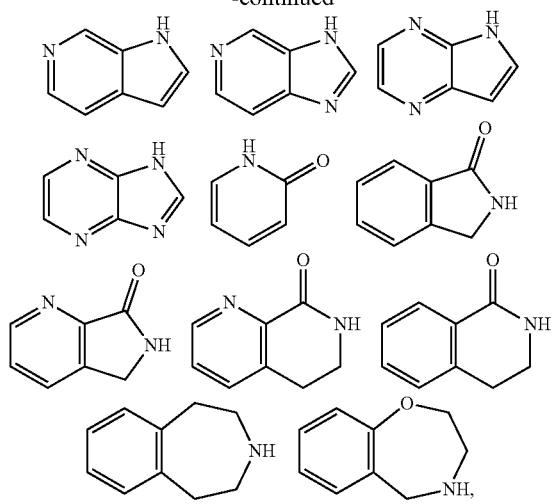
wherein each of these groups is optionally substituted.
In certain embodiments of the compounds of Formula (I), E is optionally substituted aryl, preferably optionally substituted phenyl.
In certain embodiments of the compounds of Formula (I), E is selected from the groups set forth below,
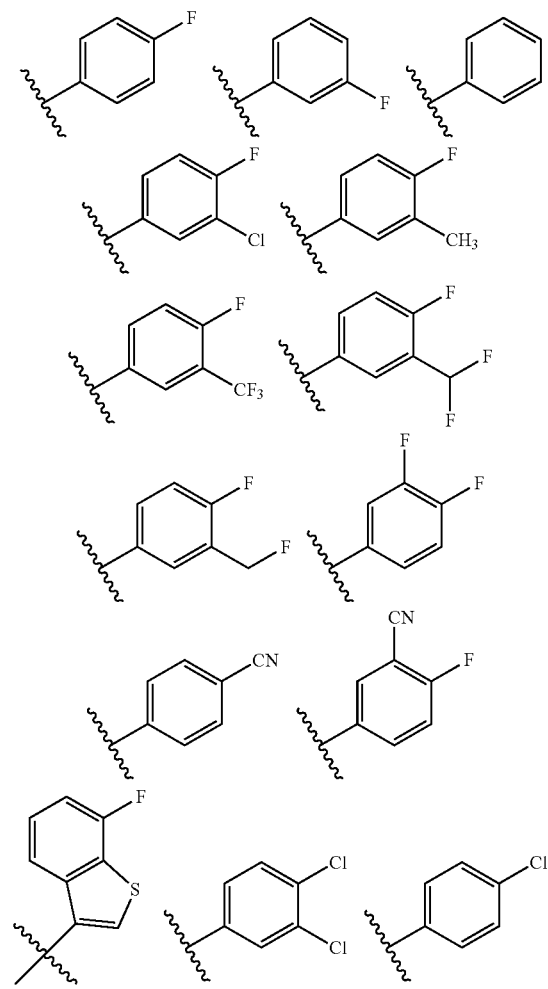
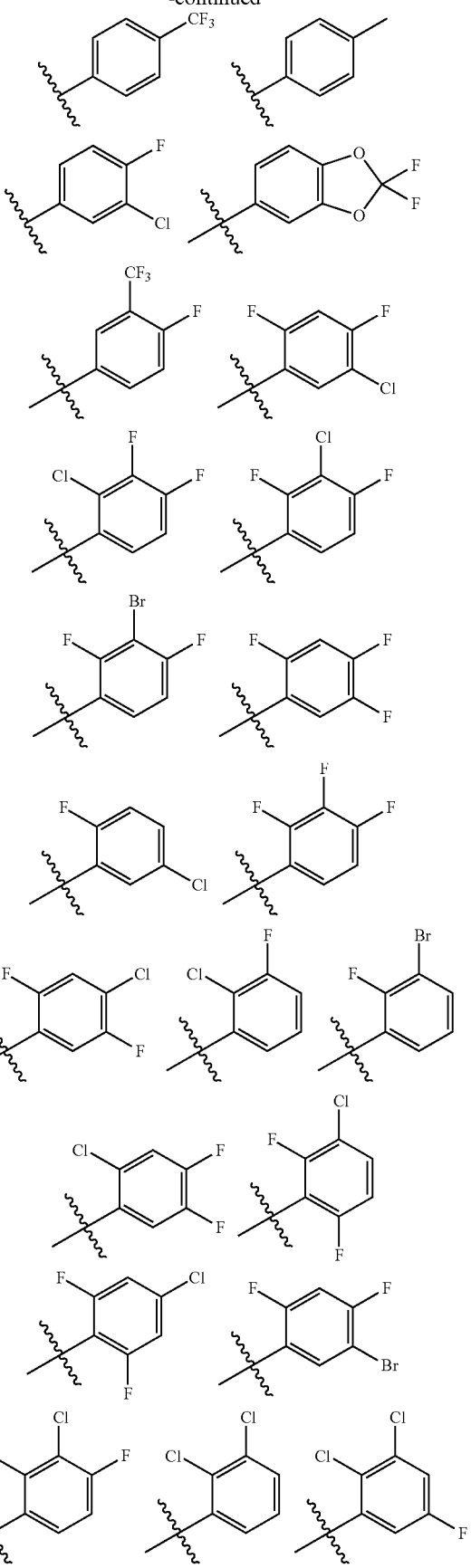

-continued

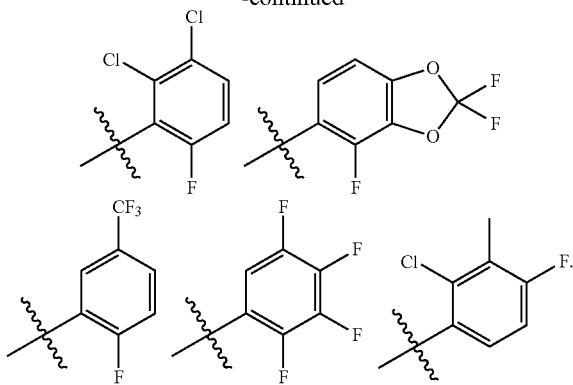

In one embodiment of the present invention, the compound of Formula (I) is represented by Formula (Ia) or Formula (Ib):

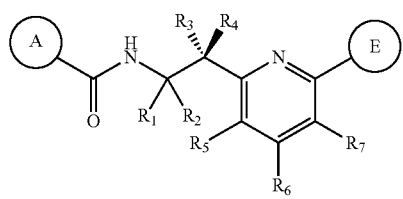

(Ia)

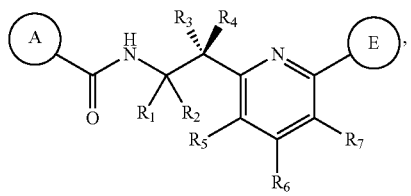

(Ib)

wherein A, E, $R_1$, $R_2$, $R_3$, $R_4$, $R_5$, $R_6$, and $R_7$ are as previously defined.

In a preferred embodiment, the compound of Formula (I) has the stereochemistry shown in Formula (Ia).

In one embodiment of the present invention, the compound of Formula (I) is represented by Formula (II):

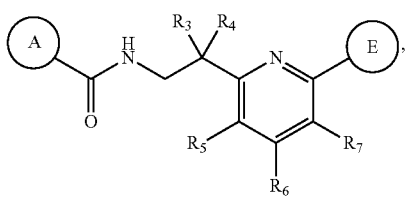

(II)

wherein A, E, $R_3$, $R_4$, $R_5$, $R_6$, and $R_7$ are as previously defined.

In one embodiment of the present invention, the compound of Formula (I) is represented by Formula (III):

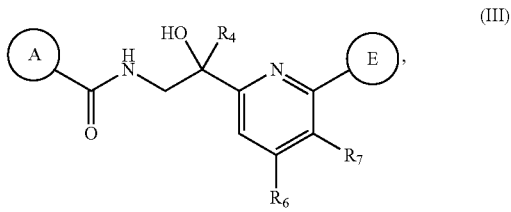

(III)

wherein A, E, $R_4$, $R_6$, and $R_7$ are as previously defined.

In one embodiment of the present invention, the compound of Formula (I) is represented by Formula (IIIa):

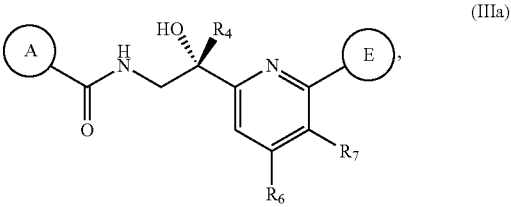

(IIIa)

wherein A, E, $R_4$, $R_6$, and $R_7$ are as previously defined.

In one embodiment of the present invention, the compound of Formula (I) is represented by Formula (IV):

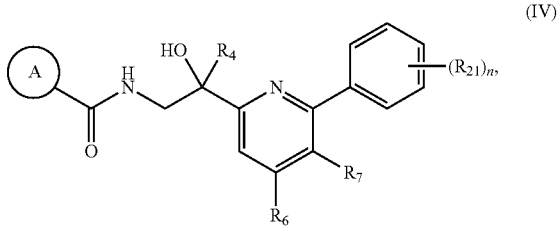

(IV)

wherein
each $R_{21}$ is independently optionally substituted methyl, halo, —CN, —$OR_{31}$, or —$NR_{31}R_{32}$;
n is 1, 2, 3, 4 or 5; preferably n is 1, 2 or 3;
each $R_{31}$ and $R_{32}$ are independently selected from the group consisting of:
1) hydrogen;
2) optionally substituted —$C_1$-$C_8$-alkyl;
3) optionally substituted —$C_3$-$C_8$-cycloalkyl;
4) optionally substituted 4- to 8-membered heterocyclic;
5) optionally substituted aryl;
6) optionally substituted arylalkyl;
7) optionally substituted heteroaryl; and
8) optionally substituted heteroarylalkyl;
and A, $R_4$, $R_6$, and $R_7$ are as previously defined. Preferably, each $R_{21}$ is independently halo or optionally substituted methyl, and n is 1, 2 or 3.

In one embodiment of the present invention, the compound of Formula (I) is represented by one of Formulae (V-1)~(V-5):

(V-1)
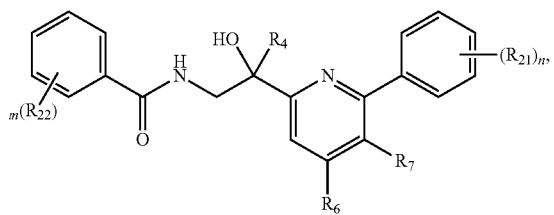

(V-2)
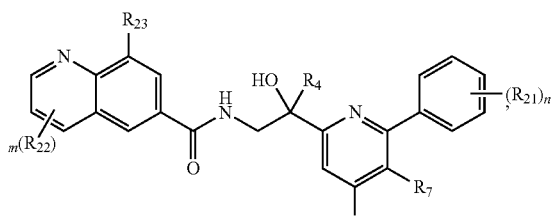

(V-3)
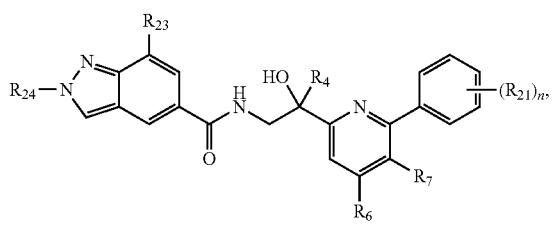

(V-4)
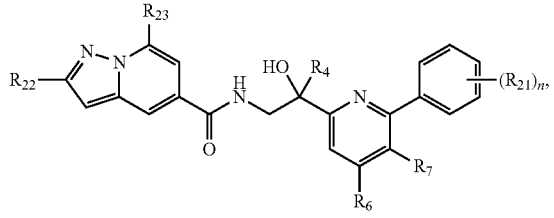

(V-5)
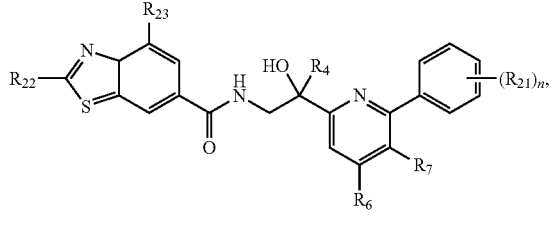

wherein
- each $R_{22}$ is independently halo; —CN; —NO$_2$, —OR$_{31}$; —NR$_{31}$R$_{32}$; —NR$_{31}$C(O)R$_{32}$; —C(O)NR$_{31}$R$_{32}$; —C(O)R$_{31}$, —C(O)OR$_{31}$; optionally substituted —C$_1$-C$_6$ alkyl; optionally substituted —C$_3$-C$_8$-cycloalkyl; optionally substituted 3- to 8-membered heterocyclic; optionally substituted aryl; or optionally substituted heteroaryl;
- m is 0, 1, 2, or 3; preferably m is 0, 1 or 2;
- each $R_{23}$ is independently hydrogen, halo; —OR$_{31}$, optionally substituted —C$_1$-C$_6$ alkyl, or optionally substituted —C$_3$-C$_8$-cycloalkyl;
- each $R_{24}$ is independently hydrogen, optionally substituted —C$_1$-C$_6$ alkyl, or optionally substituted —C$_3$-C$_8$-cycloalkyl;

and n, $R_4$, $R_6$, $R_7$, $R_{21}$, $R_{31}$, and $R_{32}$ are as previously defined.

In one embodiment of the present invention, the compound of Formula (I) is represented by one of Formulae (V-1a)~(V-5a):

(V-1a)
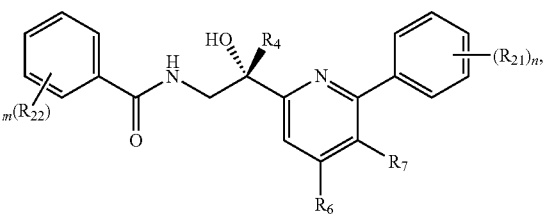

(V-2a)
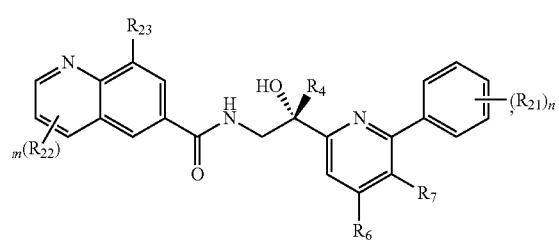

(V-3a)
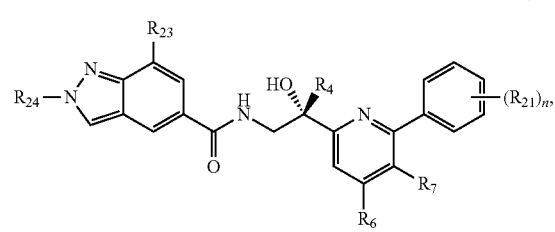

(V-4a)
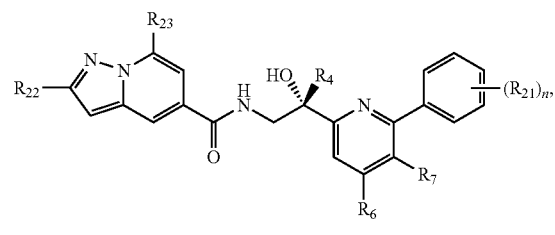

(V-5a)
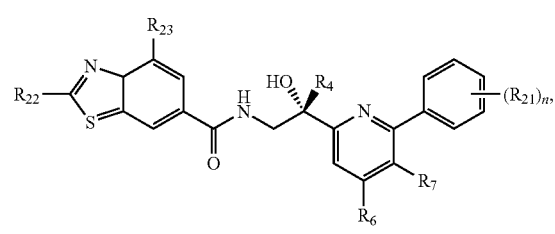

wherein n, m, $R_4$, $R_6$, $R_7$, $R_{21}$, $R_{22}$, $R_{23}$, and $R_{24}$ are as previously defined.

In one embodiment of the present invention, the compound of Formula (I) is represented by one of Formulae (V-1)~(V-5), or one of Formulae (V-1a)~(V-5a), wherein $R_4$ is

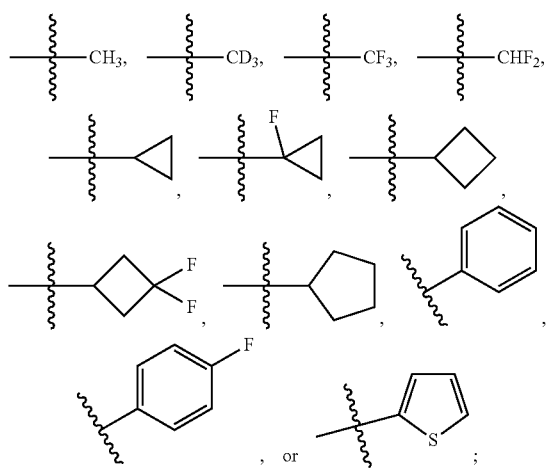
or R₄ is
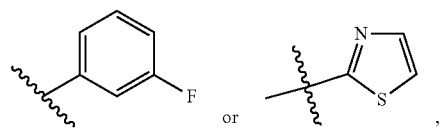 [SMILES: *c1cccc(F)c1 ; *c1nccs1]
and R₆ is selected from the following:
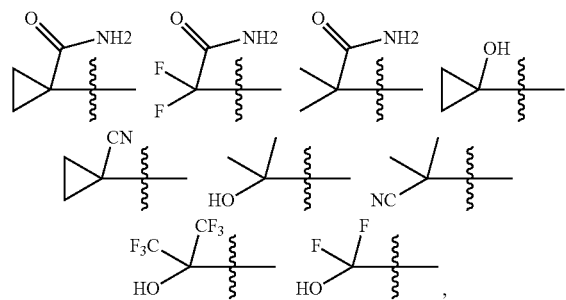
or the following
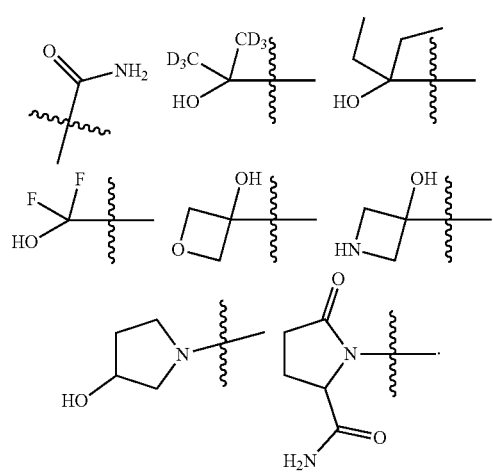
In one embodiment of the present invention, the compound of Formula (I) is represented by one of Formulae (VI-1)~(VI-10):
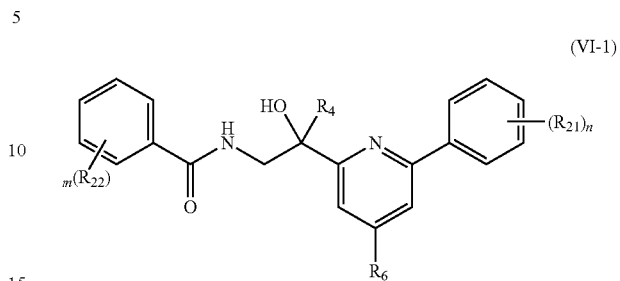
(VI-1)
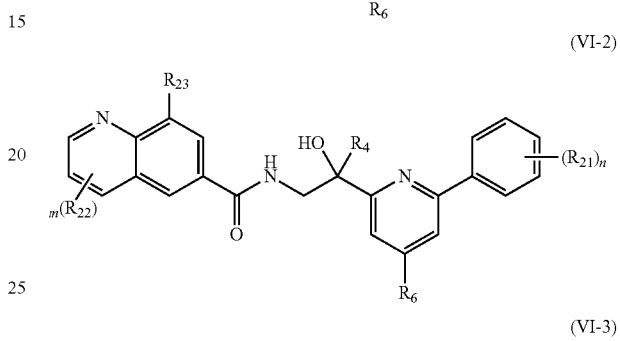
(VI-2)
(VI-3)
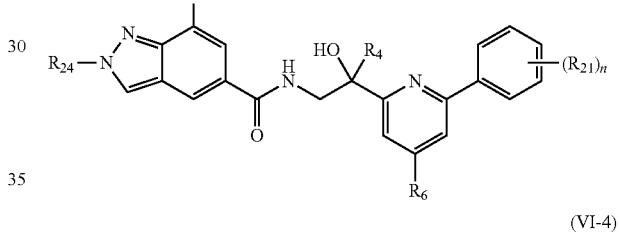
(VI-4)
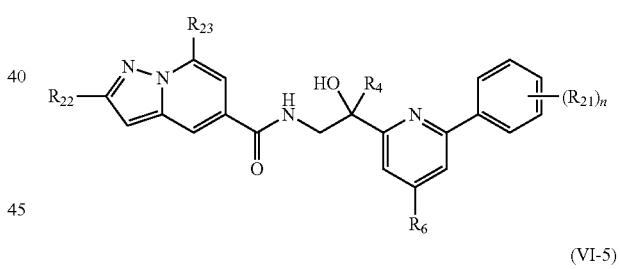
(VI-5)
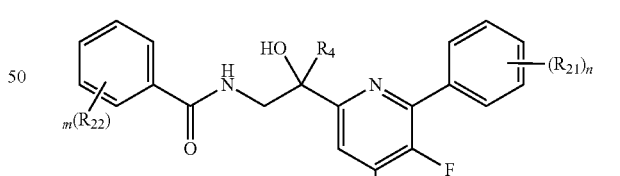
(VI-6)
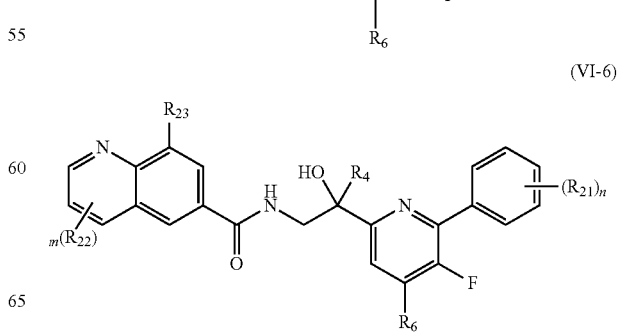

-continued (VI-7)
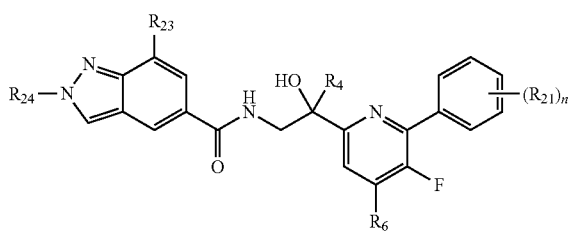

(VI-8)
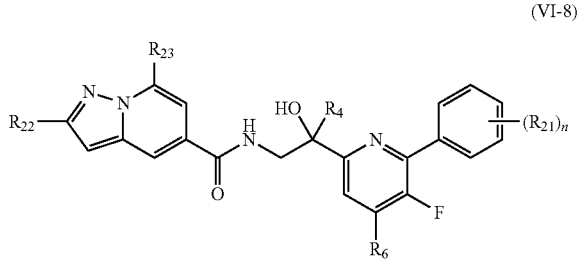

(VI-9)
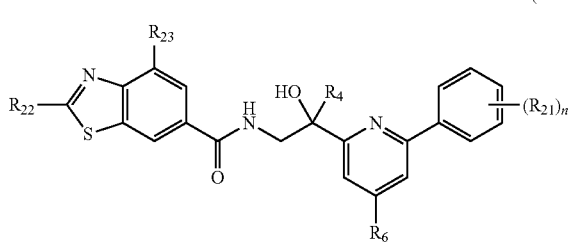

(VI-10)
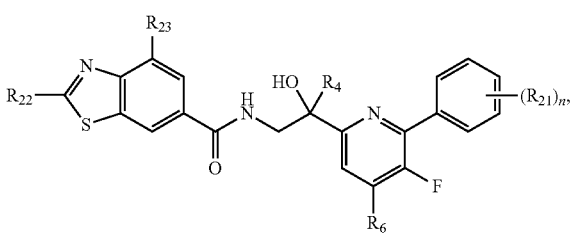

wherein n, m, $R_4$, $R_6$, $R_{21}$, $R_{22}$, $R_{23}$, and $R_{24}$ are as previously defined.

In one embodiment of the present invention, the compound of Formula (I) is represented by one of Formulae (VI-1)~(VI-10), wherein $R_4$ is selected from one of the following:

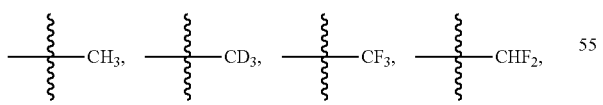

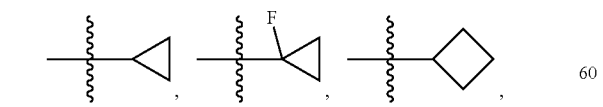

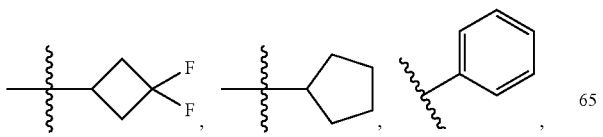

-continued

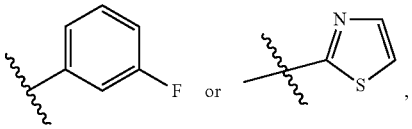 [SMILES: *c1cccc(F)c1 ; *c1nccs1], or or $R_4$ is

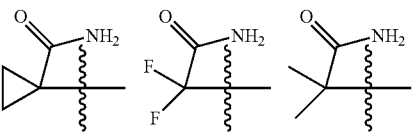, or , and $R_6$ is selected from the group below:

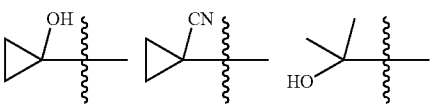

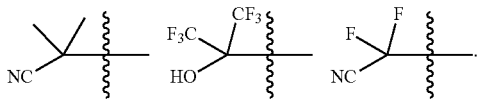

or the group below,

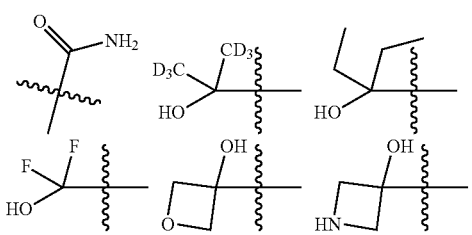

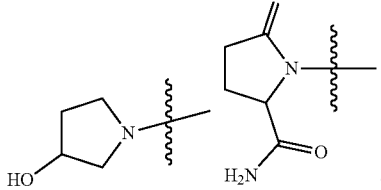.

In one embodiment of the present invention, the compound of Formula (I) is represented by one of Formulae (VII-1)~(VII-8):

(VII-1)
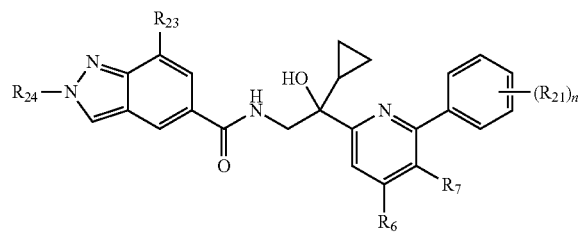
(VII-2)
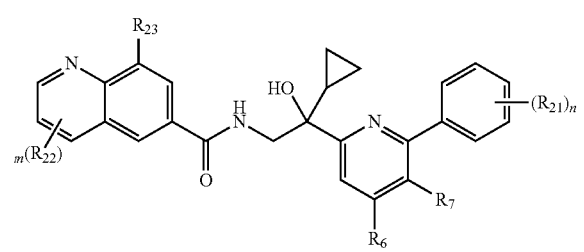
(VII-3)
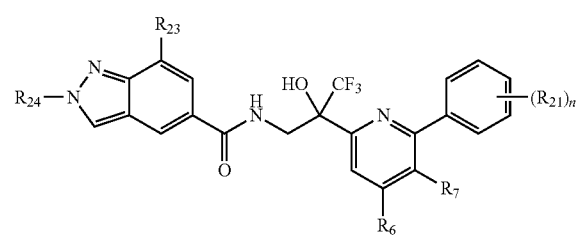
(VII-4)
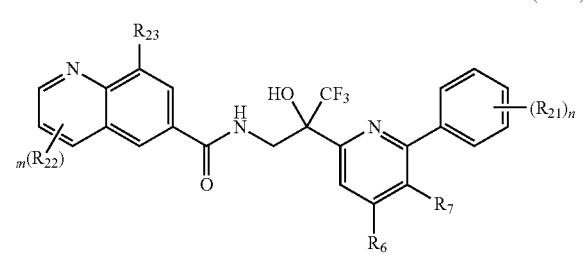
(VII-5)
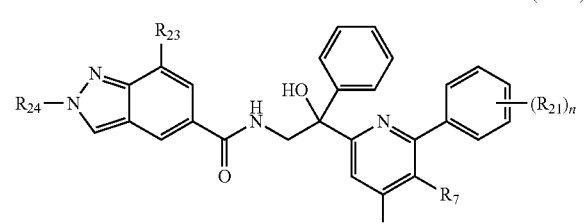
(VII-6)
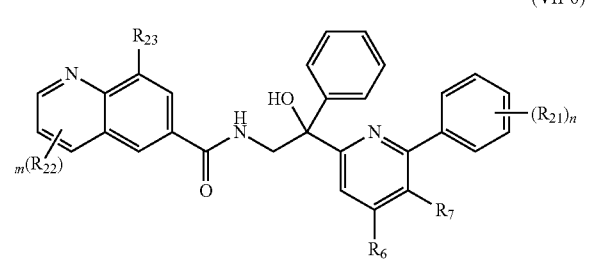
(VII-7)
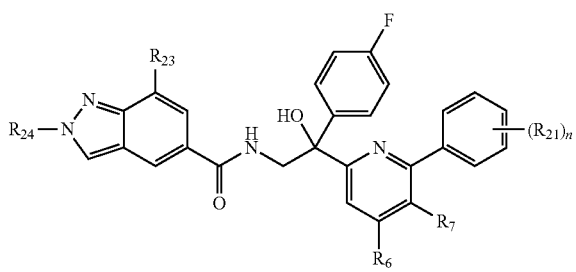
(VII-8)
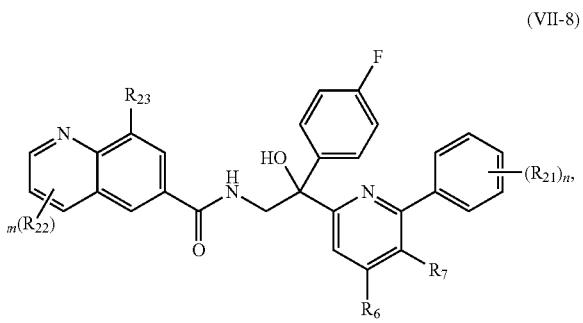
wherein n, m, $R_6$, $R_7$, $R_{21}$, $R_{22}$, $R_{23}$, and $R_{24}$ are as previously defined.
In one embodiment of the present invention, the Compound of Formula (I) is represented by one of Formulae (VII-1a)~(VII-8a)
(VII-1a)
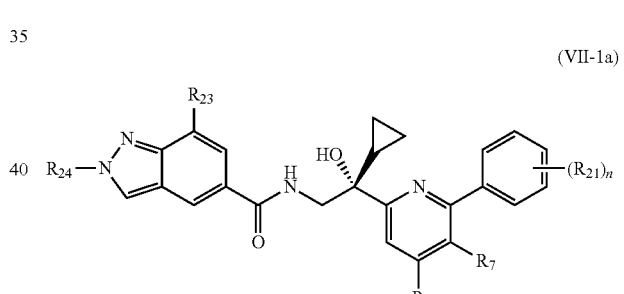
(VII-2a)
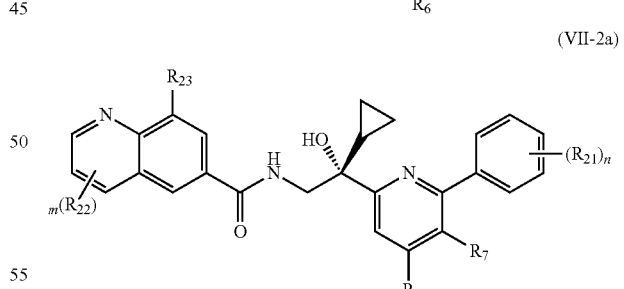
(VII-3a)
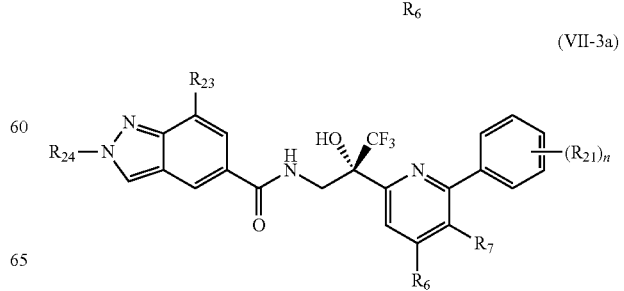

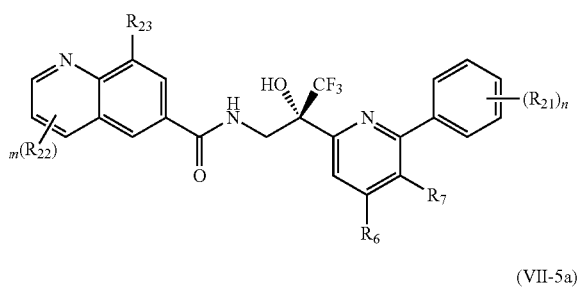
(VII-4a)

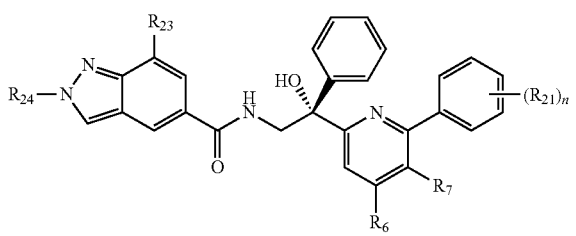
(VII-5a)

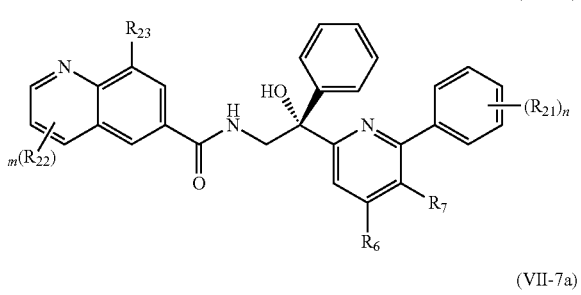
(VII-6a)

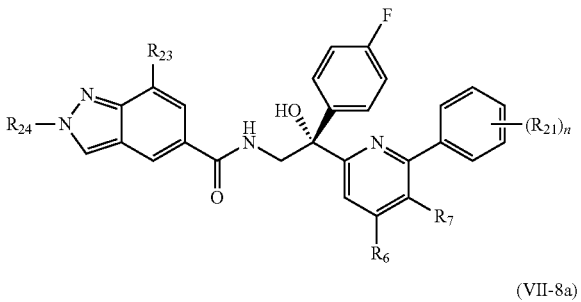
(VII-7a)

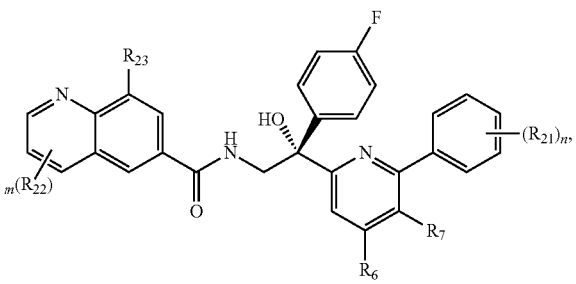
(VII-8a)

wherein n, m, $R_6$, $R_7$, $R_{21}$, $R_{22}$, $R_{23}$, and $R_{24}$ are as previously defined.

In one embodiment of the present invention, the compound of Formula (I) is represented by one of Formulae (VII-1)~(VII-8), or Formulae (VII-1a)~(VII-8a), wherein $R_7$ is hydrogen or —F; and $R_6$ is selected from one of the following:

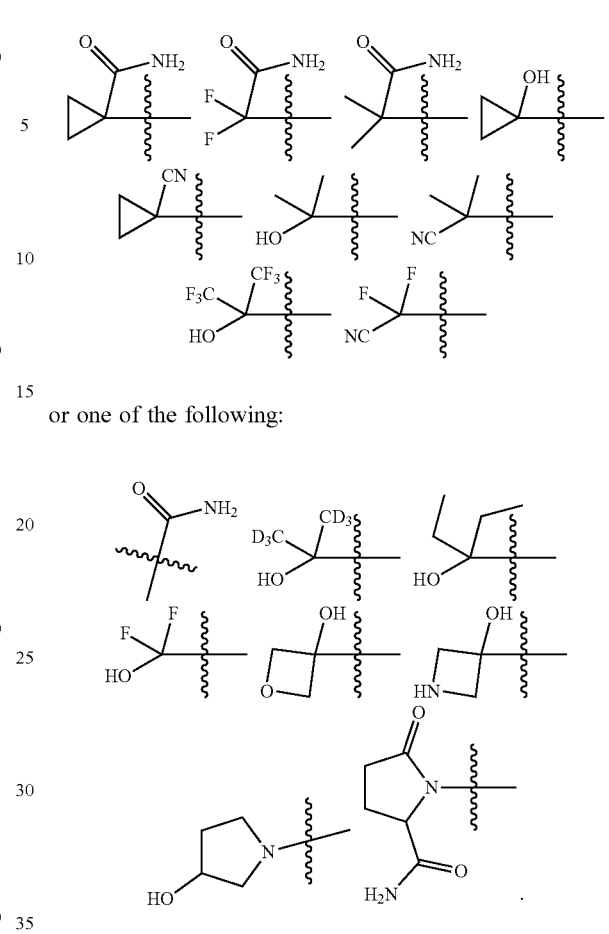

or one of the following:

It will be appreciated that the description of the present invention herein should be construed in congruity with the laws and principles of chemical bonding. In some instances, it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule.

It will be appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection in a subject in need thereof. The method comprises administering to the subject a therapeutically effective amount of a compound of Formula (I).

The present invention also provides the use of a compound of Formula (I) for the preparation of a medicament for the prevention or treatment of RSV.

Thus, in one embodiment, a compound of Formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of Formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of Formula (I) is combined with interleukin 8 or interleukin 9 inhibitors. The present invention thus also relates to a product containing a compound of Formula (I), or a pharmaceutically acceptable salt thereof, and an anti-inflammatory compound for simultaneous, separate, or sequential use in the treatment of RSV.

The present invention also relates to a combination of a compound of Formula (I), or a pharmaceutically acceptable salt thereof, with an anti-influenza compound and the use of such a combination in the treatment of concomitant RSV and influenza infections. The present invention thus also relates to a product containing a compound of Formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be achieved by concomitant administration in: (1) a unitary pharmaceutical composition including both compounds; or (2) separate pharmaceutical compositions each including one of the compounds.

In certain embodiments of the combination therapy, the additional therapeutic agent is administered at a lower dose and/or dosing frequency as compared to dose and/or dosing frequency of the additional therapeutic agent required to achieve similar results in treating or preventing RSV and/or HMPV infection.

In an embodiment, the compounds of the invention are administered by intranasal or intrabronchial administration. The present invention also provides an inhaler or nebulizer containing a medicament which comprises (a) a derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, nontoxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain a carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g. propylene glycol, and if desired, a suitable amount of lidocaine hydrochloride.

Solutions for injection or infusion may contain a carrier, for example, sterile water or preferably they may be in the form of sterile, aqueous, isotonic saline solutions.

The present invention also relates to the compounds as defined above; or a pharmaceutically acceptable salt thereof, for use in a method of treating the human or animal body. The present invention also relates to a pharmaceutical composition comprising a compound as defined above and a pharmaceutically acceptable diluent or carrier. Preferably, the pharmaceutical composition comprises a pharmaceutically acceptable salt of a compound as defined above. A pharmaceutically acceptable salt is as defined above. The compounds of the invention are typically administered in the manner defined above and the compounds are typically formulated for administration in the manner defined above.

Preferably, the pharmaceutical compositions comprise optically active isomers of the compounds of the invention. Thus, for example, preferred compounds of the invention containing only one chiral center include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the compounds of the invention can, if desired, be used in the form of solvates.

Yet a further aspect of the present invention is a process of making any of the compounds delineated herein employing any of the synthetic means delineated herein.

It is to be understood that the compounds encompassed by the present invention are those that are suitably stable for use as a pharmaceutical agent.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring. Preferred aryl groups are $C_6$-$C_{12}$-aryl groups, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. In certain embodiments, a heteroaryl group is a 5- to 10-membered heteroaryl, such as a 5- or 6-membered monocyclic heteroaryl or an 8- to 10-membered bicyclic heteroaryl. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof. A heteroaryl group can be C-attached or N-attached where possible.

In accordance with the invention, aryl and heteroaryl groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," and "$C_3$-$C_6$ alkyl," refer to alkyl groups containing from 1 to 4, 1 to 6, 1 to 8, 1 to 12, 2 to 4 and 3 to 6 carbon atoms respectively. Examples of alkyl groups include, but are not limited to, methyl, ethyl, propyl, isopropyl, n-butyl, sec-butyl, tert-butyl, n-pentyl, neopentyl, n-hexyl, n-heptyl and n-octyl radicals.

The term "alkenyl" as used herein, refers to straight- or branched-chain hydrocarbon radicals having at least one carbon-carbon double bond. "$C_2$-$C_8$ alkenyl," "$C_2$-$C_{12}$ alkenyl," "$C_2$-$C_4$ alkenyl," "$C_3$-$C_4$ alkenyl," and "$C_3$-$C_6$ alkenyl," refer to alkenyl groups containing from 2 to 8, 2 to 12, 2 to 4, 3 to 4 or 3 to 6 carbon atoms respectively. Alkenyl groups include, but are not limited to, ethenyl, propenyl, butenyl, 2-methyl-2-buten-2-yl, heptenyl, octenyl, and the like.

The term "alkynyl" as used herein, refers to straight- or branched-chain hydrocarbon radicals having at least one carbon-carbon triple bond. "$C_2$-$C_8$ alkynyl," "$C_2$-$C_{12}$ alkynyl," "$C_2$-$C_4$ alkynyl," "$C_3$-$C_4$ alkynyl," and "$C_3$-$C_6$ alkynyl," refer to alkynyl groups containing from 2 to 8, 2 to 12, 2 to 4, 3 to 4 or 3 to 6 carbon atoms respectively. Representative alkynyl groups include, but are not limited to, ethynyl, 2-propynyl, 2-butynyl, heptynyl, octynyl, and the like.

The term "cycloalkyl", as used herein, refers to a monocyclic or polycyclic saturated carbocyclic ring, such as a bi- or tri-cyclic fused, bridged or spiro system. The ring carbon atoms are optionally oxo-substituted or optionally substituted with an exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of cycloalkyl include, but are not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring, such as a bi- or tri-cyclic fused, bridged or spiro system having at least one carbon-carbon double bond. The ring carbon atoms are optionally oxo-substituted or optionally substituted with an exocyclic olefinic double bond. Preferred cycloalkenyl groups include $C_3$-$C_{12}$ cycloalkenyl, $C_4$-$C_{12}$-cycloalkenyl, $C_3$-$C_8$ cycloalkenyl, $C_4$-$C_8$ cycloalkenyl and $C_5$-$C_7$ cycloalkenyl groups.

Examples of cycloalkenyl include, but are not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-2-enyl, bicyclo[4.2.1]non-3-en-12-yl, and the like.

As used herein, the term "arylalkyl" means a functional group wherein an alkylene chain is attached to an aryl group, e.g., —$(CH_2)_n$-phenyl, where n is 1 to 12, preferably 1 to 6 and more preferably 1 or 2. The term "substituted arylalkyl" means an arylalkyl functional group in which the aryl group is substituted. Similarly, the term "heteroarylalkyl" means a functional group wherein an alkylene chain is attached to a heteroaryl group, e.g., —$(CH_2)_n$-heteroaryl, where n is 1 to 12, preferably 1 to 6 and more preferably 1 or 2. The term "substituted heteroarylalkyl" means a heteroarylalkyl functional group in which the heteroaryl group is substituted.

As used herein, the term "alkoxy" refers to a radical in which an alkyl group having the designated number of carbon atoms is connected to the rest of the molecule via an oxygen atom. Alkoxy groups include $C_1$-$C_{12}$-alkoxy, $C_1$-$C_8$-alkoxy, $C_1$-$C_6$-alkoxy, $C_1$-$C_4$-alkoxy and $C_1$-$C_3$-alkoxy groups. Examples of alkoxy groups includes, but are not limited to, methoxy, ethoxy, n-propoxy, 2-propoxy (isopropoxy) and the higher homologs and isomers. Preferred alkoxy is $C_1$-$C_3$alkoxy.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" and "heterocycloalkyl" can be used interchangeably and refer to a non-aromatic ring or a polycyclic ring system, such as a bi- or tri-cyclic fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclic or heterocycloalkyl groups may be further substituted. A heterocycloalkyl or heterocyclic group can be C-attached or N-attached where possible.

It is understood that any alkyl, alkenyl, alkynyl, alicyclic, cycloalkyl, cycloalkenyl, aryl, heteroaryl, heterocyclic, aliphatic moiety or the like described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH— heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, —$CO_2$—$C_3$-$C_{12}$-cycloalkyl, —$CO_2$-aryl, —$CO_2$-heteroaryl, —$CO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH— heterocycloalkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)— heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, —$NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)$NH_2$, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH— heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2NH$—$C_1$-$C_{12}$-alkyl, —$SO_2NH$—$C_2$-$C_8$-alkenyl, —$SO_2NH$—$C_2$-$C_8$-alkynyl, —$SO_2$—$C_1$-$C_{12}$-alkyl, —$SO_2$—$C_2$-$C_8$-alkenyl, —$SO_2$—$C_2$-$C_8$-alkynyl, —$SO_2$—$C_3$-$C_{12}$-cycloalkyl, —$SO_2$-aryl, —$SO_2$-heteroaryl, —$SO_2$-heterocycloalkyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S— heterocycloalkyl, or methylthio-methyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy; —CN; —OH; $NH_2$; $C_1$-$C_4$-alkylamino; di($C_1$-$C_4$-alkyl)amino; and $NO_2$. It is understood that an aryl, heteroaryl, alkyl, alkenyl, alkynyl, cycloalkyl, or heterocycloalkyl in a substituent can be further substituted. In certain embodiments, a substituent in a substituted moiety is additionally optionally substituted with one or more groups, each group being independently selected from $C_1$-$C_4$-alkyl; —$CF_3$, —$OCH_3$, —$OCF_3$, —F, —Cl, —Br, —I, —OH, —$NO_2$, —CN, and —$NH_2$. Preferably, a substituted alkyl group is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an element includes all isotopes of that element so long as the resulting compound is pharmaceutically acceptable. In certain embodiments, the isotopes of an element are present at a particular position according to their natural abundance. In other embodiments, one or more isotopes of an element at a particular position are enriched beyond their natural abundance.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including, but not limited to mesylate, tosylate, triflate, p-nitrobenzoate, phosphonate groups.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in P. G. M. Wuts, *Greene's Protective Groups in Organic Synthesis,* 5th edition, John Wiley & Sons, Hoboken, NJ (2014). Examples of hydroxyl protecting groups include, but are not limited to, benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including but not limited to, benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in P. G. M. Wuts, *Greene's Protective Groups in Organic Synthesis,* 5th edition, John Wiley & Sons, Hoboken, NJ (2014). Examples of amino protecting groups include, but are not limited to, methoxycarbonyl, t-butoxycarbonyl, 12-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); P. G. M. Wuts, *Greene's Protective Groups in Organic Synthesis,* 5th edition, John Wiley & Sons, Hoboken, N J (2014); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject," as used herein, refers to an animal. Preferably, the animal is a mammal. More preferably, the mammal is a human. A subject also refers to, for example, a dog, cat, horse, cow, pig, guinea pig, fish, bird and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 2-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Combination and Alternation Therapy

The compounds of the present invention may be used in combination with one or more antiviral therapeutic agents or anti-inflammatory agents useful in the prevention or treatment of viral diseases or associated pathophysiology. Thus, the compounds of the present invention and their salts, solvates, or other pharmaceutically acceptable derivatives thereof, may be employed alone or in combination with other antiviral or anti-inflammatory therapeutic agents. The compounds herein and pharmaceutically acceptable salts thereof may be used in combination with one or more other agents which may be useful in the prevention or treatment of respiratory disease, inflammatory disease, autoimmune disease, for example; anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast. pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, anthelmintic agents, antimalarial agents, antiprotozoal agents, antituberculosis agents, and antiviral agents, including those listed at https://www.drugs.com/drug-class/anti-infectives.html. In general, combination therapy is typically preferred over alternation therapy because it induces multiple simultaneous stresses on the virus.

Although the invention has been described with respect to various preferred embodiments, it is not intended to be limited thereto, but rather those skilled in the art will recognize that variations and modifications may be made therein which are within the spirit of the invention and the scope of the appended claims.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The "additional therapeutic or prophylactic agents" include but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or anti-microbial and anti-viral agents (e.g. ribavirin and amantidine). The compositions according to the invention may also be used in combination with gene replacement therapy.

Abbreviations

Abbreviations which have been used in the descriptions of the schemes and the examples that follow are:
ACN for acetonitrile;
AD-mix-β for (9S)-(9"S)-9,9"-[1,4-Phthalazinediylbis(oxy)]bis[10,11-dihydro-6'-methoxycinchonan];
BAST for (diethylamino)sulfur trifluoride;
Bn for benzyl;
BOP for (Benzotriazol-1-yloxy)tris(dimethylamino)phosphonium hexafluorophosphate;
BzCl for benzoyl chloride;
mCPBA for meta-chloroperbenzoic acid;
Cbz for benzyloxycarbonyl;
CDI for carbonyldiimidazole;
DAST for diethylaminosulfur trifluoride;
DBU for 1,8-Diazabicycloundec-7-ene;
DCM for dichloromethane;
Dess-Martin periodinane for 1,1,1-tris(acetyloxy)-1,1-dihydro-1,2-benziodoxol-3-(1H)-one;
DIAD for diisopropyl azodicarboxylate;
DIBAL-H for diisobutylaluminum hydride;
DIPEA for diisopropylethylamine;
DMAP for N,N-dimethylaminopyridine;
DME for 1,2-dimethoxyethane;
DMF for N,N-dimethyl formamide;
DMSO for dimethylsulfoxide;
DPPA for diphenylphosphoryl azide or diphenyl phosphorylazidate;
EDCI or EDC for 1-(3-diethylaminopropyl)-3-ethylcarbodiimide hydrochloride;
EtOAc for ethyl acetate;
HATU for O (7-Azabenzotriazole-1-yl)-N,N,N',N'-tetramethyluronium hexafluorophosphate;
HCl for hydrochloric acid;
HOBt for 1-hydroxybenzotriazole;
Hunig's base for diisopropylethylamine;
Pd(dppf)Cl$_2$ for 1,1'-bis(diphenylphosphino)ferrocene]dichloropalladium(II);
PyBOP for (Benzotriazol-1-yloxy)tripyrrolidinophosphonium hexafluorophosphate;
LDA for Lithium diisopropylamine;
Ms for $CH_3SO_2$—;
Pd—C for palladium carbon;
Ph for phenyl;
RT for reverse transcription;
RT-PCR for reverse transcription-polymerase chain reaction;
TBAF for tetrabutylammonium fluoride;
TBME for tert-butyl methyl ether;
TEA for triethylamine;
Tf$_2$O for trifluoromethanesulfonic anhydride;
TFA for trifluoroacetic acid;
THE for tetrahydrofuran;
(TMS)$_2$NH for hexamethyldisilazane;
TBS for tert-Butyldimethylsilyl;
TBDPS for tert-Butyldiphenylsilyl;
TMS for trimethylsilyl;
TPAP tetrapropylammonium perruthenate;
PPh$_3$ for triphenylphosphine;
Ts or tosyl for p-$CH_3C_6H_4SO_2$—;
tBOC or Boc for tert-butyloxy carbonyl; and
Xantphos for 4,5-Bis-diphenylphosphanyl-9,9-dimethyl-9H-xanthene;
XPhos Pd G2 for chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalyst.

Synthetic Methods

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

The compounds and processes of the present invention will be better understood in connection with the following synthetic schemes that illustrate the methods by which the compounds of the invention may be prepared, which are intended as an illustration only and not to limit the scope of the invention.

Scheme 1 illustrates methods to prepare compounds of formula 13 starting from compounds 1 and 2. Compound 1 is coupled with boronic acids or ester 2 using an appropriate coupling reagent such as, but not limited to, XPhos Pd G2 or Pd(dppf)Cl$_2$ or Pd(PPh$_3$)$_4$ to afford compound 3, wherein E and R$_7$ are as previously defined. After N-oxidation of 3 using m-CPBA, the obtained compound 4 is converted to 5 using POCl$_3$ at a heated condition. Compound 5 is reacted with MeMgCl or MeMgBr to afford alcohol 6. Compound 6 is coupled with vinyl boronic ester 7 using an appropriate coupling reagent such as, but not limited to, Pd(dppf)Cl$_2$ or Pd(PPh$_3$)$_4$ to afford compound 8, wherein R$_4$ is as previously defined. Using appropriate chiral dihydroxylation reagents and/or ligand such as, but no t limit to, AD-mix-beta, compound 9 can be prepared in a stereoselective or stereospecific fashion. The diol compound 9 is converted to compound 10 whereas L is a leaving group such as, but not limited to, Cl, Br, I, OMs, or OTs. Displacement of L of compound 10 with ammonia provides compound 11. Finally, amine 11 is coupled with acid 12 using a coupling reagent such as, but not limited to, HATU/DIPEA or PyBOP/DIPEA to afford 13 wherein A is as previously defined.

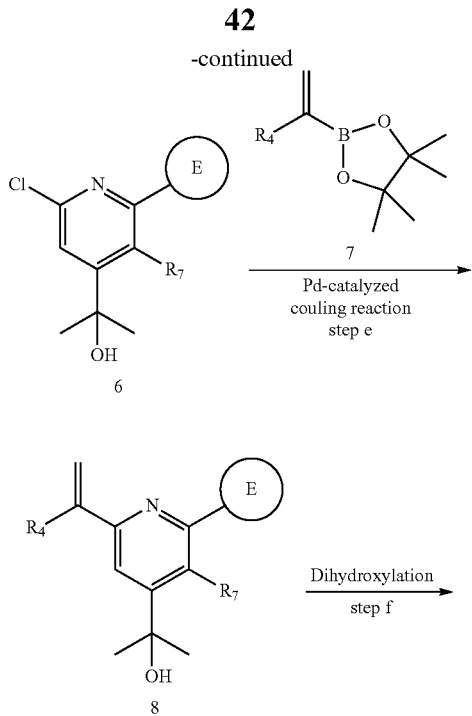

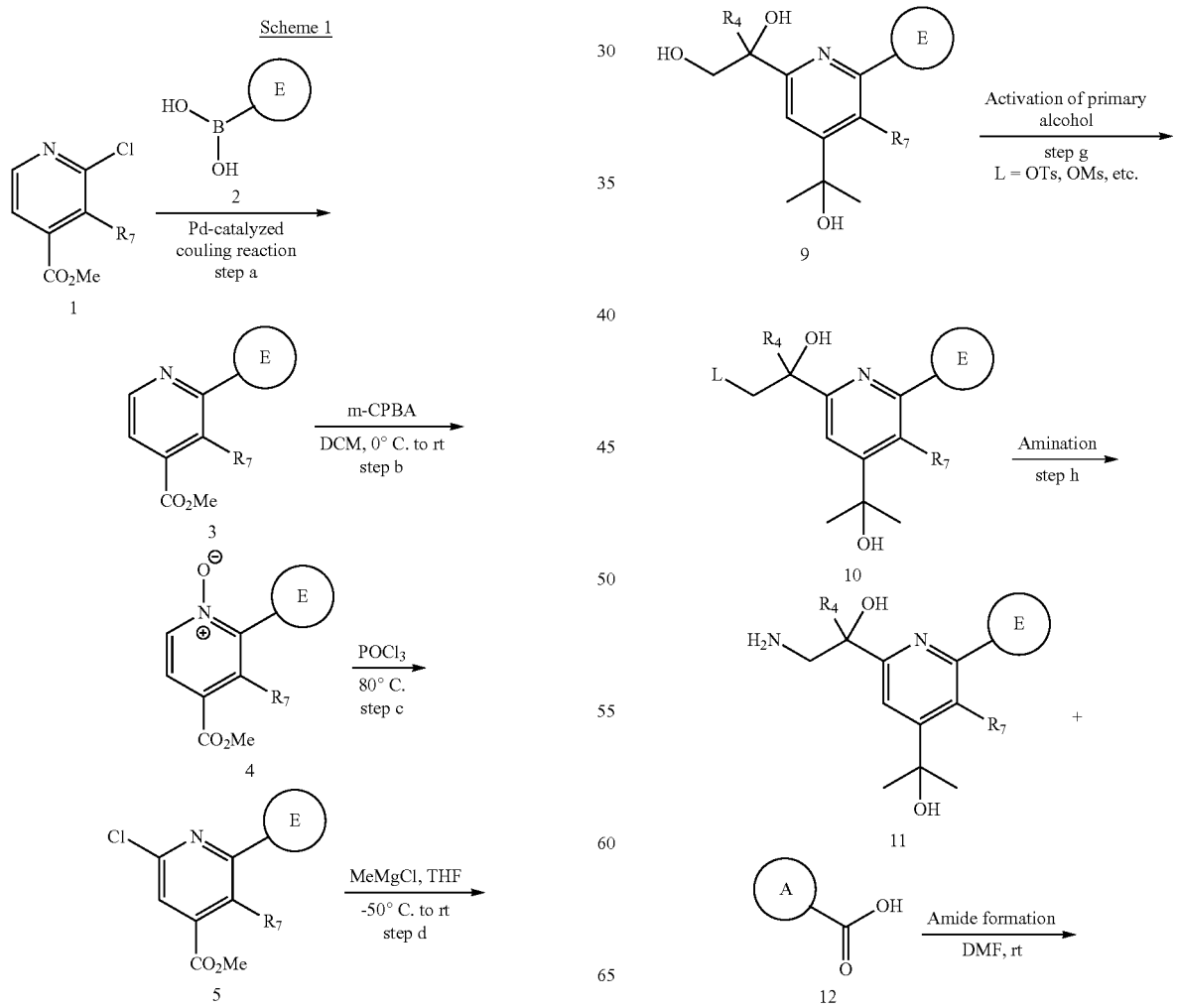

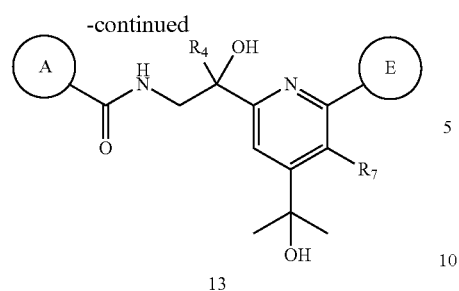

13

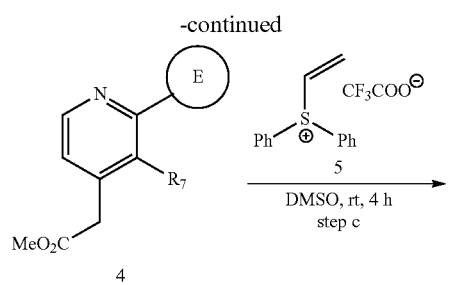

4

Scheme 2 illustrates methods to prepare compounds of formula 17 starting from compounds 1. Compound 1 is methylated to afford 2 using an appropriate methylation reagent such as, but not limited to, trimethylsilyldiazomethane to afford compound 2, wherein $R_7$ is as previously defined. Compound 2 is then coupled with boronic acids or ester 3 using an appropriate coupling reagent such as, but not limited to, XPhos Pd G2 or Pd(dppf)Cl$_2$ or Pd(PPh$_3$)$_4$ to afford compound 4, wherein E is as previously defined. Introducing a cyclopropyl group on 4 is achieved using a reagent such as, but not limited to 5 to afford 6. After N-oxidation of 6 using m-CPBA, the obtained compound 7 is converted to 8 using POCl$_3$ at a heated condition. Compound 8 is hydrolyzed using a base such as, but not limited to, NaOH, LiOH or KOH to afford 9. The free acid 9 is converted to amide 10 using an amide coupling reagent such as, but not limited to, NH$_4$Cl/HATU. Compound 10 is coupled with vinyl boronic ester 11 using an appropriate coupling reagent such as, but not limited to, Pd(dppf)Cl$_2$ or Pd(PPh$_3$)$_4$, to afford compound 12, wherein $R_4$ is as previously defined. Using appropriate chiral dihydroxylation reagents and/or ligand such as, but not limited to, AD-mix-beta, compound 13 can be prepared in a stereoselective or stereospecific fashion. The diol compound 13 is converted to compound 14, where L is a leaving group such as, but not limited to Cl, Br, I, OMs, or OTs. Displacement of L of compound 14 with ammonia provides compound 15. Finally, amine 15 is coupled with acid 16 using a coupling reagent, but not limited to, HATU/DIPEA or PyBOP/DIPEA to afford 17 wherein A is as previously defined.

Scheme 2

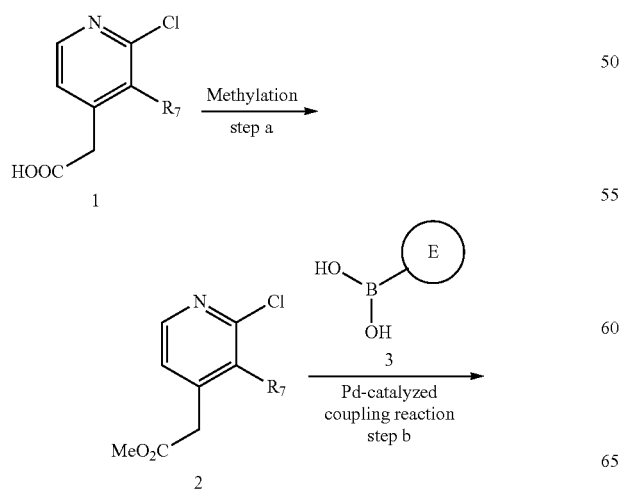

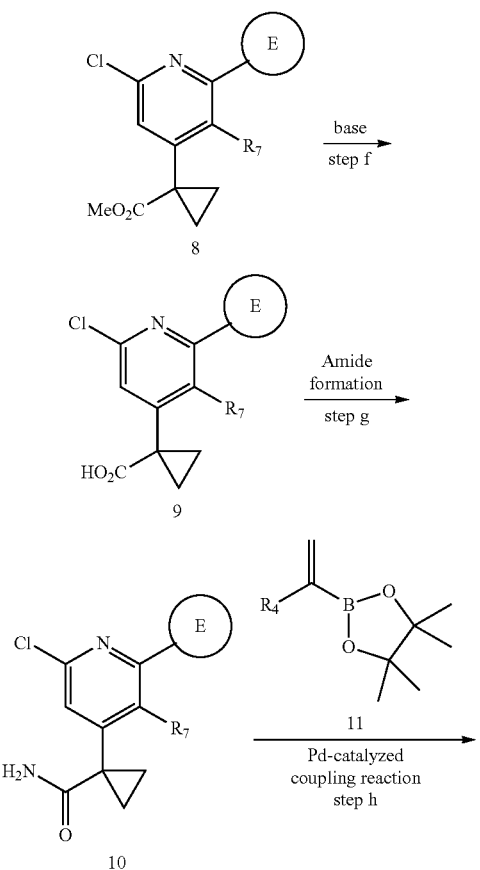

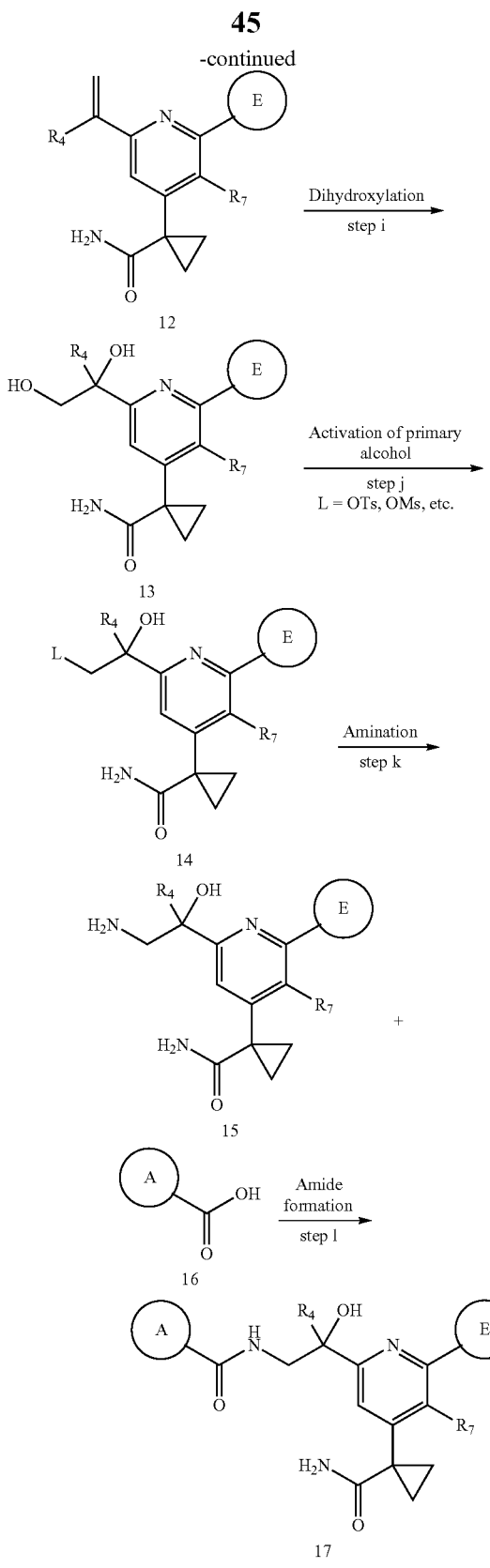

examples, which are intended as an illustration only and not limiting of the scope of the invention. Starting materials were either available from a commercial vendor or produced by methods well known to those skilled in the art.

While this invention has been particularly shown and described with references to preferred embodiments thereof, it will be understood by those skilled in the art that various changes in form and details may be made therein without departing from the scope of the invention encompassed by the appended claims.

Example 1

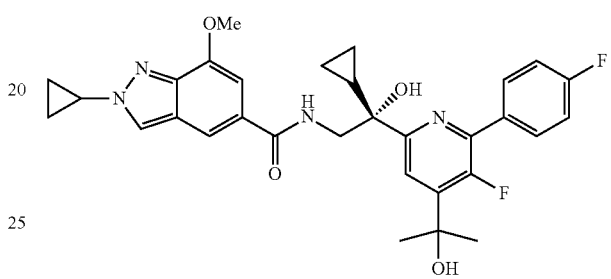

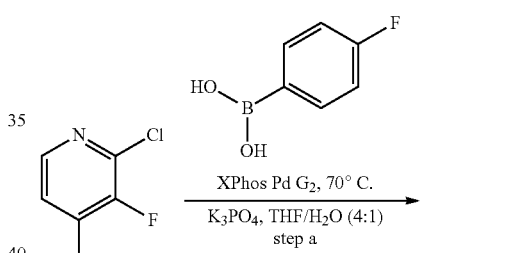

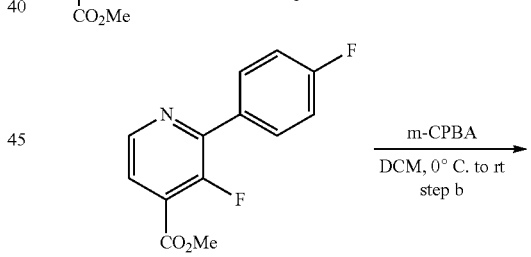

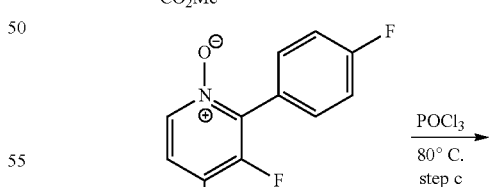

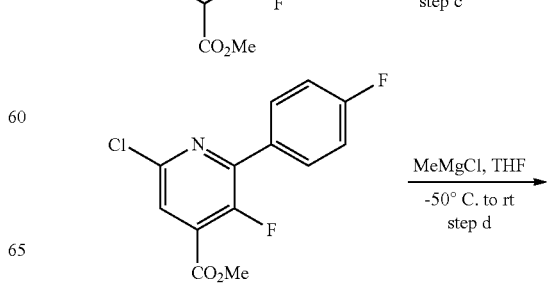

EXAMPLES

The compounds and processes of the present invention will be better understood in connection with the following -continued

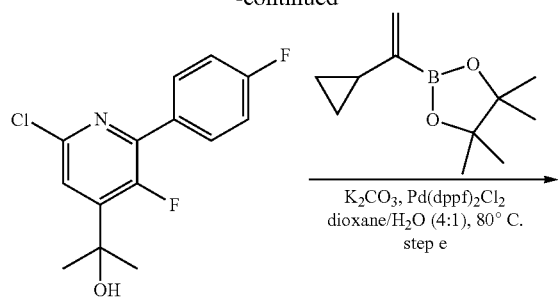

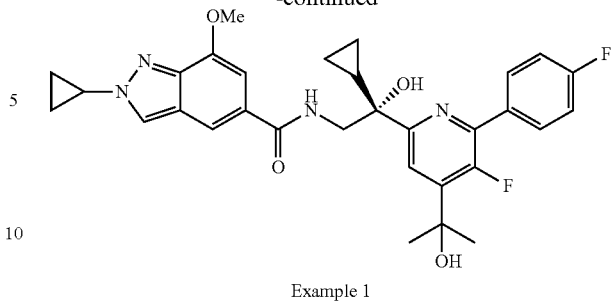

Example 1

Example 1 Step a

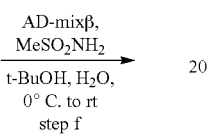

To a round-bottom flask (100 mL) were added methyl 2-chloro-3-fluoropyridine-4-carboxylate (7.0 g, 37 mmol), 4-fluorophenylboronic acid (10.33 g, 74.0 mmol), $K_3PO_4$ (23.5 g, 111.0 mmol), 2nd Generation XPhos Precatalyst (2.91 g, 3.7 mmol), THF (20 mL) and $H_2O$ (5 mL) at room temperature. After degassed, the resulting mixture was stirred at 70° C. for 2 h. The aqueous layer was extracted with EtOAc (500 mL×2). The organic layers were combined, dried and evaporated. The obtained residue was purified by silica gel column chromatography eluting with 0-40% EtOAc/hexanes to afford the desired compound (8.3 g, 90%) as a white solid. ESI-MS m/z: 250.05 [M+H]$^+$.

Example 1 Step b

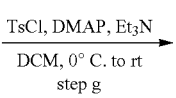

To a round-bottom flask (250 mL) were added the compound from step a (8.3 g, 12.0 mmol), m-CPBA (8.31 g, 48.0 mmol) and DCM (50 mL) at 0° C. The resulting mixture was stirred overnight at room temperature. The resulting mixture was washed with aq. NaOH (1 N) and the organic layer was further quenched with sat. $NH_4Cl$ (aq.) and $Na_2S_2O_3$ (10% wt) at room temperature. After washed with brine, the combined organic layers were dried over anhydrous $Na_2SO_4$, filtered and evaporated. The residue was purified by silica gel column chromatography eluting with 0-10% MeOH/DCM to afford the desired compound (4.45 g, 50%) as a yellow solid. ESI-MS m/z: 266.05 [M+H]$^+$.

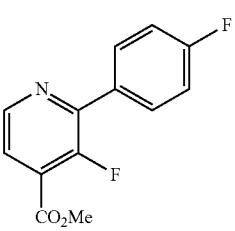 [SMILES: COC(=O)c1ccnc(-c2ccc(F)cc2)c1F]

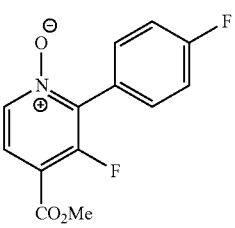 [SMILES: COC(=O)c1cc[n+]([O-])c(-c2ccc(F)cc2)c1F]

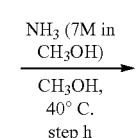

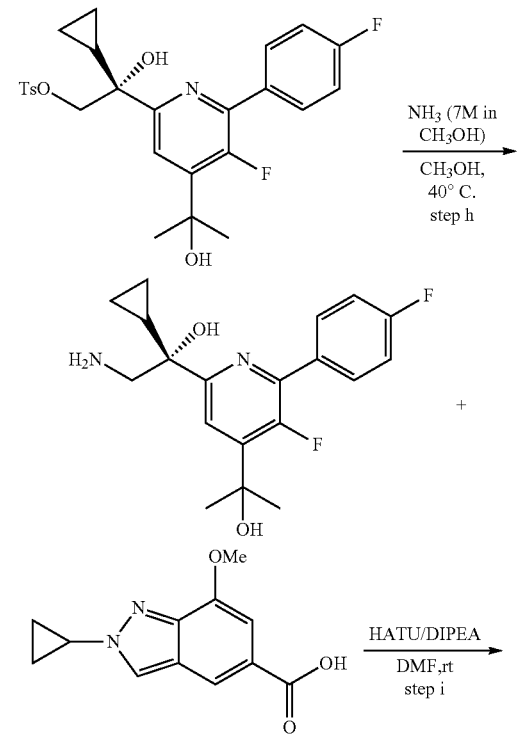

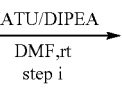

Example 1 Step c

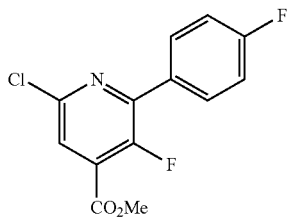 [SMILES: COC(=O)c1cc(Cl)nc(-c2ccc(F)cc2)c1F]

To a round-bottom flask (250 mL) were added the compound from step b (4.2 g, 16.0 mmol) and phosphorus oxychloride (50 mL) at room temperature. The resulting mixture was heated at 80° C. overnight and concentrated under reduced pressure. After removal most POCl$_3$, the remaining residue was diluted with EtOAc (200 mL) and brine (50 mL). The separated organic layer was washed with saturated NaHCO$_3$ (aq.) and brine. After concentrated the organic layer under vacuum, the residue was purified by silica gel column chromatography eluting with 0-40% EtOAc/hexanes to afford the desired compound (4.0 g, 87%) as a white solid. ESI-MS m/z: 284.00 [M+H]$^+$.

Example 1 Step d

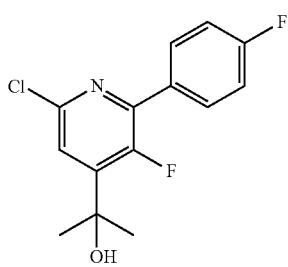 [SMILES: CC(C)(O)c1cc(Cl)nc(-c2ccc(F)cc2)c1F]

To a round-bottomed flask (50 mL) were added the compound from step c (3.87 g, 14.0 mmol), THF (20 mL, 247.0 mmol). After cooling to −50° C., CH$_3$MgBr (4.07 g, 34.0 mmol) was slowly added. The resulting mixture was slowly warmed to room temperature and stirred for 2 h under nitrogen atmosphere. The reaction was quenched with sat. NH$_4$Cl (aq.) at 0° C. and then extracted with EtOAc (100 mL×2). The combined organic layers were washed with brine, dried over Na$_2$SO$_4$, filtered and evaporated. The residue was purified by silica gel column chromatography eluting with 0-40% EtOAc/hexanes to afford the desired compound (3.6 g, 93%) as a white solid. ESI-MS m/z: 284.05 [M+H]$^+$.

Example 1 Step e

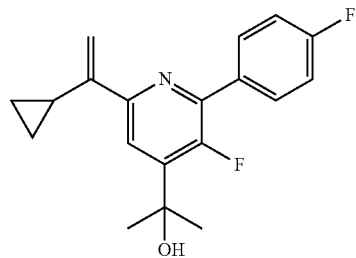 [SMILES: C=C(c1cc(C(C)(C)O)c(F)c(-c2ccc(F)cc2)n1)C1CC1]

To a round-bottom flask (100 mL) were added the compound from step d (1.8 g, 9.0 mmol), 2-[6-chloro-3-fluoro-2-(4-fluorophenyl)pyridin-4-yl]propan-2-ol (5.26 g, 19.0 mmol), K$_2$CO$_3$ (3.85 g, 28.0 mmol), Pd(dppf)Cl$_2$ (1.36 g, 1.8 mmol) and 1,4-dioxane (20 mL) at room temperature. The resulting mixture was stirred for 2 h at 80° C. under nitrogen atmosphere. The resulting mixture was extracted with EtOAc (100 mL×2). The combined organic layers were washed with brine, dried over Na$_2$SO$_4$, filtered and evaporated. The residue was purified by silica gel column chromatography eluting with 0-40% EtOAc/hexanes to afford the desired compound (1.9 g, 64%) as a yellow solid. ESI-MS m/z: 316.15 [M+H]$^+$.

Example 1 Step f

To a round-bottom flask (100 mL) were added the compound from step e (1.9 g, 6.03 mmol), AD-mix-β (14.0 g, 18.0 mmol), MeSO$_2$NH$_2$ (0.69 g, 6.0 mmol) and t-BuOH/H$_2$O (1:1, 20 mL) at 0° C. The resulting mixture was stirred for overnight at room temperature and then quenched by adding Na$_2$SO$_3$. The mixture was diluted with EtOAc (250 mL) and brine (100 mL). The organic layer was washed with brine, dried over Na$_2$SO$_3$, filtered and evaporated. The residue was purified by silica gel column chromatography eluted with 0-100% EtOAc/hexanes to afford the desired compound (2.0 g, 95%) as a white solid. ESI-MS m/z: 350.15 [M+H]$^+$.

Example 1 Step g

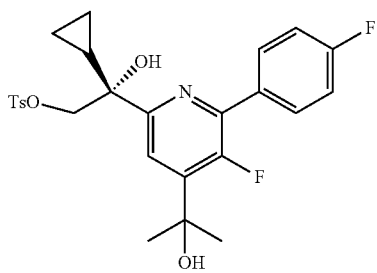 [SMILES: Cc1ccc(S(=O)(=O)OC[C@](O)(c2cc(C(C)(C)O)c(F)c(-c3ccc(F)cc3)n2)C2CC2)cc1]

To a round-bottom flask (100 mL) were added the compound from step f (1.95 g, 6.0 mmol), TsCl (1.28 g, 7.0 mmol), DMAP (0.68 g, 6.0 mmol), Et₃N (1.69 g, 16.0 mmol) and CH$_2$Cl$_2$ (20 mL) at 0° C. The resulting mixture was stirred for 2 h at room temperature under nitrogen atmosphere. The reaction was diluted with CH$_2$Cl$_2$ (100 mL) and washed with brine, dried over Na$_2$SO$_4$, filtered and evaporated. The residue was purified by silica gel column chromatography eluting with 0-30% EtOAc/hexanes to afford the desired compound (2.5 g, 88%) as a white solid. ESI-MS m/z: 504.15 [M+H]$^+$.

Example 1 Step h

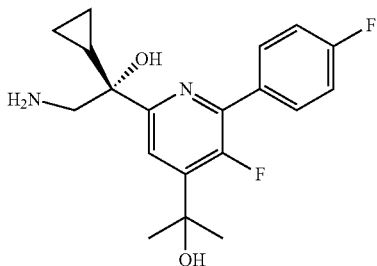

To a round-bottom flask (100 mL) were added the compound from step g (2.5 g, 5.0 mmol) and 7 N NH$_3$ in MeOH (30 mL) at room temperature. The resulting mixture was stirred for overnight at 40° C. under nitrogen atmosphere. The reaction mixture was concentrated in vacuo and dissolved in ethyl acetate. The organic layer was washed with saturated aq. NaHCO$_3$ solution and brine. The organic layer was dried, filtered and concentrated under reduced pressure to afford the desired compound (1.04 g, 60%) as a white solid. ESI-MS m/z: 349.15 [M+H]$^+$, 1H NMR (400 MHz, DMSO-d6) δ 0.11 (m, J=9.0, 5.7, 3.6 Hz, 1H), 0.23-0.40 (m, 2H), 0.42-0.52 (m, 1H), 1.26-1.37 (m, 3H), 1.55 (d, J=5.0 Hz, 6H), 2.86 (d, J=13.1 Hz, 1H), 3.19 (d, J=13.1 Hz, 1H), 4.87 (s, 1H), 5.57 (s, 1H), 7.34 (t, J=8.9 Hz, 2H), 7.86 (d, J=5.5 Hz, 1H), 7.91-8.00 (m, 2H).

Example 1 Step i

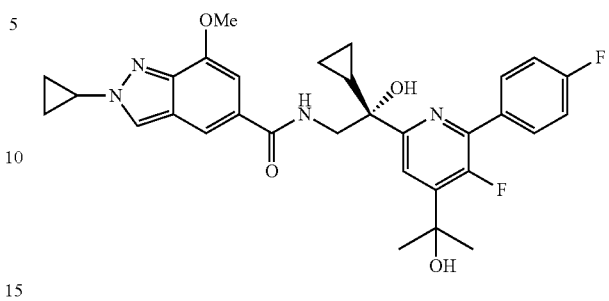

To a vial (5 mL) were added compound from step h (22 mg, 0.063 mmol), 2-cyclopropyl-7-methoxy-2H-indazole-5-carboxylic acid (18 mg, 0.076 mmol), HATU (29 mg, 0.076 mmol), DIPEA (40 mg, 0.32 mmol) and DMF (2 mL) at room temperature. The resulting mixture was stirred for 1 h at room temperature under nitrogen atmosphere. The residue was purified by reverse flash chromatography to afford the desired compound (20 mg, 56%) as a white solid. ESI-MS m/z: 563.25 [M+H]$^+$, 1H NMR (400 MHz, DMSO-d6) δ 0.13 (s, 1H), 0.27 (s, 1H), 0.39 (d, J=8.0 Hz, 1H), 0.55 (d, J=5.7 Hz, 1H), 1.11 (m, J=7.4, 5.0 Hz, 2H), 1.27 (p, J=4.9, 4.4 Hz, 2H), 1.51 (d, J=25.8 Hz, 6H), 3.89 (s, 5H), 4.14 (m, J=7.6, 3.8 Hz, 1H), 5.55 (s, 1H), 5.72 (s, 1H), 6.92 (d, J=1.3 Hz, 1H), 7.29-7.42 (m, 3H), 7.69 (d, J=1.2 Hz, 1H), 7.92 (d, J=5.6 Hz, 1H), 7.99 (t, J=7.0 Hz, 2H), 8.37 (d, J=6.2 Hz, 1H), 8.54 (s, 1H).

Example 2

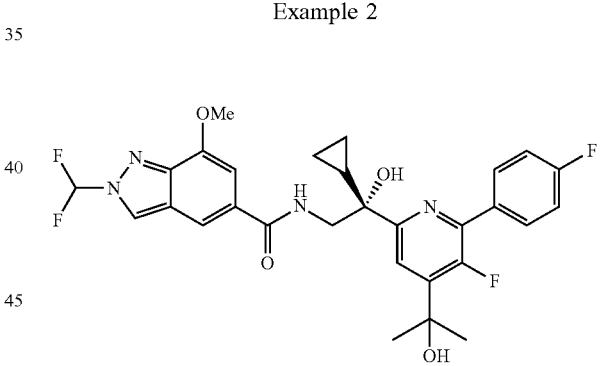

The title compound was synthesized according to the general method of Example 1 as a single enantiomer. ESI-MS m/z: 574.25 [M+H]$^+$.

Example 3

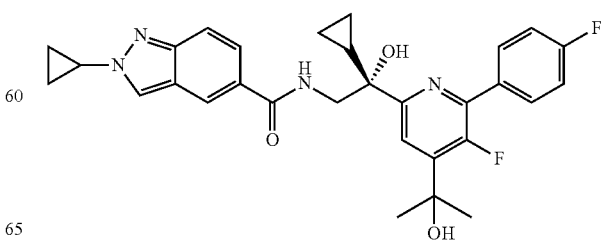

The title compound was synthesized according to the general method of Example 1 as a single enantiomer. ESI-MS m/z: 534.23 [M+H]⁺.

Example 4

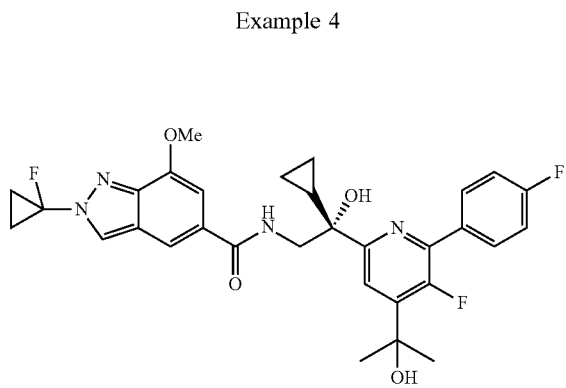

The title compound was synthesized according to the general method of Example 1 as a single enantiomer. ESI-MS m/z: 582.23 [M+H]⁺.

Example 5

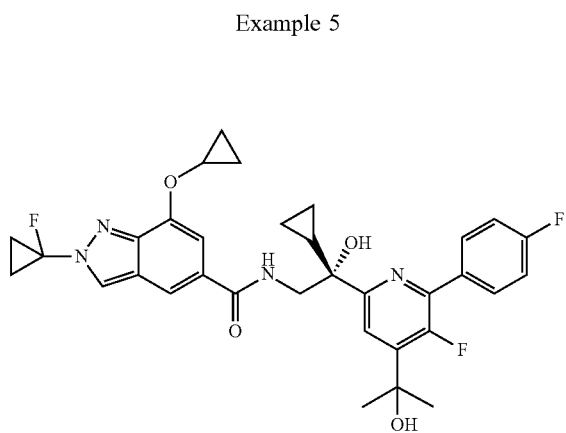

The title compound was synthesized according to the general method of Example 1 as a single enantiomer. ESI-MS m/z: 608.24 [M+H]⁺.

Example 6

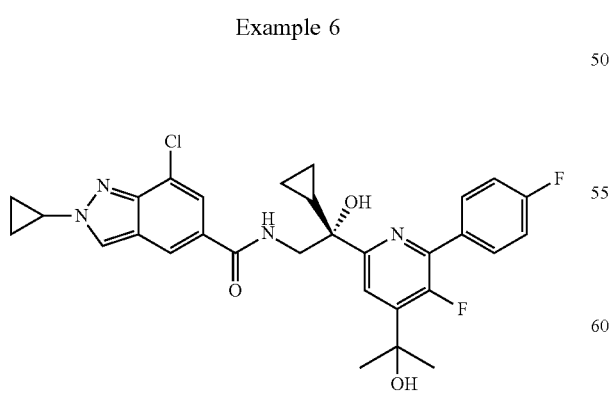

The title compound was synthesized according to the general method of Example 1 as a single enantiomer. ESI-MS m/z: 568.20 [M+H]⁺.

Example 7

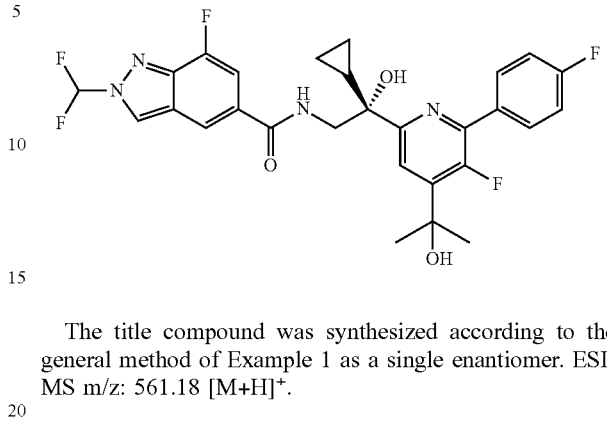

The title compound was synthesized according to the general method of Example 1 as a single enantiomer. ESI-MS m/z: 561.18 [M+H]⁺.

Example 8

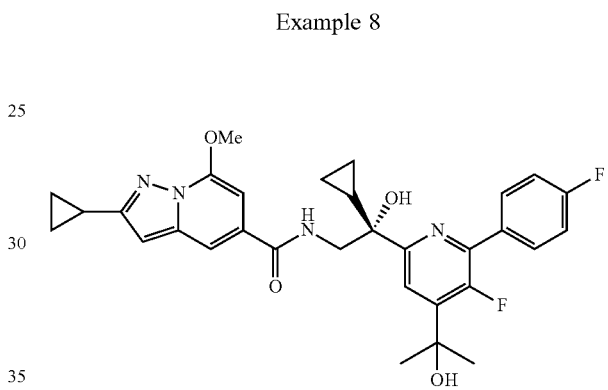

The title compound was synthesized according to the general method of Example 1 as a single enantiomer. ESI-MS m/z: 563.20 [M+H]⁺.

Example 9

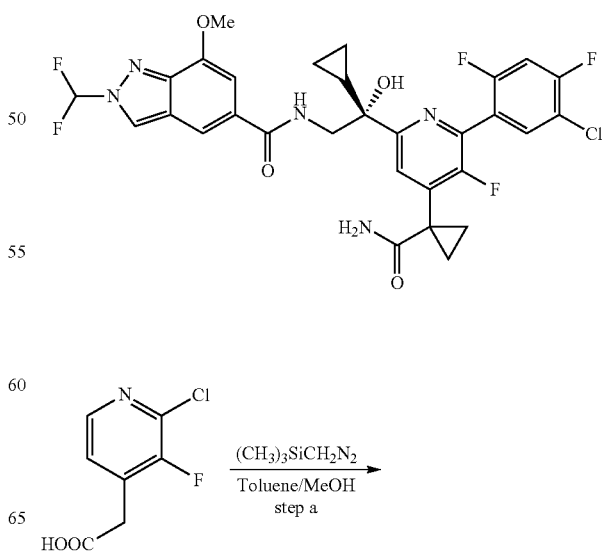

55
-continued
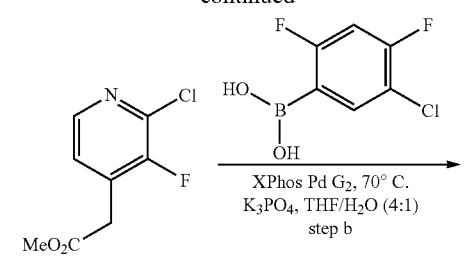
step b
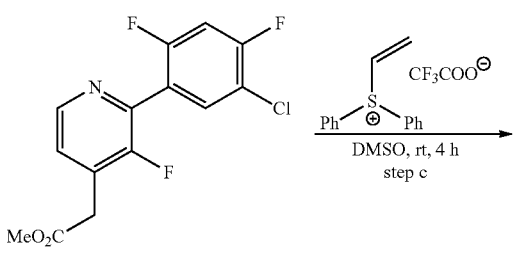
step c
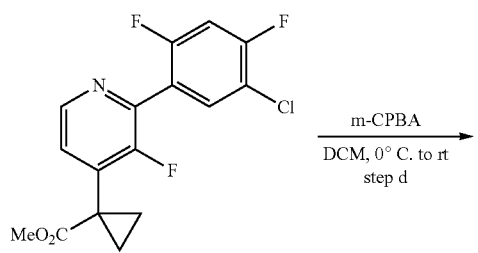
step d
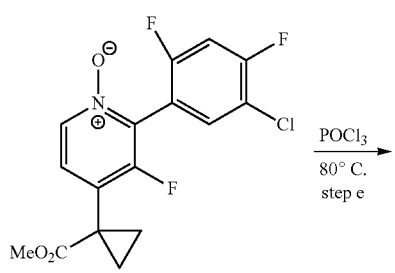
step e
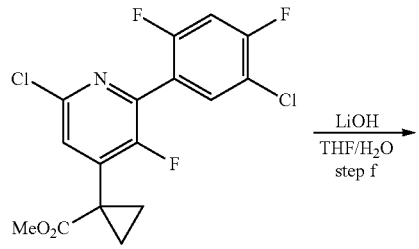
step f
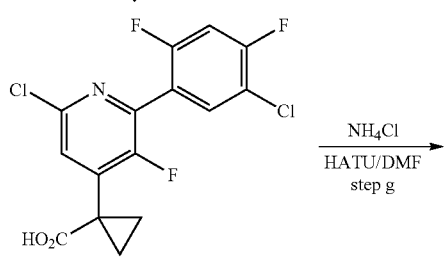
step g
56
-continued
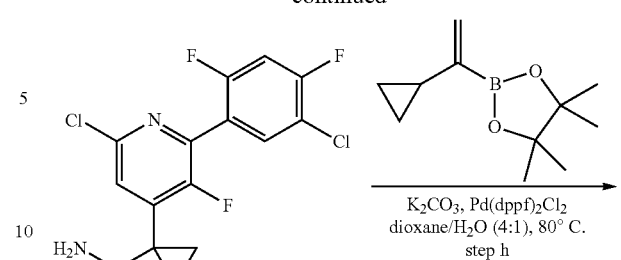
step h
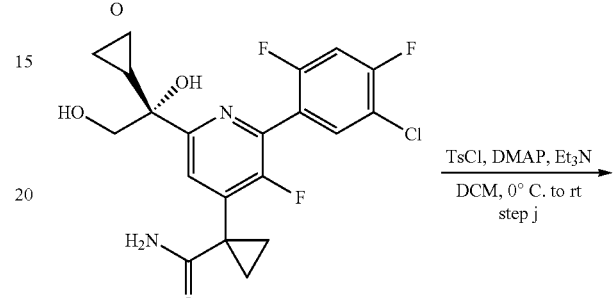
step j
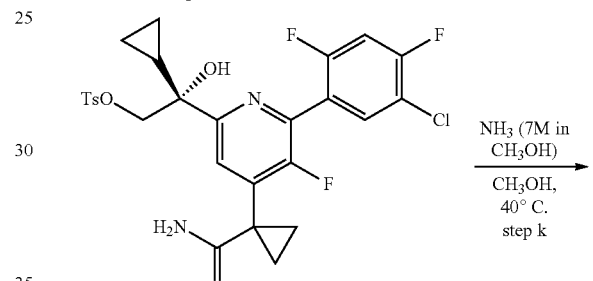
step k
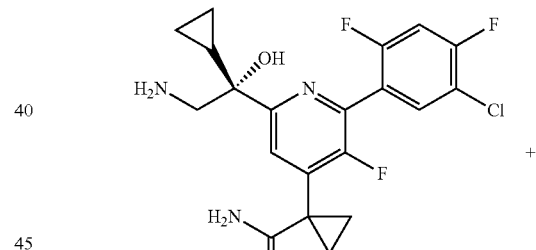
+
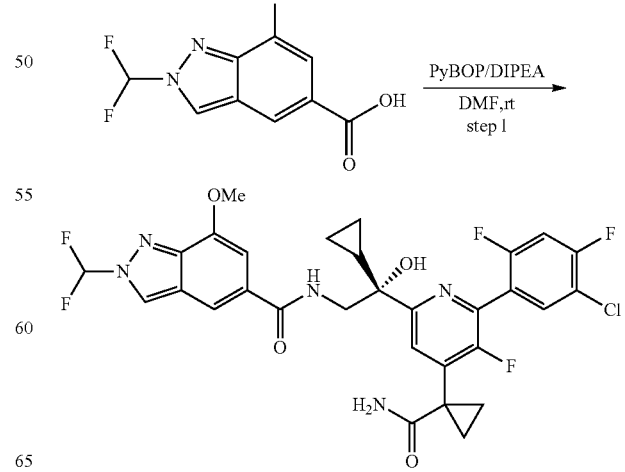

Example 9 Step a

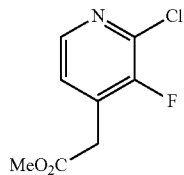 [SMILES: COC(=O)Cc1ccnc(Cl)c1F]

2-(2-Chloro-3-fluoropyridin-4-yl)acetic acid (1.5 g, 7.91 mmol) was dissolved in toluene/MeOH (20 mL/12 mL). After cooled down to 0° C., trimethylsilyldiazomethane (9.1 mL, 18.20 mmol) was slowly added. The reaction was warm to rt and stirred for 1 h and then quenched with AcOH (0.5 mL). After evaporated most of solvents, the residue was diluted with DCM (100 mL), washed with brine, dried over Na$_2$SO$_4$ and purified by silica gel column chromatography eluting with 0-20% EtOAc/hexanes to obtain the desired compound (1.4 g, 87% yield) as a colorless oil. ESI-MS m/z: 204.20 [M+H]$^+$.

Example 9 Step b

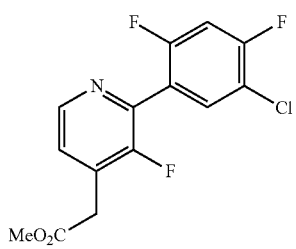 [SMILES: COC(=O)Cc1ccnc(-c2cc(Cl)c(F)cc2F)c1F]

To a round-bottom flask (100 mL) were added methyl 2-(2-chloro-3-fluoropyridin-4-yl)acetate (1.5 g, 7.37 mmol), (5-chloro-2,4-difluorophenyl)boronic acid (1.79 g, 74.0 mmol), K$_2$CO$_3$ (3.05 g, 22.1 mmol), Pd(dppf)Cl$_2$ (0.539 g, 0.737 mmol), 1,4-dioxane (45 mL) and H$_2$O (12 mL) at room temperature. After degassed, the resulting mixture was stirred at 80° C. for 2 h. The aqueous layer was extracted with EtOAc (50 mL×2). The organic layers were combined, dried and evaporated. The obtained residue was purified by silica gel column chromatography eluting with 0-10% EA/hexanes to afford the desired compound (1.8 g, 77%) as a pale-yellow oil. ESI-MS m/z: 316.20 [M+H]$^+$.

Example 9 Step c

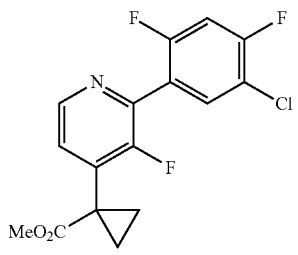 [SMILES: COC(=O)C1(c2ccnc(-c3cc(Cl)c(F)cc3F)c2F)CC1]

Methyl 2-(6-chloro-2-(5-chloro-2,4-difluorophenyl)-3-fluoropyridin-4-yl)acetate (170 mg, 0.486 mmol) and diphenyl(vinyl)sulfonium trifluoromethanesulfonate (222 mg, 0.583 mmol) and DMSO (2 mL) were added to a 5 mL vial. The resulting mixture was stirred at rt for 2 min, and then DBU (220 μl, 1.457 mmol) was added to the mixture. After stirred at rt for 4 h, reaction was completed. The reaction mixture was diluted with EtOAc (150 mL), washed with brine (20 mL×3), dried and purified by silica gel column chromatography eluting with 0-5% EtOAc/hexanes to obtain the desired compound (130 mg, 71.2% yield) as an oil. ESI-MS m/z: 376.01 [M+H]$^+$.

Example 9 Step d

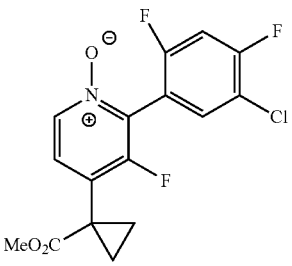

Following the same conditions as Example 1 step b, the desired compound was obtained as a white solid. ESI-MS m/z: 358.03 [M+H]$^+$.

Example 9 Step e

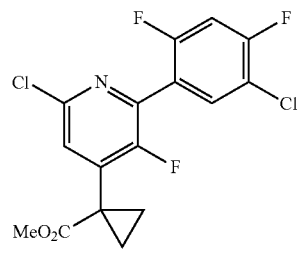

Following the same conditions as Example 1 step c, the desired compound was obtained as a white solid. ESI-MS m/z: 377.01 [M+H]$^+$.

Example 9 Step f

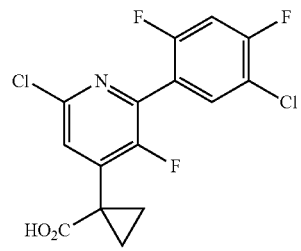 [SMILES: O=C(O)C1(c2cc(Cl)nc(-c3cc(Cl)c(F)cc3F)c2F)CC1]

To a solution of compound from step e (540 mg, 1.44 mmol) in THF (10 mL) and water (1 mL) was added LiOH (1.03 g, 43.1 mmol). The resulting mixture was stirred at rt overnight. After adjusted the pH~3, the mixture was extracted with EtOAc (100 mL×2). The combined organic layer was washed with brine, dried over Na$_2$SO$_4$, filtered and evaporated to obtain the desired product (500 mg, 96% yield) as a pale yellow solid. This crude product was used directly for the next step. ESI-MS m/z: 363.99 [M+H]$^+$.

Example 9 Step g

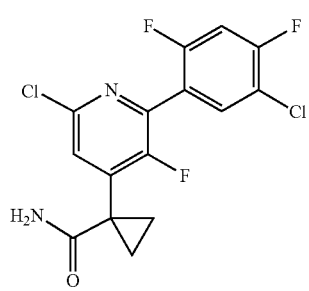 [SMILES: NC(=O)C1(c2cc(Cl)nc(-c3cc(Cl)c(F)cc3F)c2F)CC1]

To a round-bottomed flask were added compound from step f (540 mg, 1.491 mmol), HATU (1.13 g, 2.98 mmol), NH$_4$Cl (160 mg, 2.98 mmol), DIPEA (0.78 mL, 4.47 mmol) and DMSO (4 mL). The resulting mixture was stirred at rt overnight. After diluted with EtOAc (200 mL), the organic layer was washed with brine (50 mL×3), dried over Na$_2$SO$_4$ and evaporated. The residue was purified by silica gel column chromatography eluting with 0-50% EtOAc/hexanes to obtain the desired compound (460 mg, 85% yield) as a white foam. ESI-MS m/z: 361.03 [M+H]$^+$.

Example 9 Step h

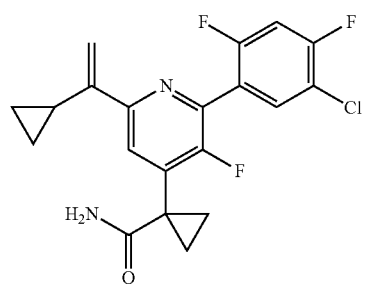 [SMILES: C=C(c1cc(C2(C(N)=O)CC2)c(F)c(-c2cc(Cl)c(F)cc2F)n1)C1CC1]

Following the same condition as Example 1 step e, the desired compound was obtained as an oil. ESI-MS m/z: 393.11 [M+H]$^+$.

Example 9 Step i

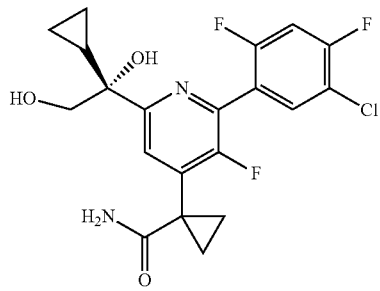 [SMILES: NC(=O)C1(c2cc([C@@](O)(CO)C3CC3)nc(-c3cc(Cl)c(F)cc3F)c2F)CC1]

Following the same condition as Example 1 step f, the desired compound was obtained as a white solid. ESI-MS m/z: 427.10 [M+H]$^+$.

Example 9 Step j

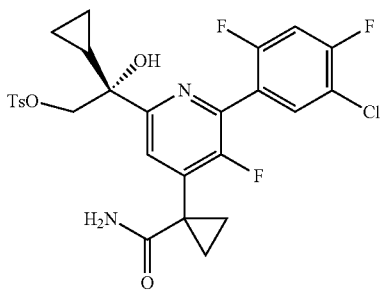

Following the same condition as Example 1 step g, the desired compound was obtained as an oil. ESI-MS m/z: 581.12 [M+H]$^+$.

Example 9 Step k

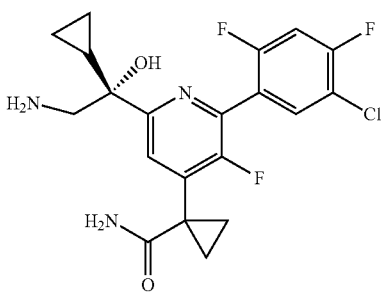 [SMILES: Cc1ccc(S(=O)(=O)OC[C@](O)(c2cc(C3(C(N)=O)CC3)c(F)c(-c3cc(Cl)c(F)cc3F)n2)C2CC2)cc1]

Following the same condition as Example 1 step h, the desired compound was obtained as a yellowish foam. ESI-MS m/z: 426.11 [M+H]$^+$.

Example 9 Step 1

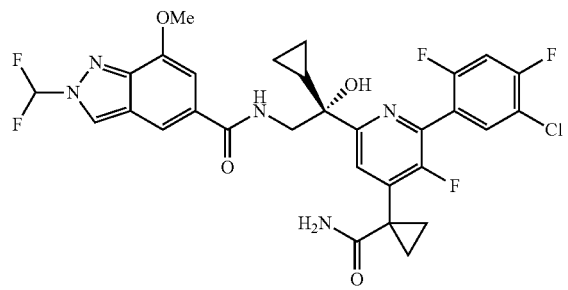 [SMILES: COc1cc(C(=O)NC[C@](O)(c2cc(C3(C(N)=O)CC3)c(F)c(-c3cc(Cl)c(F)cc3F)n2)C2CC2)cc2cn(C(F)F)nc12]

Following the same condition as Example 1 step i, the desired compound was obtained as a white foam as a single enantiomer. ESI-MS m/z: 650.17 [M+H]+.

Example 10

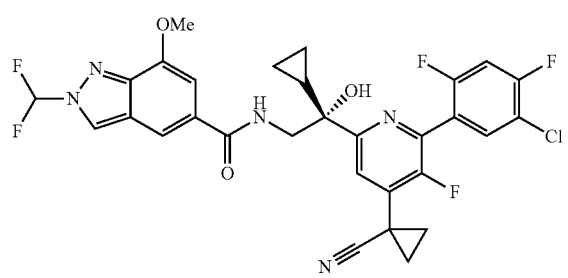 [SMILES: COc1cc(C(=O)NC[C@](O)(c2cc(C3(C#N)CC3)c(F)c(-c3cc(Cl)c(F)cc3F)n2)C2CC2)cc2cn(C(F)F)nc12]

To a solution of compound Example 9 (20 mg, 0.031 mmol) in DCM (2 mL) was added Et$_3$N (12.9 L, 0.093 mmol) and then cooled down to 0° C. After 5 min, trifluoroacetic anhydride (8.55 μL, 0.062 mmol) in DCM (0.5 mL) was slowly added. The reaction was quenched with MeOH after 10 min and then evaporated. The residue was purified by reverse flash chromatography to afford the desired compound (15 mg, 77%) as a white foam after lyophilization. ESI-MS m/z: 632.15 [M+H]+.

Example 11

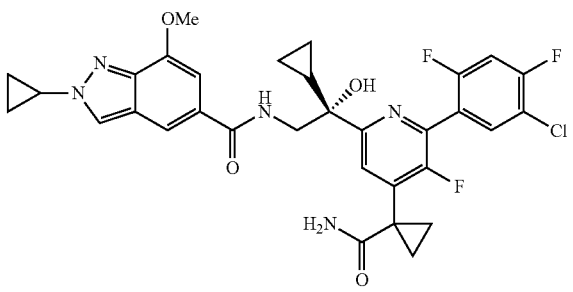 [SMILES: COc1cc(C(=O)NC[C@](O)(c2cc(C3(C(N)=O)CC3)c(F)c(-c3cc(Cl)c(F)cc3F)n2)C2CC2)cc2cn(C3CC3)nc12]

The title compound was synthesized according to the general method of Example 9 as a single enantiomer. ESI-MS m/z: 640.20 [M+H]+.

Example 12

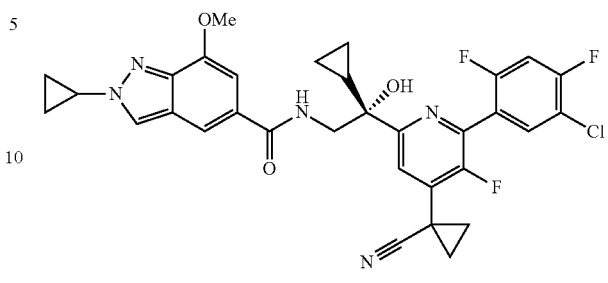

The title compound was synthesized according to the general method of Example 10 as a single enantiomer. ESI-MS m/z: 622.19 [M+H]+.

Example 13

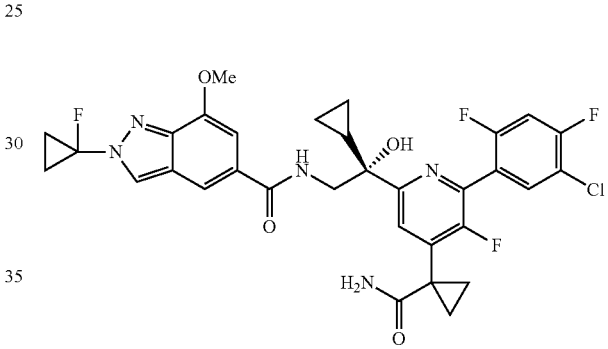

The title compound was synthesized according to the general method of Example 9 as a single enantiomer. ESI-MS m/z: 658.19 [M+H]+.

Example 14

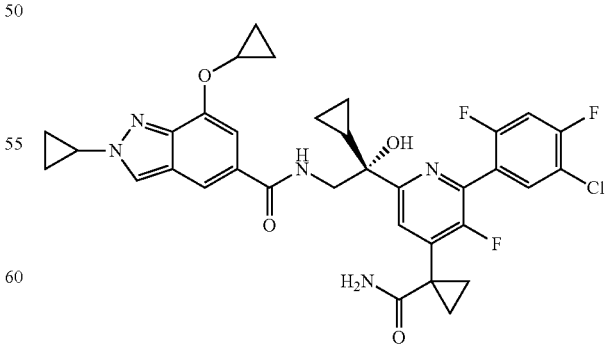

The title compound was synthesized according to the general method of Example 9 as a single enantiomer. ESI-MS m/z: 666.21 [M+H]+.

Example 15

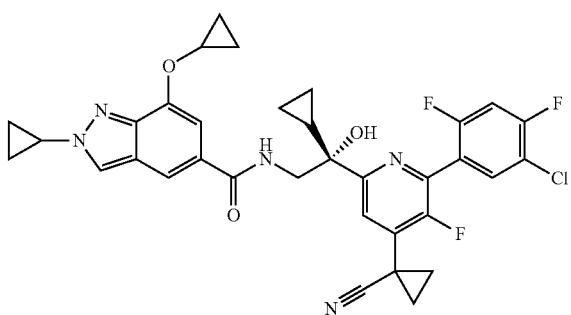 [SMILES: N#CC1(c2cc([C@@](O)(CNC(=O)c3cc(OC4CC4)c4nn(C5CC5)cc4c3)C3CC3)nc(-c3cc(Cl)c(F)cc3F)c2F)CC1]

The title compound was synthesized according to the general method of Example 10 as a single enantiomer. ESI-MS m/z: 648.21 [M+H]+.

Example 16

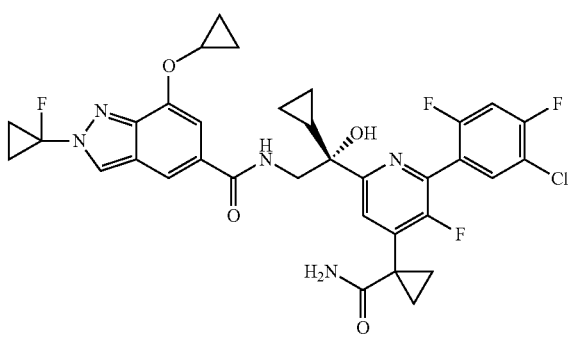 [SMILES: NC(=O)C1(c2cc([C@@](O)(CNC(=O)c3cc(OC4CC4)c4nn(C5(F)CC5)cc4c3)C3CC3)nc(-c3cc(Cl)c(F)cc3F)c2F)CC1]

The title compound was synthesized according to the general method of Example 9 as a single enantiomer. ESI-MS m/z: 684.22 [M+H]+.

Example 17

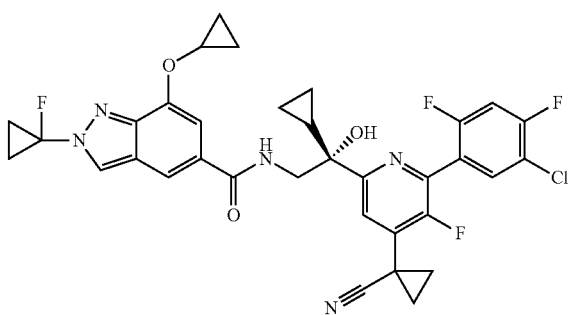 [SMILES: N#CC1(c2cc([C@@](O)(CNC(=O)c3cc(OC4CC4)c4nn(C5(F)CC5)cc4c3)C3CC3)nc(-c3cc(Cl)c(F)cc3F)c2F)CC1]

The title compound was synthesized according to the general method of Example 10 as a single enantiomer. ESI-MS m/z: 666.19 [M+H]+.

Example 18

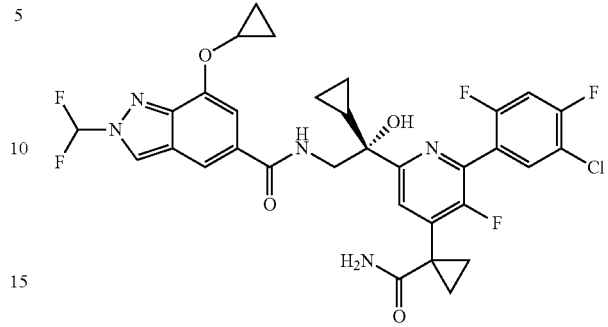

The title compound was synthesized according to the general method of Example 9 as a single enantiomer. ESI-MS m/z: 676.19 [M+H]+.

Example 19

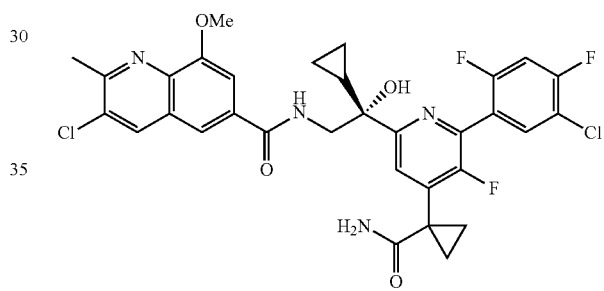

The title compound was synthesized according to the general method of Example 9 as a single enantiomer. ESI-MS m/z: 659.14 [M+H]+.

Example 20

The title compound was synthesized according to the general method of Example 9 as a single enantiomer. ESI-MS m/z: 640.20 [M+H]+.

Example 21

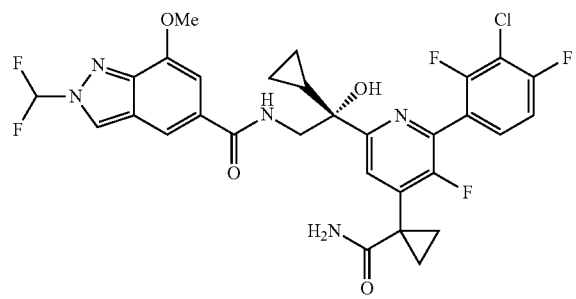 [SMILES: COc1cc(C(=O)NC[C@](O)(c2cc(C3(C(N)=O)CC3)c(F)c(-c3ccc(F)c(Cl)c3F)n2)C2CC2)cc2cn(C(F)F)nc12]

The title compound was synthesized according to the general method of Example 9 as a single enantiomer. ESI-MS m/z: 650.16 [M+H]+.

Example 22

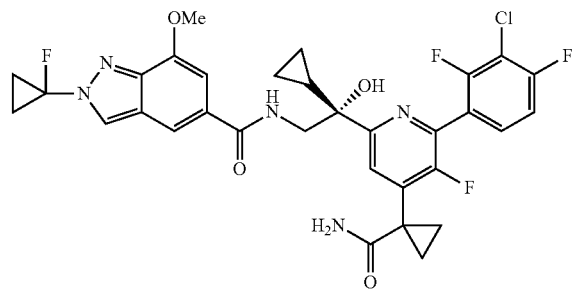 [SMILES: COc1cc(C(=O)NC[C@](O)(c2cc(C3(C(N)=O)CC3)c(F)c(-c3ccc(F)c(Cl)c3F)n2)C2CC2)cc2cn(C3(F)CC3)nc12]

The title compound was synthesized according to the general method of Example 9 as a single enantiomer. ESI-MS m/z: 658.19 [M+H]+.

Example 23

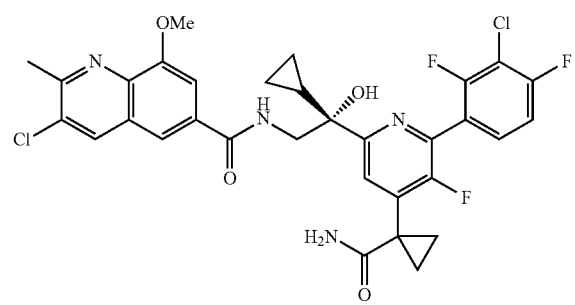 [SMILES: COc1cc(C(=O)NC[C@](O)(c2cc(C3(C(N)=O)CC3)c(F)c(-c3ccc(F)c(Cl)c3F)n2)C2CC2)cc2cc(Cl)c(C)nc12]

The title compound was synthesized according to the general method of Example 9 as a single enantiomer. ESI-MS m/z: 659.14 [M+H]+.

Example 24

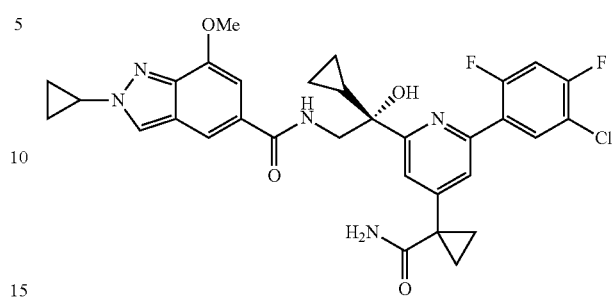

The title compound was synthesized according to the general method of Example 9 as a single enantiomer. ESI-MS m/z: 622.21 [M+H]+.

Example 25

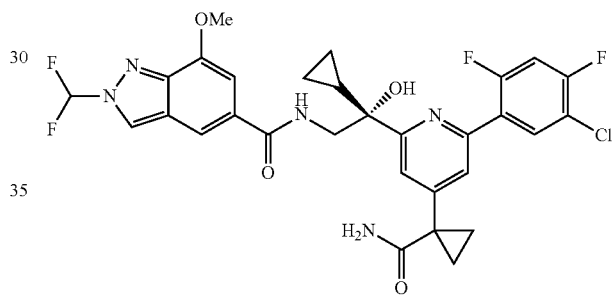

The title compound was synthesized according to the general method of Example 9 as a single enantiomer. ESI-MS m/z: 632.18 [M+H]+.

Example 26

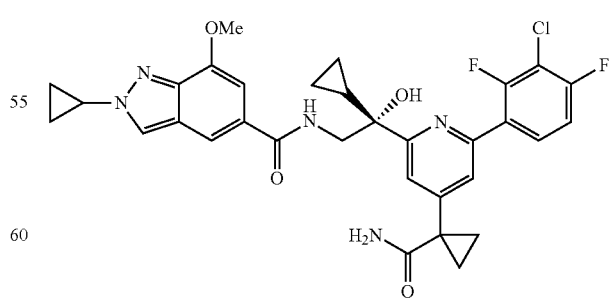

The title compound was synthesized according to the general method of Example 9 as a single enantiomer. ESI-MS m/z: 622.21 [M+H]+.

Example 27

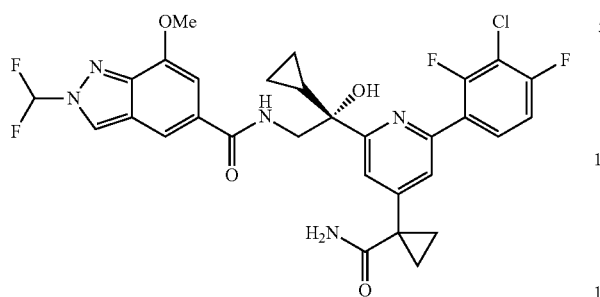

The title compound was synthesized according to the general method of Example 9 as a single enantiomer. ESI-MS m/z: 632.18 [M+H]$^+$.

Example 28

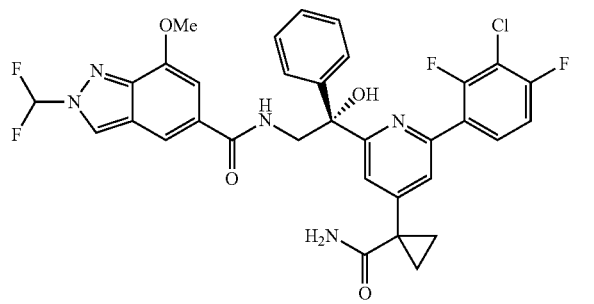 [SMILES: COc1cc(C(=O)NC[C@@](O)(c2ccccc2)c2cc(C3(C(N)=O)CC3)cc(-c3ccc(F)c(Cl)c3F)n2)cc2cn(C(F)F)nc12]

The title compound was synthesized according to the general method of Example 9 as a single enantiomer. ESI-MS m/z: 676.20 [M+H]$^+$.

Example 29

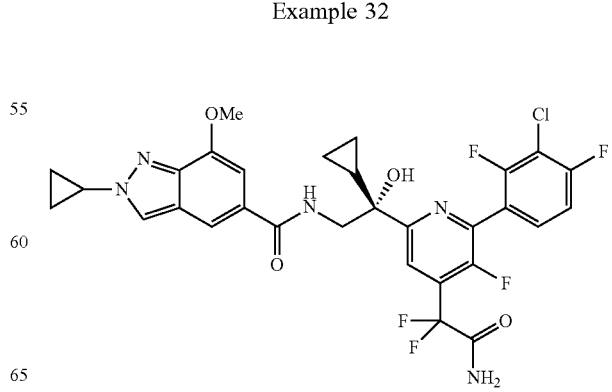

The title compound was synthesized according to the general method of Example 9 as a single enantiomer. ESI-MS m/z: 686.16 [M+H]$^+$.

Example 30

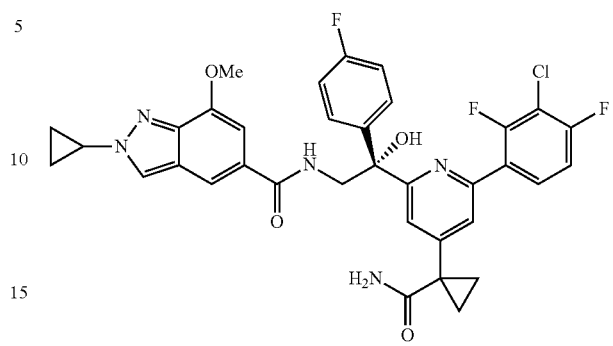

The title compound was synthesized according to the general method of Example 9 as a single enantiomer. ESI-MS m/z: 694.19 [M+H]$^+$.

Example 31

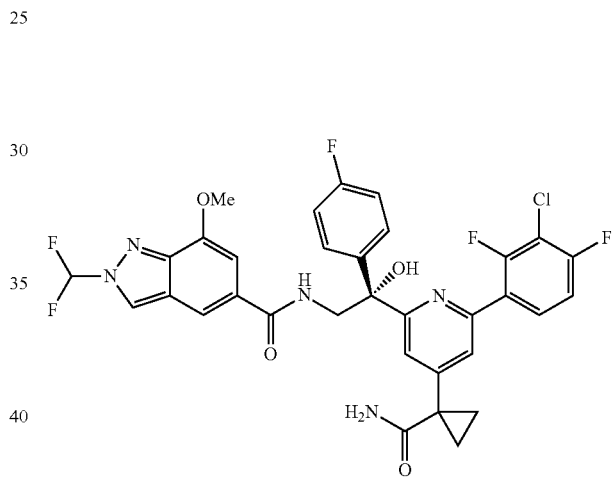

The title compound was synthesized according to the general method of Example 9 as a single enantiomer. ESI-MS m/z: 704.15 [M+H]$^+$.

Example 32

69
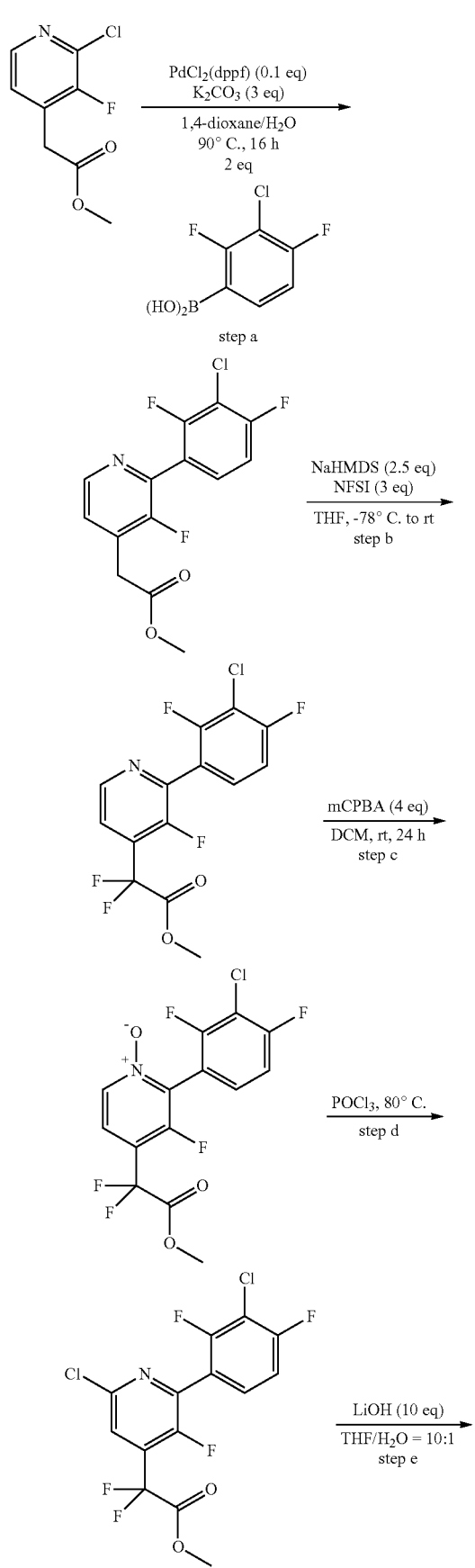
70
-continued
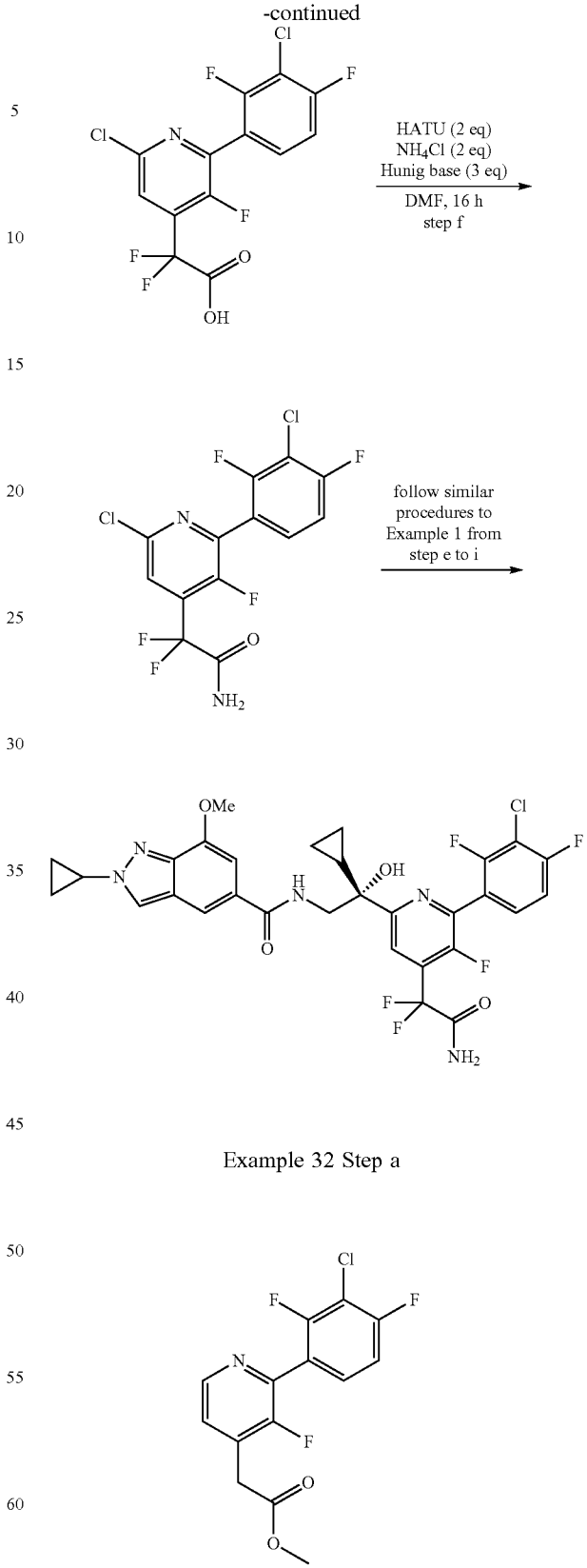
Example 32 Step a
Following the same conditions as Example 9 step b, the desired compound was obtained as a white solid. ESI-MS m/z: 361.15 [M+H]$^+$.

Example 32 Step b

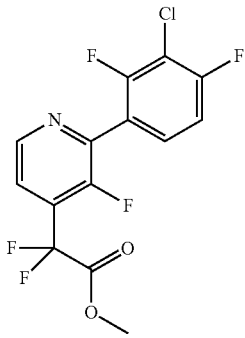 [SMILES: COC(=O)C(F)(F)c1ccnc(-c2ccc(F)c(Cl)c2F)c1F]

The compound from step a (860 mg, 2.72 mmol) was dissolved in THF (27.2 ml) in a round-bottom flask and cooled to −78° C. NaHMDS (1M in THF, 6.8 mL, 6.81 mmol) was added dropwise. The reaction mixture was allowed to stir at −78° C. for 20 min. N-fluorobenzenesulfonimide (2.58 g, 8.17 mmol) in THF (1 mL) was added and dropwise. The reaction mixture was slowly warmed to rt and allowed to stir at rt for 16 h. The reaction was quenched by sat. NH$_4$Cl (aq.) at room temperature. The aqueous layer was extracted with ethyl acetate 3 times and the combined organic layers were dried with MgSO$_4$, filtered and concentrated. The residue was purified by silica gel column chromatography eluting with 0-10% EtOAc/hexanes to afford the desired compound (919 mg, 91% yield) as an off-white solid. ESI-MS m/z: 352.09 [M+H]$^+$.

Example 32 Step c

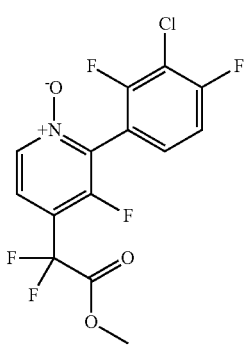

Following the same conditions as Example 1 step b, the desired compound was obtained as a white solid. ESI-MS m/z: 368.03 [M+H]$^+$.

Example 32 Step d

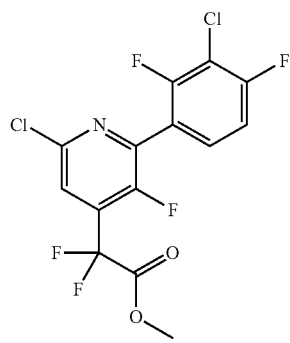 [SMILES: COC(=O)C(F)(F)c1cc(Cl)nc(-c2ccc(F)c(Cl)c2F)c1F]

Following the same conditions as Example 1 step c, the desired compound was obtained as a white solid. ESI-MS m/z: 386.02 [M+H]$^+$.

Example 32 Step e

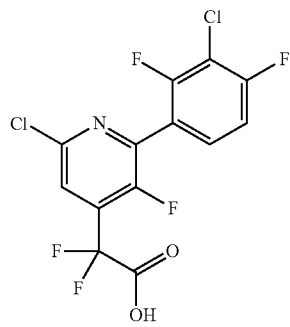 [SMILES: O=C(O)C(F)(F)c1cc(Cl)nc(-c2ccc(F)c(Cl)c2F)c1F]

Following the same conditions as Example 9 step f, the desired compound was obtained as a white solid. ESI-MS m/z: 372.10 [M+H]$^+$.

Example 32 Step f

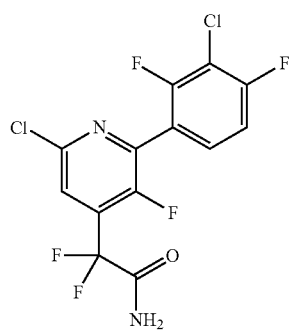 [SMILES: NC(=O)C(F)(F)c1cc(Cl)nc(-c2ccc(F)c(Cl)c2F)c1F]

Following the same conditions as Example 9 step g, the desired compound was obtained as an oil. ESI-MS m/z: 371.05 [M+H]$^+$.

Example 32 Step g

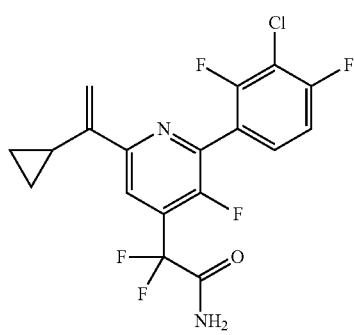 [SMILES: C=C(c1cc(C(F)(F)C(N)=O)c(F)c(-c2ccc(F)c(Cl)c2F)n1)C1CC1]

Following the same conditions as Example 1 step e, the desired compound was obtained as an oil. ESI-MS m/z: 403.11 [M+H]$^+$.

Example 32 Step h

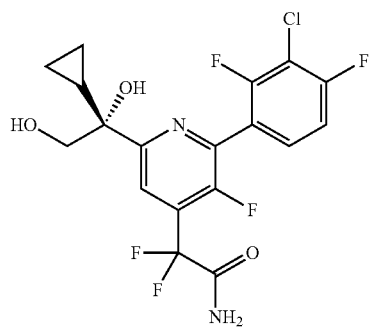 [SMILES: NC(=O)C(F)(F)c1cc([C@@](O)(CO)C2CC2)nc(-c2ccc(F)c(Cl)c2F)c1F]

Following the same conditions as Example 1 step f, the desired compound was obtained as a white solid. ESI-MS m/z: 437.18 [M+H]$^+$.

Example 32 Step i

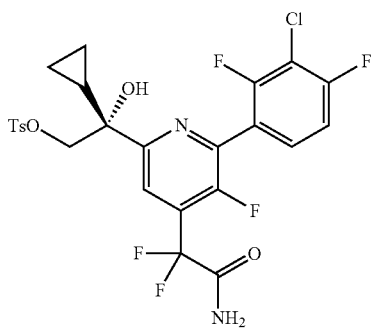 [SMILES: Cc1ccc(S(=O)(=O)OC[C@](O)(c2cc(C(F)(F)C(N)=O)c(F)c(-c3ccc(F)c(Cl)c3F)n2)C2CC2)cc1]

Following the same conditions as Example 1 step g, the desired compound was obtained as an oil. ESI-MS m/z: 591.10 [M+H]$^+$.

Example 32 Step j

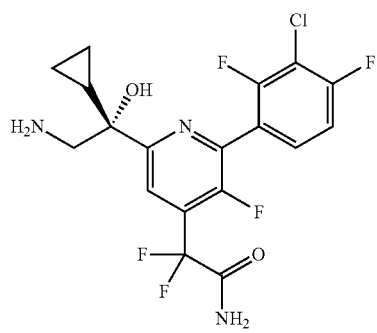

Following the same conditions as Example 1 step h, the desired compound was obtained as a yellowish foam. ESI-MS m/z: 436.08 [M+H]$^+$.

Example 32 Step k

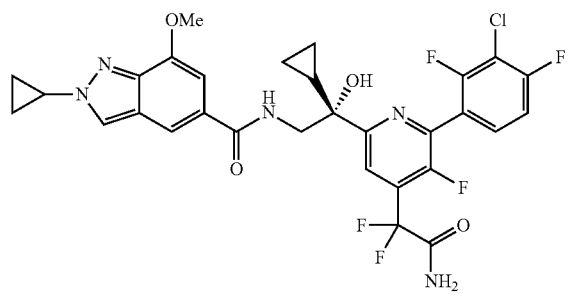 [SMILES: COc1cc(C(=O)NC[C@](O)(c2cc(C(F)(F)C(N)=O)c(F)c(-c3ccc(F)c(Cl)c3F)n2)C2CC2)cc2cn(C3CC3)nc12]

Following the same conditions as Example 1 step i, the desired compound was obtained as a white foam as a single enantiomer. ESI-MS m/z: 650.19 [M+H]$^+$.

Example 33

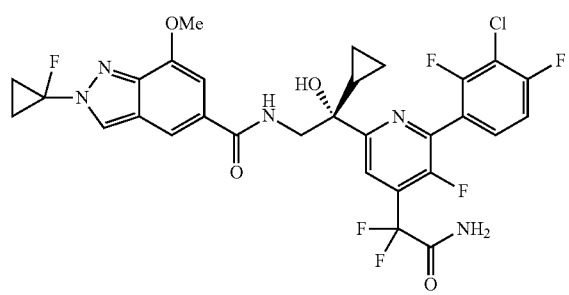 [SMILES: COc1cc(C(=O)NC[C@](O)(c2cc(C(F)(F)C(N)=O)c(F)c(-c3ccc(F)c(Cl)c3F)n2)C2CC2)cc2cn(C3(F)CC3)nc12]

The title compound was synthesized according to the general method of Example 32 as a single enantiomer. ESI-MS m/z: 668.09 [M+H]$^+$.

Example 34

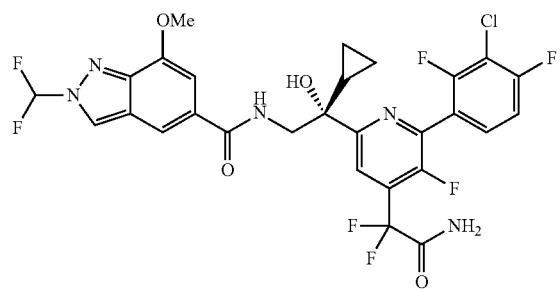 [SMILES: COc1cc(C(=O)NC[C@](O)(c2cc(C(F)(F)C(N)=O)c(F)c(-c3ccc(F)c(Cl)c3F)n2)C2CC2)cc2cn(C(F)F)nc12]

The title compound was synthesized according to the general method of Example 32 as a single enantiomer. ESI-MS m/z: 660.12 [M+H]$^+$.

Example 35

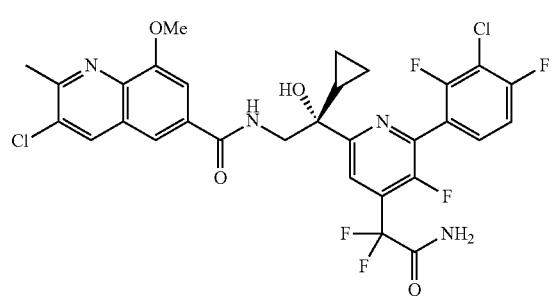 [SMILES: COc1cc(C(=O)NC[C@](O)(c2cc(C(F)(F)C(N)=O)c(F)c(-c3ccc(F)c(Cl)c3F)n2)C2CC2)cc2cc(Cl)c(C)nc12]

The title compound was synthesized according to the general method of Example 32 as a single enantiomer. ESI-MS m/z: 669.15 [M+H]$^+$.

Example 36

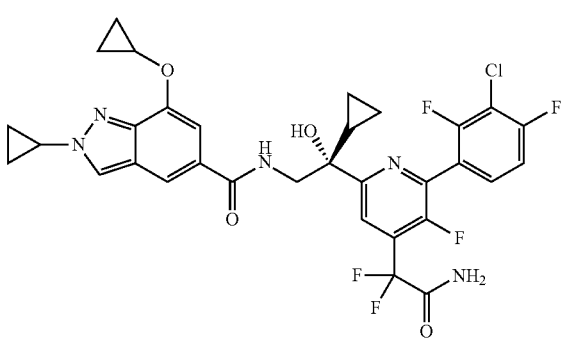 [SMILES: NC(=O)C(F)(F)c1cc([C@@](O)(CNC(=O)c2cc(OC3CC3)c3nn(C4CC4)cc3c2)C2CC2)nc(-c2ccc(F)c(Cl)c2F)c1F]

The title compound was synthesized according to the general method of Example 32 as a single enantiomer. ESI-MS m/z: 676.25 [M+H]$^+$.

Example 37

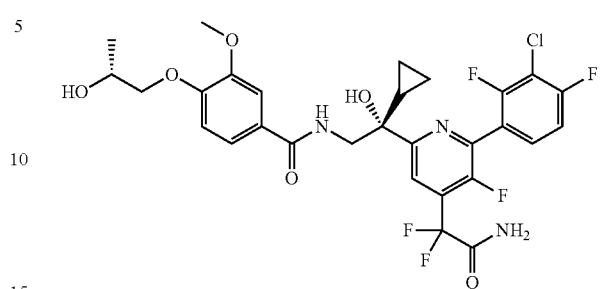

The title compound was synthesized according to the general method of Example 32 as a single enantiomer. ESI-MS m/z: 644.19 [M+H]$^+$.

Example 38

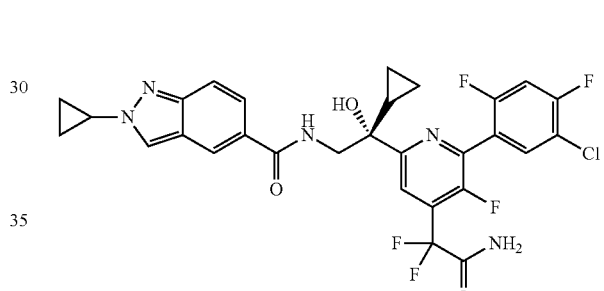

The title compound was synthesized according to the general method of Example 32 as a single enantiomer. ESI-MS m/z: 650.23 [M+H]$^+$.

Example 39

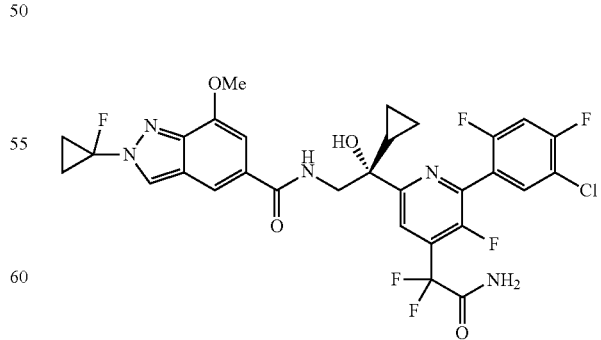

The title compound was synthesized according to the general method of Example 32 as a single enantiomer. ESI-MS m/z: 668.14 [M+H]$^+$.

Example 40

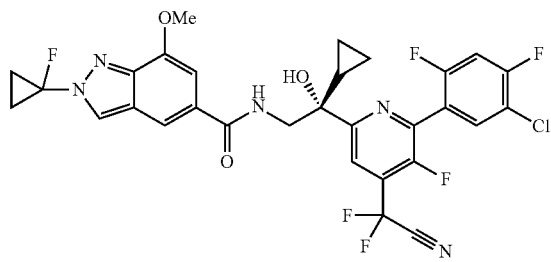 [SMILES: COc1cc(C(=O)NC[C@](O)(c2cc(C(F)(F)C#N)c(F)c(-c3cc(Cl)c(F)cc3F)n2)C2CC2)cc2cn(C3(F)CC3)nc12]

The title compound was synthesized according to the general method of Example 10 from Example 39 as a single enantiomer. ESI-MS m/z: 648.21 [M+H]$^+$.

Example 41

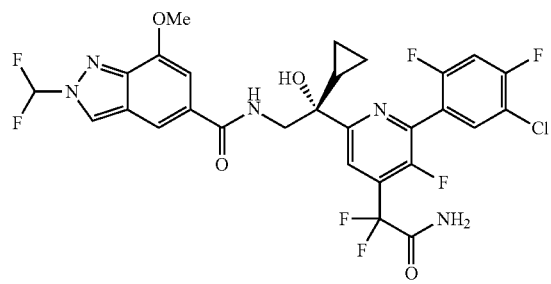 [SMILES: COc1cc(C(=O)NC[C@](O)(c2cc(C(F)(F)C(N)=O)c(F)c(-c3cc(Cl)c(F)cc3F)n2)C2CC2)cc2cn(C(F)F)nc12]

The title compound was synthesized according to the general method of Example 32 as a single enantiomer. ESI-MS m/z: 660.22 [M+H]$^+$.

Example 42

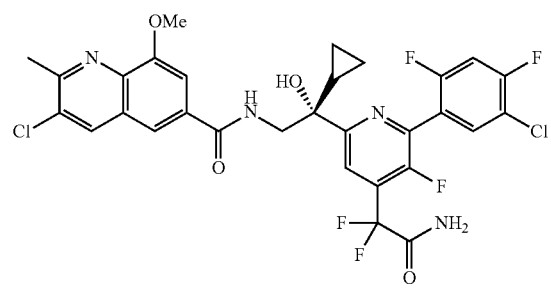 [SMILES: COc1cc(C(=O)NC[C@](O)(c2cc(C(F)(F)C(N)=O)c(F)c(-c3cc(Cl)c(F)cc3F)n2)C2CC2)cc2cc(Cl)c(C)nc12]

The title compound was synthesized according to the general method of Example 32 as a single enantiomer. ESI-MS m/z: 669.15 [M+H]$^+$.

Example 43

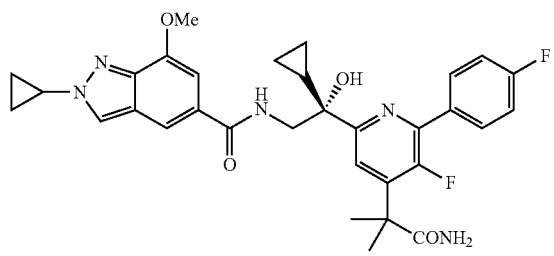 [SMILES: COc1cc(C(=O)NC[C@](O)(c2cc(C(C)(C)C(N)=O)c(F)c(-c3ccc(F)cc3)n2)C2CC2)cc2cn(C3CC3)nc12]

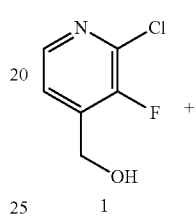

1

XPhos Pd G$_2$, (0.1 eq)
K$_3$PO$_4$ (3 eq)
———————————→
THF/H$_2$O (4/1), 70° C.
step a

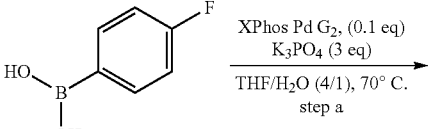

DCM, TEA (2.5 eq)
MsCl (1.2 eq)
———————→
0° C.
step b

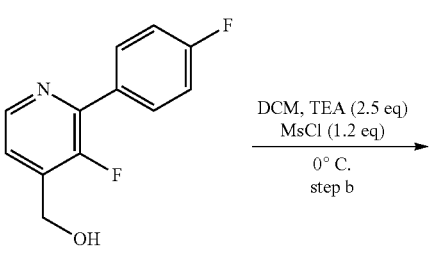

2

(2 eq)
———————→
TBAF, DMSO, rt
step c

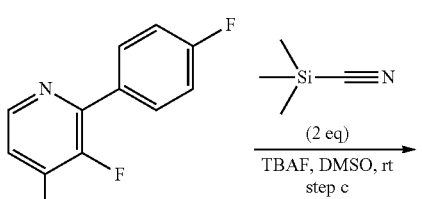

3

NaH, MeI
———————→
DMF, rt
step d

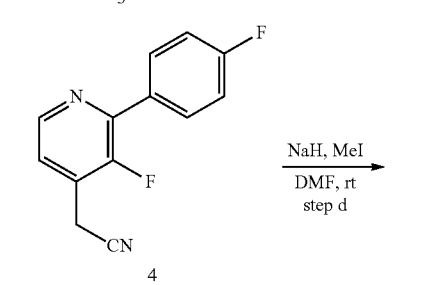

4

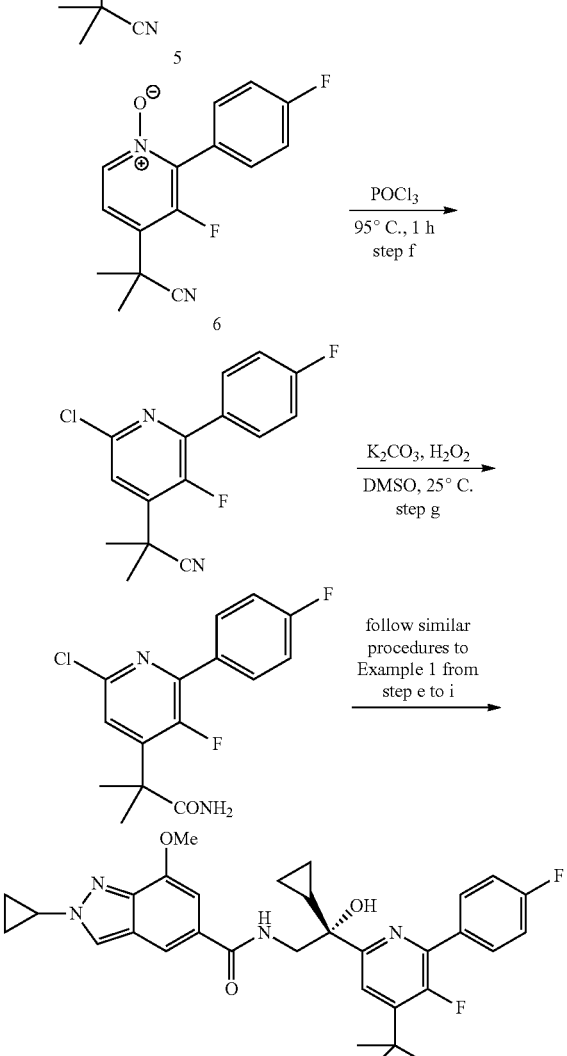

Example 43 Step b

A solution of (2-chloro-3-fluoropyridin-4-yl)methanol (5.0 g, 30.94 mmol), K₃PO₄ (19.0 g, 92.84 mmol), 2nd Generation XPhos Precatalyst (2.44 g, 3.09 mmol) and 4-fluorophenylboronic acid (8.66 g, 61.89 mmol) in THF (4 mL) and H₂O (1 mL) was stirred for 2 h at 70° C. The resulting mixture was extracted, dried, evaporated and purified by silica gel column chromatography eluting with 0-40% EtOAc/hexanes to afford the desired compound (6.0 g, 87%) as a yellow solid. ESI-MS m/z: 222.15 [M+H]⁺.

Example 43 Step b

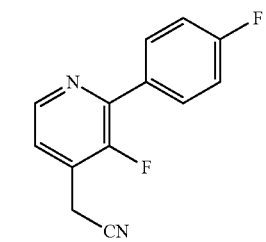 [SMILES: N#CCc1ccnc(-c2ccc(F)cc2)c1F]

A solution of compound from step a (4.0 g, 22.07 mmol), methanesulfonyl chloride (6.32 g, 55.19 mmol) in DCM (30 mL) was stirred for 2 h at 0° C. The resulting mixture was washed with aq. NaHCO₃, brine, dried, filtered and evaporated to afford the desired compound (4.0 g, 83%) as a brown crude solid which will be used for the next step directly without further purification. ESI-MS m/z: 218.05 [M+H]⁺.

Example 43 Step c

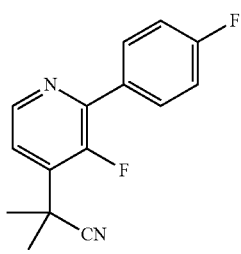 [SMILES: CC(C)(C#N)c1ccnc(-c2ccc(F)cc2)c1F]

A solution of compound from step b (5.5 g, 18.37 mmol), trimethylsilyl cyanide (3.65 g, 36.75 mmol) and TBAF (9.61 g, 36.75 mmol) in DMSO (50 mL) was stirred for 2 h at room temperature. The reaction was quenched, extracted, evaporated and purified by silica gel column chromatography eluting with 0-30% EtOAc/hexanes to afford the desired compound (1.6 g, 37%) as a white solid. ESI-MS m/z: 231.00 [M+H]⁺.

Example 43 Step d

A solution of compound from step c (1.6 g, 6.95 mmol) in DMF (10 mL) was treated with NaH (0.50 g, 20.85 mmol) for 5 min followed by the addition of MeI (5.92 g, 41.70 mmol) dropwise. The resulting mixture was stirred for 1 h at room temperature and then quenched with sat. NH₄Cl (aq.) at room temperature. The resulting mixture was extracted, dried, evaporated and purified by silica gel column chromatography eluting with 0-30% EtOAc/hexanes to afford the desired compound (1.3 g, 72%) as a yellow solid. ESI-MS m/z: 259.00 [M+H]⁺.

Example 43 Step e

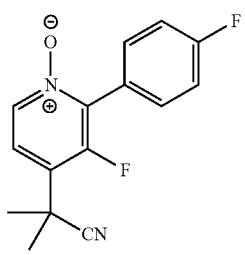 [SMILES: CC(C)(C#N)c1cc[n+]([O-])c(-c2ccc(F)cc2)c1F]

A solution of compound from step d (1.30 g, 5.03 mmol) in DCM (10 mL) was treated with m-CPBA (2.6 g, 15.09 mmol) for 5 min at 0° C. The resulting mixture was stirred for 12 h at room temperature. The resulting mixture was extracted, dried, evaporated and purified by silica gel column chromatography eluting with 0-100% EtOAc/hexanes to afford the desired compound (1.2 g, 87%) as a yellow solid. ESI-MS m/z: 275.00 [M+H]⁺.

Example 43 Step f

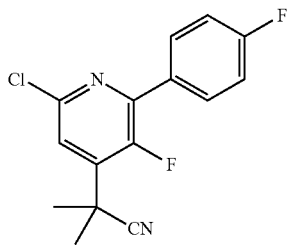 [SMILES: CC(C)(C#N)c1cc(Cl)nc(-c2ccc(F)cc2)c1F]

A solution of compound from step e (1.2 g, 4.37 mmol) and POCl₃ (8.8 g, 56.87 mmol) was heated for 1 h at 110° C. After removed most POCl₃, the remaining residue was diluted with EtOAc (200 mL) and brine (50 mL). The organic layer was washed with saturated NaHCO₃ (aq.) and brine. After concentrated the organic layer under vacuum, the residue was purified by silica gel column chromatography eluting with 0-40% EtOAc/hexanes to afford the desired compound (1.1 g, 86%) as a white solid. ESI-MS m/z: 292.95 [M+H]⁺.

Example 43 Step g

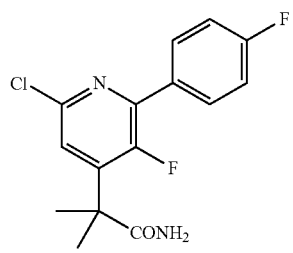 [SMILES: CC(C)(C(N)=O)c1cc(Cl)nc(-c2ccc(F)cc2)c1F]

A solution of compound from step f (1.1 g, 3.75 mmol), K₂CO₃ (1.56 g, 11.27 mmol) and H₂O₂ (255.7 mg, 7.51 mmol) in DMSO (10 mL) was stirred for 40 min at 25° C. The resulting mixture was concentrated, extracted, evaporated and purified by silica gel column chromatography eluting with 0-40% EtOAc/hexanes to afford the desired compound (800 mg, 68%) as a white solid. ESI-MS m/z: 311.10 [M+H]⁺. ¹H NMR (400 MHz, DMSO-d₆) δ 1.50 (s, 6H), 7.02 (s, 1H), 7.11 (s, 1H), 7.33-7.43 (m, 2H), 7.48 (d, J=4.6 Hz, 1H), 7.86-7.94 (m, 2H).

Example 43 Step h

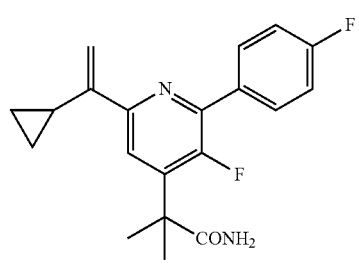 [SMILES: C=C(c1cc(C(C)(C)C(N)=O)c(F)c(-c2ccc(F)cc2)n1)C1CC1]

A solution of compound from step g (800 mg, 2.57 mmol), K₃PO₄ (1639 mg, 7.72 mmol), 2″d Generation XPhos Precatalyst (202 mg, 0.25 mmol) and 2-(1-cyclopropylethenyl)-4,4,5,5-tetramethyl-1,3,2-dioxaborolane (1.0 g, 5.15 mmol) in THF (8 mL) and H₂O (2 mL) was heated for 2 h at 70° C. The resulting mixture was extracted with EtOAc (100 mL×2). The combined organic layer was washed with brine, dried over Na₂SO₄, filtered and evaporated. The residue was purified by silica gel column chromatography eluting with 0-40% EtOAc/hexanes to afford the desired compound (600 mg, 78%) as a yellow solid. ESI-MS m/z: 343.05 [M+H]⁺.

Example 43 Step i

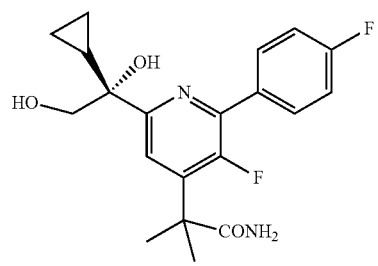 [SMILES: CC(C)(C(N)=O)c1cc([C@@](O)(CO)C2CC2)nc(-c2ccc(F)cc2)c1F]

A solution of compound from step h (600 mg, 1.75 mmol), AD-mix-β (4.09 g, 5.25 mmol) and methanesulfonamide (167 mg, 1.75 mmol) in t-BuOH (60 mL) and H₂O (60 mL) was stirred for 48 h at room temperature. After quenched with Na₂SO₃, the resulting mixture was extracted with EtOAc (200 mL×2). The combined organic layer was washed with brine, dried over Na₂SO₄, filtered and evaporated. The residue was purified by silica gel column chromatography eluting with 0-100% EtOAc/hexanes to afford the desired compound (500 mg, 75%) as a yellow solid. ESI-MS m/z: 377.05 [M+H]⁺.

Example 43 Step j

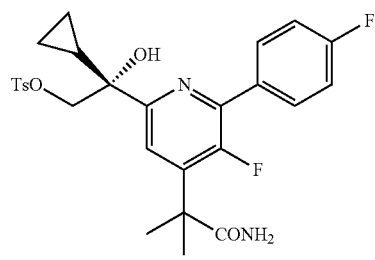 [SMILES: Cc1ccc(S(=O)(=O)OC[C@](O)(c2cc(C(C)(C)C(N)=O)c(F)c(-c3ccc(F)cc3)n2)C2CC2)cc1]

A solution of compound from step i (500 mg, 1.32 mmol), Et₃N (269 mg, 2.65 mmol), TsCl (304 mg, 1.59 mmol) and DMAP (65 mg, 0.53 mmol) in DCM (10 mL) was stirred for 2 h at room temperature. The resulting mixture was extracted with CH₂Cl₂ (100 mL×2). The combined organic layer was washed with brine, dried over Na₂SO₄, filtered and evaporated. The residue was purified by silica gel column chromatography eluting with 0-40% EtOAc/hexanes to afford the desired compound (600 mg, 73%) as a white foam. ESI-MS m/z: 531.25 [M+H]⁺.

Example 43 Step k

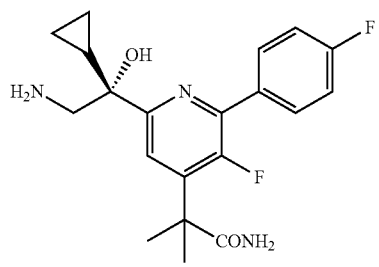 [SMILES: CC(C)(C(N)=O)c1cc([C@@](O)(CN)C2CC2)nc(-c2ccc(F)cc2)c1F]

A solution of compound from step j (600 mg, 1.31 mmol) was treated with 7 N NH₃ in MeOH (40 mL, 280.0 mmol) for 4 h at 40° C. The resulting mixture was concentrated and purified by Prep-TLC (DCM7N NH₃ in MeOH=10:1) to afford the desired compound (81 mg, 19%) as a white solid. ESI-MS m/z: 376.05 [M+H]⁺. ¹H NMR (400 MHz, DMSO-d₆) δ 0.08-0.19 (m, 1H), 0.33-0.35 (m, 2H), 0.48 (p, J=4.5 Hz, 1H), 1.23 (s, 1H), 1.50 (d, J=5.0 Hz, 6H), 2.87 (d, J=13.0 Hz, 1H), 3.23 (d, J=13.0 Hz, 1H), 7.01 (d, J=9.4 Hz, 2H), 7.35 (t, J=8.8 Hz, 2H), 7.56 (d, J=5.3 Hz, 2H), 7.95 (dd, J=8.4, 5.6 Hz, 2H).

Example 43 Step 1

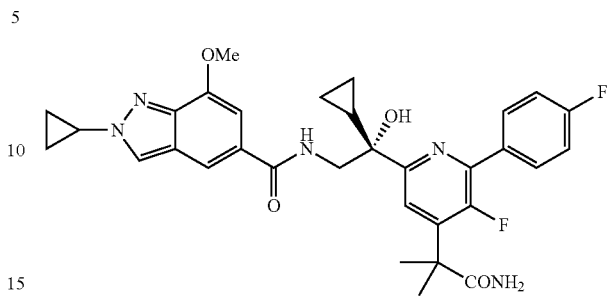

The title compound was synthesized according to Example 1 step i as a single enantiomer. ESI-MS m/z: 590.35[M+H]⁺. ¹H NMR (400 MHz, DMSO-d₆) δ 0.18 (s, 1H), 0.41 (s, 2H), 0.56 (s, 1H), 1.06-1.15 (m, 2H), 1.26-1.28 (m, 2H), 1.45 (d, J=16.7 Hz, 6H), 1.54 (d, J=6.1 Hz, 1H), 3.86 (s, 5H), 4.13 (tt, J=7.5, 3.9 Hz, 1H), 5.46 (s, 1H), 6.89 (d, J=1.3 Hz, 1H), 6.95 (s, 1H), 7.04 (s, 1H), 7.32 (t, J=8.9 Hz, 2H), 7.63 (d, J=5.3 Hz, 2H), 7.68 (d, J=1.3 Hz, 2H), 7.95 (dd, J=8.2, 5.6 Hz, 2H), 8.34 (t, J=6.0 Hz, 1H), 8.52 (s, 1H).

Example 44

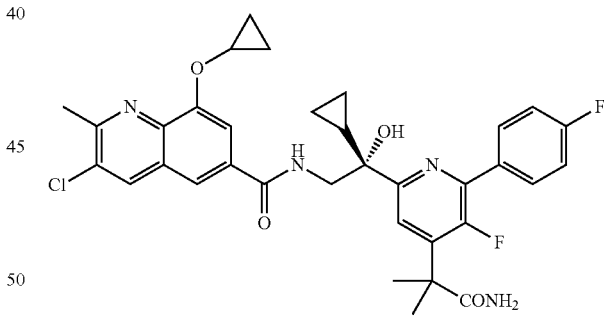

The title compound was synthesized according to Example 42 as a single enantiomer. ESI-MS m z: 635.30 [M+H]⁺. ¹H NMR (400 MHz, DMSO-d₆) δ 0.20 (s, 1H), 0.35 (s, 1H), 0.44 (s, 1H), 0.60 (s, 1H), 0.75 (s, 2H), 0.84 (d, J=6.4 Hz, 2H), 1.51 (s, 3H), 1.64 (dd, J=13.2, 5.5 Hz, 3H), 1.75-1.79 (m, 1H), 2.75 (s, 3H), 3.89-3.97 (m, 3H), 5.46 (s, 1H), 6.96 (s, 1H), 7.06 (s, 1H), 7.31 (t, J=8.9 Hz, 2H), 7.68 (dd, J=11.5, 3.5 Hz, 2H), 7.81 (d, J=1.7 Hz, 1H), 7.95 (dd, J=8.0, 5.8 Hz, 2H), 8.37 (s, 1H), 8.55 (d, J=5.8 Hz, 1H).

Example 45

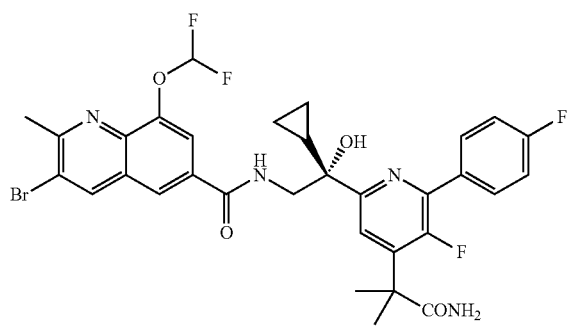 [SMILES: Cc1nc2c(OC(F)F)cc(C(=O)NC[C@](O)(c3cc(C(C)(C)C(N)=O)c(F)c(-c4ccc(F)cc4)n3)C3CC3)cc2cc1Br]

The title compound was synthesized according to Example 42 as a single enantiomer. ESI-MS m z: 689.20 [M+H]+. $^1$H NMR (400 MHz, DMSO-d$_6$) δ 0.19 (dd, J=9.0, 5.2 Hz, 1H), 0.38-0.41 (m, 1H), 0.56-0.64 (m, 1H), 0.84 (s, 1H), 1.45 (d, J=15.1 Hz, 6H), 1.53-1.64 (m, 1H), 2.81 (s, 3H), 3.85 (dd, J=13.5, 5.6 Hz, 1H), 3.94 (dd, J=13.4, 6.2 Hz, 1H), 5.40 (s, 1H), 6.97 (s, 1H), 7.05 (s, 1H), 7.27-7.36 (m, 3H), 7.48 (s, 1H), 7.62-7.69 (m, 1H), 7.81 (d, J=1.7 Hz, 2H), 7.95 (dd, J=8.3, 5.7 Hz, 1H), 8.16 (d, J=1.8 Hz, 1H), 8.53-8.65 (m, 1H), 8.73 (s, 1H).

Example 46

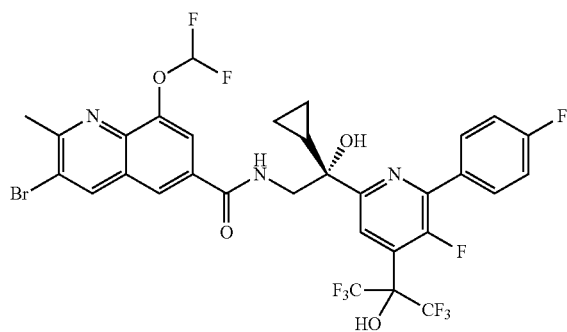 [SMILES: Cc1nc2c(OC(F)F)cc(C(=O)NC[C@](O)(c3cc(C(O)(C(F)(F)F)C(F)(F)F)c(F)c(-c4ccc(F)cc4)n3)C3CC3)cc2cc1Br]

Example 46 Step a

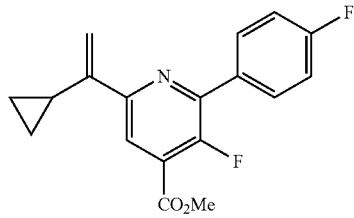 [SMILES: C=C(c1cc(C(=O)OC)c(F)c(-c2ccc(F)cc2)n1)C1CC1]

A solution of the compound from Example 1 step c (4.0 g, 14.1 mmol), 2-(1-cyclopropyl-ethenyl)-4,4,5,5-tetramethyl-1,3,2-dioxaborolane (2.74 g, 14.1 mmol), Pd(dppf)Cl$_2$ (0.21 g, 0.28 mmol) and K$_2$CO$_3$ (3.9 g, 28.20 mmol) in 1,4-dioxane (20 mL) and H$_2$O (2 mL) was heated for 2 hours at 80° C. under N$_2$ atmosphere. The resulting mixture was extracted with EtOAc (100 mL×2). The combined organic layer was washed with brine, dried over Na$_2$SO$_4$, filtered and evaporated. The residue was purified by silica gel column chromatography eluting with 0-20% EtOAc/hexanes to afford the desired compound (4.2 g, 94%) as a yellow oil. ESI-MS m/z: 316.00 [M+H]+.

Example 46 Step b

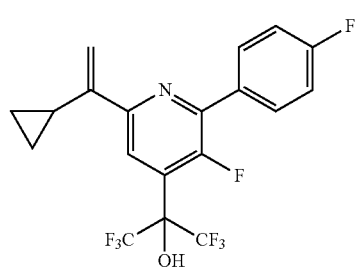 [SMILES: C=C(c1cc(C(O)(C(F)(F)F)C(F)(F)F)c(F)c(-c2ccc(F)cc2)n1)C1CC1]

To a round-bottomed flask were charged trifluoromethyl-trimethylsilane (1.5 g, 10.55 mmol), the compound from step a (1.5 g, 4.76 mmol) and anhydrous ethylene glycol dimethyl ether (2 mL). The resulting mixture was degassed and cooled down to 0° C., and then CsF (500 mg, 3.29 mmol) was added. After slowly warm to rt, the mixture was stirred overnight. The resulting mixture was extracted with EtOAc (100 mL×3). The combined organic layer was washed with brine, dried over Na$_2$SO$_4$, filtered and evaporated. The residue was purified by silica gel column chromatography eluting with 0-30% EtOAc/hexanes to afford the desired compound (1.5 g, 74%) as a yellow oil. ESI-MS m/z: 424.00 [M+H]+.

Example 46 Step c

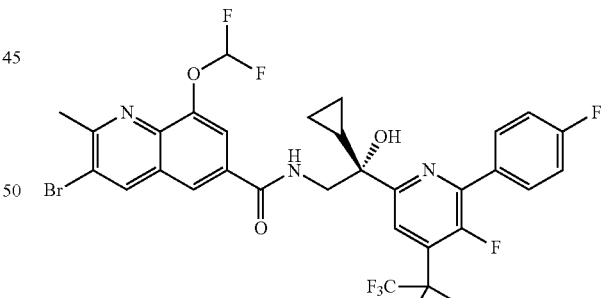

Following the same conditions as Example 1 from step f to step i, the desired compound was obtained as a single enantiomer. ESI-MS m/z: 770.00 [M+H]+. $^1$H NMR (400 MHz, DMSO-d$_6$) δ 0.15 (dd, J=8.7, 5.2 Hz, 1H), 0.23-0.36 (m, 1H), 0.41 (dd, J=11.7, 5.7 Hz, 1H), 0.61 (dd, J=10.5, 5.8 Hz, 1H), 1.54-1.62 (m, 1H), 2.81 (s, 3H), 3.86-4.01 (m, 1H), 4.06 (dd, J=13.1, 6.2 Hz, 1H), 6.05 (s, 1H), 7.28-7.41 (m, 2H), 7.50 (s, 1H), 7.80 (d, J=1.5 Hz, 1H), 7.93-8.06 (m, 2H), 8.15 (s, 1H), 8.21 (d, J=1.8 Hz, 1H), 8.48 (s, 2H), 8.82 (s, 1H).

Example 47

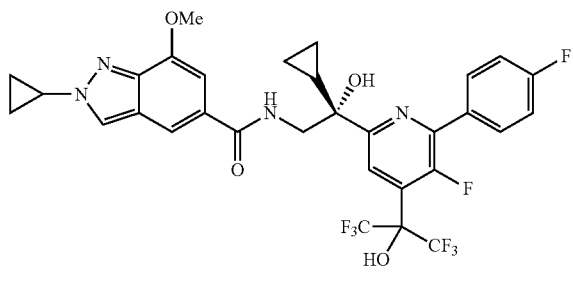 [SMILES: COc1cc(C(=O)NC[C@](O)(c2cc(C(O)(C(F)(F)F)C(F)(F)F)c(F)c(-c3ccc(F)cc3)n2)C2CC2)cc2cn(C3CC3)nc12]

The title compound was synthesized according to Example 45 as a single enantiomer. ESI-MS m/z: 671.00 [M+H]+. 1H NMR (400 MHz, DMSO-d6) δ 0.01-0.16 (m, 1H), 0.16-0.36 (m, 1H), 0.42 (d, J=7.0 Hz, 1H), 0.58 (d, J=5.1 Hz, 1H), 1.11 (td, J=7.6, 5.1 Hz, 2H), 1.18-1.42 (m, 2H), 1.54 (s, 1H), 3.88 (s, 3H), 3.94 (q, J=7.0, 6.4 Hz, 2H), 4.14 (tt, J=7.5, 4.0 Hz, 1H), 5.96 (s, 1H), 6.90 (s, 1H), 7.38 (t, J=8.9 Hz, 2H), 7.67 (d, J=1.2 Hz, 1H), 7.90-8.14 (m, 3H), 8.37-8.46 (m, 1H), 8.54 (s, 1H), 9.47 (s, 1H).

Example 48

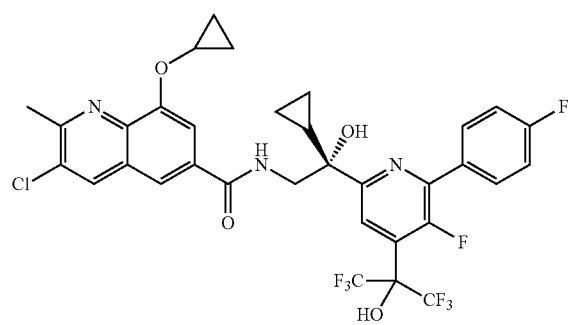 [SMILES: Cc1nc2c(OC3CC3)cc(C(=O)NC[C@](O)(c3cc(C(O)(C(F)(F)F)C(F)(F)F)c(F)c(-c4ccc(F)cc4)n3)C3CC3)cc2cc1Cl]

The title compound was synthesized according to the general method of Example 45 as a single enantiomer. ESI-MS m/z: 716.00 [M+H]+. 1H NMR (400 MHz, DMSO-d6) δ 0.17 (s, 1H), 0.28 (s, 1H), 0.44 (s, 1H), 0.57-0.66 (m, 1H), 0.78 (dd, J=5.1, 2.9 Hz, 2H), 0.85 (d, J=6.2 Hz, 2H), 1.24 (s, 1H), 2.71 (s, 3H), 3.92 (dd, J=13.6, 5.4 Hz, 1H), 3.96-4.07 (m, 2H), 5.80 (s, 1H), 7.33-7.42 (m, 2H), 7.72 (d, J=1.7 Hz, 1H), 7.80 (d, J=1.7 Hz, 1H), 7.96-8.05 (m, 2H), 8.10 (d, J=5.0 Hz, 1H), 8.37 (s, 1H), 8.60 (t, J=5.9 Hz, 1H).

Example 49

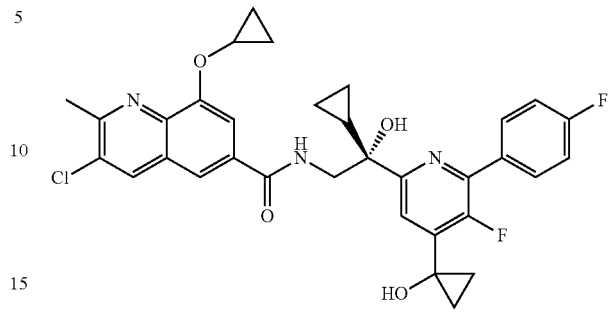

Example 49 Step a

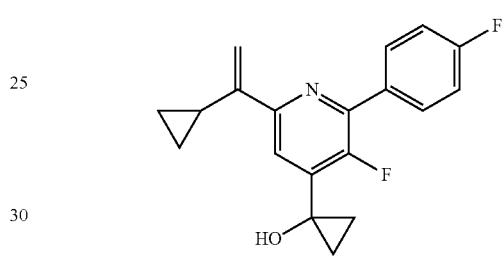

To a solution of bis(cyclopentadienyl)zirconium (IV) dichloride (2.76 g, 9.51 mmol) in toluene (20 mL) was added EtMgBr (2.54 g, 19.02 mmol) at 0° C. The mixture was further stirred at 0° C. for 1 h. The compound from Example 46 step a (1.5 g, 4.76 mmol) in toluene (5 mL) was added to the abovementioned solution dropwise at 0° C. After slowly warm to rt, the resulting mixture was stirred overnight at rt. The reaction was quenched, filtered, extracted and purified by silica gel column chromatography eluting with 0-30% EtOAc/hexanes to give the desired compound (500 mg, 33%) as a yellowish oil. ESI-MS m/z: 314.00 [M+H]+.

Example 49 Step b

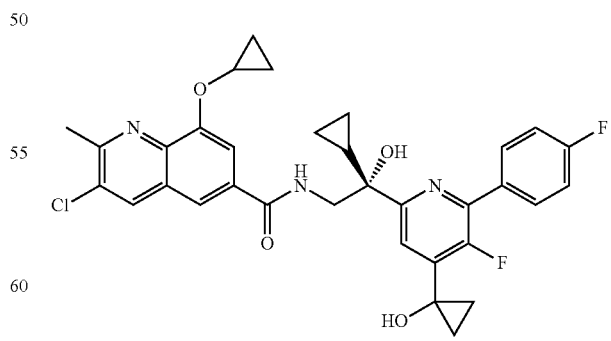

Following the same conditions as Example 1 from step f to step i, the desired compound was obtained as a single enantiomer. ESI-MS m/z: 606.20 [M+H]+. 1H NMR (400 MHz, DMSO-d6) δ 0.11-0.21 (m, 1H), 0.24-0.34 (m, 1H), 0.41 (dd, J=9.2, 5.5 Hz, 1H), 0.54-0.64 (m, 1H), 0.72-0.91 (m, 4H), 1.04-1.11 (s, 2H), 1.18-1.28 (m, 4H), 1.48-1.61 (m, 1H), 2.65-2.75 (m, 4H), 3.85-4.04 (m, 3H), 5.53 (s, 1H), 6.34 (s, 1H), 7.25-7.42 (m, 2H), 7.72 (d, J=1.8 Hz, 1H), 7.82 (d, J=1.7 Hz, 1H), 7.86 (d, J=5.5 Hz, 1H), 7.98 (dd, J=8.2, 5.6 Hz, 2H), 8.38 (s, 1H), 8.53 (t, J=5.9 Hz, 1H).

(d, J=1.3 Hz, 1H), 7.84 (d, J=5.6 Hz, 1H), 7.97 (dd, J=8.0, 5.5 Hz, 2H), 8.38 (t, J=5.8 Hz, 1H), 8.54 (s, 1H).

Example 50

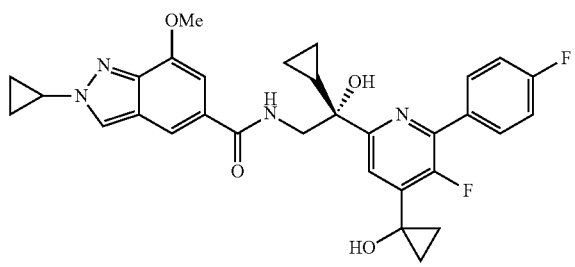 [SMILES: COc1cc(C(=O)NC[C@](O)(c2cc(C3(O)CC3)c(F)c(-c3ccc(F)cc3)n2)C2CC2)cc2cn(C3CC3)nc12]

The title compound was synthesized according to the general method of Example 48 as a single enantiomer. ESI-MS m/z: 561.15 [M+H]$^+$. $^1$H NMR (400 MHz, DMSO-d$_6$) δ 0.06-0.17 (m, 1H), 0.18-0.31 (m, 1H), 0.32-0.43 (m, 1H), 0.49-0.61 (m, 1H), 1.07-1.13 (m, 4H), 1.15-1.21 (m, 2H), 1.22-1.29 (m, 3H), 1.44-1.55 (m, 1H), 2.69 (s, 1H), 3.89 (d, J=7.5 Hz, 5H), 4.11-4.16 (m, 1H), 5.74 (s, 1H), 6.32 (s, 1H), 6.92 (d, J=1.3 Hz, 1H), 7.33 (t, J=8.9 Hz, 2H), 7.71

Example 51

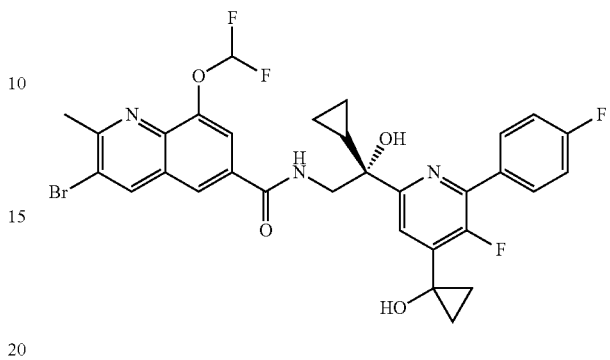

The title compound was synthesized according to the general method of Example 48 as a single enantiomer. ESI-MS m/z: 662.05 [M+H]$^+$. $^1$H NMR (400 MHz, DMSO-d$_6$) δ 0.15 (t, J=4.5 Hz, 1H), 0.25-0.33 (m, 1H), 0.34-0.44 (m, 1H), 0.52-0.63 (m, 1H), 1.08 (s, 2H), 1.17-1.26 (m, 3H), 1.50-1.59 (m, 1H), 2.81 (s, 3H), 3.83-4.04 (m, 3H), 5.45 (s, 1H), 6.33 (s, 1H), 7.25-7.36 (m, 2H), 7.26-7.70 (m, 1H), 7.81 (d, J=1.7 Hz, 1H), 7.85 (d, J=5.5 Hz, 1H), 7.93-8.00 (m, 2H), 8.19 (d, J=1.8 Hz, 1H), 8.55-8.63 (m, 1H), 8.73 (s, 1H).

The following examples in Table 1 were prepared by using procedures similar to those described in Example 1:

TABLE 1

| Entry | Example |
|---|---|
| 52 | 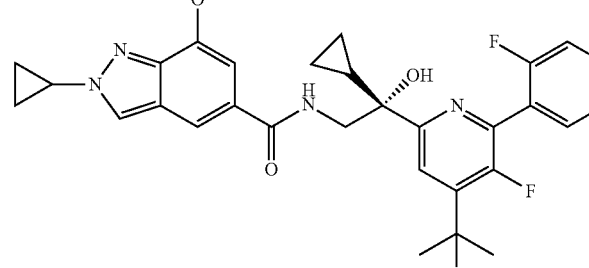 |
| 53 | 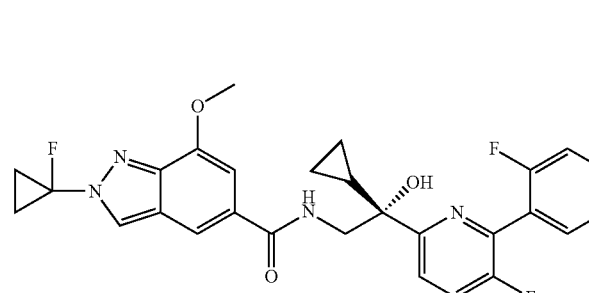 |

TABLE 1-continued
| Entry | Example |
|---|---|
| 54 | 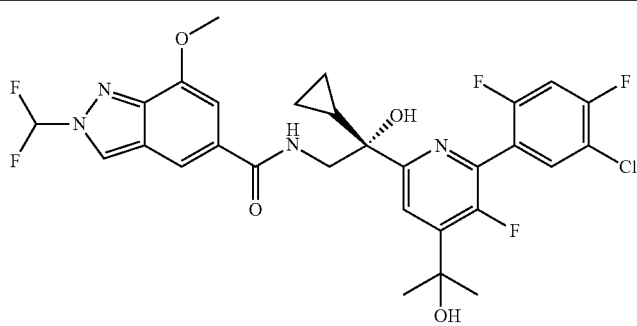 |
| 55 | 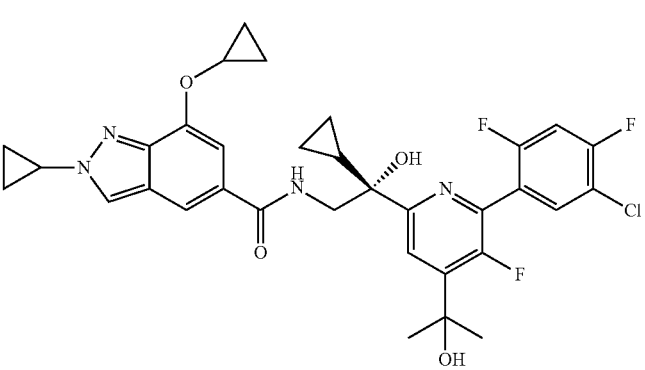 [SMILES: CC(C)(O)c1cc([C@@](O)(CNC(=O)c2cc(OC3CC3)c3nn(C4CC4)cc3c2)C2CC2)nc(-c2cc(Cl)c(F)cc2F)c1F] |
| 56 | 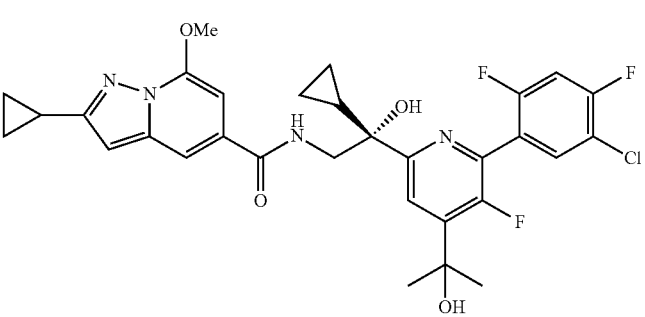 [SMILES: COc1cc(C(=O)NC[C@](O)(c2cc(C(C)(C)O)c(F)c(-c3cc(Cl)c(F)cc3F)n2)C2CC2)cc2cc(C3CC3)nn12] |
| 57 | 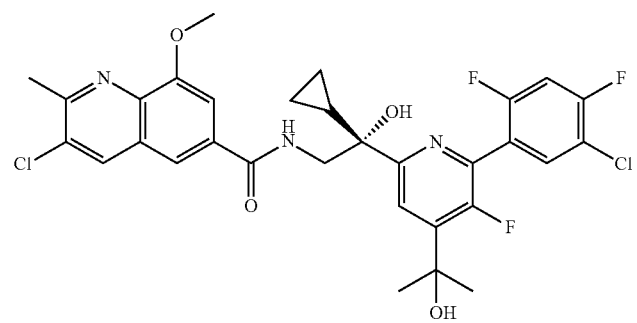 [SMILES: COc1cc(C(=O)NC[C@](O)(c2cc(C(C)(C)O)c(F)c(-c3cc(Cl)c(F)cc3F)n2)C2CC2)cc2cc(Cl)c(C)nc12] |

TABLE 1-continued
| Entry | Example |
|---|---|
| 58 | 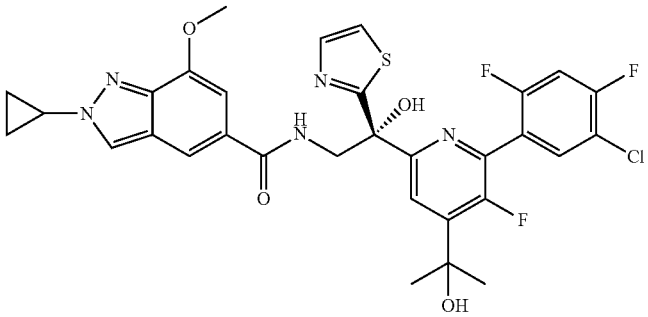 [SMILES: COc1cc(C(=O)NC[C@](O)(c2cc(C(C)(C)O)c(F)c(-c3cc(Cl)c(F)cc3F)n2)c2nccs2)cc2cn(C3CC3)nc12] |
| 59 | 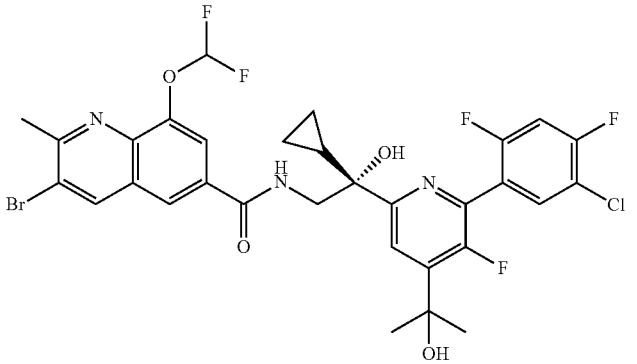 [SMILES: Cc1nc2c(OC(F)F)cc(C(=O)NC[C@](O)(c3cc(C(C)(C)O)c(F)c(-c4cc(Cl)c(F)cc4F)n3)C3CC3)cc2cc1Br] |
| 60 | 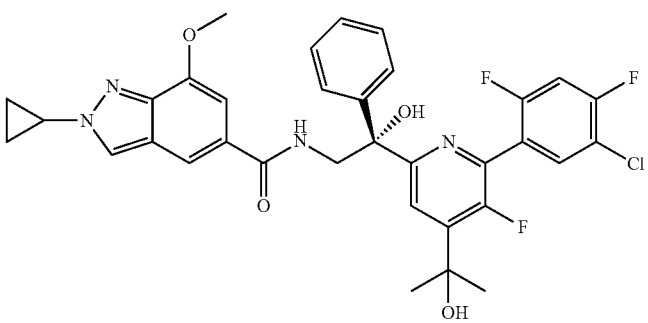 |
| 61 | 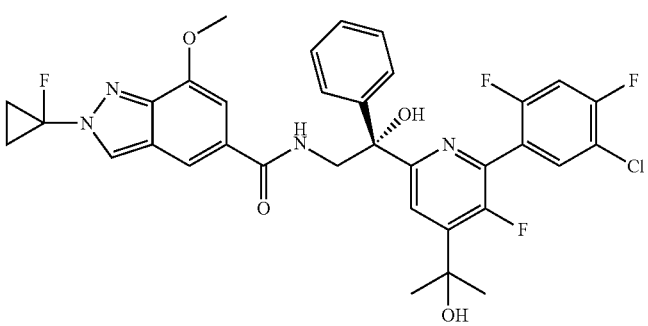 [SMILES: COc1cc(C(=O)NC[C@@](O)(c2ccccc2)c2cc(C(C)(C)O)c(F)c(-c3cc(Cl)c(F)cc3F)n2)cc2cn(C3(F)CC3)nc12] |

TABLE 1-continued
| Entry | Example |
|---|---|
| 62 | 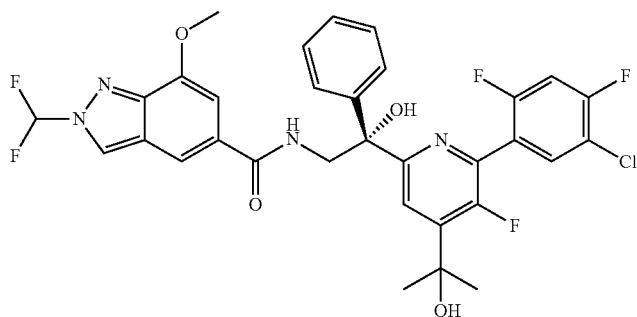 [SMILES: COc1cc(C(=O)NC[C@@](O)(c2ccccc2)c2cc(C(C)(C)O)c(F)c(-c3cc(Cl)c(F)cc3F)n2)cc2cn(C(F)F)nc12] |
| 63 | 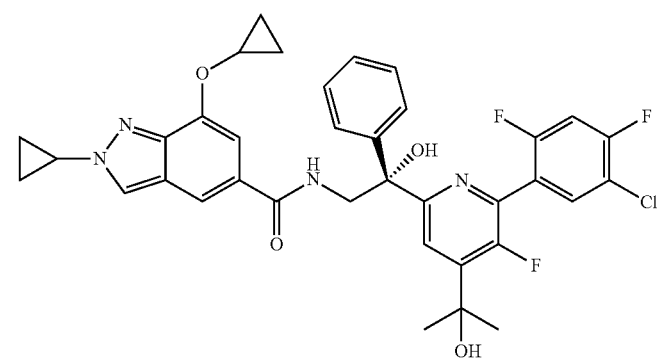 [SMILES: CC(C)(O)c1cc([C@@](O)(CNC(=O)c2cc(OC3CC3)c3nn(C4CC4)cc3c2)c2ccccc2)nc(-c2cc(Cl)c(F)cc2F)c1F] |
| 64 | 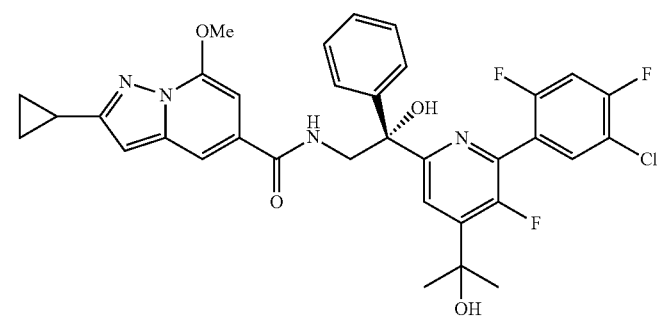 [SMILES: COc1cc(C(=O)NC[C@@](O)(c2ccccc2)c2cc(C(C)(C)O)c(F)c(-c3cc(Cl)c(F)cc3F)n2)cc2cc(C3CC3)nn12] |
| 65 | 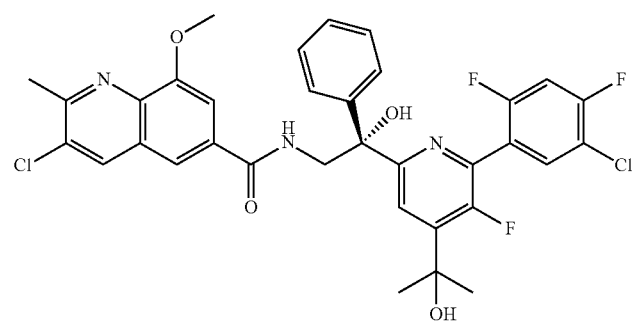 [SMILES: COc1cc(C(=O)NC[C@@](O)(c2ccccc2)c2cc(C(C)(C)O)c(F)c(-c3cc(Cl)c(F)cc3F)n2)cc2cc(Cl)c(C)nc12] |

TABLE 1-continued

| Entry | Example |
|---|---|
| 66 | (structure) |
| 67 | (structure) |
| 68 | (structure) |
| 69 | (structure) |

TABLE 1-continued

| Entry | Example |
|---|---|
| 70 | (structure) |
| 71 | (structure) |
| 72 | (structure) |
| 73 | (structure) |
| 74 | (structure) |

TABLE 1-continued

| Entry | Example |
|---|---|
| 75 | (structure) |
| 76 | (structure) |
| 77 | (structure) |
| 78 | (structure) |

TABLE 1-continued

| Entry | Example |
|---|---|
| 79 | (structure) |
| 80 | (structure) |
| 81 | (structure) |
| 82 | (structure) |
| 83 | (structure) |

TABLE 1-continued
| Entry | Example |
|---|---|
| 84 | 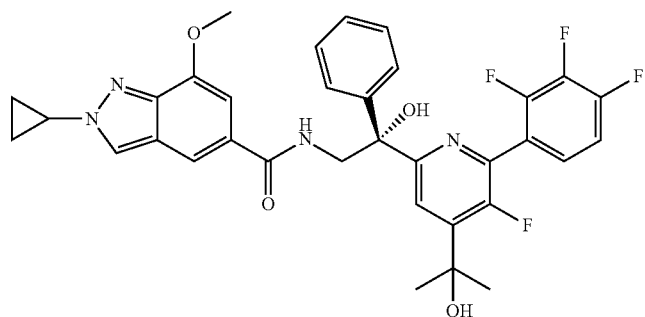 [SMILES: COc1cc(C(=O)NC[C@@](O)(c2ccccc2)c2cc(C(C)(C)O)c(F)c(-c3ccc(F)c(F)c3F)n2)cc2cn(C3CC3)nc12] |
| 85 | 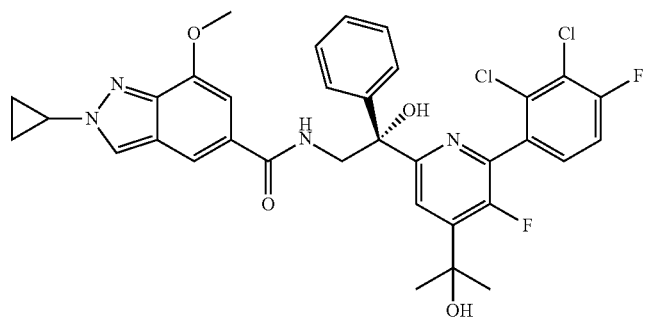 [SMILES: COc1cc(C(=O)NC[C@@](O)(c2ccccc2)c2cc(C(C)(C)O)c(F)c(-c3ccc(F)c(Cl)c3Cl)n2)cc2cn(C3CC3)nc12] |
| 86 | 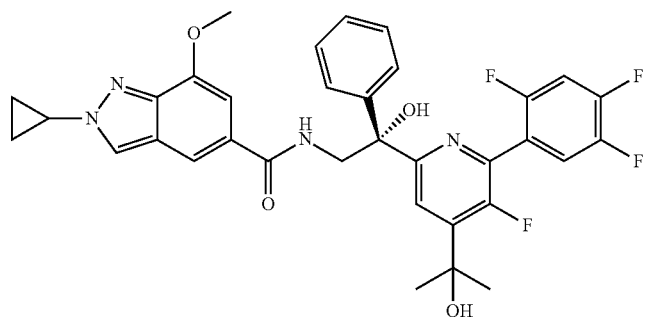 [SMILES: COc1cc(C(=O)NC[C@@](O)(c2ccccc2)c2cc(C(C)(C)O)c(F)c(-c3cc(F)c(F)cc3F)n2)cc2cn(C3CC3)nc12] |
| 87 | 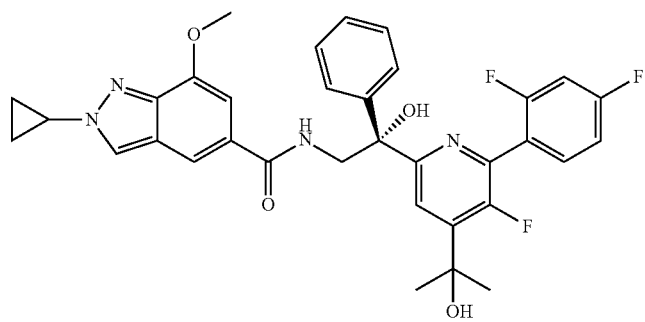 [SMILES: COc1cc(C(=O)NC[C@@](O)(c2ccccc2)c2cc(C(C)(C)O)c(F)c(-c3ccc(F)cc3F)n2)cc2cn(C3CC3)nc12] |

TABLE 1-continued

| Entry | Example |
|---|---|
| 88 | (structure) |
| 89 | (structure) |
| 90 | (structure) |
| 91 | (structure) |

TABLE 1-continued

| Entry | Example |
|---|---|
| 92 | (structure) |
| 93 | (structure) |
| 94 | (structure) |
| 95 | (structure) |

TABLE 1-continued
| Entry | Example |
|---|---|
| 96 | 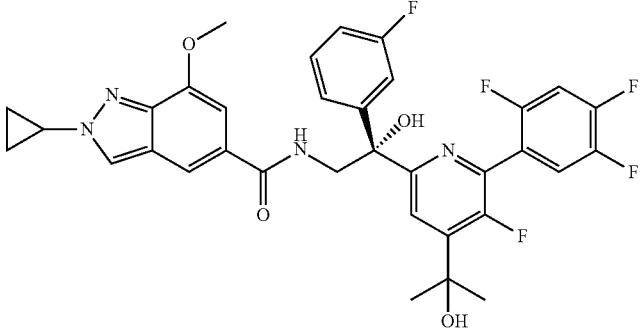 [SMILES: COc1cc(C(=O)NC[C@@](O)(c2cccc(F)c2)c2cc(C(C)(C)O)c(F)c(-c3cc(F)c(F)cc3F)n2)cc2cn(C3CC3)nc12] |
| 97 | 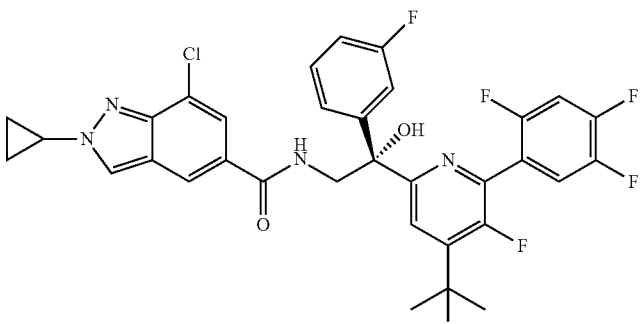 |
| 98 | 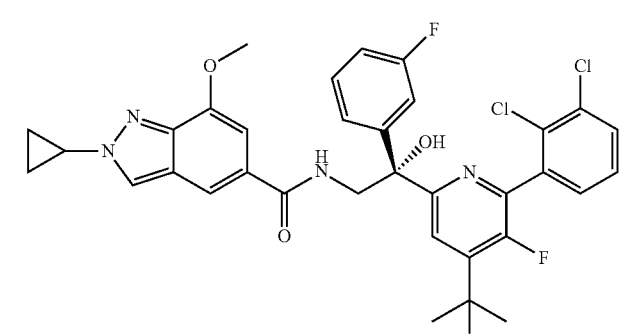 |
| 99 | 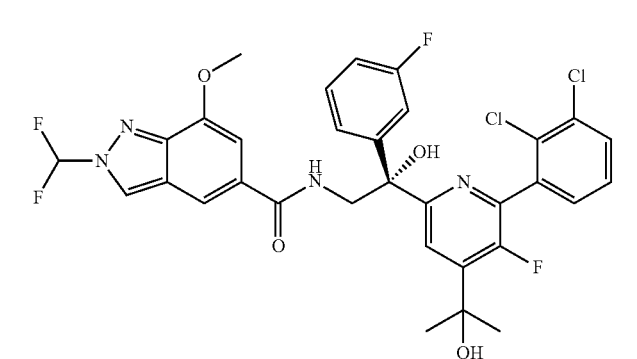 [SMILES: COc1cc(C(=O)NC[C@@](O)(c2cccc(F)c2)c2cc(C(C)(C)O)c(F)c(-c3cccc(Cl)c3Cl)n2)cc2cn(C(F)F)nc12] |

TABLE 1-continued

| Entry | Example |
|---|---|
| 100 | (structure) |
| 101 | (structure) |
| 102 | (structure) |
| 103 | (structure) |

TABLE 1-continued
| Entry | Example |
|---|---|
| 104 | 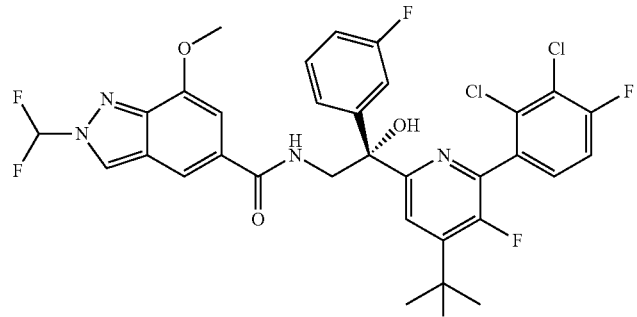 |
| 105 | 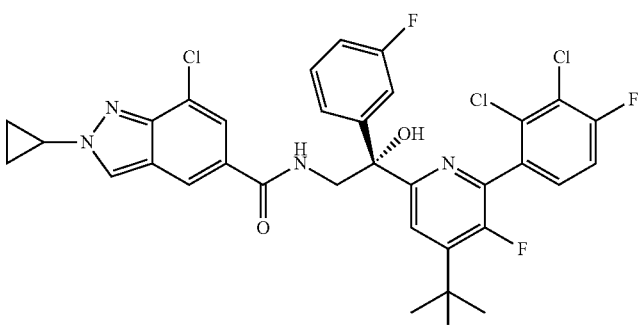 |
| 106 | 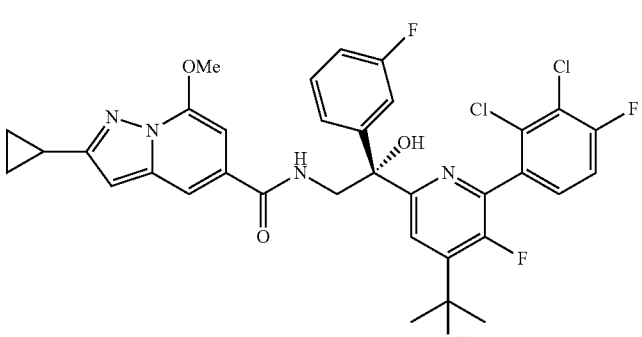 |
| 107 | 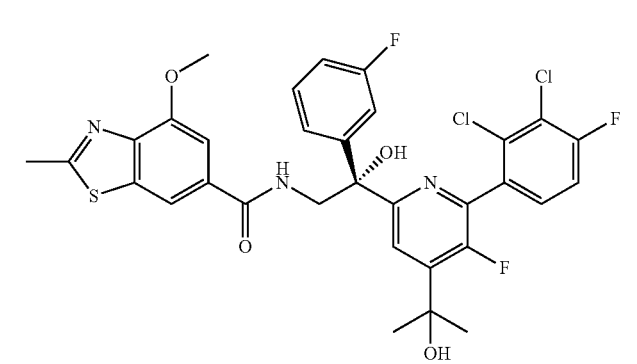 [SMILES: COc1cc(C(=O)NC[C@@](O)(c2cccc(F)c2)c2cc(C(C)(C)O)c(F)c(-c3ccc(F)c(Cl)c3Cl)n2)cc2sc(C)nc12] |

TABLE 1-continued
| Entry | Example |
|---|---|
| 108 | 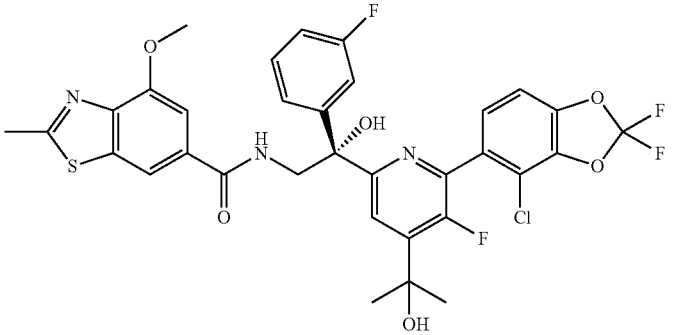 [SMILES: COc1cc(C(=O)NC[C@@](O)(c2cccc(F)c2)c2cc(C(C)(C)O)c(F)c(-c3ccc4c(c3Cl)OC(F)(F)O4)n2)cc2sc(C)nc12] |
| 109 | 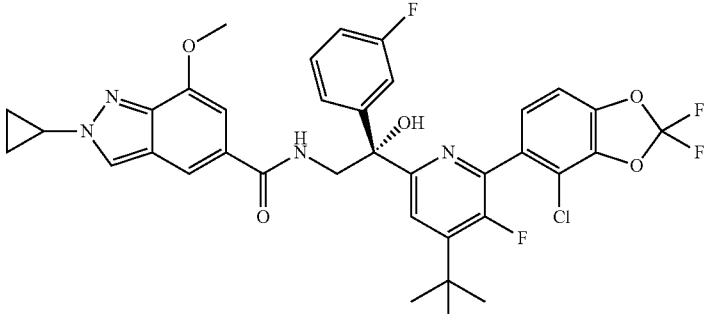 |
| 110 | 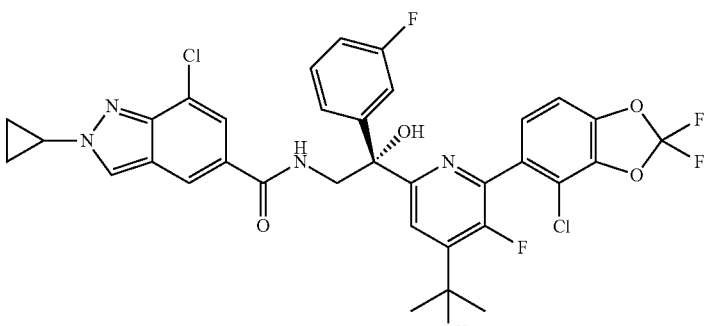 |
| 111 | 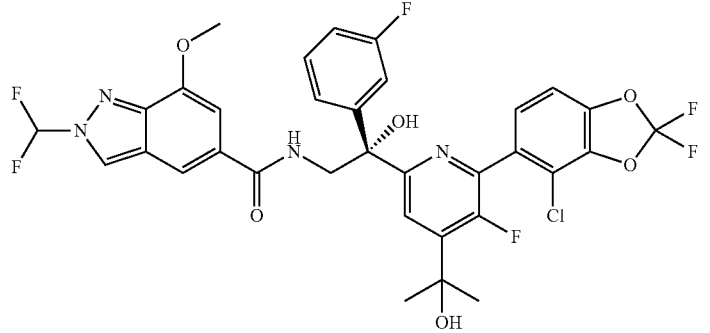 [SMILES: COc1cc(C(=O)NC[C@@](O)(c2cccc(F)c2)c2cc(C(C)(C)O)c(F)c(-c3ccc4c(c3Cl)OC(F)(F)O4)n2)cc2cn(C(F)F)nc12] |

TABLE 1-continued

| Entry | Example |
|---|---|
| 112 | (structure) |
| 113 | (structure) |
| 114 | (structure) |
| 115 | (structure) |
| 116 | (structure) |

TABLE 1-continued
| Entry | Example |
|---|---|
| 117 | 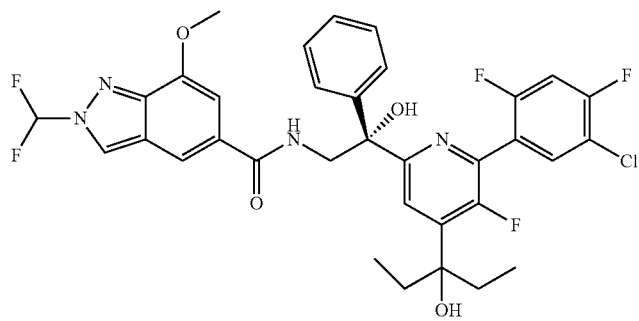 [SMILES: CCC(O)(CC)c1cc([C@@](O)(CNC(=O)c2cc(OC)c3nn(C(F)F)cc3c2)c2ccccc2)nc(-c2cc(Cl)c(F)cc2F)c1F] |
| 118 | 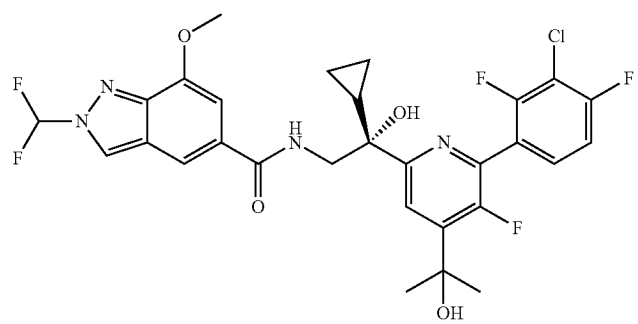 [SMILES: COc1cc(C(=O)NC[C@](O)(c2cc(C(C)(C)O)c(F)c(-c3ccc(F)c(Cl)c3F)n2)C2CC2)cc2cn(C(F)F)nc12] |
| 119 | 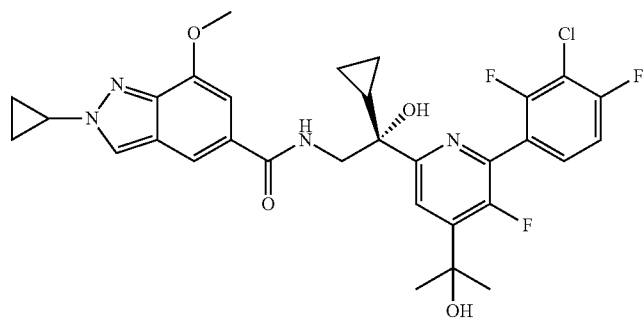 [SMILES: COc1cc(C(=O)NC[C@](O)(c2cc(C(C)(C)O)c(F)c(-c3ccc(F)c(Cl)c3F)n2)C2CC2)cc2cn(C3CC3)nc12] |
| 120 | 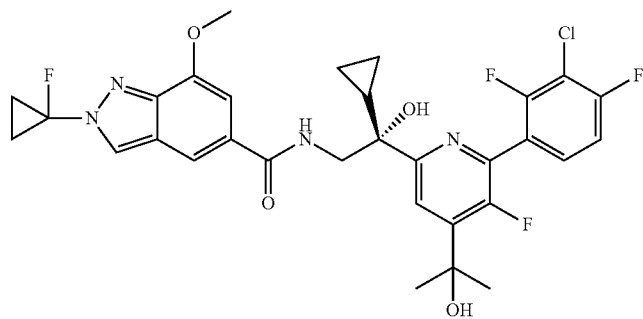 [SMILES: COc1cc(C(=O)NC[C@](O)(c2cc(C(C)(C)O)c(F)c(-c3ccc(F)c(Cl)c3F)n2)C2CC2)cc2cn(C3(F)CC3)nc12] |

TABLE 1-continued
| Entry | Example |
|---|---|
| 121 | 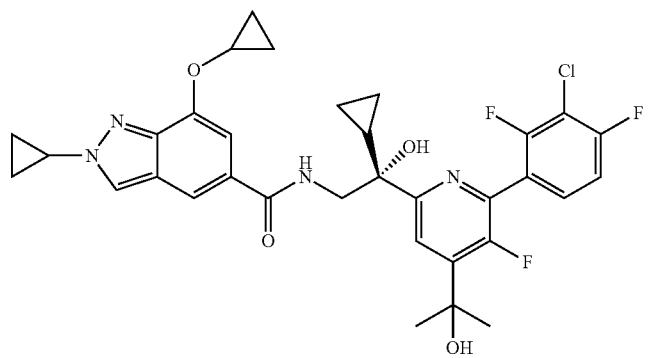 [SMILES: CC(C)(O)c1cc([C@@](O)(CNC(=O)c2cc(OC3CC3)c3nn(C4CC4)cc3c2)C2CC2)nc(-c2ccc(F)c(Cl)c2F)c1F] |
| 122 | 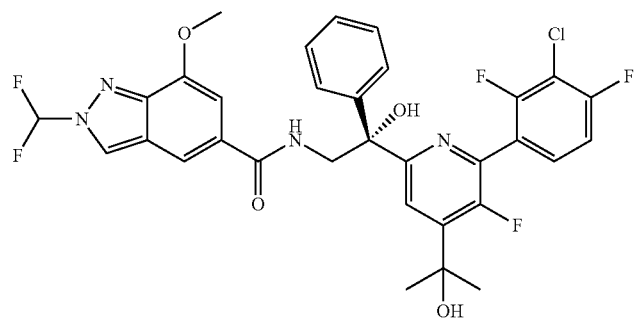 [SMILES: COc1cc(C(=O)NC[C@@](O)(c2ccccc2)c2cc(C(C)(C)O)c(F)c(-c3ccc(F)c(Cl)c3F)n2)cc2cn(C(F)F)nc12] |
| 123 | 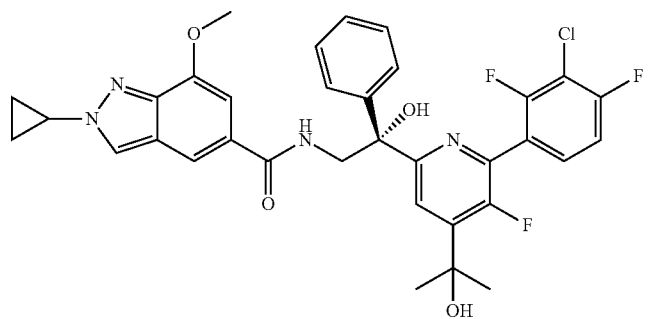 [SMILES: COc1cc(C(=O)NC[C@@](O)(c2ccccc2)c2cc(C(C)(C)O)c(F)c(-c3ccc(F)c(Cl)c3F)n2)cc2cn(C3CC3)nc12] |
| 124 | 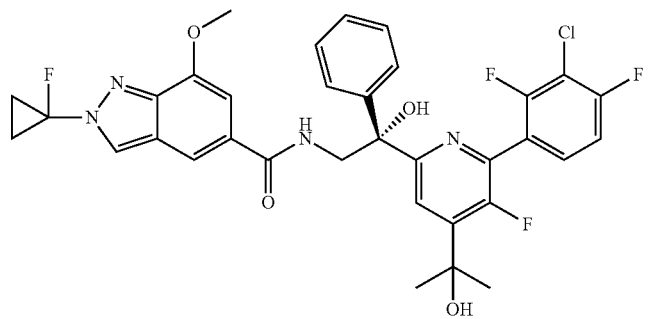 [SMILES: COc1cc(C(=O)NC[C@@](O)(c2ccccc2)c2cc(C(C)(C)O)c(F)c(-c3ccc(F)c(Cl)c3F)n2)cc2cn(C3(F)CC3)nc12] |

TABLE 1-continued
| Entry | Example |
|---|---|
| 125 | 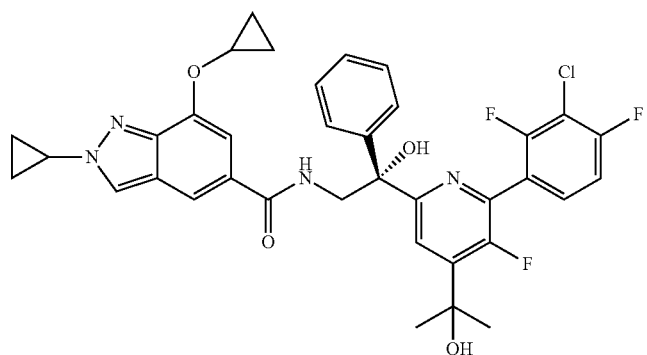 [SMILES: CC(C)(O)c1cc([C@@](O)(CNC(=O)c2cc(OC3CC3)c3nn(C4CC4)cc3c2)c2ccccc2)nc(-c2ccc(F)c(Cl)c2F)c1F] |
| 126 | 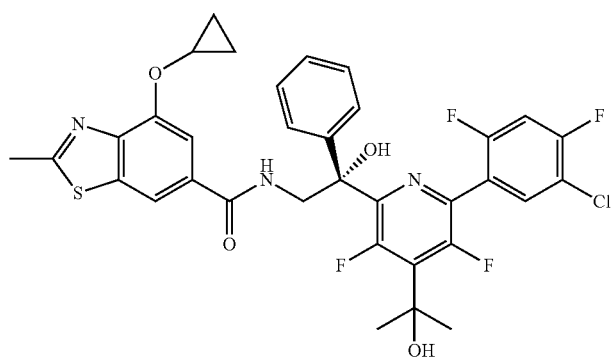 [SMILES: Cc1nc2c(OC3CC3)cc(C(=O)NC[C@@](O)(c3ccccc3)c3nc(-c4cc(Cl)c(F)cc4F)c(F)c(C(C)(C)O)c3F)cc2s1] |
| 127 | 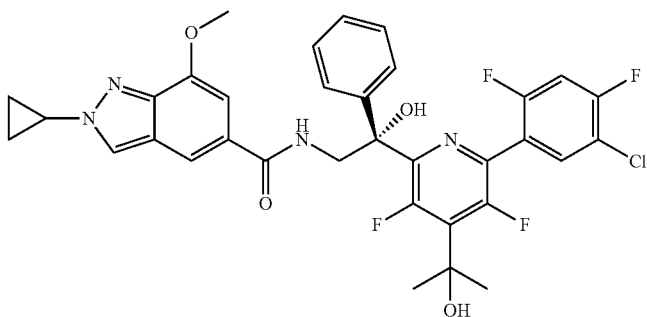 [SMILES: COc1cc(C(=O)NC[C@@](O)(c2ccccc2)c2nc(-c3cc(Cl)c(F)cc3F)c(F)c(C(C)(C)O)c2F)cc2cn(C3CC3)nc12] |
| 128 | 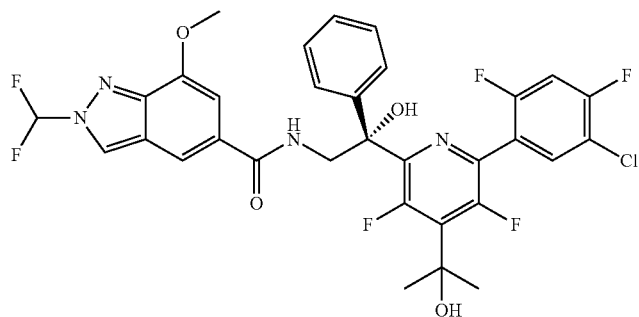 [SMILES: COc1cc(C(=O)NC[C@@](O)(c2ccccc2)c2nc(-c3cc(Cl)c(F)cc3F)c(F)c(C(C)(C)O)c2F)cc2cn(C(F)F)nc12] |

TABLE 1-continued
| Entry | Example |
|---|---|
| 129 | 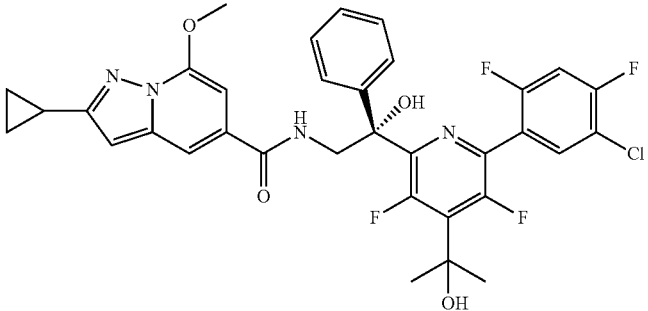 [SMILES: COc1cc(C(=O)NC[C@@](O)(c2ccccc2)c2nc(-c3cc(Cl)c(F)cc3F)c(F)c(C(C)(C)O)c2F)cc2cc(C3CC3)nn12] |
| 130 | 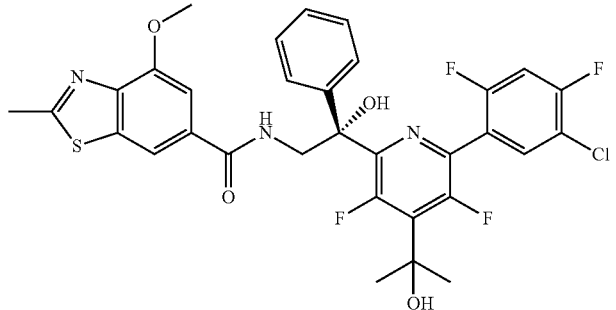 [SMILES: COc1cc(C(=O)NC[C@@](O)(c2ccccc2)c2nc(-c3cc(Cl)c(F)cc3F)c(F)c(C(C)(C)O)c2F)cc2sc(C)nc12] |
| 131 | 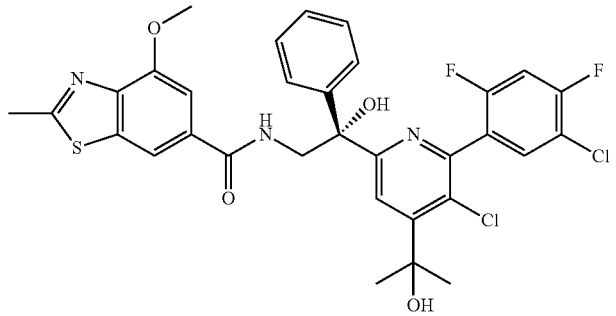 [SMILES: COc1cc(C(=O)NC[C@@](O)(c2ccccc2)c2cc(C(C)(C)O)c(Cl)c(-c3cc(Cl)c(F)cc3F)n2)cc2sc(C)nc12] |
| 132 | 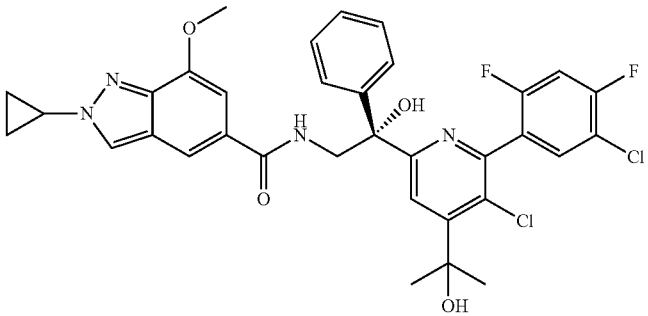 [SMILES: COc1cc(C(=O)NC[C@@](O)(c2ccccc2)c2cc(C(C)(C)O)c(Cl)c(-c3cc(Cl)c(F)cc3F)n2)cc2cn(C3CC3)nc12] |
| 133 | 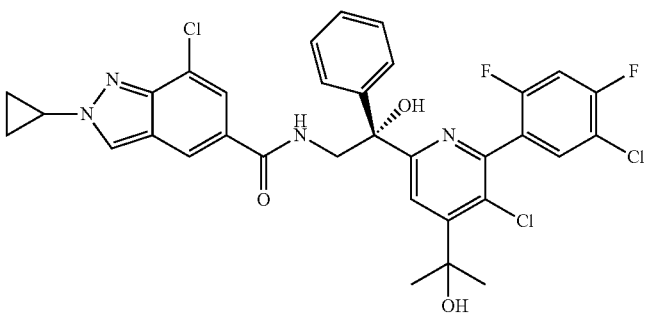 |

TABLE 1-continued

| Entry | Example |
|---|---|
| 134 | (structure) |
| 135 | (structure) |
| 136 | (structure) |
| 137 | (structure) |
| 138 | (structure) |

TABLE 1-continued
| Entry | Example |
|---|---|
| 139 | 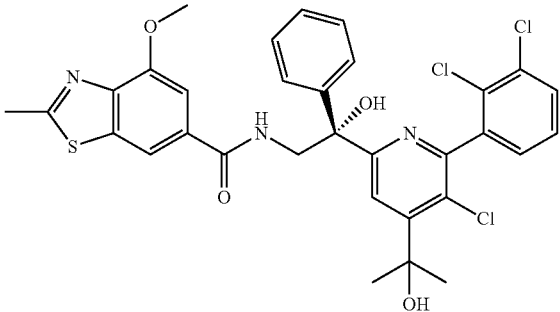 [SMILES: COc1cc(C(=O)NC[C@@](O)(c2ccccc2)c2cc(C(C)(C)O)c(Cl)c(-c3cccc(Cl)c3Cl)n2)cc2sc(C)nc12] |
| 140 | 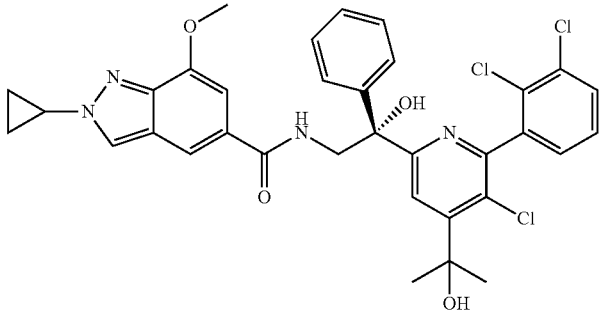 [SMILES: COc1cc(C(=O)NC[C@@](O)(c2ccccc2)c2cc(C(C)(C)O)c(Cl)c(-c3cccc(Cl)c3Cl)n2)cc2cn(C3CC3)nc12] |
| 141 | 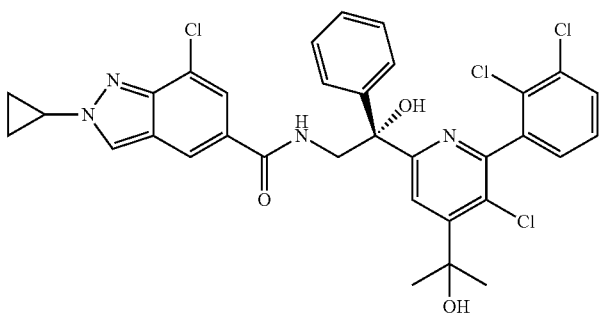 [SMILES: CC(C)(O)c1cc([C@@](O)(CNC(=O)c2cc(Cl)c3nn(C4CC4)cc3c2)c2ccccc2)nc(-c2cccc(Cl)c2Cl)c1Cl] |
| 142 | 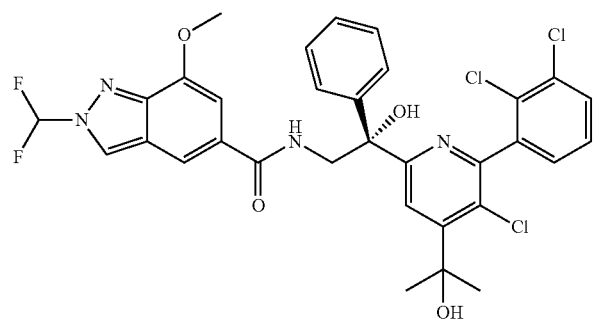 [SMILES: COc1cc(C(=O)NC[C@@](O)(c2ccccc2)c2cc(C(C)(C)O)c(Cl)c(-c3cccc(Cl)c3Cl)n2)cc2cn(C(F)F)nc12] |
| 143 | 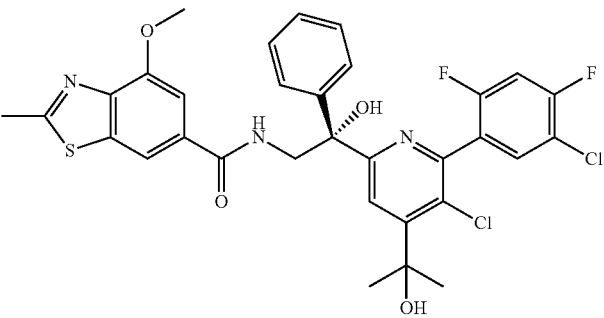 [SMILES: COc1cc(C(=O)NC[C@@](O)(c2ccccc2)c2cc(C(C)(C)O)c(Cl)c(-c3cc(Cl)c(F)cc3F)n2)cc2sc(C)nc12] |

TABLE 1-continued

| Entry | Example |
|---|---|
| 144 | (structure) |
| 145 | (structure) |
| 146 | (structure) |
| 147 | (structure) |
| 148 | (structure) |

TABLE 1-continued

| Entry | Example |
|---|---|
| 149 | (structure) |
| 150 | (structure) |
| 151 | (structure) |
| 152 | (structure) |
| 153 | (structure) |

TABLE 1-continued

| Entry | Example |
|---|---|
| 154 | |
| 155 | |
| 156 | |
| 157 | |
| 158 | |

TABLE 1-continued

| Entry | Example |
|---|---|
| 159 | (structure) |

The following examples in Table 2 were prepared by using procedures similar to those described in Example 43:

TABLE 2

| Entry | Example |
|---|---|
| 160 | (structure) |
| 161 | (structure) |
| 162 | (structure) |
| 163 | (structure) |

Example 164

(reaction scheme)

step a: LDA (1.5 equiv), then acetone (4.25 equiv), THF, −78° C. to rt, 1 h step b: 1.4 equiv, Pd(dppf)Cl₂ (0.1 equiv), K₂CO₃ (3.0 equiv), 1,4-dioxane/H₂O 8:1, 90° C., 75 min step c: 1.4 equiv, Pd(dppf)Cl₂ (0.1 equiv), K₂CO₃ (3.0 equiv), 1,4-dioxane/H₂O 8:1, 90° C., 75 min

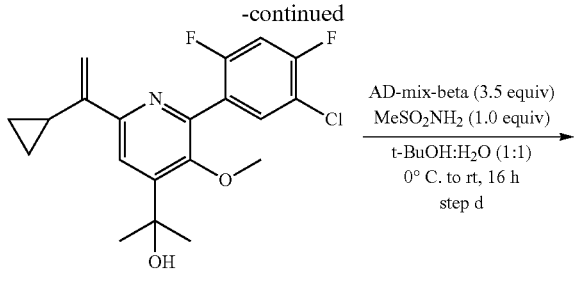

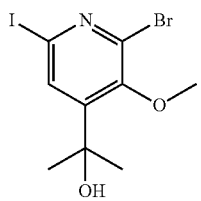

Example 164 Step a

A solution of 2-bromo-6-iodo-3-methoxypyridine (500 mg, 1.59 mmol) in THF (1.6 mL) was added dropwise to a stirring solution of LDA (1.20 mL, 2.39 mmol), in THF (0.5 mL) at −78° C. The mixture was stirred at that temperature for 45 minutes, before the addition of acetone (0.497 mL, 6.8 mmol). The reaction was warmed to room temperature and allowed to stir for 15 minutes before being quenched with saturated aqueous ammonium chloride, and then diluted with water and EtOAc. The layers were separated, and the aqueous layer was extracted with EtOAc (3×10 mL), dried over sodium sulfate, filtered, and concentrated. The crude residue was purified by automated flash chromatography on silica gel eluting with 0-70% EtOAc/hexanes to afford the desired product (229 mg, 39%). ESI-MS m/z: 374.01 [M+H]$^+$.

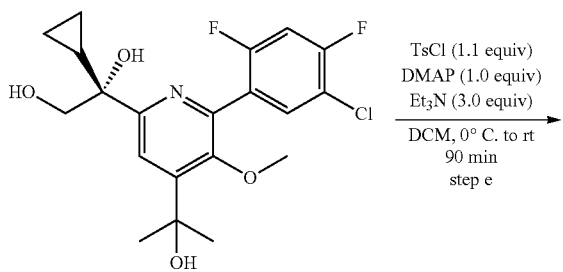

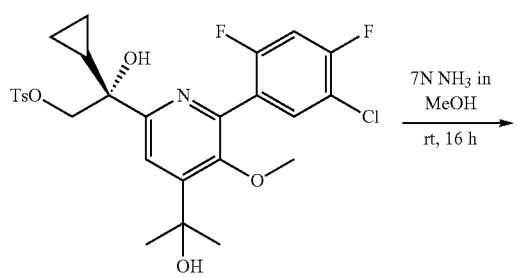

Example 164 Step b

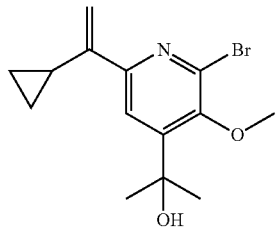 [SMILES: C=C(c1cc(C(C)(C)O)c(OC)c(Br)n1)C1CC1]

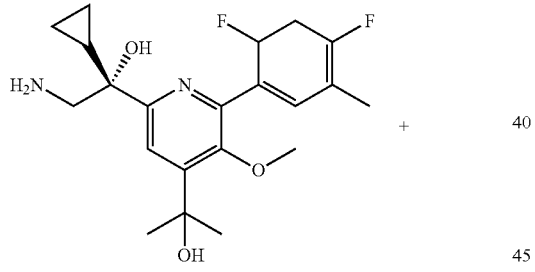

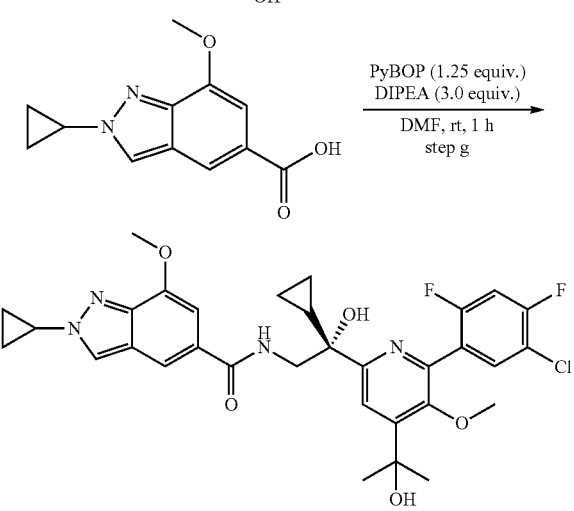

Example 164

The compound from step a (229 mg, 0.616 mmol) was dissolved in 1,4-Dioxane (2.7 mL) in a vial with a stirbar. To this solution was added PdCl$_2$(dppf) (45.0 mg, 0.062 mmol), K$_2$CO$_3$ (255 mg, 1.847 mmol), 2-(1-cyclopropylvinyl)-4,4,5,5-tetramethyl-1,3,2-dioxaborolane (163 µL, 0.800 mmol) and water (0.34 mL). The mixture was sparged with nitrogen for 5 minutes, and the vial was sealed and heated to 80° C. with stirring for 90 minutes. The reaction mixture was cooled to room temperature and diluted with water and EtOAc. The layers were separated, and the aqueous layer was extracted with EtOAc (3×5 mL). The combined organic extracts were dried over sodium sulfate, filtered, and concentrated. The crude residue was purified by flash chromatography on silica gel eluting with 0-60% EtOAc/hexanes to afford the desired product (98 mg, 51%). ESI-MS m/z: 314.18 [M+H]$^+$.

Example 164 Step c

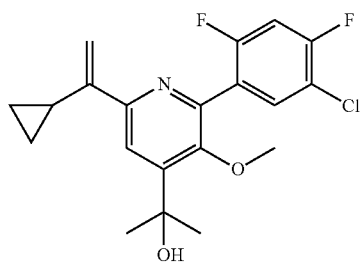 [SMILES: C=C(c1cc(C(C)(C)O)c(OC)c(-c2cc(Cl)c(F)cc2F)n1)C1CC1]

The compound from step b (98 mg, 0.314 mmol) was dissolved in 1,4-Dioxane (1.4 mL) in a vial with a stirbar. To this solution was added PdCl$_2$(dppf) (33 mg, 0.046 mmol), K$_2$CO$_3$ (130 mg, 0.942 mmol), (5-chloro-2,4-difluorophenyl)boronic acid (91 mg, 0.471 mmol), and water (0.17 mL). The resulting mixture was sparged with nitrogen for 5 minutes, and the vial was sealed and heated to 90° C. with stirring. After 3 h, the reaction mixture was cooled to rt and diluted with water and EtOAc. The layers were separated, and the aqueous layer extracted with EtOAc (3×5 mL). The combined organic extracts were dried over sodium sulfate, filtered, and concentrated. The crude residue was purified by flash chromatography on silica gel eluting with 0-40% EtOAc/hexanes to afford the desired product (54 mg, 46%). ESI-MS m/z: 380.27 [M+H]$^+$.

Example 164 Step d

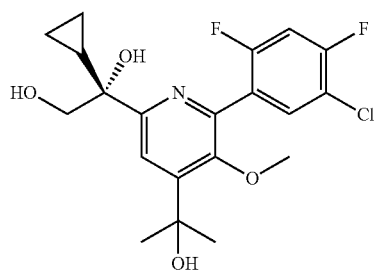 [SMILES: COc1c(C(C)(C)O)cc([C@@](O)(CO)C2CC2)nc1-c1cc(Cl)c(F)cc1F]

The compound from step c (54 mg, 0.14 mmol) was dissolved in a 1:1 mixture of t-butanol and water (2.4 mL). The solution was cooled to 0° C. and AD-mix-beta (653 mg, 0.839 mmol) and methanesulfonamide (22.79 mg, 0.240 mmol) were added. The mixture was warmed to room temperature and allowed to stir vigorously overnight. After this time, the reaction was quenched by the addition of solid sodium sulfite, and then diluted with water and EtOAc. The layers were separated, and the aqueous layer extracted with EtOAc (3×10 mL). The combined organic extracts were dried over sodium sulfate, filtered, and concentrated. The crude residue was purified by flash chromatography on silica gel eluting with 0-100% EtOAc/hexanes to afford the desired product (36 mg, 61%). ESI-MS m/z: 414.24 [M+H]$^+$.

Example 164 Step e

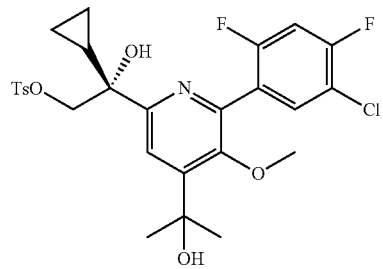 [SMILES: COc1c(C(C)(C)O)cc([C@@](O)(COS(=O)(=O)c2ccc(C)cc2)C2CC2)nc1-c1cc(Cl)c(F)cc1F]

The compound from step d (36 mg, 0.089 mmol) was dissolved in DCM (0.5 mL) and the solution was cooled to 0° C. Et$_3$N (37.2 µl, 0.267 mmol) was added, followed by the addition of TsCl (22.04 mg, 0.116 mmol) and DMAP (10.86 mg, 0.089 mmol). The reaction was warmed to room temperature and allowed to stir for 3 h. After this time, the reaction mixture was concentrated, and the residue directly purified by flash chromatography on silica gel eluting with 0-100% EtOAc/hexanes to afford the desired product (46 mg, 91%). ESI-MS m/z: 568.16 [M+H]$^+$.

Example 164 Step f

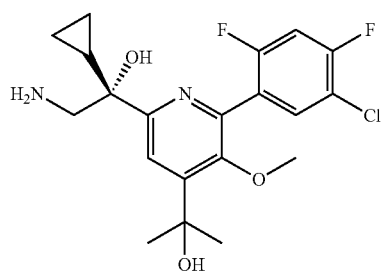 [SMILES: COc1c(C(C)(C)O)cc([C@@](O)(CN)C2CC2)nc1-c1cc(Cl)c(F)cc1F]

The compound from step e (46 mg, 0.081 mmol) was dissolved in a minimum amount of MeOH (0.5 mL) and the solution was cooled to 0° C. Ammonia solution (7N in MeOH, 1.8 mL, 13 mmol) was added, and the solution was allowed to stir at room temperature overnight. After this time, the reaction mixture was concentrated, and the residue dissolved in EtOAc. This organic solution was washed with saturated aqueous sodium bicarbonate (2×10 mL), dried over sodium sulfate, filtered, and concentrated to afford the desired product (34 mg, 95%). ESI-MS m/z: 413.25 [M+H]$^+$. This material was used directly for the next step without further purification.

Example 164 Step g

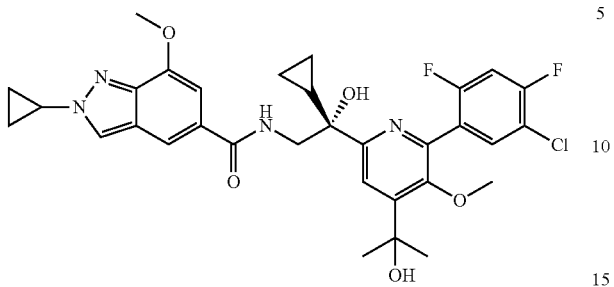

The compound from step f (34 mg, 0.082 mmol) and 2-cyclopropyl-7-methoxy-2H-indazole-5-carboxylic acid (23 mg, 0.099 mmol) were added to a vial with a stirbar and dissolved in DMF (0.4 mL). To this solution were added diisopropylethylamine (0.043 mL, 0.25 mmol) and PyBOP (54 mg, 0.10 mmol). The reaction mixture was allowed to stir at room temperature for 1 h before quenched with saturated aqueous sodium bicarbonate and diluted with water and EtOAc. The layers were separated, and the aqueous layer extracted with EtOAc (5 mL×3). The combined organic extracts were dried over sodium sulfate, filtered, and concentrated. The crude residue was purified by reverse phase HPLC to afford the desired product as a white solid (8.7 mg, 17%). ESI-MS m/z: 628.95 [M+H]$^+$; $^1$H NMR (400 MHz, DMSO-d6): δ −0.05-0.03 (m, 1H), 0.10-0.18 (m, 1H), 0.19-0.26 (m, 1H), 0.35-0.42 (m, 1H), 0.99 (td, J=7.4, 5.0 Hz, 2H), 1.10-1.17 (m, 2H), 1.26-1.33 (m, 1H), 1.35 (s, 3H), 1.39 (s, 3H), 3.62-3.75 (m, 2H), 3.77 (s, 3H), 4.01 (septet, J=3.7 Hz, 1H), 5.20 (s, 1H), 5.49 (s, 1H), 6.80 (s, 1H), 7.49-7.58 (m, 2H), 7.68-7.77 (t, f=8.2 Hz, 1H), 7.86 (s, 1H), 8.23 (t, J=5.8 Hz, 1H), 8.40 (s, 1H).

Example 165

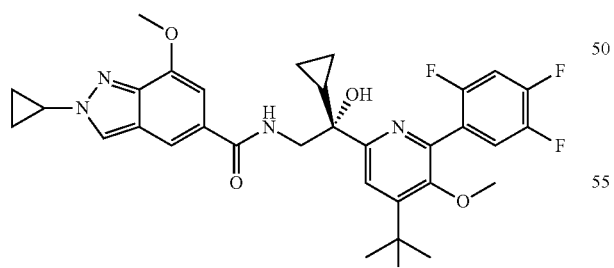

The title compound was synthesized according to the general method of Example 164 as a single enantiomer. ESI-MS m/z: 611.26 [M+H]$^+$.

Example 166

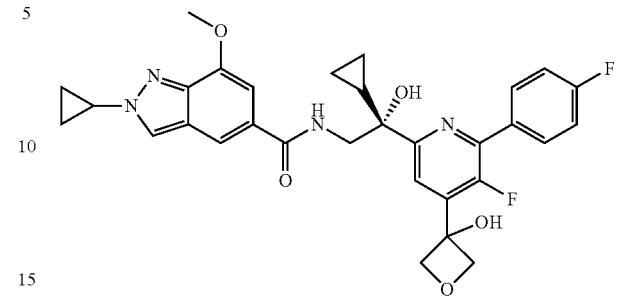

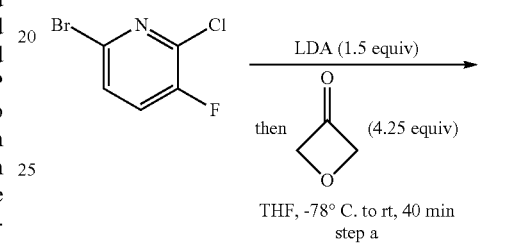

THF, -78° C. to rt, 40 min
step a

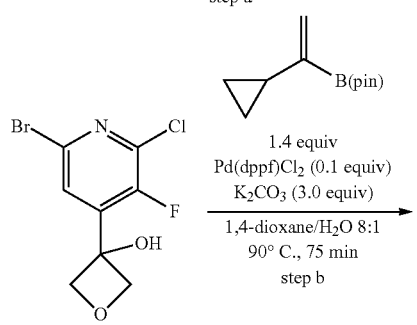

1,4-dioxane/H$_2$O 8:1
90° C., 75 min
step b

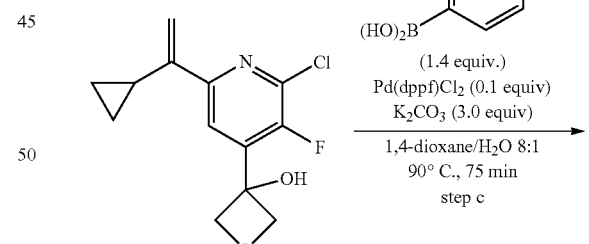

1,4-dioxane/H$_2$O 8:1
90° C., 75 min
step c

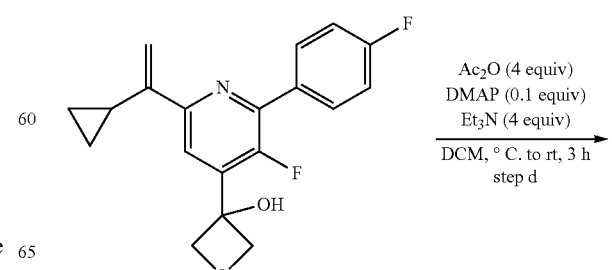

Ac$_2$O (4 equiv)
DMAP (0.1 equiv)
Et$_3$N (4 equiv)
DCM, ° C. to rt, 3 h
step d

147

-continued

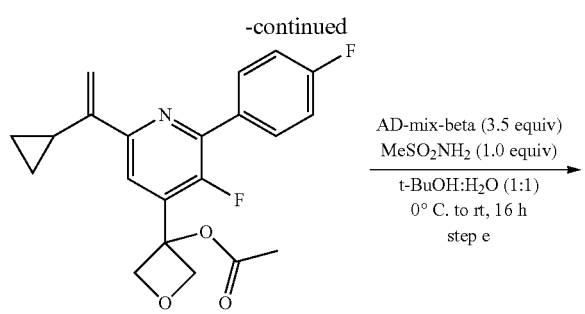

AD-mix-beta (3.5 equiv)
MeSO₂NH₂ (1.0 equiv)
———————————→
t-BuOH:H₂O (1:1)
0° C. to rt, 16 h
step e

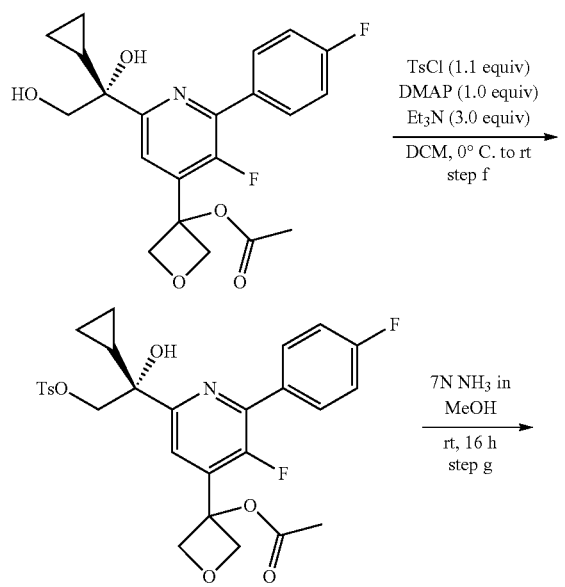

TsCl (1.1 equiv)
DMAP (1.0 equiv)
Et₃N (3.0 equiv)
———————————→
DCM, 0° C. to rt
step f 7N NH₃ in
MeOH
———————→
rt, 16 h
step g

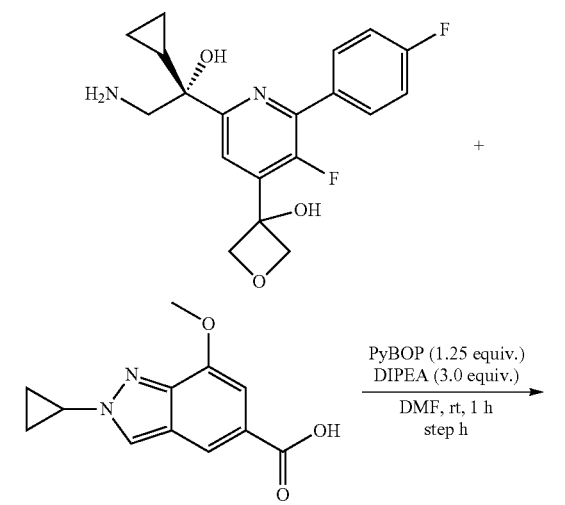

+

PyBOP (1.25 equiv.)
DIPEA (3.0 equiv.)
———————————→
DMF, rt, 1 h
step h

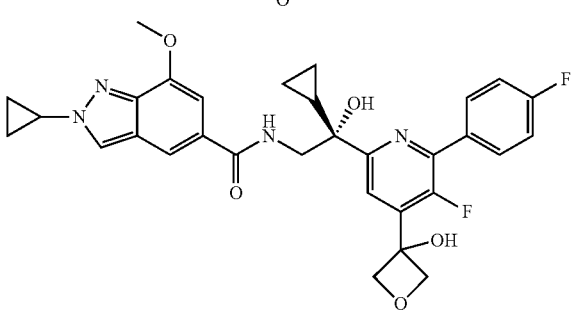

Example 166

148

Example 166 Step a

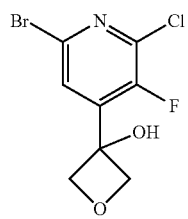 [SMILES: OC1(c2cc(Br)nc(Cl)c2F)COC1]

A solution of 6-bromo-2-chloro-3-fluoropyridine (500 mg, 2.38 mmol) in THF (2.4 mL) was added dropwise to a stirring solution of LDA (1.78 mL, 3.56 mmol), in additional THF (0.5 mL) at −78° C. The resultant mixture was stirred at that temperature for 45 minutes, at which point oxetan-3-one (0.647 mL, 10.1 mmol) was added. The reaction mixture was warmed to room temperature, and after stirring at room temperature for 15 minutes, quenched with saturated aqueous ammonium chloride and diluted with water and EtOAc. The layers were separated, and the aqueous layer was extracted with EtOAc (3×10 mL). The combined organic extracts were dried over sodium sulfate, filtered, and concentrated. The crude residue was purified by flash chromatography on silica gel eluting with 0-70% EtOAc/hexanes to afford the desired product (544 mg, 81%). ESI-MS m/z: 283.95 [M+H]⁺.

Example 166 Step b

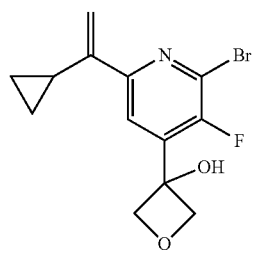 [SMILES: C=C(c1cc(C2(O)COC2)c(F)c(Br)n1)C1CC1]

Following the same conditions as used in Example 164 step b, the above compound was obtained as a white solid. ESI-MS m/z: 272.30 [M+H]⁺.

Example 166 Step c

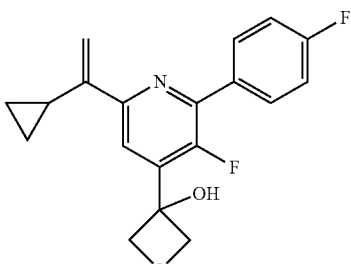

Following the same conditions as used in Example 164 step c, the above compound was obtained as a white solid. ESI-MS m/z: 330.45 [M+H]⁺.

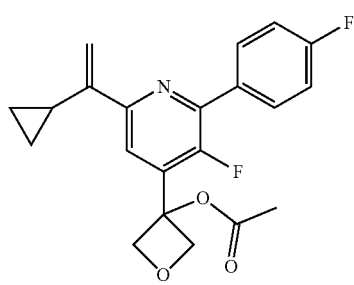 [SMILES: C=C(c1cc(C2(OC(C)=O)COC2)c(F)c(-c2ccc(F)cc2)n1)C1CC1]

The compound from step c (210 mg, 0.638 mmol) was dissolved in DCM (1.3 mL) and the solution was cooled to 0° C. Et₃N (356 μL, 2.55 mmol) was added, followed by the addition of DMAP (7.79 mg, 0.064 mmol), and acetic anhydride (241 μL, 2.55 mmol). The reaction mixture was allowed to warm to room temperature and stir for 3 h. After this time, the reaction was quenched with saturated aqueous sodium bicarbonate. The layers were separated, and the aqueous layer was extracted with EtOAc (3×5 mL). The combined organic extracts were dried over sodium sulfate, filtered, and concentrated. The crude residue was purified by flash chromatography on silica gel eluting with 0-50% EtOAc/hexanes to afford the desired product (220 mg. 93%). ESI-MS m/z: 372.30 [M+H]⁺.

Example 166 Step e

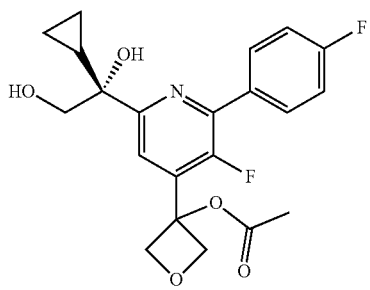 [SMILES: CC(=O)OC1(c2cc([C@@](O)(CO)C3CC3)nc(-c3ccc(F)cc3)c2F)COC1]

Following the same conditions as used in Example 164 step d, the above compound was obtained as a white solid. ESI-MS m/z: 406.27 [M+H]⁺.

Example 166 Step f

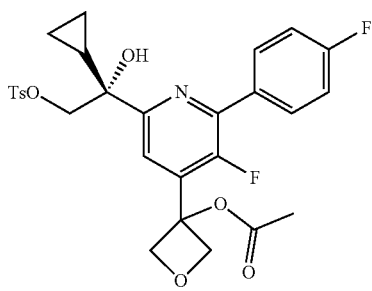 [SMILES: CC(=O)OC1(c2cc([C@@](O)(COS(=O)(=O)c3ccc(C)cc3)C3CC3)nc(-c3ccc(F)cc3)c2F)COC1]

Following the same conditions as used in Example 164 step e, the above compound was obtained as a white solid. ESI-MS m/z: 560.28 [M+H]⁺.

Example 166 Step g

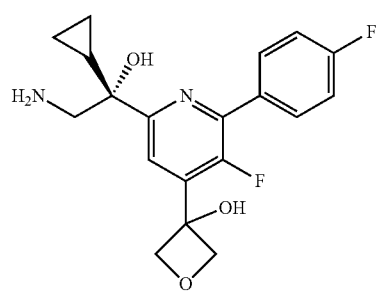 [SMILES: NC[C@](O)(c1cc(C2(O)COC2)c(F)c(-c2ccc(F)cc2)n1)C1CC1]

The compound from step f (277 mg, 0.495 mmol) was dissolved in a minimum amount of MeOH (0.5 mL) and the solution was cooled to 0° C. Ammonia solution (7 N in MeOH, 10.6 mL, 74.3 mmol) was added, and the solution was allowed to stir at room temperature overnight. After this time, the reaction mixture was concentrated, and the residue dissolved in EtOAc. This organic solution was washed with saturated aqueous sodium bicarbonate (10 mL×2), dried over sodium sulfate, filtered, and concentrated to afford the product (146 mg, 81%). ESI-MS m/z: 363.32 [M+H]⁺. This material was used directly for the next step without further purification.

Example 166 Step h

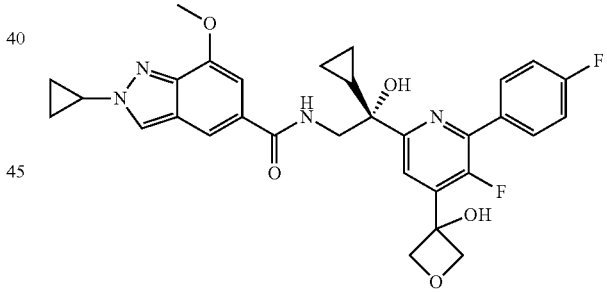

Following the same conditions as used in Example 164 step g, the above compound was obtained as a white solid. ESI-MS m/z: 577.45 [M+H]⁺; ¹H NMR (400 MHz, DMSO-d₆): δ 0.06-0.15 (m, 1H), 0.21-0.30 (m, 1H), 0.34-0.43 (m, 1H), 0.52-0.60 (m, 1H), 1.11 (td, J=7.5, 5.0 Hz, 2H), 1.22-1.28 (m, 2H), 1.51 (ddd, J=13.6, 8.5, 5.3 Hz, 1H), 3.88 (s, 3H), 3.85-3.95 (m, 2H), 4.13 (septet, J=3.7 Hz, 1H), 4.71 (t, J=7.2 Hz, 2H), 5.01 (t, J=7.5 Hz, 2H), 5.74 (s, 1H), 6.73 (s, 1H), 6.92 (s, 1H), 7.36 (t, J=8.9 Hz, 2H), 7.66 (d, J=5.2 Hz, 1H), 7.70 (d, J=1.0 Hz, 1H), 8.03 (dd, J=8.2, 5.6 Hz, 2H), 8.36 (t, J=5.8 Hz, 1H), 8.53 (s, 1H).

Example 167

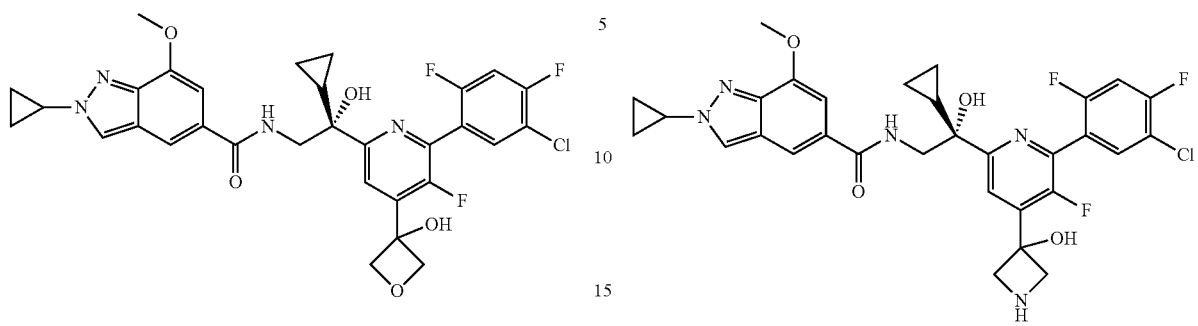

The title compound was synthesized according to the general method of Example 166 as a white solid. ESI-MS m/z: 629.40 [M+H]$^+$.

Example 168

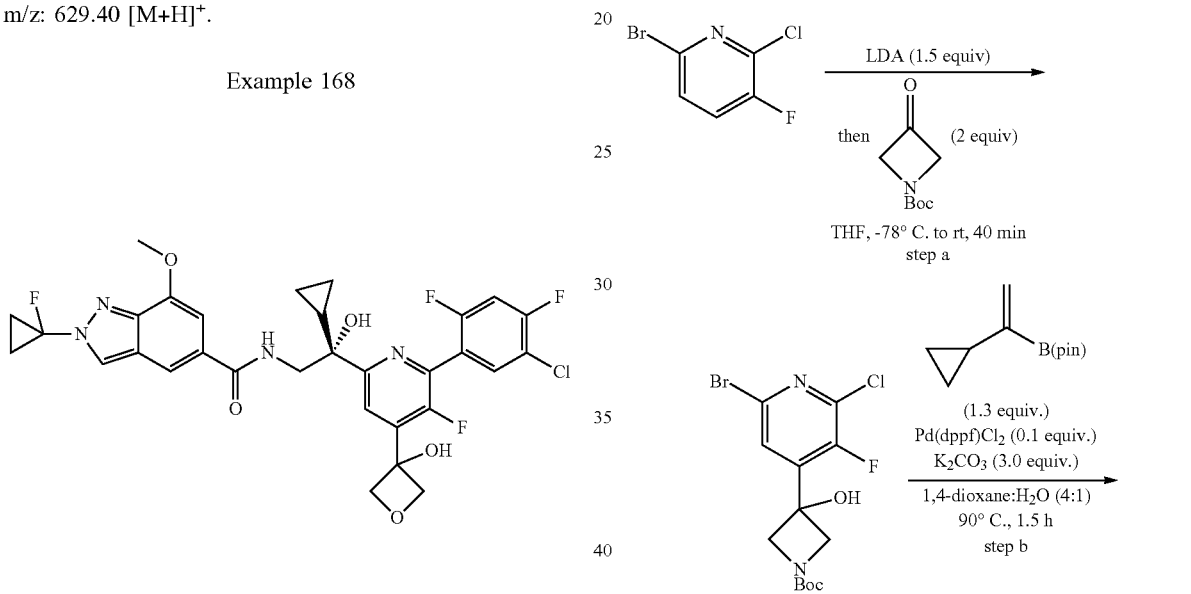

The title compound was synthesized according to the general method of Example 166 as a white solid. ESI-MS m/z: 647.38 [M+H]$^+$.

Example 169

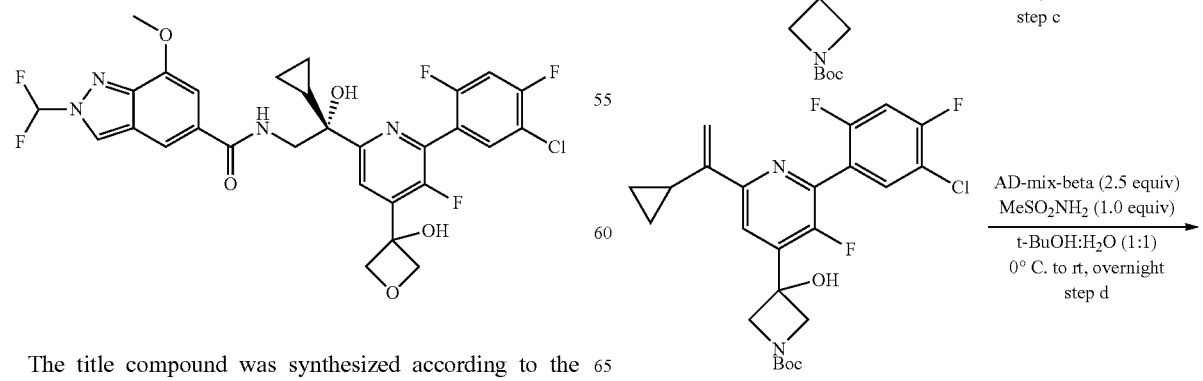

The title compound was synthesized according to the general method of Example 166 as a white solid. ESI-MS m/z: 639.36 [M+H]$^+$.

Example 170

153
-continued

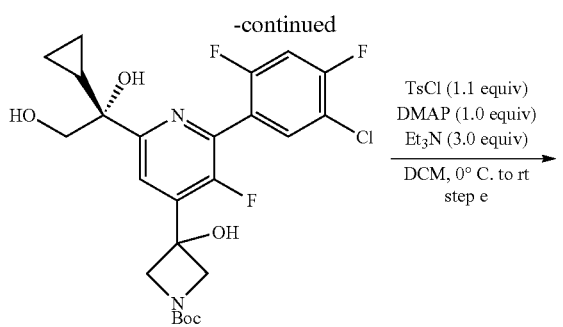

TsCl (1.1 equiv)
DMAP (1.0 equiv)
Et₃N (3.0 equiv)
DCM, 0° C. to rt
step e

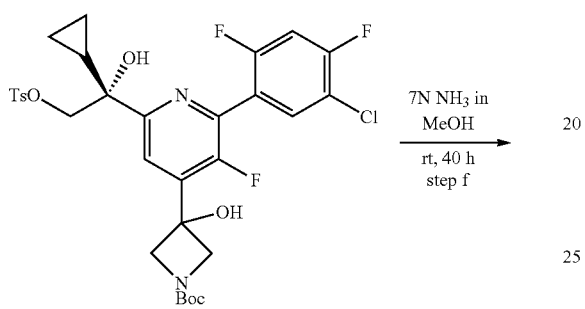

7N NH₃ in MeOH
rt, 40 h
step f

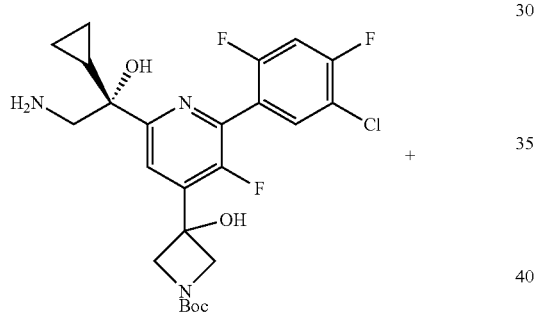
+

1. PyBOP (1.2 equiv)
DIPEA (2.0 equiv)
DMF, rt, 1 h
2. TFA (15 equiv)
DMF, rt, 3 h
step g

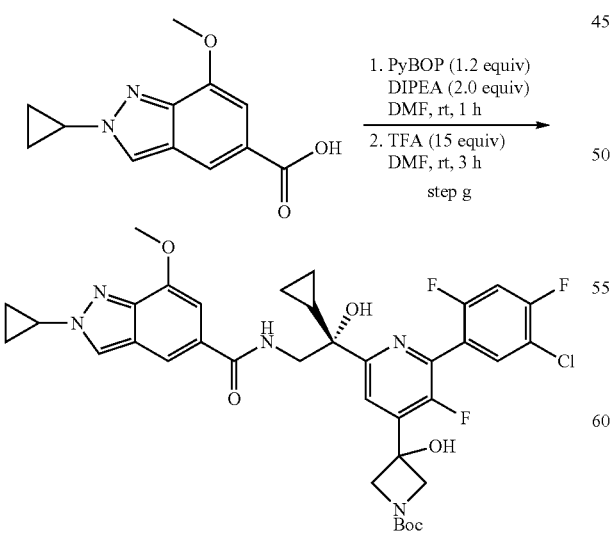

Example 170

154
Example 170 Step a

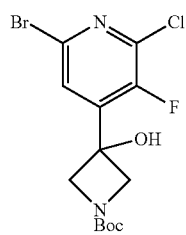 [SMILES: CC(C)(C)OC(=O)N1CC(O)(c2cc(Br)nc(Cl)c2F)C1]

Following the same conditions as used in Example 166 step a, the above compound was obtained as a white solid.

Example 170 Step b

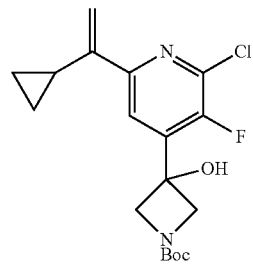 [SMILES: C=C(c1cc(C2(O)CN(C(=O)OC(C)(C)C)C2)c(F)c(Cl)n1)C1CC1]

Following the same conditions as used in Example 166 step b, the above compound was obtained as a white solid.

Example 170 Step c

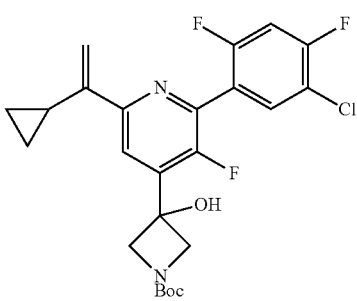 [SMILES: C=C(c1cc(C2(O)CN(C(=O)OC(C)(C)C)C2)c(F)c(-c2cc(Cl)c(F)cc2F)n1)C1CC1]

Following the same conditions as used in Example 166 step c, the above compound was obtained as a white solid.
ESI-MS m/z: 481.30 [M+H]⁺.

Example 170 Step d

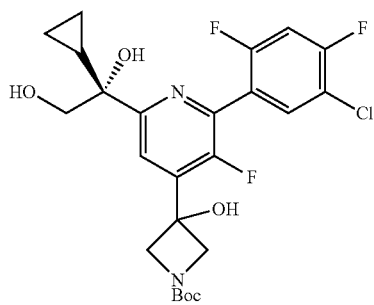 [SMILES: CC(C)(C)OC(=O)N1CC(O)(c2cc([C@@](O)(CO)C3CC3)nc(-c3cc(Cl)c(F)cc3F)c2F)C1]

Following the same conditions as used in Example 166 step e, the above compound was obtained as a white solid. ESI-MS m/z: 515.28 [M+H]+.

Example 170 Step e

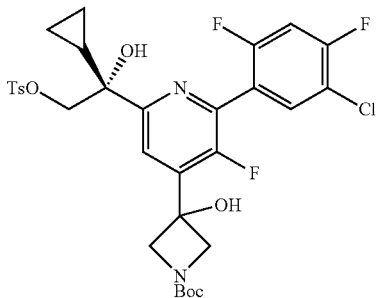 [SMILES: Cc1ccc(S(=O)(=O)OC[C@](O)(c2cc(C3(O)CN(C(=O)OC(C)(C)C)C3)c(F)c(-c3cc(Cl)c(F)cc3F)n2)C2CC2)cc1]

Following the same conditions as used in Example 166 step f, the above compound was obtained as a white solid. ESI-MS m/z: 669.46 [M+H]+.

Example 170 Step f

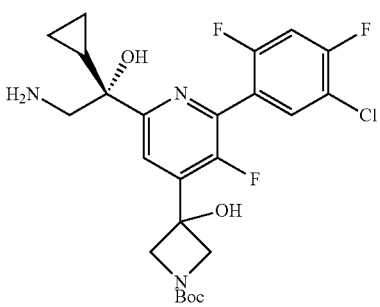

Following the same conditions as used in Example 166 step f, the above compound was obtained as a white solid. ESI-MS m/z: 514.36 [M+H]+.

Example 170 Step g

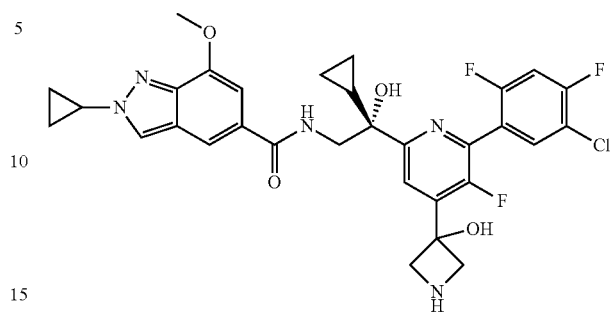

The compound from step f (35 mg, 0.068 mmol) and 2-cyclopropyl-7-methoxy-2H-indazole-5-carboxylic acid (17 mg, 0.075 mmol) were added to a vial with a stirbar and dissolved in DMF (0.34 mL). To this solution were added diisopropylethylamine (0.036 mL, 0.20 mmol) and PyBOP (44 mg, 0.085 mmol). The reaction mixture was stirred at room temperature for 1 h before quenched with saturated aqueous sodium bicarbonate and diluted with water and EtOAc. The layers were separated, and the aqueous layer extracted with EtOAc (5 mL×3). The combined organic extracts were dried over sodium sulfate, filtered, and concentrated. The crude residue was purified by flash chromatography on silica gel eluting with 0-7% MeOH/DCM to afford the Boc-protected product, which was taken on to the next step. ESI-MS m/z: 728.51 [M+H]+. The Boc-protected material was dissolved in DCM (0.5 mL) and the solution was cooled to 0° C. TFA (26.5 µL, 0.343 mmol) was added and the cooling bath was removed. After 2 h of stirring at room temperature, an additional aliquot of TFA (60 µL, 0.777 mmol) was added, and the reaction mixture was allowed to continue stirring at room temperature for an additional 2 h. After this time, the reaction was quenched with saturated aqueous sodium bicarbonate. The layers were separated, and the aqueous layer was extracted with EtOAc (3 mL×3) and 10% MeOH in DCM (3 mL). The combined organic extracts were dried over sodium sulfate, filtered, and concentrated. The crude residue was purified by reverse phase HPLC to afford the desired product as a white solid (3.5 mg, 8%). ESI-MS m/z: 628.55 [M+H]+; 1H NMR (400 MHz, DMSO-d6): δ 0.07-0.16 (m, 1H), 0.22-0.30 (m, 1H), 0.43-0.42 (m, 1H), 0.51-0.58 (m, 1H), 1.07-1.14 (m, 2H), 1.22-1.29 (m, 2H), 1.41-1.50 (m, 1H), 3.82 (dd, J=13.6, 5.3 Hz, 1H), 3.89 (s, 3H), 3.94 (dd, J=13.4, 6.4 Hz, 1H), 4.12 (septet, J=3.7 Hz, 1H), 6.31 (s, 1H), 6.92 (s, 1H), 7.67 (d, J=0.8 Hz, 1H), 7.71 (t, J=9.6 Hz, 1H), 7.78 (d, J=5.6 Hz, 1H), 7.94 (t, J=7.8 Hz, 1H), 8.37 (t, J=6.0 Hz, 1H), 8.54 (s, 1H).

Example 171

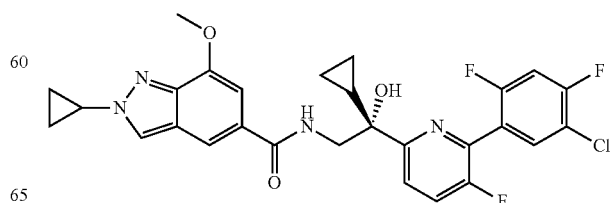

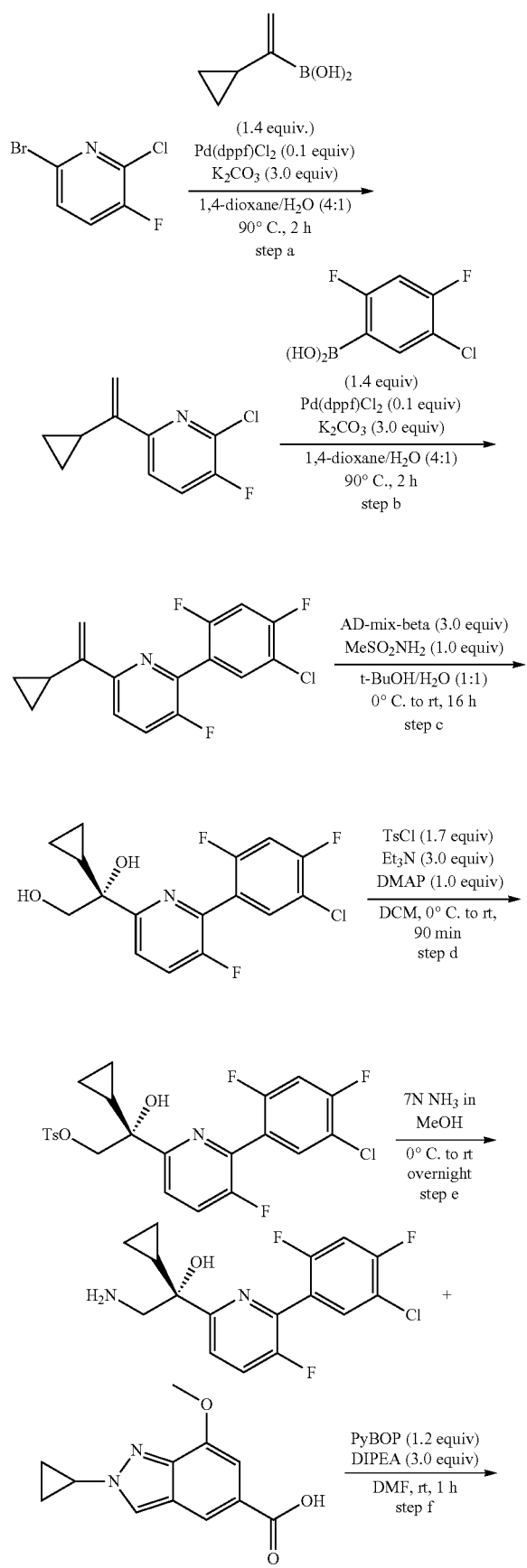

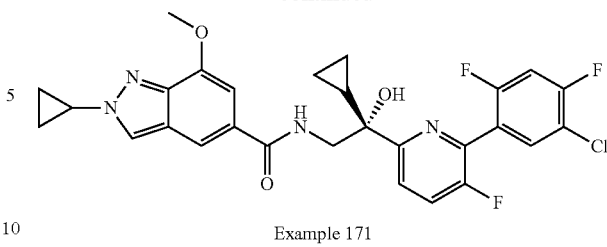

Example 171

Example 171 Step a

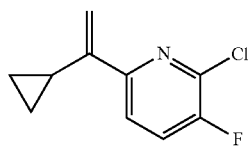

Following the same conditions as used in Example 166 step b, the above compound was obtained as a white solid. ESI-MS m/z: 198.13 [M+H]$^+$.

Example 171 Step b

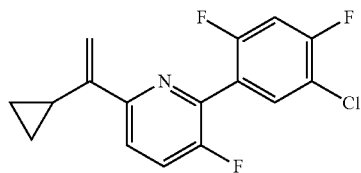 [SMILES: C=C(c1ccc(F)c(-c2cc(Cl)c(F)cc2F)n1)C1CC1]

Following the same conditions as used in Example 166 step c, the above compound was obtained as a white solid. ESI-MS m/z: 294.15 [M+H]$^+$.

Example 171 Step c

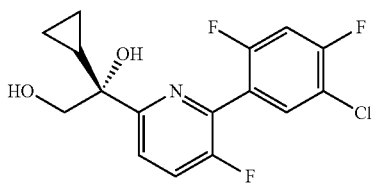 [SMILES: OC[C@](O)(c1ccc(F)c(-c2cc(Cl)c(F)cc2F)n1)C1CC1]

Following the same conditions as used in Example 166 step d, the above compound was obtained as a white solid. ESI-MS m/z: 328.15 [M+H]$^+$.

Example 171 Step d

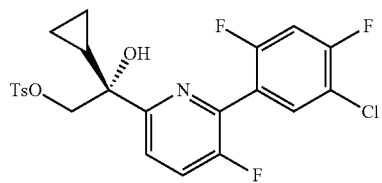 [SMILES: Cc1ccc(S(=O)(=O)OC[C@](O)(c2ccc(F)c(-c3cc(Cl)c(F)cc3F)n2)C2CC2)cc1]

Following the same conditions as used in Example 166 step e, the above compound was obtained as a white solid. ESI-MS m/z: 482.35 [M+H]$^+$.

Example 171 Step e

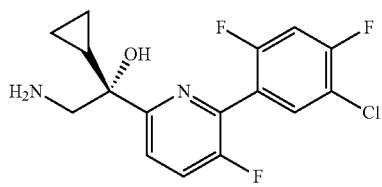

Following the same conditions as used in Example 166 step f, the above compound was obtained as a white solid. ESI-MS m/z: 327.18 [M+H]$^+$.

Example 171 Step f

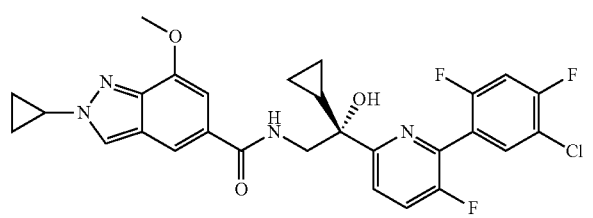 [SMILES: COc1cc(C(=O)NC[C@](O)(c2ccc(F)c(-c3cc(Cl)c(F)cc3F)n2)C2CC2)cc2cn(C3CC3)nc12]

Following the same conditions as used in Example 166 step g, the above compound was obtained as a white solid. ESI-MS m/z: 557.37 [M+H]$^+$; $^1$H NMR (400 MHz, DMSO-d6): δ 0.08-0.17 (m, 1H), 0.22-0.31 (m, 1H), 0.34-0.45 (m, 1H), 0.52-0.60 (m, 1H), 1.06-1.14 (m, 2H), 1.21-1.29 (m, 2H), 1.42-1.52 (m, 1H), 3.80 (dd, J=13.5, 5.2 Hz, 1H), 3.88 (s, 3H), 3.97 (dd, J=13.6, 6.5 Hz, 1H), 4.12 (septet, J=3.7 Hz, 1H), 5.74 (s, 1H), 7.66 (d, J=1.3 Hz, 1H), 7.71 (t, J=9.7 Hz, 1H), 7.75 (dd, J=8.7, 4.0 Hz, 1H), 7.82 (dd, J=9.8, 8.7 Hz, 1H), 7.94 (dd, J=8.4, 7.2 Hz, 1H), 8.35 (t, J=5.9 Hz, 1H), 8.54 (s, 1H).

Example 172

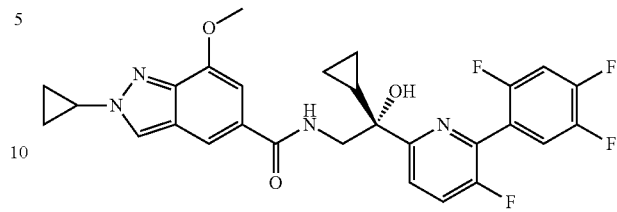

The title compound was synthesized according to the general method of Example 171 as a white solid. ESI-MS m/z: 541.38 [M+H]$^+$.

Example 173

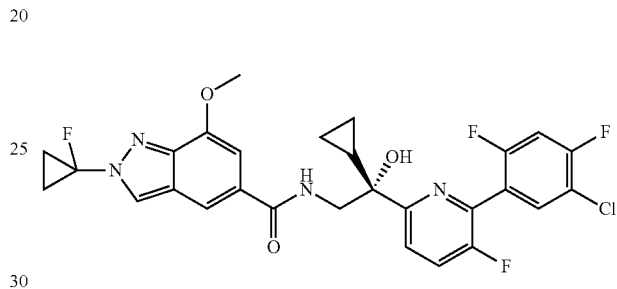

The title compound was synthesized according to the general method of Example 171 as a white solid. ESI-MS m/z: 575.40 [M+H]$^+$.

Example 174

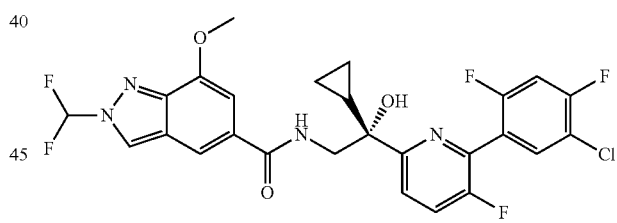

The title compound was synthesized according to the general method of Example 171 as a white solid. ESI-MS m/z: 567.31 [M+H]$^+$.

Example 175

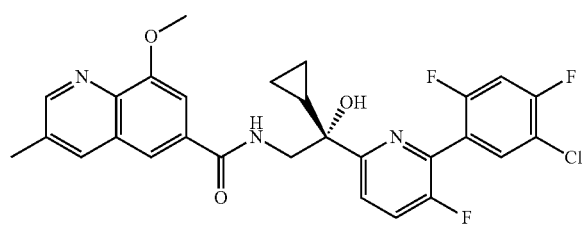 [SMILES: COc1cc(C(=O)NC[C@](O)(c2ccc(F)c(-c3cc(Cl)c(F)cc3F)n2)C2CC2)cc2cc(C)cnc12]

The title compound was synthesized according to the general method of Example 171 as a white solid. ESI-MS m/z: 542.36 [M+H]+.

Example 176

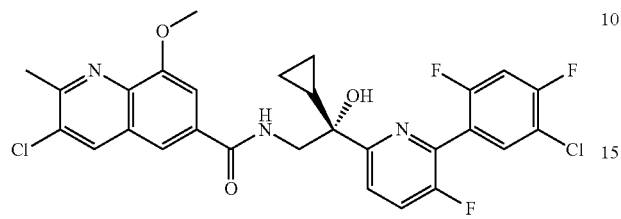

The title compound was synthesized according to the general method of Example 171 as a white solid. ESI-MS m/z: 576.31 [M+H]+.

Example 177

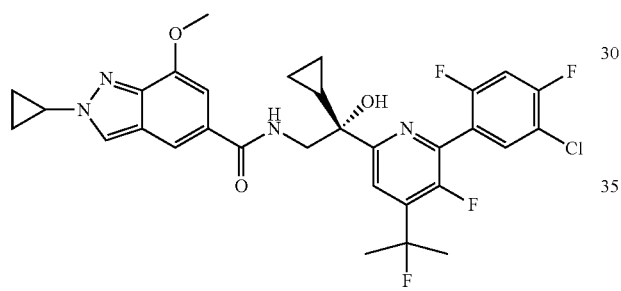

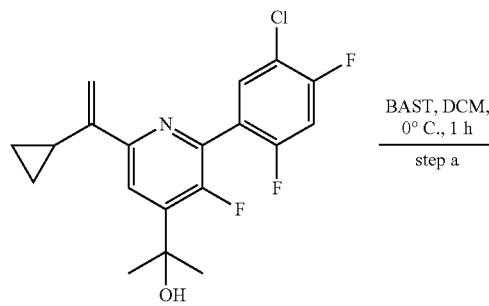

BAST, DCM,
0° C., 1 h
step a
→

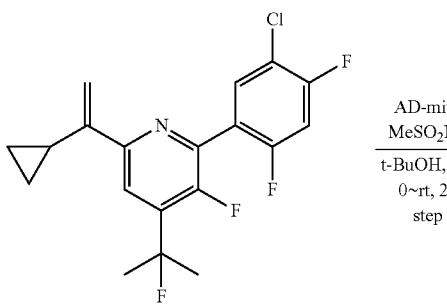

AD-mix-β,
MeSO₂NH₂,
t-BuOH, H₂O,
0~rt, 24 h
step b
→

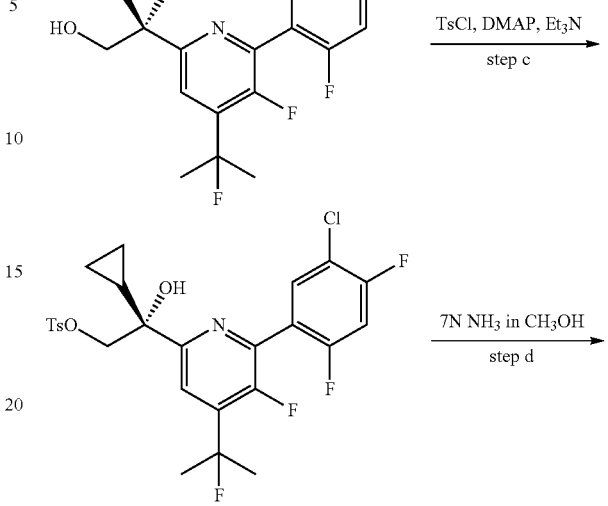

TsCl, DMAP, Et₃N
step c
→

7N NH₃ in CH₃OH
step d
→

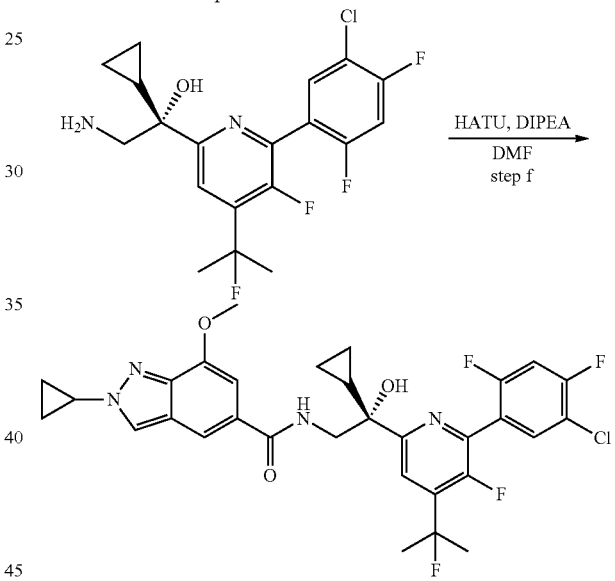

HATU, DIPEA
DMF
step f
→

Example 177

Example 177 Step a

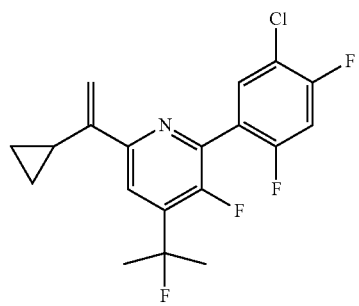 [SMILES: C=C(c1cc(C(C)(C)F)c(F)c(-c2cc(Cl)c(F)cc2F)n1)C1CC1]

To a stirred solution of 2-(2-(5-chloro-2,4-difluorophenyl)-6-(1-cyclopropylvinyl)-3-fluoropyridin-4-yl)propan-2- ol (prepared by the similar method to Example 1 steps a-e) (450 mg, 1.22 mmol) in DCM (10 mL) was added BAST (812 mg, 3.67 mmol) dropwise at 0° C. The resulting mixture was stirred for 1 h at 0° C. The reaction was quenched with water. The resulting mixture was extracted with DCM. The combined organic layers were concentrated under reduced pressure. The residue was purified by Prep-TLC (EtOAc/hexanes=1/15) to afford the desired product (370 mg, 81%) as a light yellowish oil. ESI-MS m/z: 370.20 [M+H]⁺.

Example 177 Step b

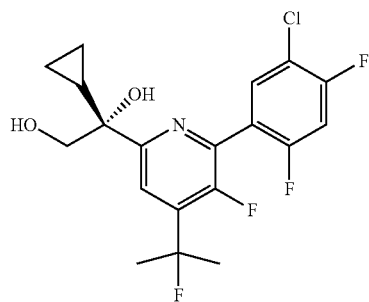 [SMILES: CC(C)(F)c1cc([C@@](O)(CO)C2CC2)nc(-c2cc(Cl)c(F)cc2F)c1F]

A mixture of the compound from step a (370 mg, 1.00 mmol), methanesulfonamide (95 mg, 1.00 mmol) and AD-mix-β (2.34 g, 3.00 mmol) in t-BuOH (6 mL), H₂O (6 mL) was stirred overnight at room temperature. The resulting mixture was poured into water, extracted with EtOAc. The combined organic layers were concentrated under reduced pressure. The residue was purified by silica gel column chromatography eluting with 0-40% EtOAc/hexanes to afford the desired product (280 mg, 69%) as a light yellowish oil. ESI-MS m/z: 404.15 [M+H]⁺.

Example 177 Step c

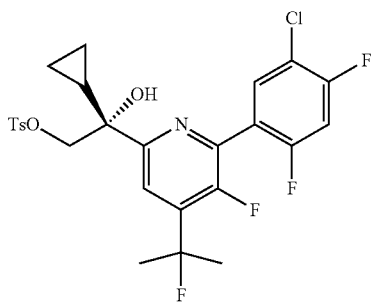 [SMILES: Cc1ccc(S(=O)(=O)OC[C@](O)(c2cc(C(C)(C)F)c(F)c(-c3cc(Cl)c(F)cc3F)n2)C2CC2)cc1]

To a stirred solution of the compound from step b (280 mg, 0.69 mmol) in DCM (5 mL) was added TsCl (198 mg, 1.04 mmol), DMAP (84 mg, 0.69 mmol), TEA (210 mg, 2.08 mmol) at 0° C. The resulting mixture was stirred for 2 h at 0° C. The mixture was acidified to pH 4 with HCl (2 M aq.). The resulting mixture was extracted with CH₂Cl₂. The combined organic layers were concentrated under reduced pressure. The residue was purified by Prep-TLC (hexanes/EtOAc=3:1) to afford the desired product (350 mg, 90%) as a light yellowish oil. ESI-MS m/z: 558.00 [M+H]⁺.

Example 177 Step d

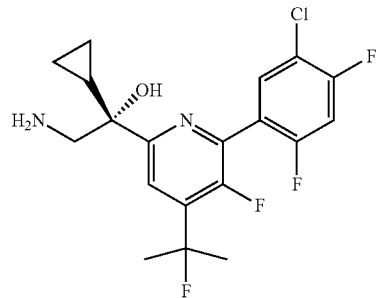 [SMILES: CC(C)(F)c1cc([C@@](O)(CN)C2CC2)nc(-c2cc(Cl)c(F)cc2F)c1F]

Into a 40 mL sealed tube were added 7 N NH₃ in MeOH (15 mL). The compound from step c (350 mg, 0.62 mmol) in MeOH was added dropwise and stirred overnight at 40° C. The resulting mixture was concentrated under reduced pressure. The residue was purified by Prep-TLC (CH₂Cl₂/7 N NH₃ in MeOH=15:1) to afford the desired product (200 mg, 79%) as a white solid. ESI-MS m/z: 403.05 [M+H]⁺. ¹H NMR (400 MHz, DMSO-d₆) δ 0.12 (dtd, J=8.9, 5.5, 2.9 Hz, 1H), 0.21-0.41 (m, 2H), 0.47 (ddd, J=9.1, 6.3, 3.7 Hz, 1H), 1.27 (ddt, J=12.6, 9.6, 4.7 Hz, 1H), 1.50 (s, 2H), 1.75 (dd, J=22.9, 4.4 Hz, 6H), 2.82 (d, J=13.1 Hz, 1H), 3.20 (d, J=13.1 Hz, 1H), 4.99 (s, 1H), 7.69-7.79 (m, 2H), 7.93 (t, J=7.8 Hz, 1H).

Example 177 Step e

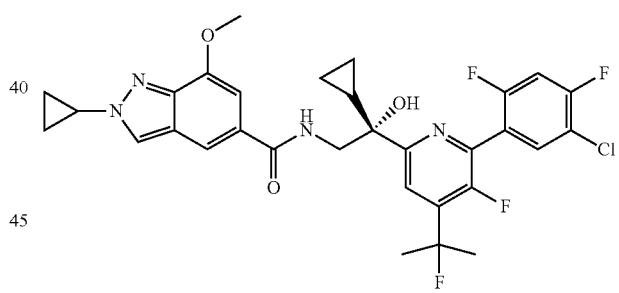

A mixture of compound from step d (17 mg, 0.04 mmol), 2-cyclopropyl-7-methoxy-2H-indazole-5-carboxylic acid (10 mg, 0.043 mmol), HATU (16. mg, 0.04 mmol) and DIPEA (11 mg, 0.08 mmol) in DMF (1 mL) was stirred for 1 h at room temperature. The residue was purified by reverse flash chromatography to afford the desired product (16.4 mg, 61%) as a white solid. ESI-MS m/z: 617.15 [M+H]⁺. ¹H NMR (400 MHz, DMSO-d₆) δ 0.15 (tt, J=9.2, 4.1 Hz, 1H), 0.29 (dq, J=9.1, 4.7, 4.3 Hz, 1H), 0.40 (dq, J=12.9, 4.7, 3.9 Hz, 1H), 0.57 (dq, J=9.8, 5.2 Hz, 1H), 1.07-1.15 (m, 2H), 1.26 (p, J=4.6 Hz, 2H), 1.52 (td, J=8.4, 4.3 Hz, 1H), 1.68 (dd, J=32.8, 22.9 Hz, 6H), 3.77 (dd, J=13.6, 5.3 Hz, 1H), 3.89 (s, 3H), 3.92-4.01 (m, 1H), 4.13 (tt, J=7.6, 3.9 Hz, 1H), 5.76 (s, 1H), 6.89 (s, 1H), 7.66 (s, 1H), 7.73 (t, J=9.7 Hz, 1H), 7.79 (d, J=5.6 Hz, 1H), 7.95 (t, J=7.8 Hz, 1H), 8.36 (t, J=6.0 Hz, 1H), 8.55 (s, 1H).

Example 178

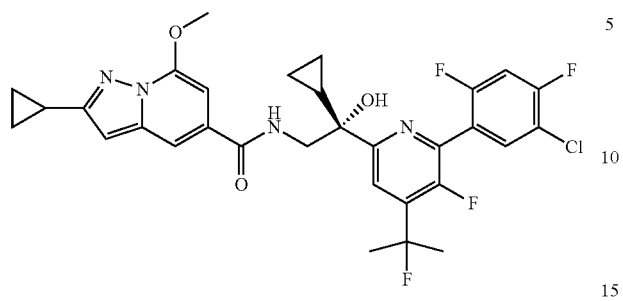

The title compound was synthesized according to the general method of Example 177 as white solid. ESI-MS m/z: 617.15 [M+H]e. $^1$H NMR (400 MHz, DMSO-d$_6$) δ 0.12-0.21 (m, 1H), 0.31 (dq, J=10.2, 5.8, 5.1 Hz, 1H), 0.36-0.46 (m, 1H), 0.57 (dq, J=9.3, 5.6, 4.5 Hz, 1H), 0.78-0.86 (m, 2H), 0.99 (dt, J=8.8, 3.2 Hz, 2H), 1.50-1.81 (m, 7H), 2.07 (tt, J=8.6, 4.2 Hz, 1H), 3.76 (dd, J=13.4, 5.4 Hz, 1H), 3.94 (dd, J=13.5, 6.5 Hz, 1H), 4.06 (s, 3H), 5.53 (s, 1H), 6.46 (d, J=18.9 Hz, 2H), 7.51 (s, 1H), 7.71 (t, J=9.6 Hz, 1H), 7.80 (d, J=5.6 Hz, 1H), 7.90 (t, J=7.7 Hz, 1H), 8.49 (t, J=6.1 Hz, 1H).

Example 179

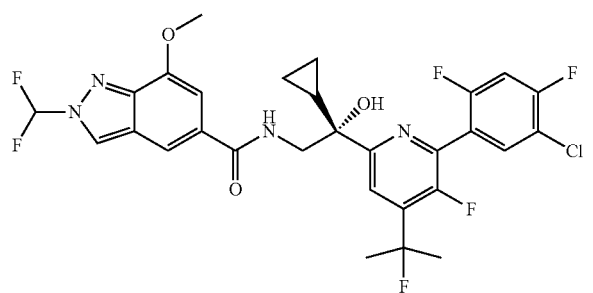 [SMILES: COc1cc(C(=O)NC[C@](O)(c2cc(C(C)(C)F)c(F)c(-c3cc(Cl)c(F)cc3F)n2)C2CC2)cc2cn(C(F)F)nc12]

The title compound was synthesized according to the general method of Example 177 as a white solid. ESI-MS m/z: 627.10 [M+H]$^+$. $^1$H NMR (400 MHz, DMSO-d$_6$) δ 0.17 (dt, J=14.0, 4.8 Hz, 1H), 0.30 (dq, J=9.2, 4.9 Hz, 1H), 0.41 (td, J=9.0, 8.2, 3.9 Hz, 1H), 0.58 (dq, J=9.6, 4.8 Hz, 1H), 1.51-1.60 (m, 1H), 1.68 (dd, J=32.2, 22.9 Hz, 6H), 3.77 (dd, J=13.6, 5.5 Hz, 1H), 3.93 (s, 4H), 5.64 (s, 1H), 6.98 (d, J=1.3 Hz, 1H), 7.68-7.78 (m, 2H), 7.80 (d, J=5.6 Hz, 1H), 7.88-7.96 (m, 1H), 8.13 (t, J=59.0 Hz, 1H), 8.44 (t, J=6.0 Hz, 1H), 9.00 (s, 1H).

Example 180

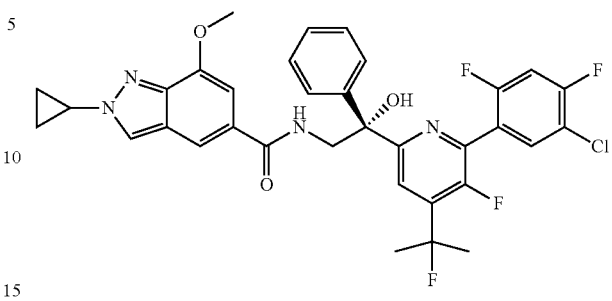

The title compound was synthesized according to the general method of Example 177 as a white solid. ESI-MS m/z: 653.25 [M+H]$^+$. $^1$H NMR (400 MHz, DMSO-d6) δ 1.07-1.14 (m, 2H), 1.22-1.29 (m, 2H), 1.68 (dd, J=23.0, 8.0 Hz, 6H), 3.88 (s, 3H), 4.13 (tt, J=7.6, 3.9 Hz, 1H), 4.28 (d, J=5.7 Hz, 2H), 6.82-6.87 (m, 2H), 7.20 (t, J=7.4 Hz, 1H), 7.31 (t, J=7.7 Hz, 2H), 7.58-7.66 (m, 3H), 7.76 (t, J=9.7 Hz, 1H), 7.91 (d, J=5.5 Hz, 1H), 7.99 (t, J=7.8 Hz, 1H), 8.19 (t, J=5.6 Hz, 1H), 8.56 (s, 1H).

Example 181

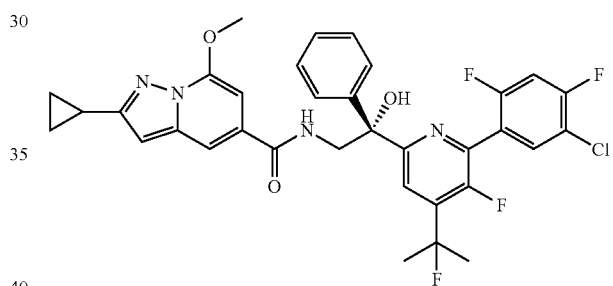

The title compound was synthesized according to the general method of Example 177 as a white solid. ESI-MS m/z: 653.25 [M+H]$^+$. $^1$H NMR (400 MHz, DMSO-d6) δ 0.77-0.84 (m, 2H), 0.94-1.02 (m, 2H), 1.68 (dd, J=22.9, 8.5 Hz, 6H), 2.06 (tt, J=8.3, 5.0 Hz, 1H), 4.05 (s, 3H), 4.23-4.34 (m, 2H), 6.40-6.46 (m, 2H), 6.67 (s, 1H), 7.18-7.24 (m, 1H), 7.31 (t, J=7.7 Hz, 2H), 7.45 (d, J=1.6 Hz, 1H), 7.59-7.64 (m, 2H), 7.75 (t, J=9.7 Hz, 1H), 7.89 (d, J=5.6 Hz, 1H), 7.98 (dd, J=8.4, 7.2 Hz, 1H), 8.34 (t, J=5.8 Hz, 1H).

Example 182

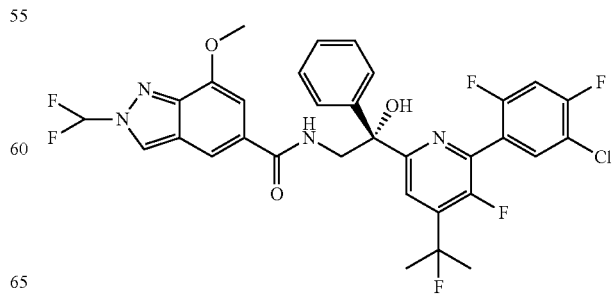

The title compound was synthesized according to the general method of Example 177 as a white solid. ESI-MS m/z: 663.25 [M+H]+. 1H NMR (400 MHz, DMSO-d6) δ 1.68 (dd, J=22.9, 9.4 Hz, 6H), 3.92 (s, 3H), 4.29 (d, J=5.8 Hz, 2H), 6.75 (s, 1H), 6.92 (d, J=1.2 Hz, 1H), 7.21 (t, J=7.3 Hz, 1H), 7.32 (t, J=7.7 Hz, 2H), 7.60-7.67 (m, 2H), 7.69 (d, J=1.2 Hz, 1H), 7.75 (t, J=9.7 Hz, 1H), 7.90 (d, J=5.5 Hz, 1H), 7.96-8.02 (m, 1H), 8.12 (s, 1H), 8.24-8.30 (m, 1H), 9.00 (s, 1H).

Example 183

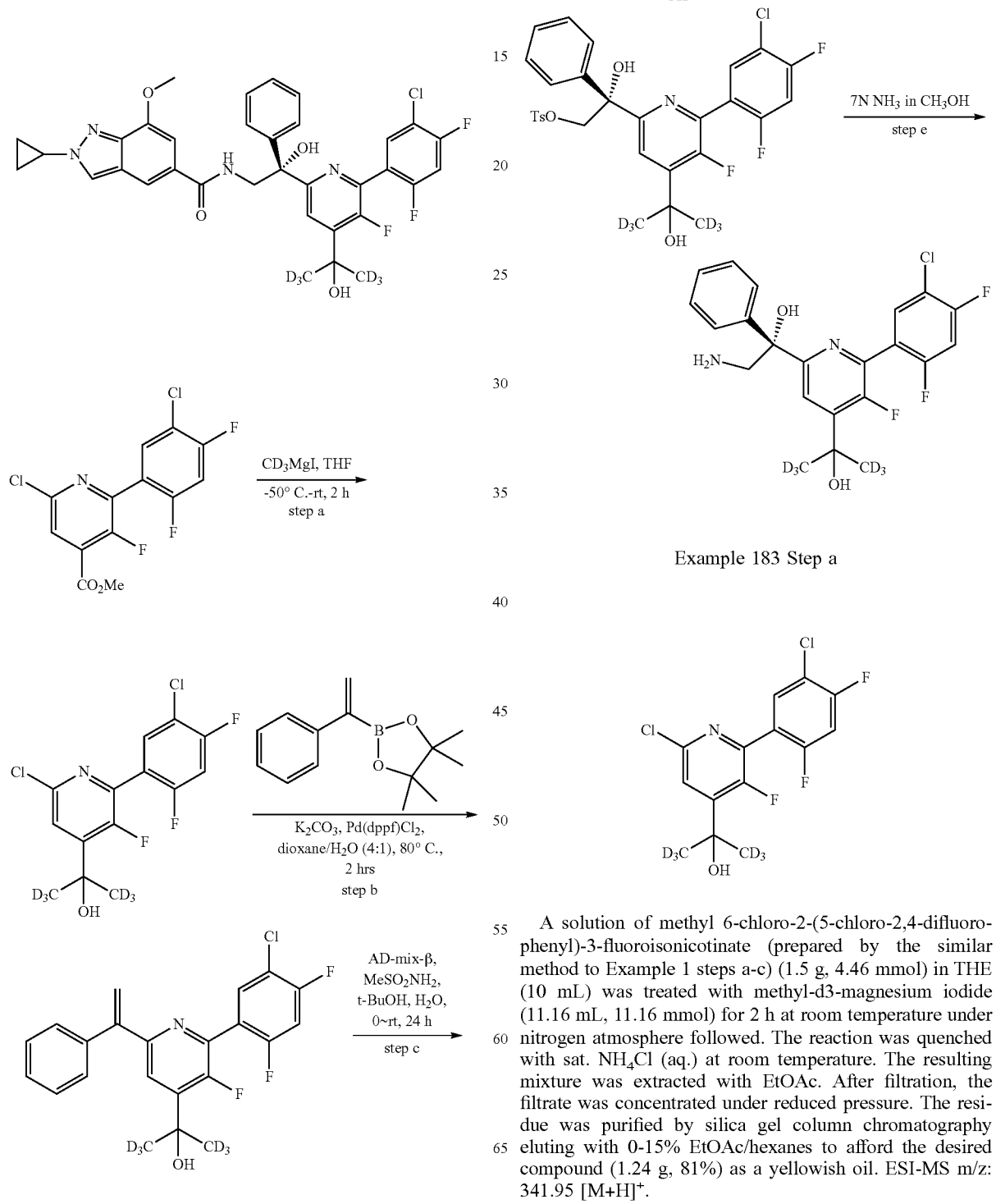

Example 183 Step a

A solution of methyl 6-chloro-2-(5-chloro-2,4-difluorophenyl)-3-fluoroisonicotinate (prepared by the similar method to Example 1 steps a-c) (1.5 g, 4.46 mmol) in THF (10 mL) was treated with methyl-d3-magnesium iodide (11.16 mL, 11.16 mmol) for 2 h at room temperature under nitrogen atmosphere followed. The reaction was quenched with sat. NH4Cl (aq.) at room temperature. The resulting mixture was extracted with EtOAc. After filtration, the filtrate was concentrated under reduced pressure. The residue was purified by silica gel column chromatography eluting with 0-15% EtOAc/hexanes to afford the desired compound (1.24 g, 81%) as a yellowish oil. ESI-MS m/z: 341.95 [M+H]+.

Example 183 Step b

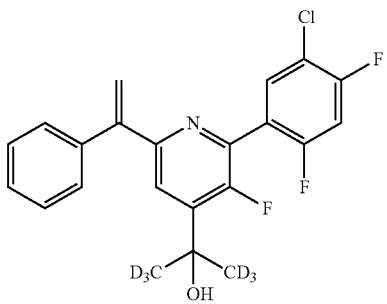 [SMILES: [2H]C([2H])([2H])C(O)(c1cc(C(=C)c2ccccc2)nc(-c2cc(Cl)c(F)cc2F)c1F)C([2H])([2H])[2H]]

Example 183 Step d

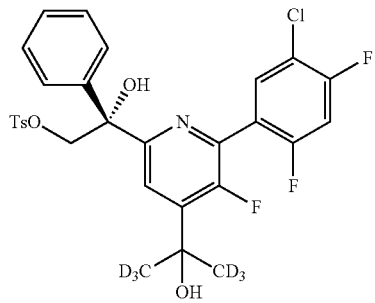

A solution of the compound from step a (600 mg, 1.75 mmol) in dioxane (8 mL) and H₂O (2 mL) was treated with 4,4,5,5-tetramethyl-2-(1-phenylethenyl)-1,3,2-dioxaborolane (404 mg, 1.75 mmol), Pd(dppf)Cl₂ (257 mg, 0.35 mmol) and K₂CO₃ (727 mg, 5.26 mmol) for 2 h at 80° C. under nitrogen atmosphere. The resulting mixture was extracted with EtOAc. After filtration, the filtrate was concentrated under reduced pressure. The residue was purified by silica gel column chromatography eluting with 0-15% EtOAc/hexanes to afford the desired compound (520 mg, 72%) as a yellowish oil. ESI-MS m/z: 410.15 [M+H]⁺.

A solution of the compound from step c (570 mg, 1.28 mmol) in DCM (5 mL) was treated with TsCl (294 mg, 1.54 mmol), DMAP (157 mg, 1.28 mmol) and Et₃N (390 mg, 3.85 mmol) for 2 hours at room temperature. The mixture was acidified to pH 4 with conc. HCl. The resulting mixture was extracted with DCM. After filtration, the filtrate was concentrated under reduced pressure. The residue was purified by silica gel column chromatography eluting with 0-50% EtOAc/hexanes to afford the desired compound (600 mg, 78%) as a white oil. ESI-MS m/z: 598.15 [M+H]⁺.

Example 183 Step c

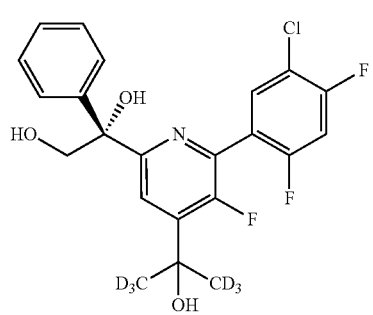 [SMILES: [2H]C([2H])([2H])C(O)(c1cc([C@@](O)(CO)c2ccccc2)nc(-c2cc(Cl)c(F)cc2F)c1F)C([2H])([2H])[2H]]

Example 183 Step e

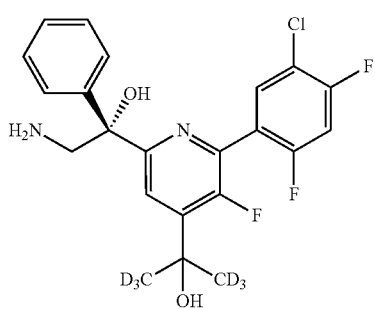 [SMILES: [2H]C([2H])([2H])C(O)(c1cc([C@@](O)(CN)c2ccccc2)nc(-c2cc(Cl)c(F)cc2F)c1F)C([2H])([2H])[2H]]

To a solution of the compound from step b (520 mg, 1.27 mmol) in t-BuOH (10 mL) and H₂O (10 mL) were added AD-mix-β (2.96 g, 3.81 mmol) and methanesulfonamide (121 mg, 1.27 mmol). The resulting mixture was stirred at 0° C. for 2 h and then overnight at room temperature. The resulting mixture was quenched with Na₂SO₃ and then extracted with EtOAc (50 mL×3). The combined organic layer was washed with brine, dried, filtrated and concentrated under reduced pressure. The residue was purified by silica gel column chromatography eluting with 0-40% EtOAc/hexanes to afford the desired compound (570 mg, 100%) as a dark green solid. ESI-MS m z: 444.20 [M+H]⁺.

A solution of 7 N NH₃ in MeOH (20 mL) and the compound from step d (600 mg, 1.00 mmol) was stirred for overnight at 40° C. The resulting mixture was concentrated under reduced pressure. The residue was purified by silica gel column chromatography eluting with DCM/7N NH₃ in MeOH (10:1) to afford the titled compound (228.2 mg, 46%) as a white solid. ESI-MS m z: 443.15 [M+H]⁺. ¹H NMR (400 MHz, DMSO-d6) δ 1.66 (d, J=50.7 Hz, 2H), 3.00 (d, J=13.2 Hz, 1H), 3.58 (d, J=13.2 Hz, 1H), 5.59 (s, 1H), 5.96 (s, 1H), 7.16-7.23 (m, 1H), 7.29 (dd, J=8.4, 6.9 Hz, 2H), 7.48-7.54 (m, 2H), 7.74 (t, J=9.7 Hz, 1H), 7.96 (dd, J=8.4, 7.3 Hz, 1H), 8.01 (d, J=5.9 Hz, 1H).

Example 183 Step f

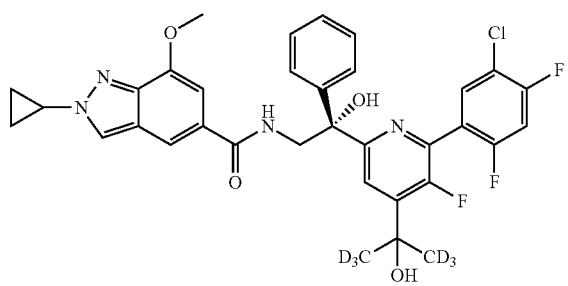 [SMILES: [2H]C([2H])([2H])C(O)(c1cc([C@@](O)(CNC(=O)c2cc(OC)c3nn(C4CC4)cc3c2)c2ccccc2)nc(-c2cc(Cl)c(F)cc2F)c1F)C([2H])([2H])[2H]]

A solution of compound from step e (19 mg, 0.04 mmol) in DMF (1 mL) was treated with 2-cyclopropyl-7-methoxy-2H-indazole-5-carboxylic acid (10 mg, 0.04 mmol), HATU (16 mg, 0.04 mmol) and DIPEA (11 mg, 0.09 mmol) for 1 h at room temperature. The residue was purified by reversed-phase flash chromatography to afford the titled compound (15.3 mg, 54%) as a white solid. ESI-MS m/z: 657.45 [M+H]$^+$. $^1$H NMR (400 MHz, DMSO-d6) δ 1.07-1.14 (m, 2H), 1.26 (m, 2H), 3.88 (s, 3H), 4.13 (tt, J=7.6, 3.9 Hz, 1H), 4.24 (dd, J=13.7, 5.4 Hz, 1H), 4.32 (dd, J=13.8, 5.7 Hz, 1H), 5.61 (s, 1H), 6.80-6.86 (m, 2H), 7.19 (t, J=7.3 Hz, 1H), 7.30 (t, J=7.6 Hz, 2H), 7.58-7.66 (m, 3H), 7.73 (t, J=9.7 Hz, 1H), 7.93-8.01 (m, 1H), 8.11 (d, J=5.8 Hz, 1H), 8.17 (t, J=5.7 Hz, 1H), 8.55 (s, 1H).

Example 184

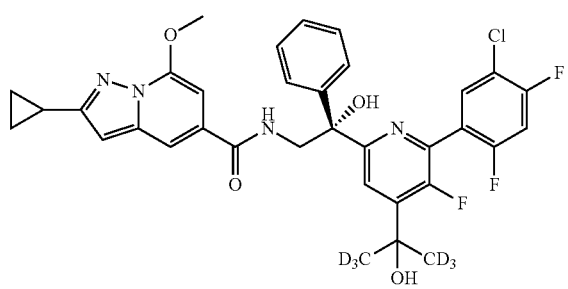 [SMILES: [2H]C([2H])([2H])C(O)(c1cc([C@@](O)(CNC(=O)c2cc(OC)n3nc(C4CC4)cc3c2)c2ccccc2)nc(-c2cc(Cl)c(F)cc2F)c1F)C([2H])([2H])[2H]]

The title compound was synthesized according to the general method of Example 183 as a white solid. ESI-MS m/z: 657.45 [M+H]$^+$. $^1$H NMR (400 MHz, DMSO-d6) δ 0.76-0.85 (m, 2H), 0.94-1.03 (m, 2H), 2.07 (tt, J=8.4, 4.9 Hz, 1H), 4.06 (s, 3H), 4.25 (dd, J=13.7, 5.6 Hz, 1H), 4.31 (dd, J=13.7, 5.8 Hz, 1H), 5.61 (s, 1H), 6.39-6.46 (m, 2H), 6.61 (s, 1H), 7.17-7.24 (m, 1H), 7.31 (dd, J=8.4, 7.0 Hz, 2H), 7.44 (d, J=1.7 Hz, 1H), 7.58-7.64 (m, 2H), 7.72 (t, J=9.7 Hz, 1H), 7.95 (dd, J=8.4, 7.2 Hz, 1H), 8.09 (d, J=5.9 Hz, 1H), 8.31 (t, J=5.8 Hz, 1H).

Example 185

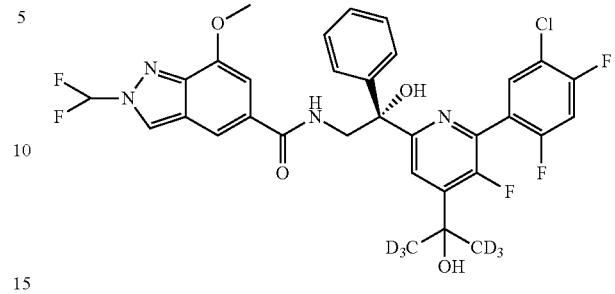

The title compound was synthesized according to the general method of Example 183 as a white solid. ESI-MS m/z: 667.45 [M+H]$^+$. $^1$H NMR (400 MHz, DMSO-d6) δ 3.92 (s, 3H), 4.24 (dd, J=13.7, 5.5 Hz, 1H), 4.32 (dd, J=13.7, 5.8 Hz, 1H), 5.61 (s, 1H), 6.72 (d, J=3.0 Hz, 1H), 6.91 (d, J=1.2 Hz, 1H), 7.15-7.23 (m, 1H), 7.30 (dd, J=8.4, 7.0 Hz, 2H), 7.57-7.65 (m, 2H), 7.66-7.77 (m, 2H), 7.93-8.00 (m, 1H), 8.06-8.14 (m, 1H), 8.25 (d, J=7.7 Hz, 1H), 8.98 (s, 1H).

Example 186

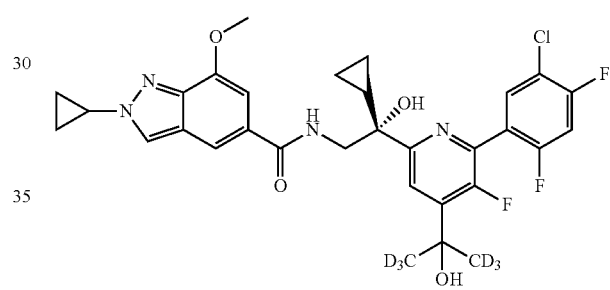

The title compound was synthesized according to the general method of Example 183 as a white solid. ESI-MS m/z: 621.00 [M+H]$^+$. $^1$H NMR (400 MHz, DMSO-d6) δ 0.09-0.16 (m, 1H), 0.25-0.32 (m, 1H), 0.38 (s, 1H), 0.51-0.58 (m, 1H), 1.11 (td, J=7.5, 5.0 Hz, 2H), 1.27 (p, J=4.8, 4.4 Hz, 2H), 1.41-1.51 (m, 1H), 3.81 (dd, J=13.6, 5.4 Hz, 1H), 3.89 (s, 3H), 3.94 (dd, J=13.6, 6.4 Hz, 1H), 4.14 (tt, J=7.5, 3.8 Hz, 1H), 5.59 (s, 1H), 5.75 (s, 1H), 6.91 (d, J=1.3 Hz, 1H), 7.66 (d, J=1.3 Hz, 1H), 7.70 (t, J=9.7 Hz, 1H), 7.90-7.98 (m, 1H), 8.01 (d, J=6.0 Hz, 1H), 8.38 (t, J=5.9 Hz, 1H), 8.55 (s, 1H).

Example 187

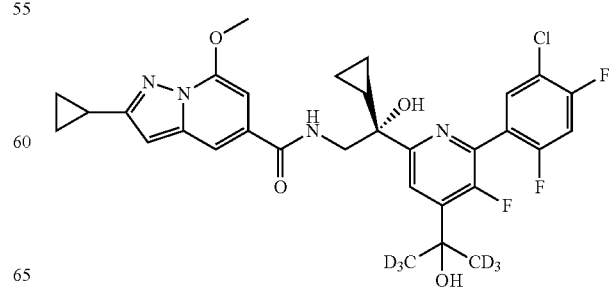

The title compound was synthesized according to the general method of Example 183 as a white solid. ESI-MS m/z: 621.00 [M+H]+. 1H NMR (400 MHz, DMSO-d6) δ 0.12-0.18 (m, 1H), 0.27-0.34 (m, 1H), 0.39 (d, J=8.1 Hz, 1H), 0.52-0.59 (m, 1H), 0.77-0.86 (m, 2H), 0.95-1.04 (m, 2H), 1.45-1.55 (m, 1H), 2.08 (ddd, J=13.3, 8.6, 4.9 Hz, 1H), 3.80 (dd, J=13.5, 5.4 Hz, 1H), 3.92 (dd, J=13.3, 6.3 Hz, 1H), 4.07 (s, 3H), 5.50 (s, 1H), 5.60 (s, 1H), 6.43 (s, 1H), 6.49 (d, J=1.6 Hz, 1H), 7.51 (d, J=1.6 Hz, 1H), 7.69 (t, J=9.6 Hz, 1H), 7.85-7.94 (m, 1H), 8.01 (d, J=5.9 Hz, 1H), 8.49 (t, J=5.9 Hz, 1H).

Example 188

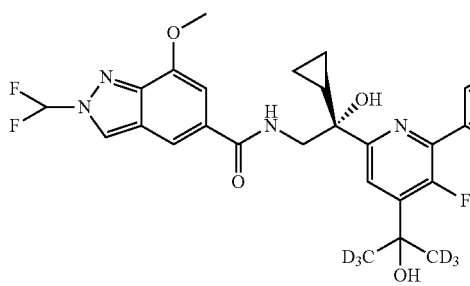

The title compound was synthesized according to the general method of Example 183 as a white solid. ESI-MS m/z: 631.00 [M+H]+. 1H NMR (400 MHz, DMSO-d6) δ 0.11-0.18 (m, 1H), 0.26-0.34 (m, 1H), 0.39 (s, 1H), 0.53-0.61 (m, 1H), 1.49 (dd, J=9.6, 4.4 Hz, 1H), 3.82 (dd, J=13.5, 5.3 Hz, 1H), 3.94 (s, 3H), 3.90-3.99 (m, 1H), 5.62 (s, 2H), 6.99 (d, J=1.2 Hz, 1H), 7.69 (t, J=9.6 Hz, 1H), 7.76 (d, J=1.2 Hz, 1H), 7.88-7.96 (m, 1H), 7.96-8.05 (m, 1H), 8.13 (s, 1H), 8.44 (t, J=6.0 Hz, 1H), 8.99 (s, 1H).

Example 189

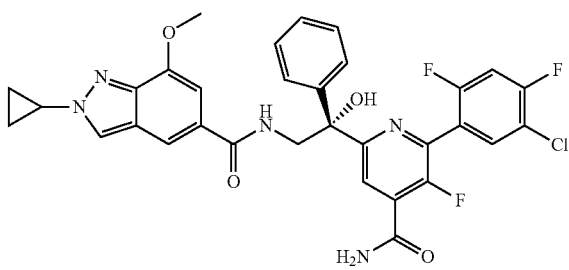 [SMILES: COc1cc(C(=O)NC[C@@](O)(c2ccccc2)c2cc(C(N)=O)c(F)c(-c3cc(Cl)c(F)cc3F)n2)cc2cn(C3CC3)nc12]

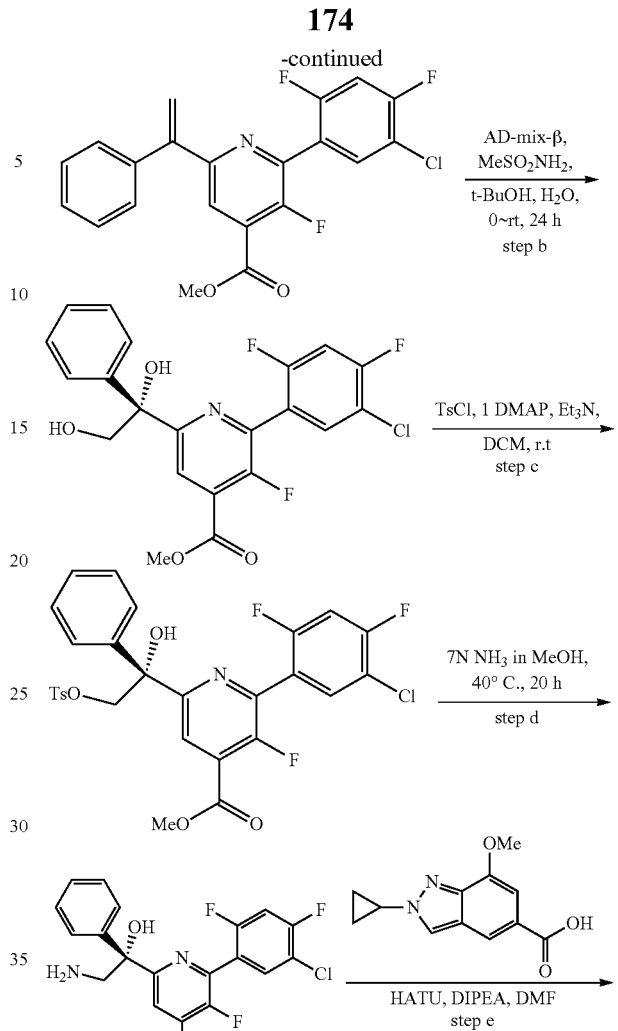

Example 189

Example 189 Step a

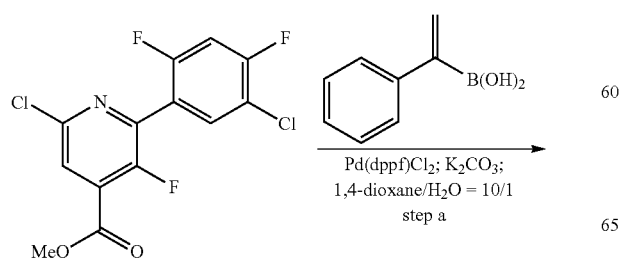

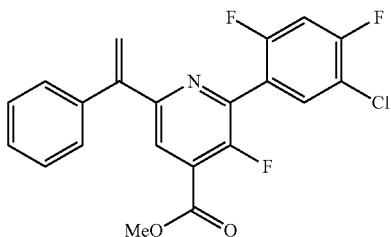 [SMILES: C=C(c1ccccc1)c1cc(C(=O)OC)c(F)c(-c2cc(Cl)c(F)cc2F)n1]

A solution of methyl 6-chloro-2-(5-chloro-2,4-difluorophenyl)-3-fluoroisonicotinate (prepared by the similar method to Example 1 steps a-c) (1.5 g, 4.46 mmol), 1-phenylethenylboronic acid (0.79 g, 5.37 mmol), Pd(dppf)Cl$_2$ (0.33 g, 0.45 mmol) and K$_2$CO$_3$ (1.23 g, 8.93 mmol) in 1,4-dioxane (20 mL) and H$_2$O (2 mL) was stirred for 2 h at 80° C. under N$_2$ atmosphere. The residue was purified by silica gel column chromatography eluting with 0-20% EtOAc/hexanes to afford the desired product (1.2 g, 67%) as a yellow oil. ESI-MS m/z: 404.00 [M+H]$^+$.

Example 189 Step b

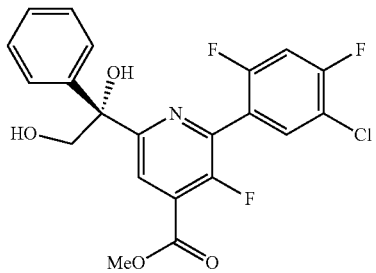 [SMILES: COC(=O)c1cc([C@@](O)(CO)c2ccccc2)nc(-c2cc(Cl)c(F)cc2F)c1F]

A solution of the compound from step a (1.5 g, 3.72 mmol), AD-mix-β (8.68 g, 11.15 mmol) and methanesulfonamide (0.35 g, 3.72 mmol) in t-BuOH (20 mL) and H$_2$O (20 mL) was stirred for overnight at room temperature. The resulting mixture was extracted with EA (100 mL×3). The combined organic layers were washed with water, dried over anhydrous Na$_2$SO$_4$. The residue was purified by silica gel column chromatography eluting with 0-50% EtOAc/hexanes to afford the desired product (1.2 g, 74%) as a yellow oil. ESI-MS m/z: 438.00 [M+H]$^+$.

Example 189 Step c

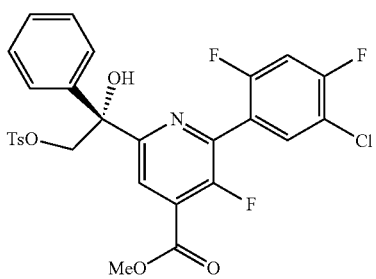 [SMILES: COC(=O)c1cc([C@@](O)(COS(=O)(=O)c2ccc(C)cc2)c2ccccc2)nc(-c2cc(Cl)c(F)cc2F)c1F]

A solution of the compound from step b (1.5 g, 3.43 mmol), TsCl (0.78 g, 4.11 mmol), DMAP (0.17 g, 1.37 mmol) and Et$_3$N (0.69 g, 6.85 mmol) in DCM (20 mL) was stirred for 2 h at room temperature. The mixture acidified to pH 4-5 with 1 N HCl (aq.). The organic layer was washed with brine, dried and concentrated. The residue was purified by silica gel column chromatography eluting with 0-20% EtOAc/hexanes to afford the desired product (700 mg, 35%) as a white solid. ESI-MS m/z: 592.00 [M+H]$^+$.

Example 189 Step d

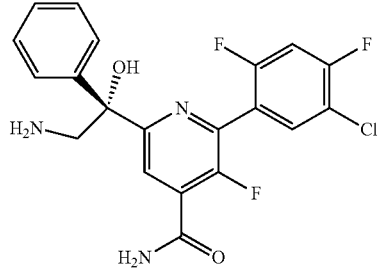 [SMILES: NC[C@@](O)(c1ccccc1)c1cc(C(N)=O)c(F)c(-c2cc(Cl)c(F)cc2F)n1]

A solution of the compound from step c (50 mg, 0.08 mmol) in 7 N NH$_3$ in MeOH (2 mL) was stirred for overnight at 40° C. After evaporated the solvent, the residue was purified by Prep-TLC (DCM/7 N NH$_3$ in MeOH=15/1) to afford the desired product (25 mg, 68%) as a white solid. ESI-MS m/z: 422.00 [M+H]$^+$.

Example 189 Step e

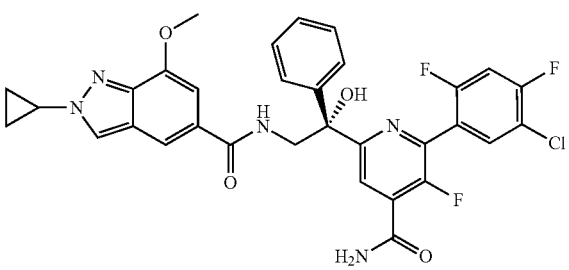 [SMILES: COc1cc(C(=O)NC[C@@](O)(c2ccccc2)c2cc(C(N)=O)c(F)c(-c3cc(Cl)c(F)cc3F)n2)cc2cn(C3CC3)nc12]

A solution of the compound from step d (40 mg, 0.09 mmol), 2-cyclopropyl-7-methoxy-2H-indazole-5-carboxylic acid (22 mg, 0.10 mmol), HATU (54 mg, 0.14 mmol) and DIPEA (25 mg, 0.19 mmol) in DMF (1 mL) was stirred for 2 h at room temperature under N$_2$ atmosphere. The residue product was purified by reverse phase flash with the following conditions to afford the desired product (21.7 mg, 36%) as a white solid. ESI-MS m/z: 636.00 [M+H]$^+$. $^1$H NMR (400 MHz, DMSO-d6) δ −1.05-1.14 (m, 2H), 1.21-1.39 (m, 2H), 3.88 (s, 3H), 4.12 (tt, J=7.5, 3.9 Hz, 1H), 4.18-4.36 (m, 2H), 6.83-6.92 (m, 2H), 7.20 (t, J=7.3 Hz, 1H), 7.30 (t, J=7.6 Hz, 2H), 7.59-7.70 (m, 3H), 7.78 (t, J=9.7 Hz, 1H), 7.93 (d, J=4.8 Hz, 1H), 7.95-8.03 (m, 2H), 8.10 (s, 1H), 8.20 (t, J=5.6 Hz, 1H), 8.56 (s, 1H).

Example 190
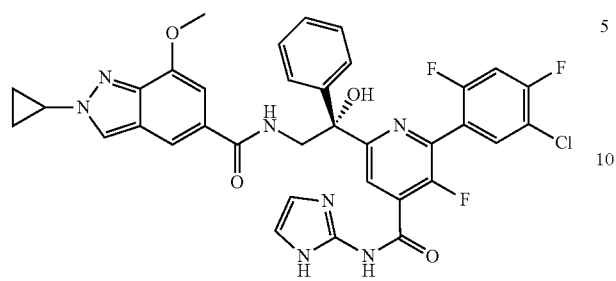
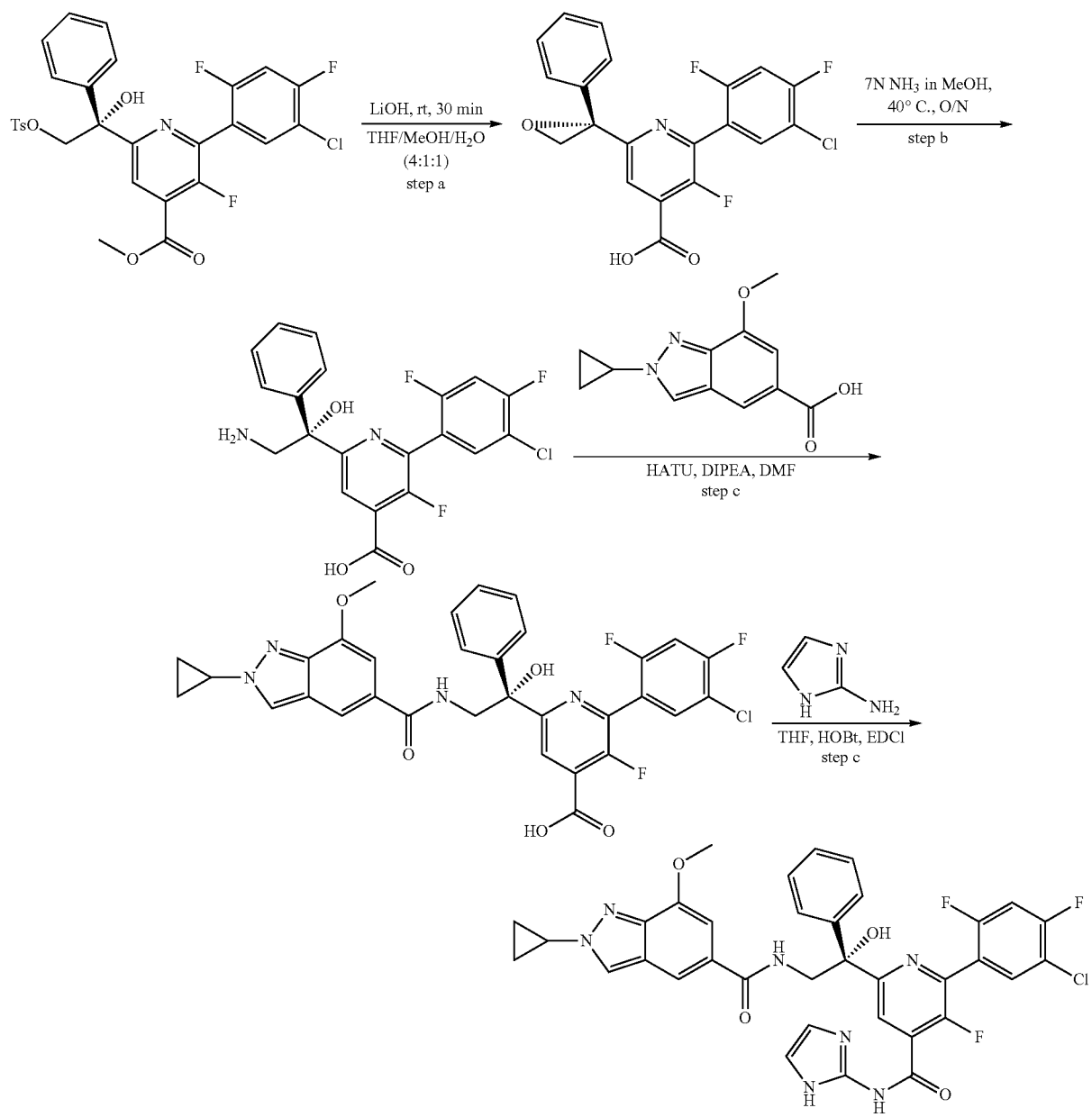
Example 190

Example 190 Step a

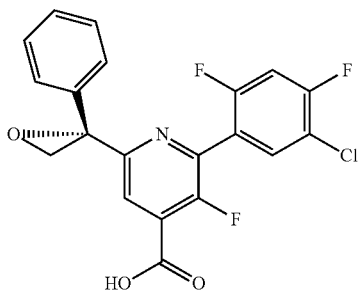 [SMILES: O=C(O)c1cc([C@]2(c3ccccc3)CO2)nc(-c2cc(Cl)c(F)cc2F)c1F]

A mixture of the compound from Example 189 step c (300 mg, 0.51 mmol) and LiOH (121 mg, 5.07 mmol) in THF (10 mL), MeOH (2.5 mL), H₂O (2.5 mL) was stirred for 30 min at room temperature. The resulting mixture was concentrated under vacuum to afford the crude product (300 mg) as a white solid. ESI-MS m/z: 405.90 [M+H]⁺.

Example 190 Step b

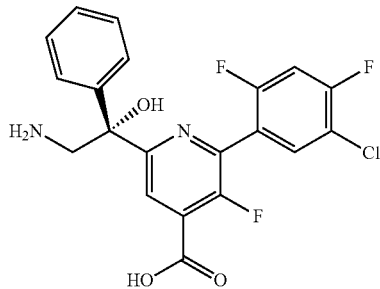 [SMILES: NC[C@@](O)(c1ccccc1)c1cc(C(=O)O)c(F)c(-c2cc(Cl)c(F)cc2F)n1]

A solution the compound from step a (300 mg, 0.74 mmol) and 7 N NH₃ in MeOH (10 mL) was stirred for overnight at 40° C. The resulting mixture was concentrated under vacuum to afford the crude product (390 mg) as a yellowish solid. ESI-MS m/z: 423.05 [M+H]⁺.

Example 190 Step c

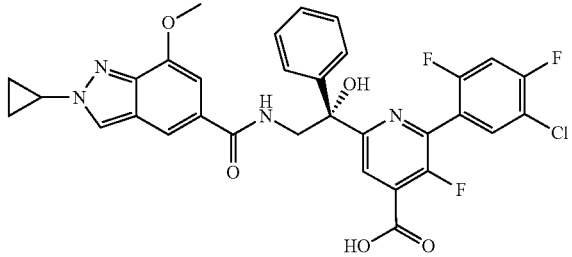 [SMILES: COc1cc(C(=O)NC[C@@](O)(c2ccccc2)c2cc(C(=O)O)c(F)c(-c3cc(Cl)c(F)cc3F)n2)cc2cn(C3CC3)nc12]

A mixture of the compound from step b (390 mg, 0.92 mmol), 2-cyclopropyl-7-methoxy-2H-indazole-5-carboxylic acid (214 mg, 0.92 mmol), HATU (350 mg, 0.92 mmol) and DIPEA (238 mg, 1.84 mmol) in DMF (2 mL) was stirred for 1 h at room temperature. The crude product was purified by Prep-HPLC to afford the desired product (15.1 mg, 2.51%) as a white solid. ESI-MS m z: 636.95 [M+H]⁺. ¹H NMR (400 MHz, DMSO-d₆) δ 1.10 (td, J=7.5, 5.0 Hz, 2H), 1.25 (m, 2H), 3.87 (s, 3H), 4.12 (tt, J=7.6, 4.0 Hz, 1H), 4.28 (dq, J=15.1, 8.0, 6.8 Hz, 2H), 6.81-6.88 (m, 2H), 7.20 (t, J=7.3 Hz, 1H), 7.31 (t, J=7.7 Hz, 2H), 7.58-7.64 (m, 3H), 7.76 (t, J=9.7 Hz, 1H), 7.98 (t, J=7.8 Hz, 1H), 8.05 (s, 1H), 8.17 (t, J=6.3 Hz, 1H), 8.55 (s, 1H).

Example 190 Step d

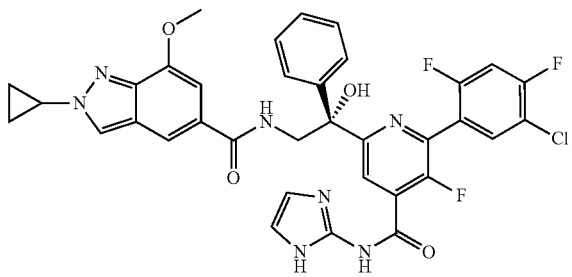 [SMILES: COc1cc(C(=O)NC[C@@](O)(c2ccccc2)c2cc(C(=O)Nc3ncc[nH]3)c(F)c(-c3cc(Cl)c(F)cc3F)n2)cc2cn(C3CC3)nc12]

A mixture of the compound from step c (20 mg, 0.03 mmol), tert-butyl 2-aminoimidazole-1-carboxylate (6 mg, 0.03 mmol), HOBt (6 mg, 0.04 mmol) and EDCI (9 mg, 0.04 mmol) in THF (1 mL) was stirred for 1 h at room temperature. The resulting mixture was poured into water and extracted with EtOAc. The combined organic layers were concentrated under reduced pressure. The residue was purified by reversed-phase flash chromatography to afford the desired product (8 mg, 31.39%) as a white solid. ESI-MS m/z: 701.90 [M+H]⁺. ¹H NMR (400 MHz, DMSO-d₆) δ 1.06-1.14 (m, 2H), 1.22-1.28 (m, 2H), 3.87 (s, 3H), 4.12 (tt, J=7.5, 3.9 Hz, 1H), 4.29 (d, J=5.6 Hz, 2H), 6.83-6.90 (m, 4H), 7.20 (t, J=7.3 Hz, 1H), 7.31 (t, J=7.7 Hz, 2H), 7.58-7.66 (m, 3H), 7.76 (t, J=9.6 Hz, 1H), 7.95-8.03 (m, 1H), 8.08 (d, J=5.0 Hz, 1H), 8.20 (t, J=5.2 Hz, 1H), 8.55 (s, 1H), 12.18 (s, 2H).

Example 191

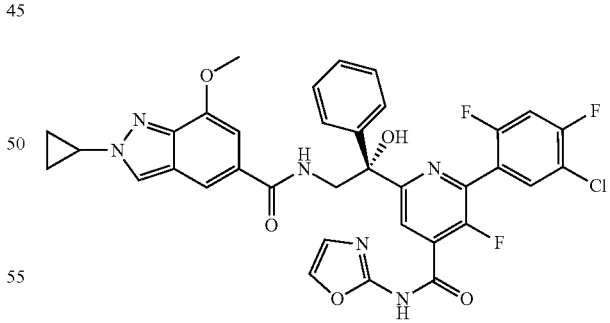

The title compound was synthesized according to the general method of Example 190 as a white solid. ESI-MS m/z: 702.95 [M+H]⁺. ¹H NMR (400 MHz, DMSO-d₆) δ 1.06-1.13 (m, 2H), 1.24 (dd, J=6.9, 3.4 Hz, 2H), 3.88 (s, 3H), 4.12 (td, J=7.5, 3.8 Hz, 1H), 4.30 (d, J=5.7 Hz, 2H), 6.86 (s, 1H), 6.89 (s, 1H), 7.19 (dd, J=16.8, 9.8 Hz, 2H), 7.31 (t, J=7.6 Hz, 2H), 7.63 (d, J=8.5 Hz, 3H), 7.78 (t, J=9.6 Hz, 1H), 7.87 (s, 1H), 7.96-8.06 (m, 2H), 8.14-8.23 (m, 1H), 8.55 (s, 1H).

Example 192

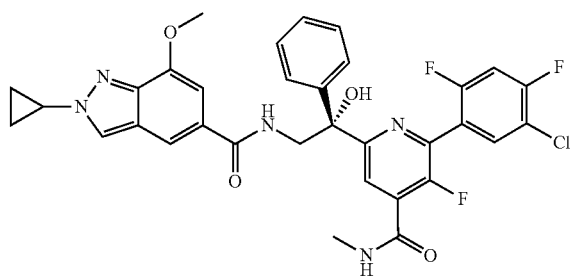 [SMILES: CNC(=O)c1cc([C@@](O)(CNC(=O)c2cc(OC)c3nn(C4CC4)cc3c2)c2ccccc2)nc(-c2cc(Cl)c(F)cc2F)c1F]

The title compound was synthesized according to the general method of Example 190 as a white solid. ESI-MS m/z: 650.20 [M+H]+. 1H NMR (400 MHz, DMSO-d6) δ 1.10 (td, J=7.5, 5.0 Hz, 2H), 1.21-1.29 (m, 2H), 2.77 (d, J=4.6 Hz, 3H), 3.88 (s, 3H), 4.12 (tt, J=7.5, 3.9 Hz, 1H), 4.22-4.36 (m, 2H), 6.83-6.92 (m, 2H), 7.16-7.24 (m, 1H), 7.30 (t, J=7.7 Hz, 2H), 7.59-7.66 (m, 3H), 7.77 (t, J=9.7 Hz, 1H), 7.91 (d, J=4.8 Hz, 1H), 7.99 (t, J=7.8 Hz, 1H), 8.19 (t, J=5.6 Hz, 1H), 8.55 (s, 1H), 8.61 (d, J=5.0 Hz, 1H).

Example 193

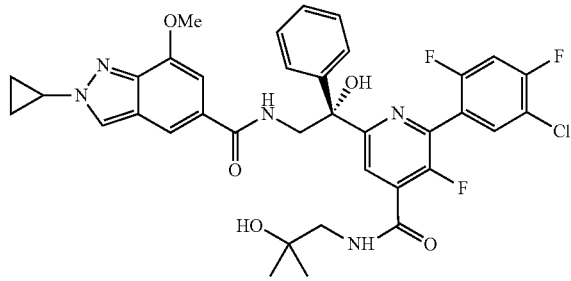 [SMILES: COc1cc(C(=O)NC[C@@](O)(c2ccccc2)c2cc(C(=O)NCC(C)(C)O)c(F)c(-c3cc(Cl)c(F)cc3F)n2)cc2cn(C3CC3)nc12]

The title compound was synthesized according to the general method of Example 190 as a white solid. ESI-MS m/z: 708.00 [M+H]+. 1H NMR (400 MHz, DMSO-d6) δ 1.09 (s, 6H), 1.08-1.15 (m, 2H), 1.25 (m, 2H), 3.21 (d, J=6.1 Hz, 2H), 3.88 (s, 3H), 4.11 (dq, J=7.5, 3.8 Hz, 1H), 4.30 (dq, J=15.1, 8.3, 7.1 Hz, 2H), 4.52 (s, 1H), 6.88 (d, J=15.5 Hz, 2H), 7.20 (t, J=7.2 Hz, 1H), 7.30 (t, J=7.6 Hz, 2H), 7.63 (d, J=7.0 Hz, 3H), 7.77 (t, J=9.6 Hz, 1H), 7.90 (d, J=4.6 Hz, 1H), 7.98 (t, J=7.8 Hz, 1H), 8.11-8.23 (m, 1H), 8.53 (d, J=13.3 Hz, 2H).

Example 194

The title compound was synthesized according to the general method of Example 190 as a white solid. ESI-MS m/z: 675.95 [M+H]+. 1H NMR (400 MHz, DMSO-d6) δ 0.48-0.55 (m, 2H), 0.66-0.73 (m, 2H), 1.10 (h, J=4.9 Hz, 2H), 1.24 (d, J=3.9 Hz, 2H), 2.79-2.86 (m, 1H), 3.88 (s, 3H), 4.12 (dt, J=7.5, 3.7 Hz, 1H), 4.28 (s, 2H), 6.88 (d, J=15.2 Hz, 2H), 7.19 (t, J=7.4 Hz, 1H), 7.30 (t, J=7.6 Hz, 2H), 7.59-7.65 (m, 2H), 7.77 (t, J=9.7 Hz, 1H), 7.86 (d, J=4.6 Hz, 1H), 7.98 (t, J=7.7 Hz, 1H), 8.19 (s, 1H), 8.55 (s, 1H), 8.74 (d, J=4.3 Hz, 1H).

Example 195

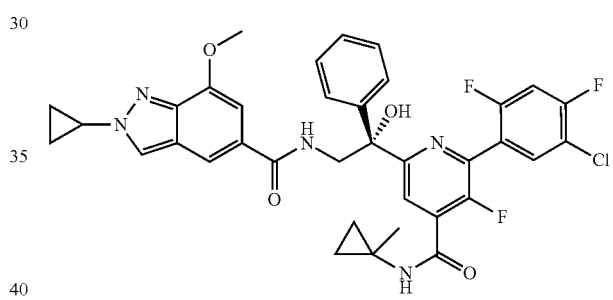

The title compound was synthesized according to the general method of Example 190 as a white solid. ESI-MS m/z: 689.95 [M+H]+. 1H NMR (400 MHz, DMSO-d6) δ 0.55-0.63 (m, 2H), 0.67-0.74 (m, 2H), 1.07-1.13 (m, 2H), 1.21-1.29 (m, 2H), 1.35 (s, 3H), 3.88 (s, 3H), 4.12 (tt, J=7.5, 3.9 Hz, 1H), 4.28 (d, J=5.7 Hz, 2H), 6.86 (d, J=1.3 Hz, 1H), 6.95 (s, 1H), 7.16-7.23 (m, 1H), 7.30 (dd, J=8.4, 7.0 Hz, 2H), 7.58-7.65 (m, 3H), 7.78 (t, J=9.7 Hz, 1H), 7.84 (d, J=4.6 Hz, 1H), 7.98 (t, J=7.8 Hz, 1H), 8.23 (s, 1H), 8.56 (s, 1H), 8.91 (s, 1H).

Example 196

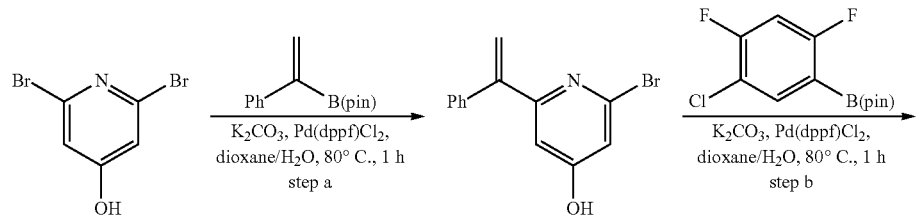

-continued
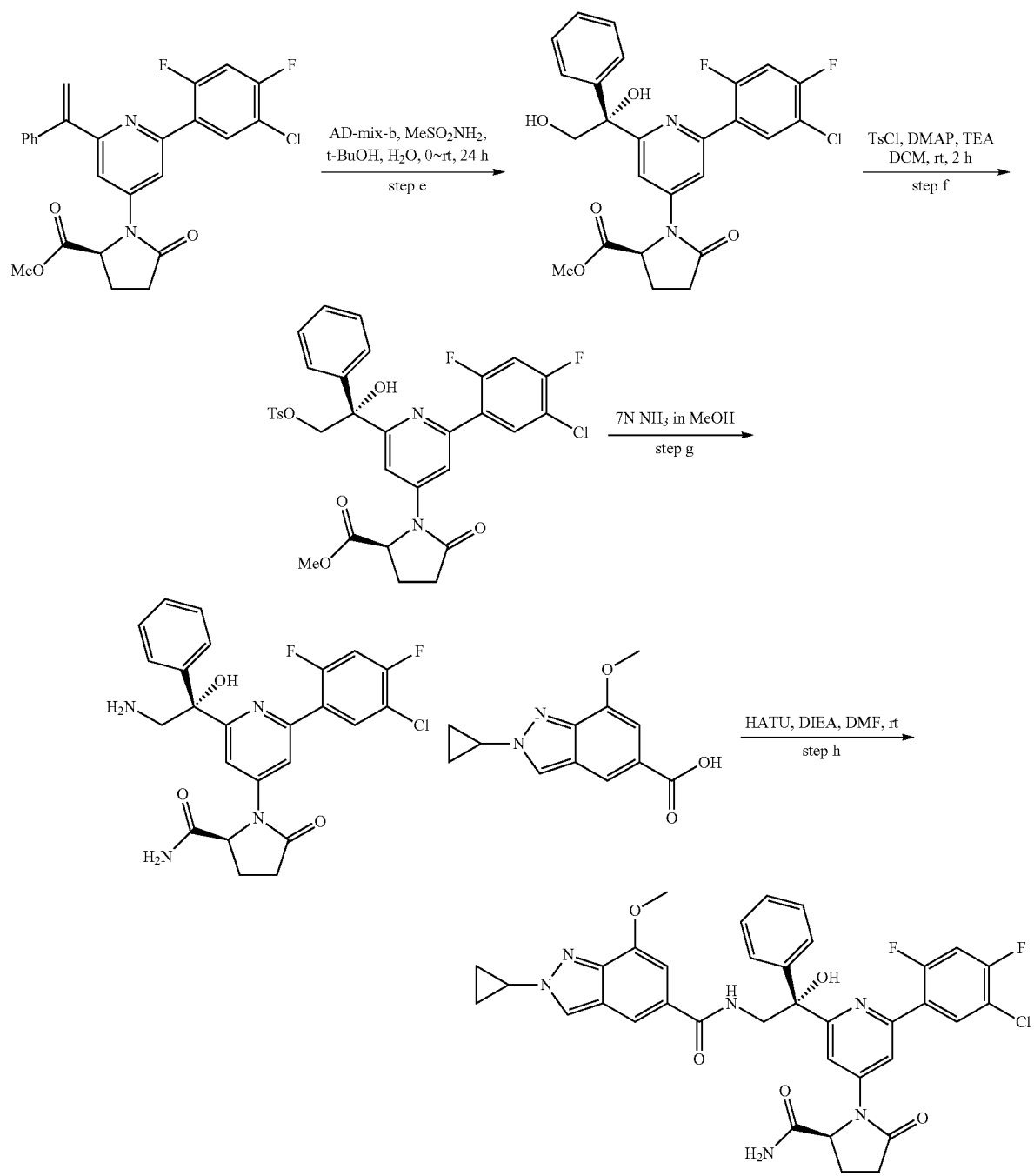
Example 196

Example 196 Step a

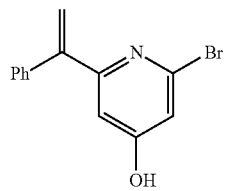 [SMILES: C=C(c1ccccc1)c1cc(O)cc(Br)n1]

A solution of 2,6-dibromopyridin-4-ol (4.0 g, 15.81 mmol), 4,4,5,5-tetramethyl-2-(1-phenylethenyl)-1,3,2-dioxaborolane (4.0 g, 17.41 mmol), Pd(dppf)Cl$_2$ (1.16 g, 1.58 mmol) and K$_2$CO$_3$ (4.37 g, 31.63 mmol) in 1,4-dioxane (20 mL) and H$_2$O (5 mL) was stirred for 2 h at 80° C. under N$_2$ atmosphere. After diluted with EtOAc (100 mL), the organic layer was washed with brine, dried and evaporated. The residue was purified by silica gel column chromatography eluting with 0-30% EtOAc/hexanes to afford the desired product (1.5 g, 34%) as a yellowish oil. ESI-MS m/z: 276.00 [M+H]$^+$.

Example 196 Step b

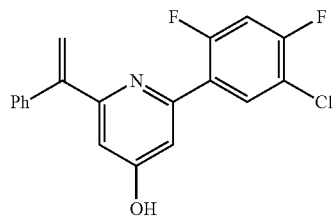 [SMILES: C=C(c1ccccc1)c1cc(O)cc(-c2cc(Cl)c(F)cc2F)n1]

A mixture of the compound from step a (1.4 g, 5.07 mmol), 2-(5-chloro-2,4-difluorophenyl)-4,4,5,5-tetramethyl-1,3,2-dioxaborolane (1.39 g, 5.07 mmol), Pd(dppf)Cl$_2$ (4100 mg, 0.51 mmol) and K$_2$CO$_3$ (1.4 g, 10.14 mmol) in dioxane (20 mL) and H$_2$O (2 mL) was stirred for 2 h at 80° C. under N$_2$ atmosphere. After diluted with EtOAc (100 mL), the organic layer was washed with brine, dried and evaporated. The residue was purified by silica gel column chromatography eluting with 0-30% EtOAc/hexanes to afford the desired product (1.3 g, 62%) as a white solid. ESI-MS m/z: 344.15 [M+H]$^+$.

Example 196 Step c

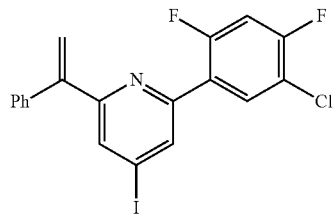 [SMILES: C=C(c1ccccc1)c1cc(I)cc(-c2cc(Cl)c(F)cc2F)n1]

A solution of the compound from step b (1.3 g, 3.78 mmol), and Tf$_2$O (1.17 g, 4.16 mmol) in MeOH was added pyridine (344 mg, 4.35 mmol) in portions at 0° C. The resulting mixture was stirred for 2 h at room temperature under nitrogen atmosphere. To the above mixture was added NaI (2.83 g, 18.91 mmol) and HCl (58 mg, 1.60 mmol) dropwise at room temperature. The resulting mixture was stirred for additional 12 h at room temperature. The mixture was basified to pH 8 with NaOH. After diluted with EtOAc (100 mL), the organic layer was washed with brine, dried and evaporated. The residue was purified by reverse flash chromatography to afford the desired product (1.1 g, 64%) as a white solid. ESI-MS m/z: 454.00 [M+H]$^+$.

Example 196 Step d

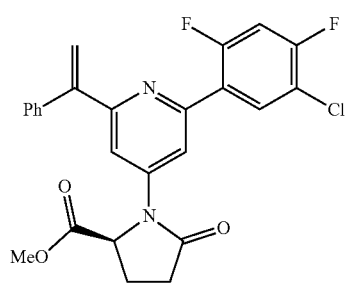 [SMILES: C=C(c1ccccc1)c1cc(N2C(=O)CC[C@H]2C(=O)OC)cc(-c2cc(Cl)c(F)cc2F)n1]

A solution of the compound from step c (400 mg, 0.88 mmol) and methyl (2S)-5-oxopyrrolidine-2-carboxylate (252 mg, 1.76 mmol) in 1,4-dioxane were added DMEDA (77 mg, 0.88 mmol), Cs$_2$CO$_3$ (574 mg, 1.76 mmol) and CuI (84 mg, 0.44 mmol) in portions at 80° C. under nitrogen atmosphere for 2 h. The resulting mixture was extracted with EtOAc (200 mL×3). The combined organic layers were washed with brine (200 mL×3) and dried. The organic layer was concentrated under reduced pressure. The residue was purified by silica gel column chromatography eluting with 0-30% EtOAc/hexanes to afford the desired product (410 mg, 99%) as a white solid. ESI-MS m/z: 469.20 [M+H]$^+$.

Example 196 Step e

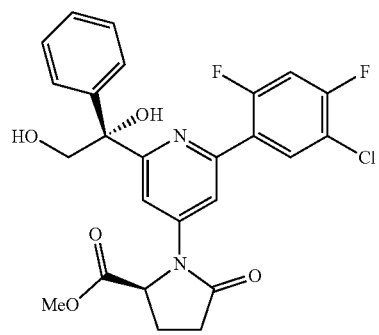 [SMILES: COC(=O)[C@@H]1CCC(=O)N1c1cc(-c2cc(Cl)c(F)cc2F)nc([C@@](O)(CO)c2ccccc2)c1]

A solution of the compound from step d (400 mg, 0.85 mmol), AD-mix-β (1.9 g, 2.43 mmol) and methanesulfonamide (77 mg, 0.81 mmol) in t-BuOH (10 mL) and H$_2$O (10 mL) was stirred for 2 days at room temperature under N$_2$ atmosphere. The reaction was quenched by adding sat. aqueous NaHSO$_3$ solution. The resulting mixture was extracted with EA (200 mL×3). The combined organic layers were washed with brine (200 mL×3), dried and evaporated. The residue was purified by silica gel column chromatography eluting with 0-50% EtOAc/hexanes to afford the desired product (310 mg, 76%) as a white solid. ESI-MS m/z: 503.05 [M+H]⁺.

Example 196 Step f

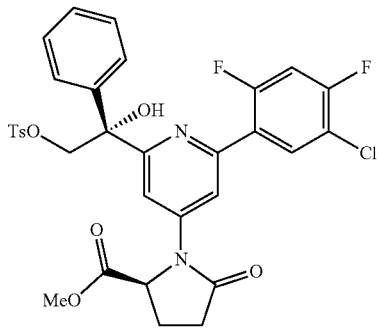 [SMILES: COC(=O)[C@@H]1CCC(=O)N1c1cc(-c2cc(Cl)c(F)cc2F)nc([C@@](O)(COS(=O)(=O)c2ccc(C)cc2)c2ccccc2)c1]

A solution of the compound from step e (310 mg, 0.61 mmol), TsCl (136 mg, 0.73 mmol), DMAP (73 mg, 0.61 mmol) and Et₃N (182 mg, 1.83 mmol) in DCM (5 mL) was stirred for 2 h at room temperature. The mixture was acidified to pH 4 with HCl (1 M aq.). The resulting mixture was extracted with DCM (50 mL×2). The combined organic layers were washed with brine, dried and concentrated under reduced pressure. The residue was purified by silica gel column chromatography eluting with 0-30% EtOAc/hexanes to afford the desired product (250 mg, 63%) as a white solid. ESI-MS m/z: 657.15 [M+H]⁺.

Example 196 Step g

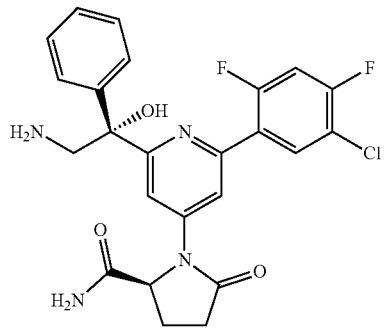 [SMILES: NC[C@@](O)(c1ccccc1)c1cc(N2C(=O)CC[C@H]2C(N)=O)cc(-c2cc(Cl)c(F)cc2F)n1]

A solution of the compound from step f (250 mg, 0.32 mmol) and 7 N NH₃ in MeOH (10 mL) was stirred overnight at 50° C. After evaporated the solvent, the residue was purified by Prep-TLC (DCM/NH₃ in MeOH=15/1) to afford the desired product (55 mg, 33%) as a white solid. ESI-MS m/z: 487.05 [M+H]⁺.

Example 196 Step h

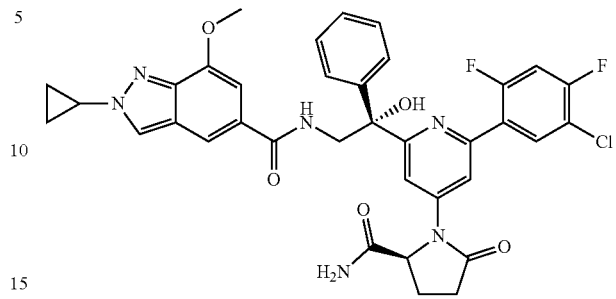

A solution of the compound from step g (25 mg, 0.05 mmol), 2-cyclopropyl-7-methoxy-2H-indazole-5-carboxylic acid (12 mg, 0.05 mmol), HATU (20 mg, 0.05 mmol) and DIPEA (20 mg, 0.15 mmol) in DMF (1 mL) was stirred for 2 h at room temperature. After diluted with EtOAc (20 mL) and water (10 mL), the organic layer was washed with brine (20 mL×3), dried and evaporated. The residue was purified by reverse flash chromatography to afford the desired product (21 mg, 50%) as a white solid. ESI-MS m/z: 701.25 [M+H]⁺. ¹H NMR (400 MHz, DMSO-d₆) δ 1.10 (td, J=7.5, 5.0 Hz, 2H), 1.20-1.33 (m, 2H), 1.92-2.02 (m, 1H), 2.40 (ddd, J=18.6, 8.7, 5.9 Hz, 2H), 2.59 (dt, J=16.5, 9.5 Hz, 1H), 3.87 (s, 3H), 4.11 (tt, J=7.6, 3.9 Hz, 1H), 4.31 (d, J=5.6 Hz, 2H), 4.75 (dd, J=8.9, 2.6 Hz, 1H), 6.80 (d, J=6.4 Hz, 1H), 6.87 (s, 1H), 7.18 (t, J=7.3 Hz, 1H), 7.29 (t, J=7.6 Hz, 2H), 7.37 (s, 1H), 7.64 (dd, J=10.5, 3.2 Hz, 3H), 7.72 (dd, J=10.9, 9.4 Hz, 1H), 7.87 (s, 1H), 7.93 (s, 1H), 8.06 (d, J=2.0 Hz, 1H), 8.25 (dt, J=17.9, 7.0 Hz, 2H), 8.55 (s, 1H).

Example 197

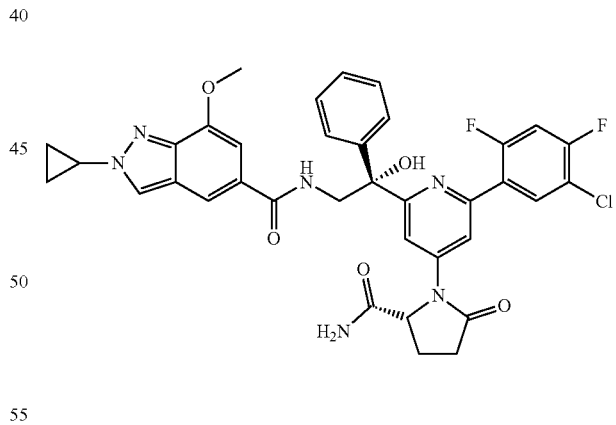

The title compound was synthesized according to Example 196 as a white solid. ESI-MS m/z: 701.15 [M+H]⁺. ¹H NMR (400 MHz, DMSO-d₆) δ 1.10 (td, J=7.5, 5.0 Hz, 2H), 1.24 (q, J=4.4, 3.7 Hz, 2H), 1.97 (dd, J=12.1, 9.4 Hz, 1H), 2.32-2.44 (m, 2H), 2.56-2.64 (m, 1H), 3.87 (s, 3H), 4.11 (tt, J=7.5, 3.9 Hz, 1H), 4.24-4.33 (m, 1H), 4.38 (dd, J=13.8, 5.6 Hz, 1H), 4.76 (dd, J=9.0, 2.7 Hz, 1H), 6.80 (s, 1H), 6.86 (d, J=1.3 Hz, 1H), 7.18 (t, J=7.3 Hz, 1H), 7.29 (t, J=7.6 Hz, 2H), 7.37 (s, 1H), 7.58-7.66 (m, 3H), 7.69-7.76 (m, 1H), 7.80 (s, 1H), 7.94 (s, 1H), 8.11 (d, J=2.0 Hz, 1H), 8.20-8.31 (m, 2H), 8.55 (s, 1H).

Example 198

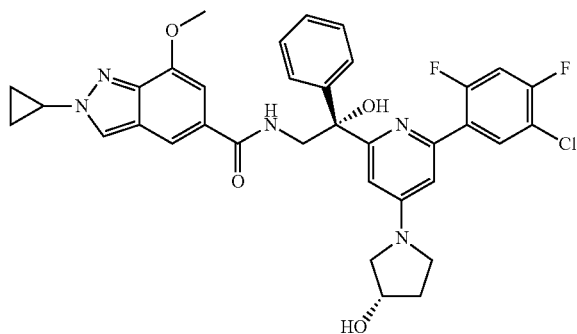 [SMILES: COc1cc(C(=O)NC[C@@](O)(c2ccccc2)c2cc(N3CC[C@H](O)C3)cc(-c3cc(Cl)c(F)cc3F)n2)cc2cn(C3CC3)nc12]

The title compound was synthesized according to Example 196 as a white solid. ESI-MS m/z: 661.22 [M+H]+.

Example 199

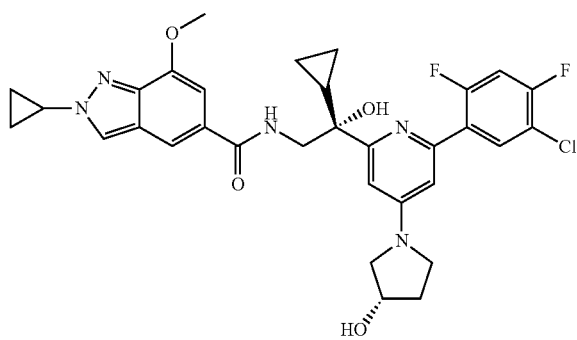 [SMILES: COc1cc(C(=O)NC[C@](O)(c2cc(N3CC[C@H](O)C3)cc(-c3cc(Cl)c(F)cc3F)n2)C2CC2)cc2cn(C3CC3)nc12]

The title compound was synthesized according to Example 196 as a white solid. ESI-MS m/z: 425.22 [M+H]+.

Example 200

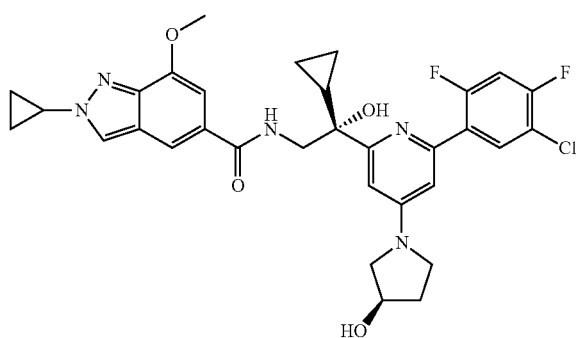 [SMILES: COc1cc(C(=O)NC[C@](O)(c2cc(N3CC[C@@H](O)C3)cc(-c3cc(Cl)c(F)cc3F)n2)C2CC2)cc2cn(C3CC3)nc12]

The title compound was synthesized according to Example 196 as a white solid. ESI-MS m/z: 425.22 [M+H]+.

Assays

Methods for RSV-A Assay

Hep-2 cells, (originally derived from tumors grown in irradiated-cortisonised weanling rats that had been injected with epidermoid carcinoma tissue from a 56 year-old male's larynx, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 3-fold viral dilutions across a 96-well plate, cultured for 4 days. Viral stock titers were also quantified by a plaque forming unit assay, as described elsewhere.

Following extensive parameter testing, the final assay is run as follows: Hep-2 cells are seeded into the inner 60 wells of a 96-well plate at 8,000 cells per well in a volume of 50 μL using Growth Media (DMEM without phenol red, 1% L-Glut, 1% Penn/Strep, 1% nonessential amino acids, 10% heat-inactivated FBS). 2-fold serial dilutions of control and test compounds are added to the wells in duplicate in a total volume of 25 μL. Viral stock is then added to the wells at a multiplicity of infection (MOI) of 0.1 in a volume of 25 μL, bringing the total volume of each well to 100 μL. The MOI is calculated using the PFU/mL, or $TCID_{50}$ if unavailable. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 μL of growth media containing an equal quantity of sucrose as those wells receiving the viral stock in order to keep consistent in media and volume conditions. The outer wells of the plate are filled with 125 μL of moat media (DMEM, 100 Penn/Strep) to act as a thermal and evaporative moat around the test wells. Following a 5-day incubation period, the plates are read using ATPlite (50 uL added per well), which quantifies the amount of ATP (a measure of cell health) present in each well. Assay plates are read using the Envision luminometer. These data (Table 3) are used to calculate the $EC_{50}$ of each compound. $EC_{50}$ ranges are as follows: A<0.01 μM; B 0.01-0.05 μM; C>0.05 μM.

TABLE 3

Summary of Activities for RSV-A

| Example | Human RSV-A ("Long" strain) $EC_{50}$ | Example | Human RSV-A ("Long" strain) $EC_{50}$ |
|---|---|---|---|
| 1 | A | 2 | A |
| 3 | B | 4 | A |
| 5 | A | 6 | A |
| 7 | C | 8 | A |
| 9 | B | 10 | B |
| 11 | B | 12 | B |
| 13 | B | 14 | B |
| 15 | B | 16 | B |
| 17 | B | 18 | B |
| 19 | A | 20 | B |
| 21 | A | 22 | A |
| 23 | B | 24 | B |
| 25 | B | 26 | A |
| 27 | A | 28 | B |
| 29 | A | 30 | A |
| 31 | B | 32 | B |
| 33 | A | 34 | B |
| 35 | C | 36 | B |
| 37 | C | 38 | B |
| 39 | A | 40 | B |
| 41 | B | 42 | C |

TABLE 3-continued

Summary of Activities for RSV-A

| Example | Human RSV-A ("Long" strain) $EC_{50}$ | Example | Human RSV-A ("Long" strain) $EC_{50}$ |
|---|---|---|---|
| 43 | A | 44 | A |
| 45 | B | 46 | B |
| 47 | B | 48 | C |
| 49 | A | 50 | A |
| 51 | B | 52 | A |
| 57 | A | 59 | A |
| 62 | A | 64 | A |
| 65 | B | 66 | C |
| 67 | A | 74 | A |
| 79 | A | 86 | A |
| 123 | A | 127 | A |
| 132 | A | 136 | A |
| 144 | A | 164 | C |
| 170 | C | 177 | B |
| 183 | A | 184 | A |
| 185 | A | 189 | B |
| 195 | C | 199 | C |
| 200 | C | | |

Methods for HMPV Antiviral Assay

In vitro HMPV antiviral activity was evaluated using the clinical isolate A2 strain TN 94-49 and LLC-MK2 cells (ATCC #CCL-7), an immortalized kidney epithelial cell line from *Macaca mulatta*.

Compounds were resuspended in dimethyl sulfoxide (DMSO) at 10 mM, serially diluted and added to a 384-well source plate. Subsequently, the compounds were diluted and transferred onto 384-well assay plates using the Echo-650 automated liquid handling system (Beckman Coulter, Indiana). The test compounds were assessed in duplicate at a top concentration of 2 µM followed by 2.5-fold serial dilutions to give a total of 10 concentration points. DMSO control wells were also included on the assay plates and were either infected or not, acting as positive and negative controls.

A2 TN 94-49 virus infections were performed in-suspension with LLC-MK2 cells. The cells were washed twice with PBS and removed from the cell-culture flask with 0.25% trypsin-EDTA (Thermo Fisher Scientific, MA). The trypsin-EDTA was inactivated by resuspending in 2% fetal bovine serum (FBS) and OptiMEM (ThermoFisher Scientific, MA) containing 1% penicillin-streptomycin. Cells were pelleted by centrifuging for 5 minutes at 800 rpm, the supernatant was removed, and cells were re-suspended and washed in PBS plus 100 µg/mL $CaCl_2$). This step was performed twice. Cells were then re-suspended in serum-free (SF)-OptiMEM containing 4 µg/mL TPCK-Trypsin (Sigma Aldrich, MO), 1% penicillin-streptomycin (ThermoFisher Scientific, MA) and 100 µg/mL $CaCl_2$). Cells were counted and seeded at a density of 5,000 cells/well, 12.5 µL/well.

Virus infections were done at a multiplicity of infection (MOI) of 0.005 with 12.5 µL added per well. Virus infections were performed in infection media which contained SF-OptiMEM, 100 µg/mL $CaCl_2$) and 1% penicillin-streptomycin. HMPV viral stocks are suspended in infection media+5% glycerol, thus an equal volume of infection media+5% glycerol was added to uninfected wells to equalize the final % glycerol across all wells of the assay plate. The final concentration of TPCK-trypsin was 2 µg/mL. The assay plates were incubated at 37° C., 5% $CO_2$ for 7 days.

After 7 days incubation, 12.5 µL of ATP-Lite (PerkinElmer, MA) was added to each well and the raw luminescence values were determined using the Envision 2104 (Perkin Elmer, MA). The average of the raw luminescence values for the cells and virus only positive control wells was subtracted from all conditions tested and the percent cell health was determined by dividing these values by the average of the cells only negative control wells. $EC_{50}$ values were then calculated by non-linear regression using a four-parameter curve logistic equation. The curve fit model employed was XLFit Dose Response One Site Model 200: $y=(A+(B/(1+((x/C)^D))))$, where A is the minimum y value, B is the maximum y value, C is the log $EC_{50}$ value, and D is the slope factor.

These data are used to calculate the $EC_{50}$ each compound (Table 4). $EC_{50}$ ranges are as follows: A<1 µM; B>1 µM.

TABLE 4

Summary of Activities for HMPV

| Compound | HMPV A2 TN/94-49 $EC_{50}$ | Compound | HMPV A2 TN/94-49 $EC_{50}$ |
|---|---|---|---|
| 1 | A | 2 | A |
| 3 | B | 4 | A |
| 5 | A | 6 | A |
| 7 | B | 8 | A |
| 9 | B | 10 | B |
| 18 | B | 19 | B |
| 20 | B | 21 | B |
| 22 | B | 23 | B |
| 24 | B | 25 | B |
| 26 | B | 47 | B |
| 48 | B | 49 | B |
| 50 | B | 51 | B |
| 52 | A | 53 | A |
| 54 | A | 55 | A |
| 56 | A | 57 | A |
| 58 | A | 59 | B |
| 60 | A | 61 | A |
| 62 | A | 63 | A |
| 64 | A | 65 | A |
| 66 | A | 67 | A |
| 68 | A | 69 | A |
| 70 | A | 71 | A |
| 72 | A | 73 | A |
| 74 | A | 75 | B |
| 76 | A | 77 | B |
| 78 | A | 79 | A |
| 80 | A | 81 | A |
| 82 | A | 83 | B |
| 84 | A | 85 | B |
| 86 | B | 87 | B |
| 89 | A | 90 | A |
| 91 | A | 92 | A |
| 93 | A | 94 | A |
| 95 | A | 96 | A |
| 97 | A | 98 | A |
| 99 | A | 100 | B |
| 101 | A | 102 | A |
| 103 | A | 104 | A |
| 105 | A | 106 | B |
| 107 | A | 108 | A |
| 109 | A | 110 | B |
| 111 | A | 112 | A |
| 113 | A | 114 | A |
| 115 | A | 116 | A |
| 117 | B | 118 | A |
| 119 | A | 120 | A |
| 121 | A | 122 | A |
| 123 | A | 124 | A |
| 125 | A | 127 | A |
| 128 | A | 129 | A |
| 130 | A | 131 | B |
| 132 | A | 133 | B |
| 134 | B | 135 | B |
| 136 | A | 137 | B |
| 138 | A | 139 | A |
| 140 | B | 141 | B |
| 142 | B | 143 | B |
| 144 | A | 145 | B |
| 146 | B | 147 | A |

TABLE 4-continued

Summary of Activities for HMPV

| Compound | HMPV A2 TN/94-49 EC$_{50}$ | Compound | HMPV A2 TN/94-49 EC$_{50}$ |
|---|---|---|---|
| 148 | A | 149 | A |
| 150 | A | 151 | A |
| 152 | A | 153 | A |
| 154 | A | 155 | A |
| 156 | A | 157 | A |
| 158 | A | 159 | B |
| 160 | A | 161 | B |
| 162 | A | 163 | B |
| 164 | B | 165 | B |
| 166 | B | 167 | B |
| 168 | B | 169 | B |
| 170 | B | 171 | B |
| 172 | B | 173 | B |
| 174 | B | 175 | B |
| 176 | B | 177 | B |
| 178 | B | 179 | B |
| 180 | B | 181 | B |
| 182 | B | 183 | A |
| 184 | A | 185 | A |
| 186 | A | 187 | A |
| 188 | A | 189 | B |
| 190 | B | 191 | B |
| 192 | B | 193 | B |
| 194 | B | 195 | B |
| 196 | B | 197 | B |
| 198 | B | 199 | B |
| 200 | B | | |

While this invention has been particularly shown and described with reference to preferred embodiments thereof, it will be understood by those skilled in the art that various changes in form and details may be made therein without departing from the scope of the invention encompassed by the appended claims.

What is claimed:

1. A compound represented by Formula (V-3):

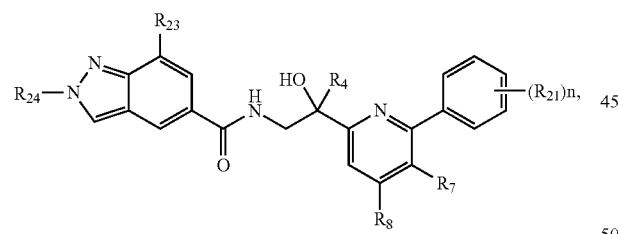

(V-3)

or a pharmaceutically acceptable salt thereof, wherein:

$R_4$ is selected from the group consisting of:
1) optionally substituted —$C_1$-$C_6$ alkyl;
2) optionally substituted —$C_3$-$C_8$ cycloalkyl;
3) optionally substituted 3- to 8-membered heterocyclic;
4) optionally substituted aryl;
5) optionally substituted arylalkyl;
6) optionally substituted heteroaryl; and
7) optionally substituted heteroarylalkyl;

$R_7$ is selected from the group consisting of:
1) hydrogen;
2) halogen;
3) optionally substituted —$C_1$-$C_6$ alkyl;
4) optionally substituted —$C_1$-$C_6$ alkoxy; and
5) optionally substituted —$C_3$-$C_8$ cycloalkyl;

$R_6$ is selected from the group consisting of:
1) —C(O)NH$_2$;
2) optionally substituted —$C_1$-$C_8$-alkyl;
3) optionally substituted —$C_3$-$C_8$-cycloalkyl;
4) hydrogen;
5) optionally substituted 4- and 5-membered heterocyclic ring;
6) —C(O)NHR$_{11}$; and
7) —C(O)NR$_{11}$R$_{12}$;

$R_{11}$ and $R_{12}$ are each independently selected from the group consisting of:
1) optionally substituted —$C_1$-$C_8$ alkyl;
2) optionally substituted —$C_2$-$C_8$ alkenyl;
3) optionally substituted —$C_2$-$C_8$ alkynyl;
4) optionally substituted —$C_3$-$C_8$ cycloalkyl;
5) optionally substituted 3- to 8-membered heterocycloalkyl;
6) optionally substituted aryl;
7) optionally substituted arylalkyl;
8) optionally substituted heteroaryl; and
9) optionally substituted heteroarylalkyl;

alternatively, $R_{11}$ and $R_{12}$ are taken together with the nitrogen atom to which they are attached to form an optionally substituted heterocyclic ring;

each $R_{21}$ is independently optionally substituted methyl, halo, —CN, —OR$_{31}$, or —NR$_{31}$R$_{32}$;

$R_{23}$ is hydrogen, halo, —OR$_{31}$, optionally substituted —$C_1$-$C_6$ alkyl, or optionally substituted —$C_3$-$C_8$-cycloalkyl;

$R_{24}$ is optionally substituted —$C_1$-$C_6$ alkyl, or optionally substituted —$C_3$-$C_8$-cycloalkyl;

each $R_{31}$ and $R_{32}$ is independently selected from the group consisting of hydrogen; optionally substituted —$C_1$-$C_8$-alkyl; optionally substituted —$C_3$-$C_8$-cycloalkyl; optionally substituted 4- to 8-membered heterocyclic; optionally substituted aryl; optionally substituted arylalkyl;

optionally substituted heteroaryl; and optionally substituted heteroarylalkyl; and n is 1, 2, 3, 4 or 5.

2. The compound of claim 1, wherein $R_4$ is selected from one of the following:

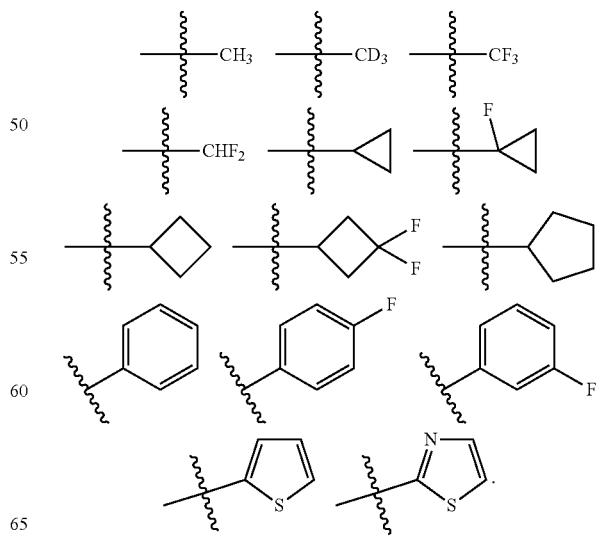

3. The compound of claim 1, wherein $R_6$ is selected from the groups below:
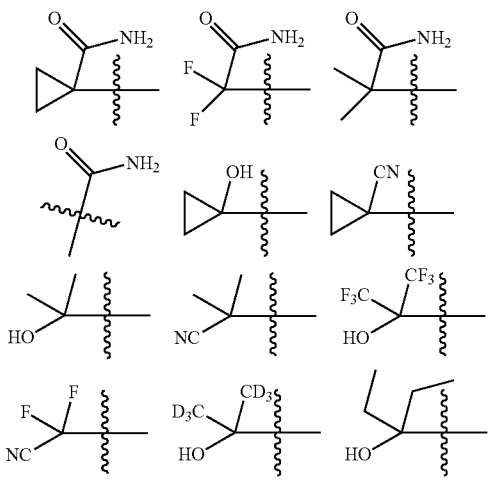
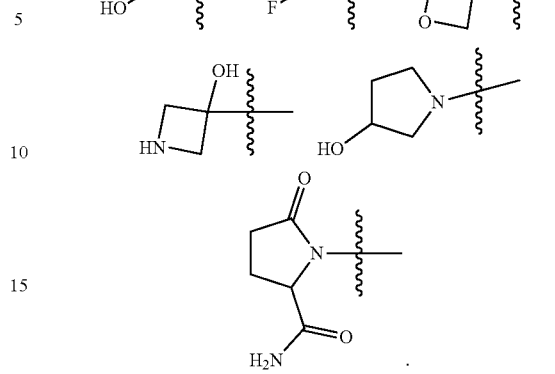
4. The compound of claim 1, selected from the compounds set forth below, or a pharmaceutically acceptable salt thereof:
| Compound | Structure |
|---|---|
| 1 | 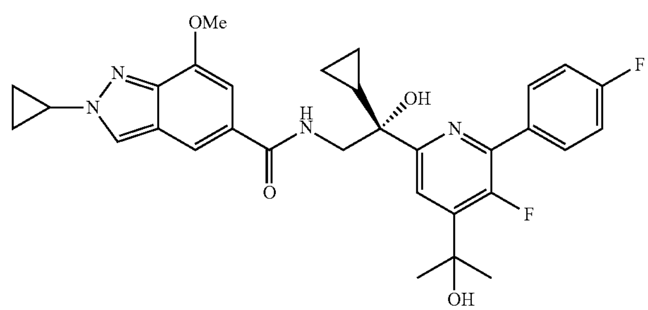 [SMILES: COc1cc(C(=O)NC[C@](O)(c2cc(C(C)(C)O)c(F)c(-c3ccc(F)cc3)n2)C2CC2)cc2cn(C3CC3)nc12] |
| 2 | 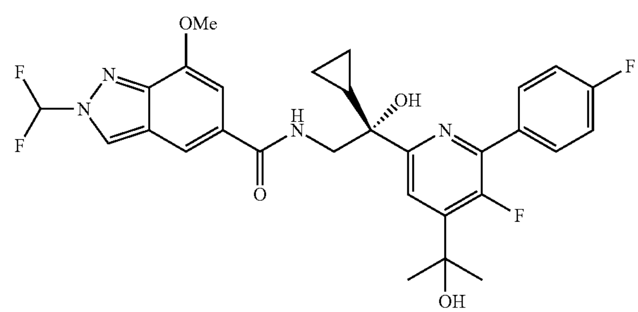 [SMILES: COc1cc(C(=O)NC[C@](O)(c2cc(C(C)(C)O)c(F)c(-c3ccc(F)cc3)n2)C2CC2)cc2cn(C(F)F)nc12] |
| 3 | 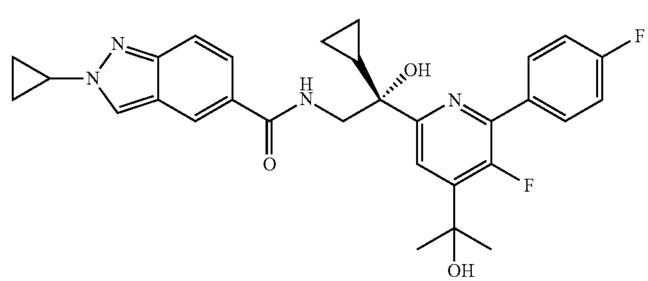 [SMILES: CC(C)(O)c1cc([C@@](O)(CNC(=O)c2ccc3nn(C4CC4)cc3c2)C2CC2)nc(-c2ccc(F)cc2)c1F] |

-continued

| Compound | Structure |
|---|---|
| 4 | 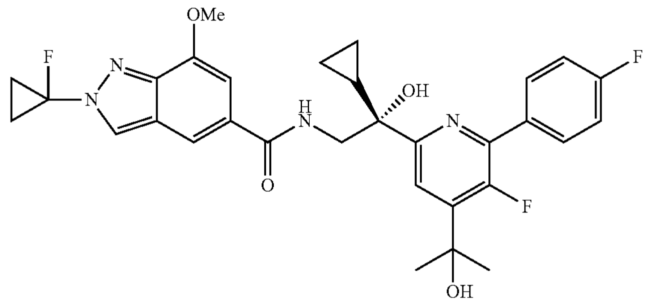 [SMILES: COc1cc(C(=O)NC[C@](O)(c2cc(C(C)(C)O)c(F)c(-c3ccc(F)cc3)n2)C2CC2)cc2cn(C3(F)CC3)nc12] |
| 5 | 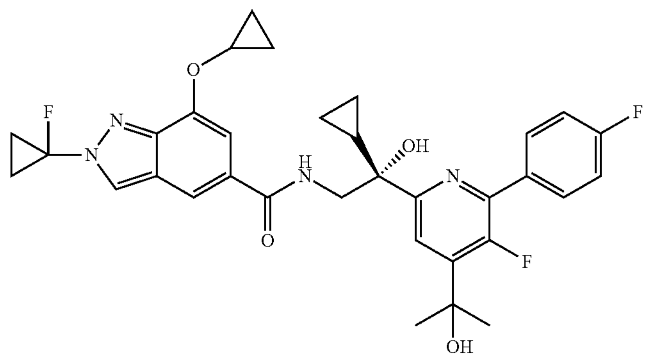 [SMILES: CC(C)(O)c1cc([C@@](O)(CNC(=O)c2cc(OC3CC3)c3nn(C4(F)CC4)cc3c2)C2CC2)nc(-c2ccc(F)cc2)c1F] |
| 6 | 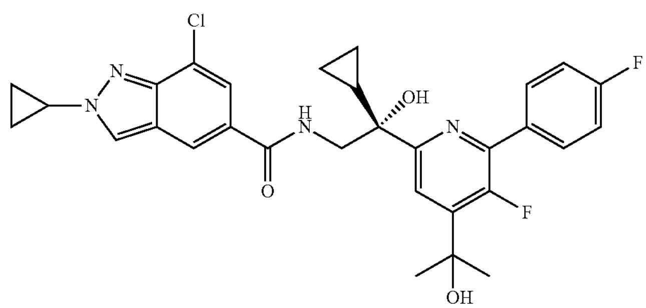 [SMILES: CC(C)(O)c1cc([C@@](O)(CNC(=O)c2cc(Cl)c3nn(C4CC4)cc3c2)C2CC2)nc(-c2ccc(F)cc2)c1F] |
| 7 | 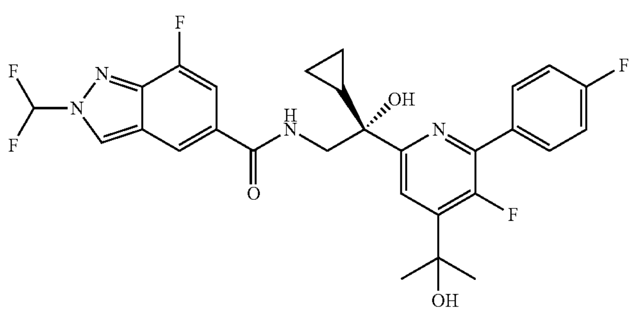 [SMILES: CC(C)(O)c1cc([C@@](O)(CNC(=O)c2cc(F)c3nn(C(F)F)cc3c2)C2CC2)nc(-c2ccc(F)cc2)c1F] |
| 9 | 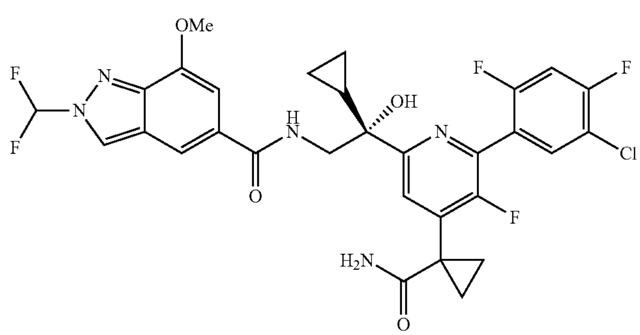 [SMILES: COc1cc(C(=O)NC[C@](O)(c2cc(C3(C(N)=O)CC3)c(F)c(-c3cc(Cl)c(F)cc3F)n2)C2CC2)cc2cn(C(F)F)nc12] |

| Compound | Structure |
|---|---|
| 10 | 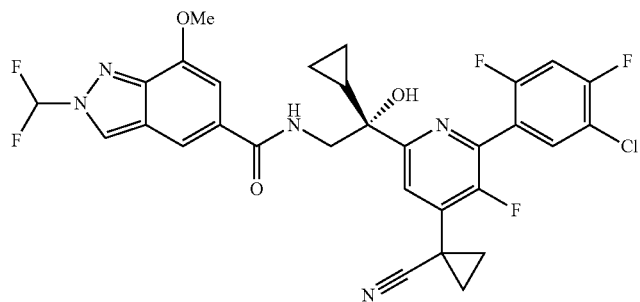 [SMILES: COc1cc(C(=O)NC[C@](O)(c2cc(C3(C#N)CC3)c(F)c(-c3cc(Cl)c(F)cc3F)n2)C2CC2)cc2cn(C(F)F)nc12] |
| 11 | 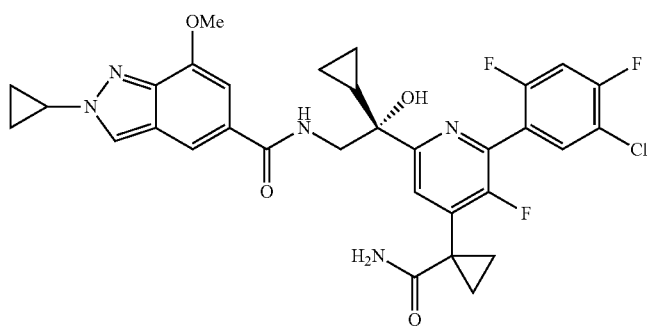 [SMILES: COc1cc(C(=O)NC[C@](O)(c2cc(C3(C(N)=O)CC3)c(F)c(-c3cc(Cl)c(F)cc3F)n2)C2CC2)cc2cn(C3CC3)nc12] |
| 12 | 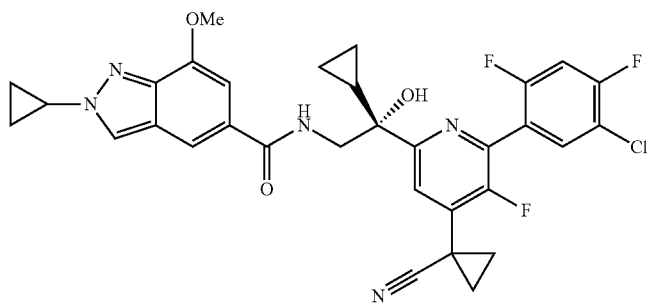 [SMILES: COc1cc(C(=O)NC[C@](O)(c2cc(C3(C#N)CC3)c(F)c(-c3cc(Cl)c(F)cc3F)n2)C2CC2)cc2cn(C3CC3)nc12] |
| 13 | 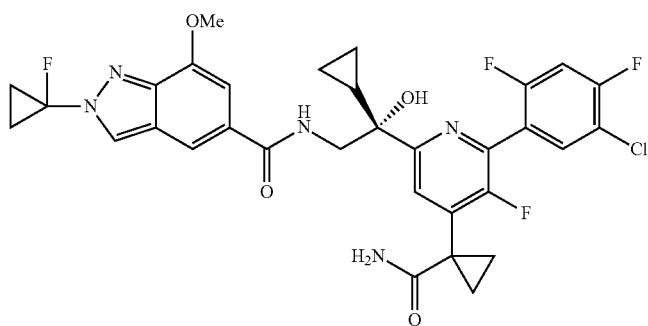 [SMILES: COc1cc(C(=O)NC[C@](O)(c2cc(C3(C(N)=O)CC3)c(F)c(-c3cc(Cl)c(F)cc3F)n2)C2CC2)cc2cn(C3(F)CC3)nc12] |

-continued
| Compound | Structure |
|---|---|
| 14 | 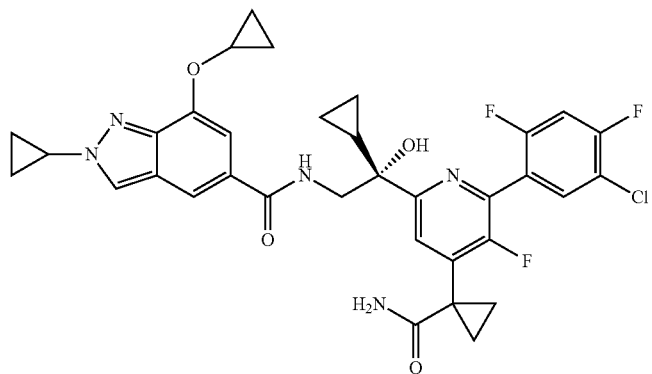 [SMILES: NC(=O)C1(c2cc([C@@](O)(CNC(=O)c3cc(OC4CC4)c4nn(C5CC5)cc4c3)C3CC3)nc(-c3cc(Cl)c(F)cc3F)c2F)CC1] |
| 15 | 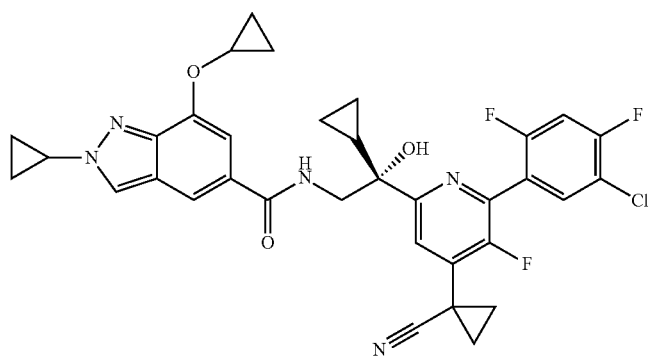 [SMILES: N#CC1(c2cc([C@@](O)(CNC(=O)c3cc(OC4CC4)c4nn(C5CC5)cc4c3)C3CC3)nc(-c3cc(Cl)c(F)cc3F)c2F)CC1] |
| 16 | 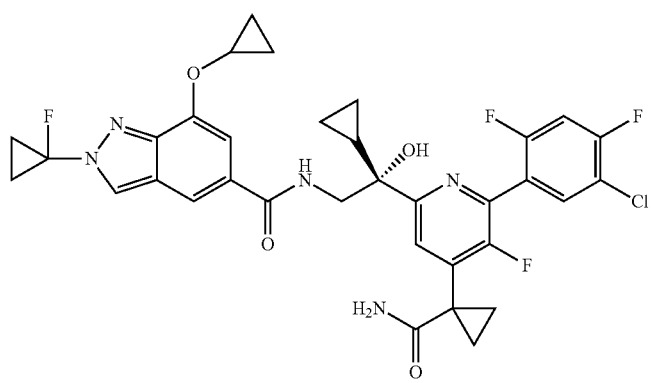 [SMILES: NC(=O)C1(c2cc([C@@](O)(CNC(=O)c3cc(OC4CC4)c4nn(C5(F)CC5)cc4c3)C3CC3)nc(-c3cc(Cl)c(F)cc3F)c2F)CC1] |
| 17 | 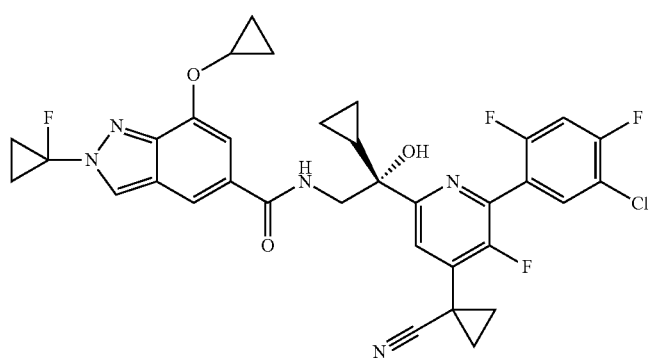 [SMILES: N#CC1(c2cc([C@@](O)(CNC(=O)c3cc(OC4CC4)c4nn(C5(F)CC5)cc4c3)C3CC3)nc(-c3cc(Cl)c(F)cc3F)c2F)CC1] |

-continued
| Compound | Structure |
|---|---|
| 18 | 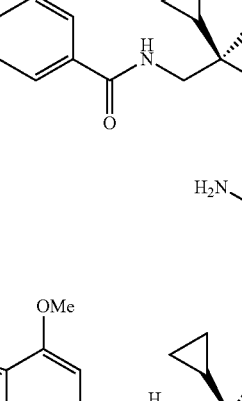 |
| 20 | 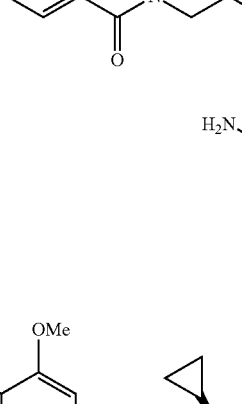 |
| 21 | 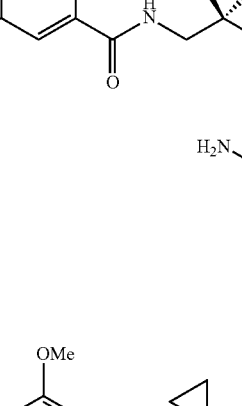 |
| 22 | 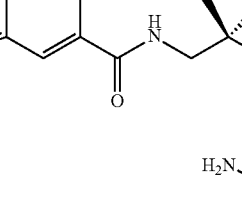 |

-continued
| Compound | Structure |
|---|---|
| 24 | 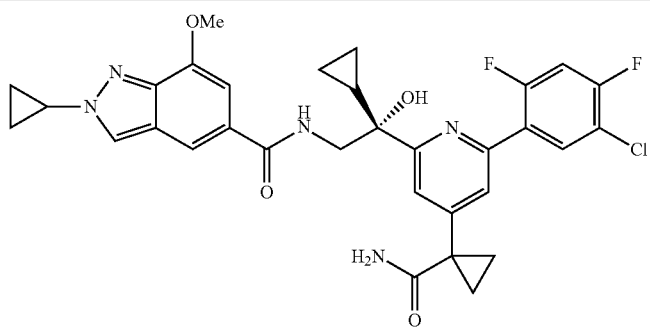 [SMILES: COc1cc(C(=O)NC[C@](O)(c2cc(C3(C(N)=O)CC3)cc(-c3cc(Cl)c(F)cc3F)n2)C2CC2)cc2cn(C3CC3)nc12] |
| 25 | 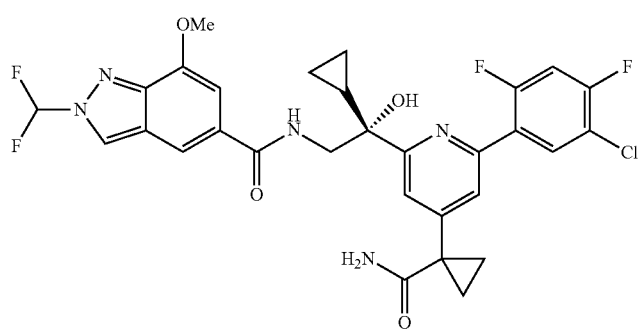 [SMILES: COc1cc(C(=O)NC[C@](O)(c2cc(C3(C(N)=O)CC3)cc(-c3cc(Cl)c(F)cc3F)n2)C2CC2)cc2cn(C(F)F)nc12] |
| 26 | 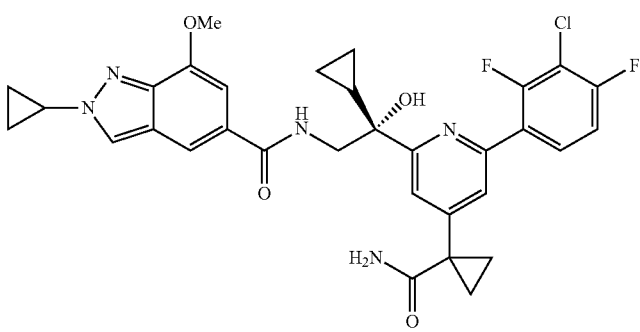 [SMILES: COc1cc(C(=O)NC[C@](O)(c2cc(C3(C(N)=O)CC3)cc(-c3ccc(F)c(Cl)c3F)n2)C2CC2)cc2cn(C3CC3)nc12] |
| 27 | 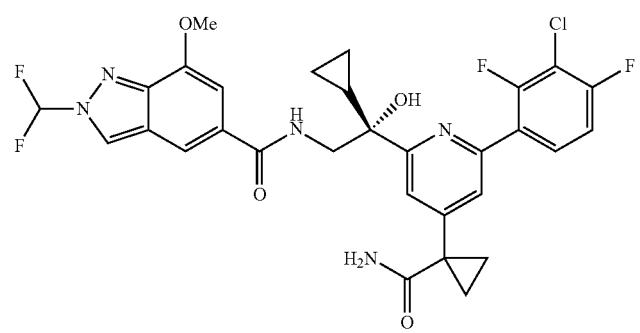 [SMILES: COc1cc(C(=O)NC[C@](O)(c2cc(C3(C(N)=O)CC3)cc(-c3ccc(F)c(Cl)c3F)n2)C2CC2)cc2cn(C(F)F)nc12] |

| Compound | Structure |
|---|---|
| 28 | 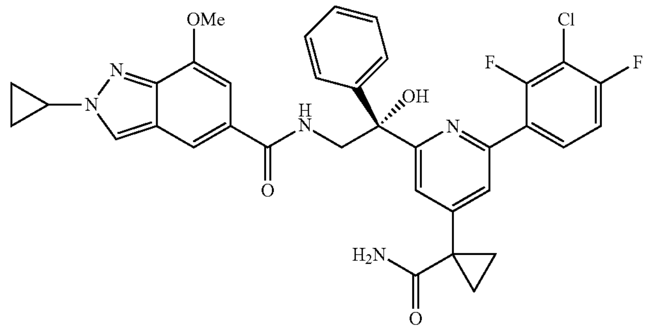 [SMILES: COc1cc(C(=O)NC[C@@](O)(c2ccccc2)c2cc(C3(C(N)=O)CC3)cc(-c3ccc(F)c(Cl)c3F)n2)cc2cn(C3CC3)nc12] |
| 29 | 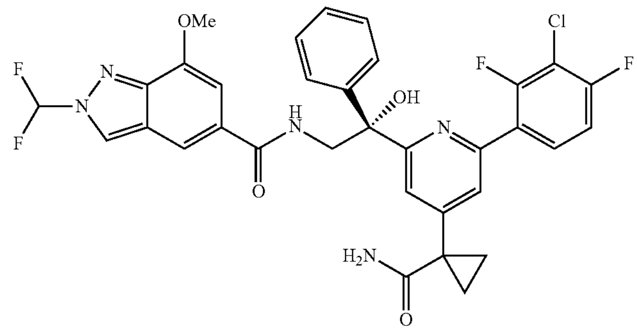 [SMILES: COc1cc(C(=O)NC[C@@](O)(c2ccccc2)c2cc(C3(C(N)=O)CC3)cc(-c3ccc(F)c(Cl)c3F)n2)cc2cn(C(F)F)nc12] |
| 30 | 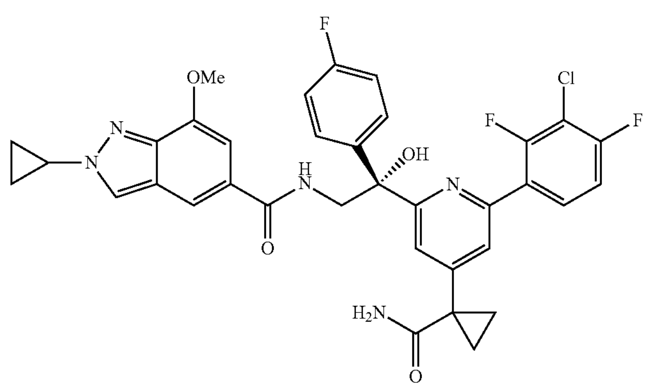 [SMILES: COc1cc(C(=O)NC[C@@](O)(c2ccc(F)cc2)c2cc(C3(C(N)=O)CC3)cc(-c3ccc(F)c(Cl)c3F)n2)cc2cn(C3CC3)nc12] |
| 31 | 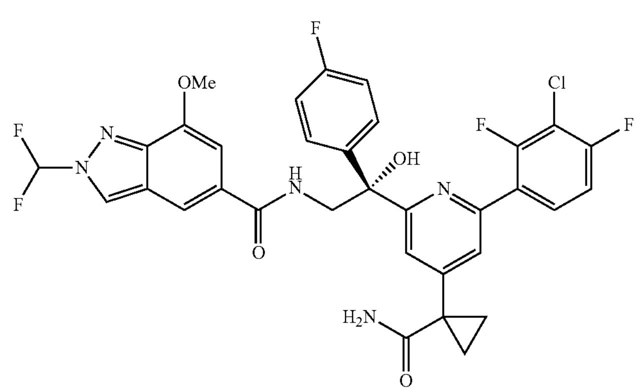 [SMILES: COc1cc(C(=O)NC[C@@](O)(c2ccc(F)cc2)c2cc(C3(C(N)=O)CC3)cc(-c3ccc(F)c(Cl)c3F)n2)cc2cn(C(F)F)nc12] |

| Compound | Structure |
|---|---|
| 32 | 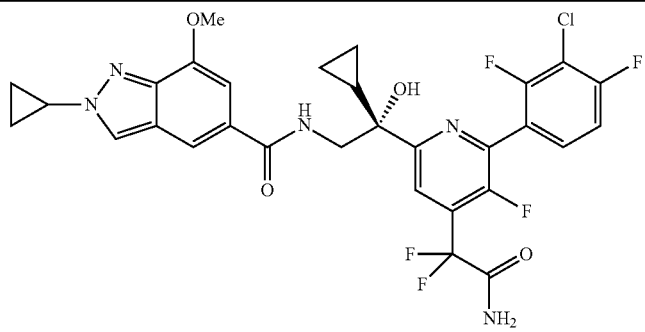 |
| 33 | 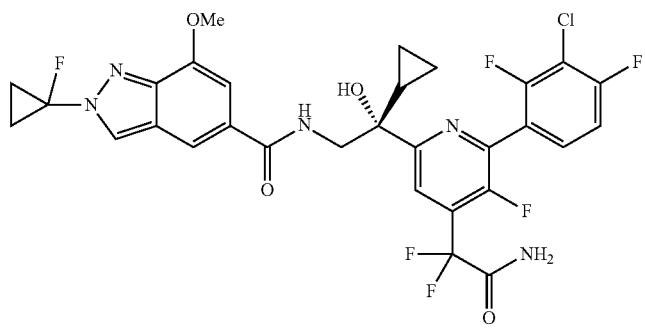 [SMILES: COc1cc(C(=O)NC[C@](O)(c2cc(C(F)(F)C(N)=O)c(F)c(-c3ccc(F)c(Cl)c3F)n2)C2CC2)cc2cn(C3(F)CC3)nc12] |
| 34 | 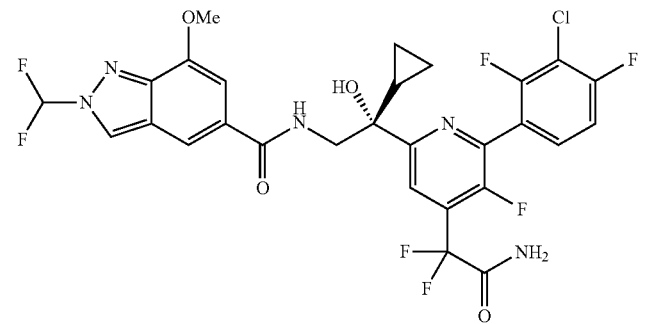 [SMILES: COc1cc(C(=O)NC[C@](O)(c2cc(C(F)(F)C(N)=O)c(F)c(-c3ccc(F)c(Cl)c3F)n2)C2CC2)cc2cn(C(F)F)nc12] |
| 36 | 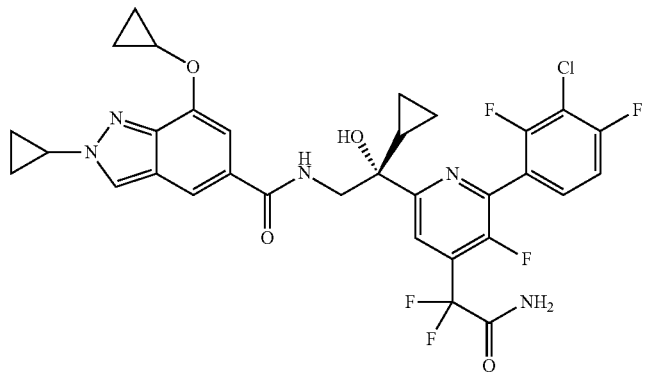 [SMILES: NC(=O)C(F)(F)c1cc([C@@](O)(CNC(=O)c2cc(OC3CC3)c3nn(C4CC4)cc3c2)C2CC2)nc(-c2ccc(F)c(Cl)c2F)c1F] |

| Compound | Structure |
|---|---|
| 38 | (structure) |
| 39 | (structure) |
| 40 | (structure) |
| 41 | (structure) |
| 43 | (structure) |

-continued
| Compound | Structure |
|---|---|
| 47 | 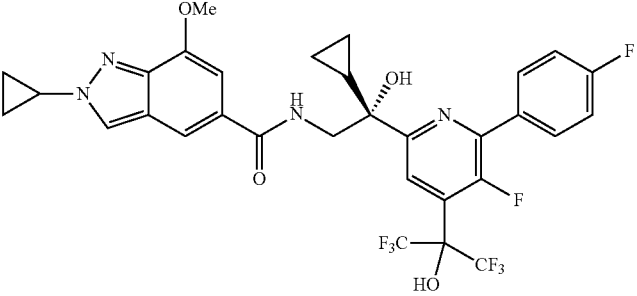 [SMILES: COc1cc(C(=O)NC[C@](O)(c2cc(C(O)(C(F)(F)F)C(F)(F)F)c(F)c(-c3ccc(F)cc3)n2)C2CC2)cc2cn(C3CC3)nc12] |
| 50 | 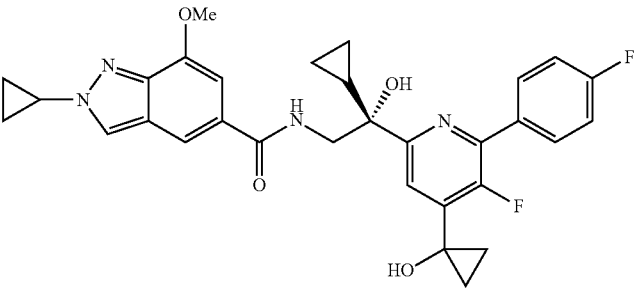 [SMILES: COc1cc(C(=O)NC[C@](O)(c2cc(C3(O)CC3)c(F)c(-c3ccc(F)cc3)n2)C2CC2)cc2cn(C3CC3)nc12] |
| 52 | 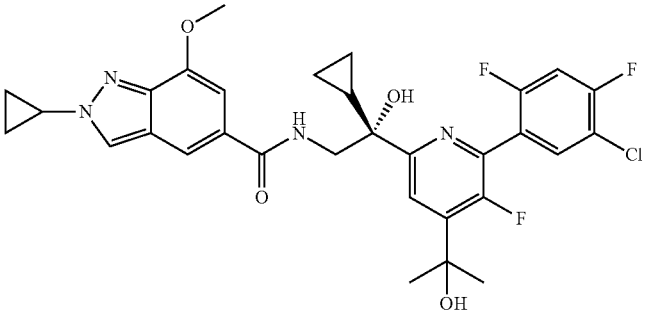 [SMILES: COc1cc(C(=O)NC[C@](O)(c2cc(C(C)(C)O)c(F)c(-c3cc(Cl)c(F)cc3F)n2)C2CC2)cc2cn(C3CC3)nc12] |
| 53 | 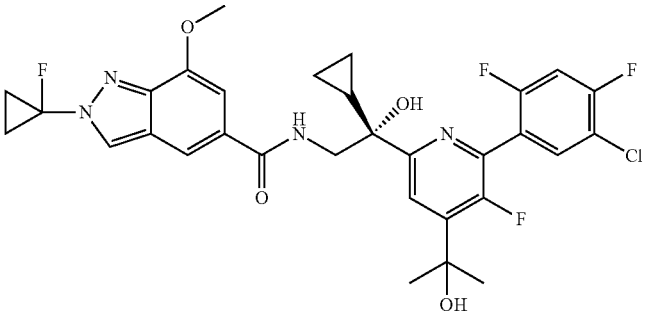 [SMILES: COc1cc(C(=O)NC[C@](O)(c2cc(C(C)(C)O)c(F)c(-c3cc(Cl)c(F)cc3F)n2)C2CC2)cc2cn(C3(F)CC3)nc12] |
| 54 | 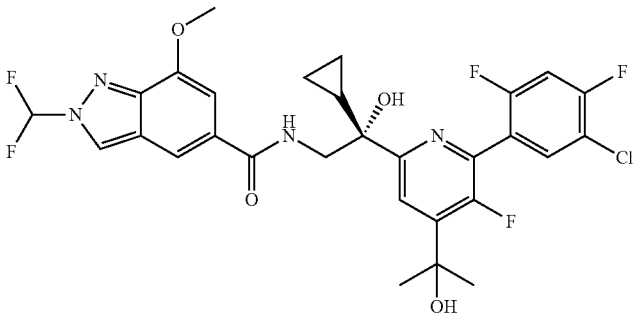 [SMILES: COc1cc(C(=O)NC[C@](O)(c2cc(C(C)(C)O)c(F)c(-c3cc(Cl)c(F)cc3F)n2)C2CC2)cc2cn(C(F)F)nc12] |

-continued
| Compound | Structure |
|---|---|
| 55 | 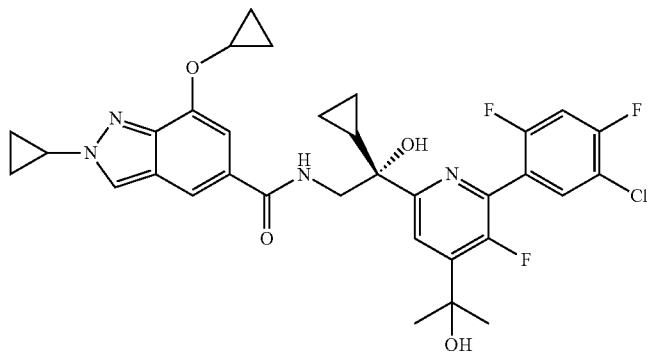 [SMILES: CC(C)(O)c1cc([C@@](O)(CNC(=O)c2cc(OC3CC3)c3nn(C4CC4)cc3c2)C2CC2)nc(-c2cc(Cl)c(F)cc2F)c1F] |
| 58 | 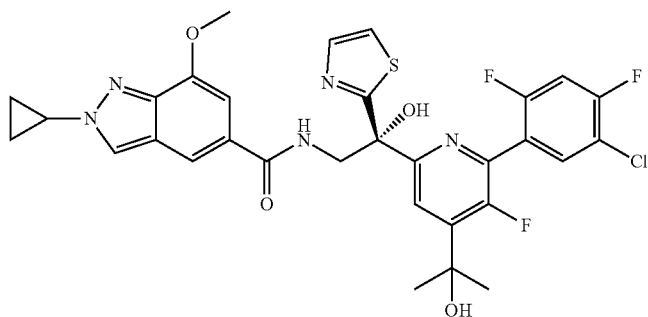 [SMILES: COc1cc(C(=O)NC[C@](O)(c2cc(C(C)(C)O)c(F)c(-c3cc(Cl)c(F)cc3F)n2)c2nccs2)cc2cn(C3CC3)nc12] |
| 60 | 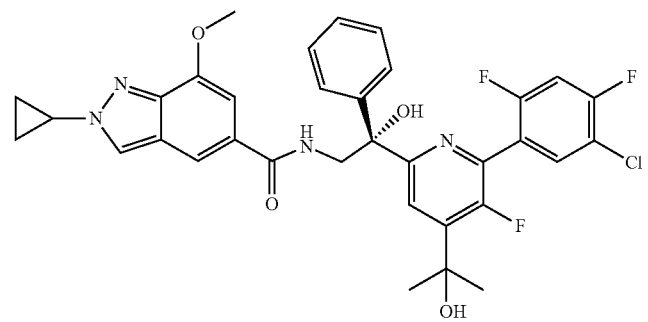 [SMILES: COc1cc(C(=O)NC[C@@](O)(c2ccccc2)c2cc(C(C)(C)O)c(F)c(-c3cc(Cl)c(F)cc3F)n2)cc2cn(C3CC3)nc12] |
| 61 | 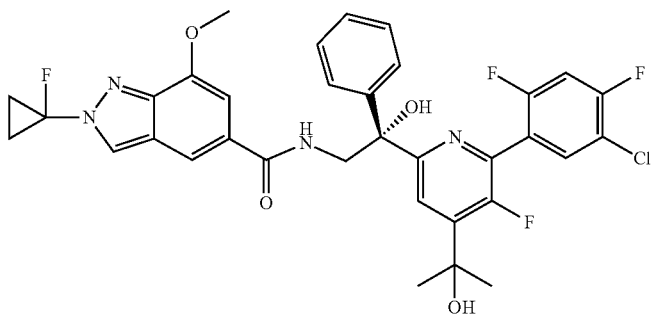 [SMILES: COc1cc(C(=O)NC[C@@](O)(c2ccccc2)c2cc(C(C)(C)O)c(F)c(-c3cc(Cl)c(F)cc3F)n2)cc2cn(C3(F)CC3)nc12] |

-continued
| Compound | Structure |
|---|---|
| 62 | 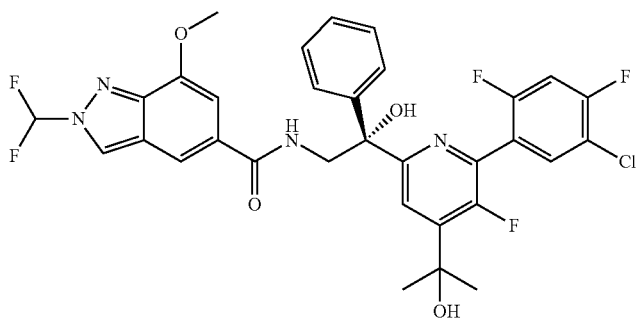 |
| 63 | 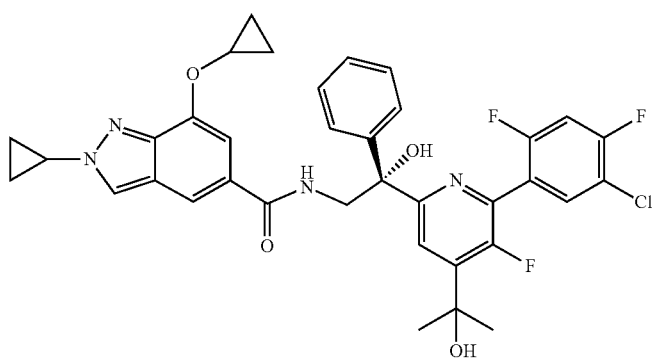 [SMILES: CC(C)(O)c1cc([C@@](O)(CNC(=O)c2cc(OC3CC3)c3nn(C4CC4)cc3c2)c2ccccc2)nc(-c2cc(Cl)c(F)cc2F)c1F] |
| 67 | 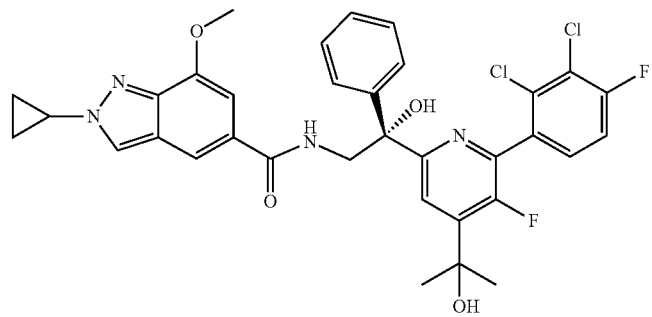 [SMILES: COc1cc(C(=O)NC[C@@](O)(c2ccccc2)c2cc(C(C)(C)O)c(F)c(-c3ccc(F)c(Cl)c3Cl)n2)cc2cn(C3CC3)nc12] |
| 68 | 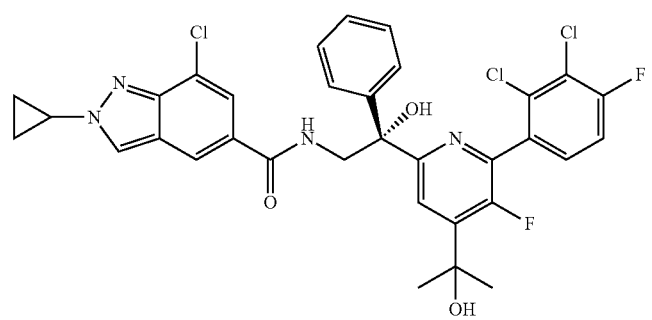 [SMILES: CC(C)(O)c1cc([C@@](O)(CNC(=O)c2cc(Cl)c3nn(C4CC4)cc3c2)c2ccccc2)nc(-c2ccc(F)c(Cl)c2Cl)c1F] |

-continued

| Compound | Structure |
|---|---|
| 70 | 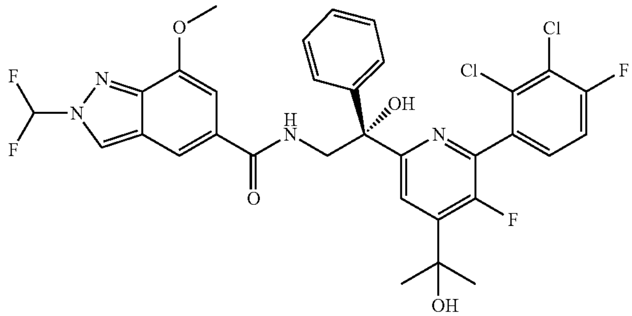 [SMILES: COc1cc(C(=O)NC[C@@](O)(c2ccccc2)c2cc(C(C)(C)O)c(F)c(-c3ccc(F)c(Cl)c3Cl)n2)cc2cn(C(F)F)nc12] |
| 74 | 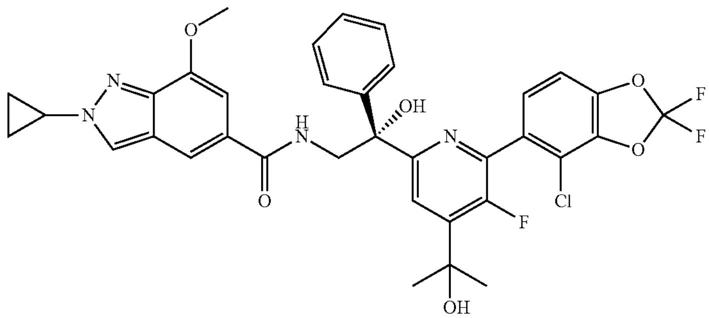 [SMILES: COc1cc(C(=O)NC[C@@](O)(c2ccccc2)c2cc(C(C)(C)O)c(F)c(-c3ccc4c(c3Cl)OC(F)(F)O4)n2)cc2cn(C3CC3)nc12] |
| 75 | 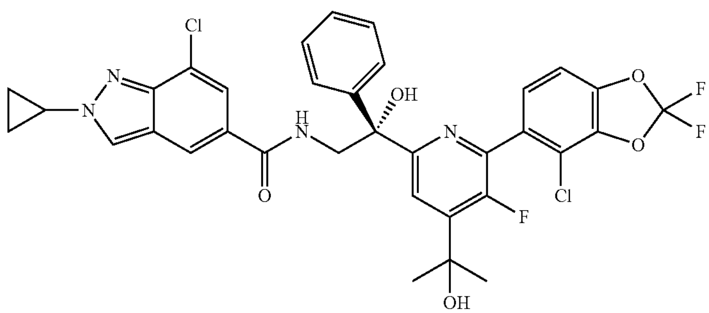 [SMILES: CC(C)(O)c1cc([C@@](O)(CNC(=O)c2cc(Cl)c3nn(C4CC4)cc3c2)c2ccccc2)nc(-c2ccc3c(c2Cl)OC(F)(F)O3)c1F] |
| 76 | 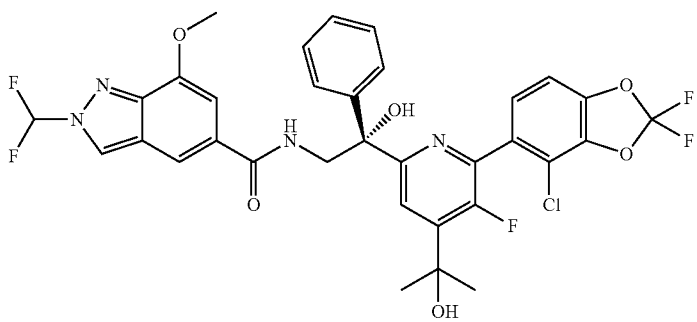 [SMILES: COc1cc(C(=O)NC[C@@](O)(c2ccccc2)c2cc(C(C)(C)O)c(F)c(-c3ccc4c(c3Cl)OC(F)(F)O4)n2)cc2cn(C(F)F)nc12] |
| 77 | 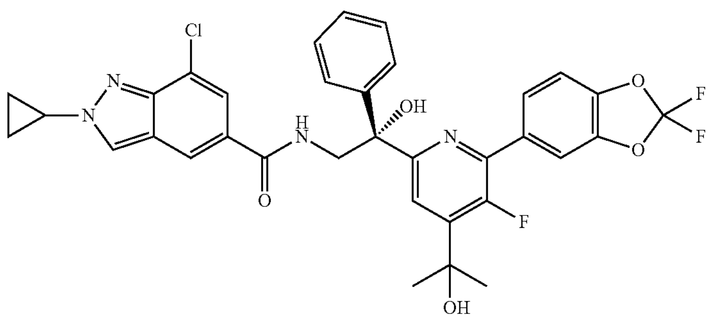 [SMILES: CC(C)(O)c1cc([C@@](O)(CNC(=O)c2cc(Cl)c3nn(C4CC4)cc3c2)c2ccccc2)nc(-c2ccc3c(c2)OC(F)(F)O3)c1F] |

-continued
| Compound | Structure |
|---|---|
| 79 | 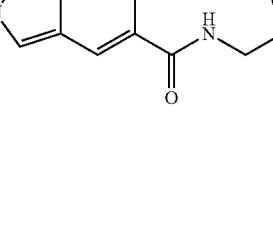 |
| 80 | 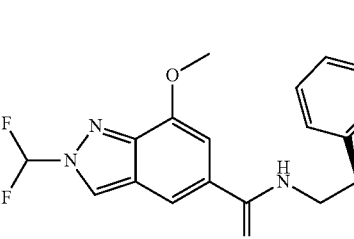 |
| 82 | 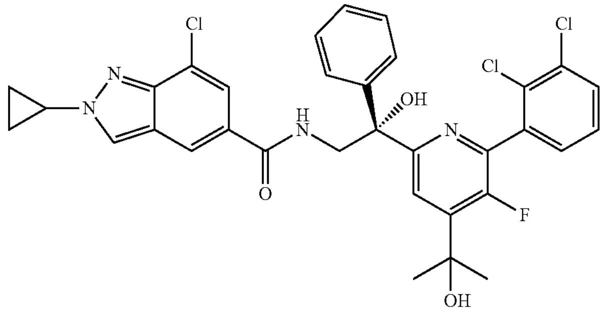 [SMILES: CC(C)(O)c1cc([C@@](O)(CNC(=O)c2cc(Cl)c3nn(C4CC4)cc3c2)c2ccccc2)nc(-c2cccc(Cl)c2Cl)c1F] |
| 83 | 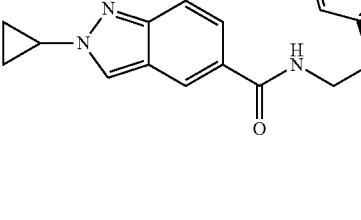 |

-continued
| Compound | Structure |
|---|---|
| 84 | 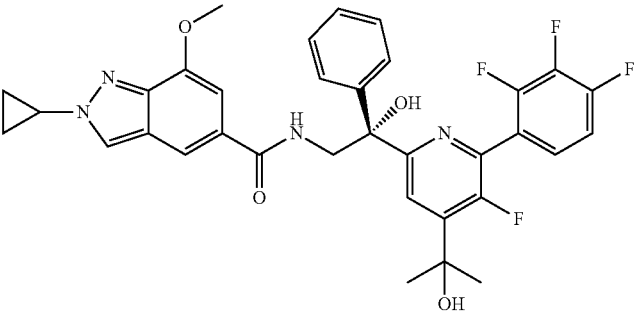 [SMILES: COc1cc(C(=O)NC[C@@](O)(c2ccccc2)c2cc(C(C)(C)O)c(F)c(-c3ccc(F)c(F)c3F)n2)cc2cn(C3CC3)nc12] |
| 85 | 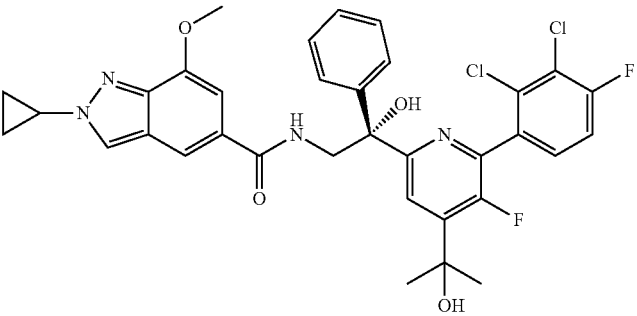 [SMILES: COc1cc(C(=O)NC[C@@](O)(c2ccccc2)c2cc(C(C)(C)O)c(F)c(-c3ccc(F)c(Cl)c3Cl)n2)cc2cn(C3CC3)nc12] |
| 86 | 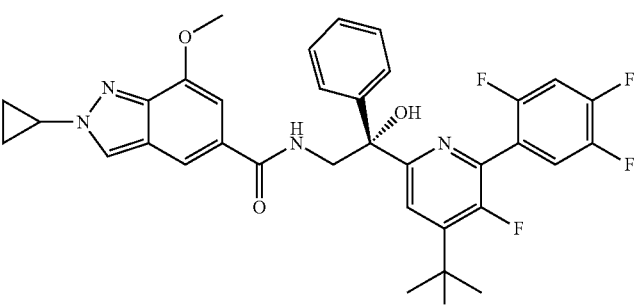 |
| 87 | 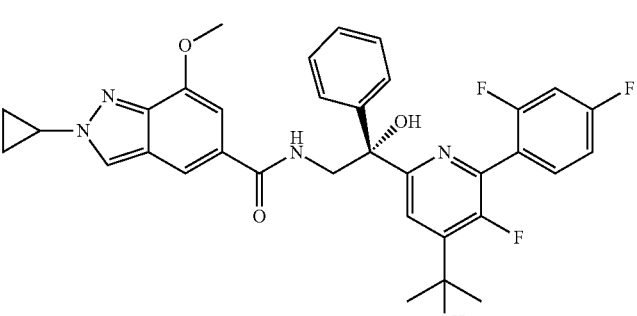 |
| 88 | 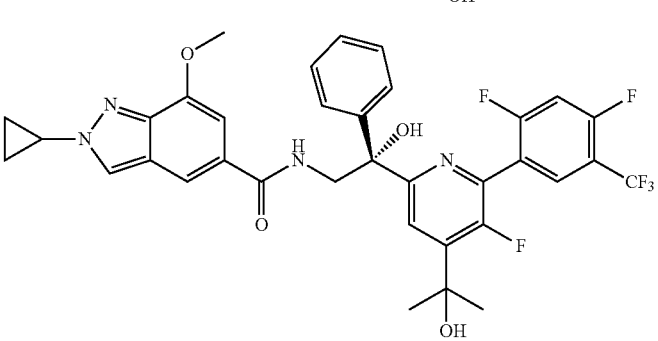 |

-continued
| Compound | Structure |
|---|---|
| 90 | 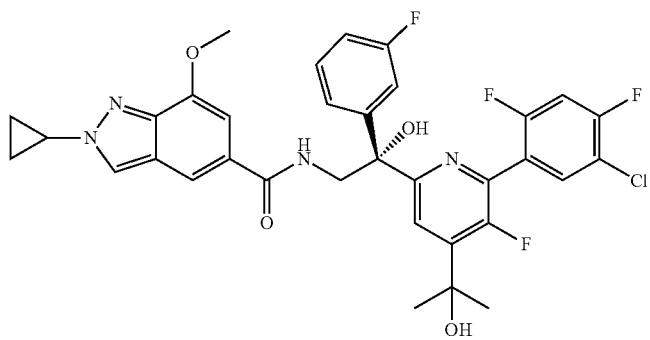 [SMILES: COc1cc(C(=O)NC[C@@](O)(c2cccc(F)c2)c2cc(C(C)(C)O)c(F)c(-c3cc(Cl)c(F)cc3F)n2)cc2cn(C3CC3)nc12] |
| 91 | 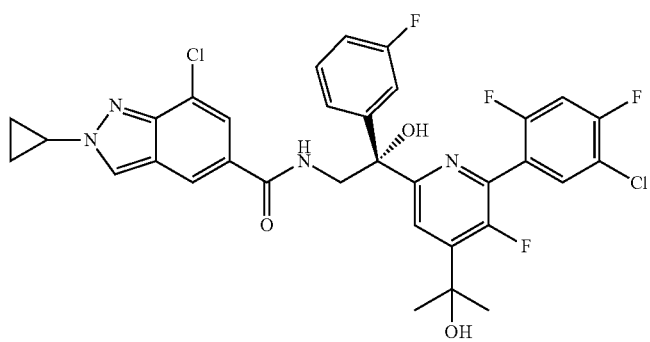 [SMILES: CC(C)(O)c1cc([C@@](O)(CNC(=O)c2cc(Cl)c3nn(C4CC4)cc3c2)c2cccc(F)c2)nc(-c2cc(Cl)c(F)cc2F)c1F] |
| 92 | 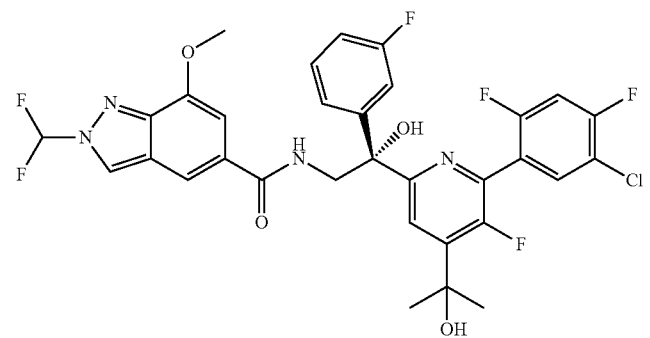 [SMILES: COc1cc(C(=O)NC[C@@](O)(c2cccc(F)c2)c2cc(C(C)(C)O)c(F)c(-c3cc(Cl)c(F)cc3F)n2)cc2cn(C(F)F)nc12] |
| 94 | 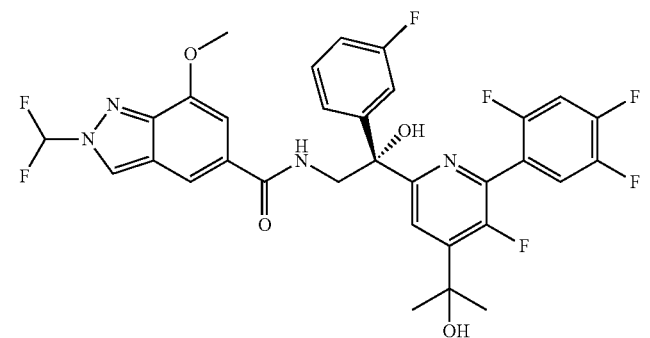 [SMILES: COc1cc(C(=O)NC[C@@](O)(c2cccc(F)c2)c2cc(C(C)(C)O)c(F)c(-c3cc(F)c(F)cc3F)n2)cc2cn(C(F)F)nc12] |

-continued
| Compound | Structure |
|---|---|
| 96 | 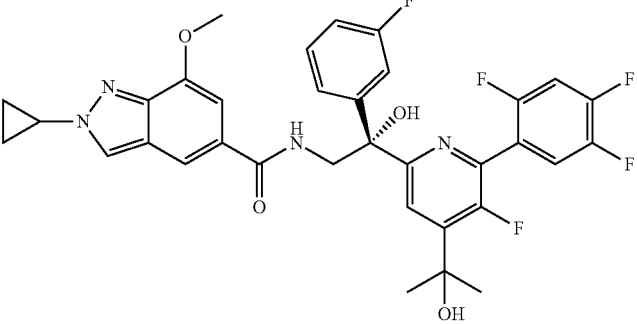 |
| 97 | 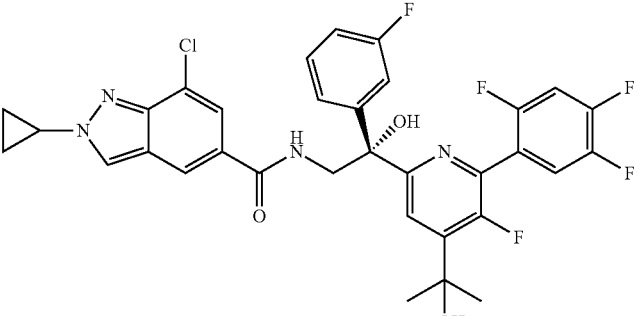 |
| 98 | 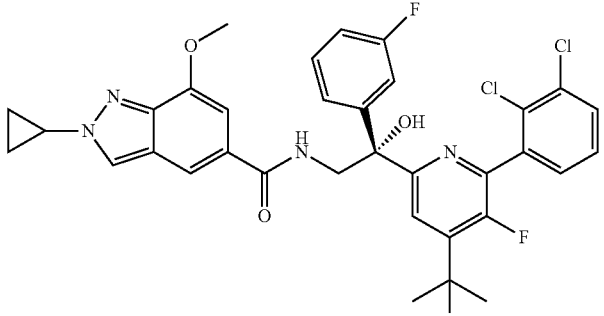 |
| 99 | 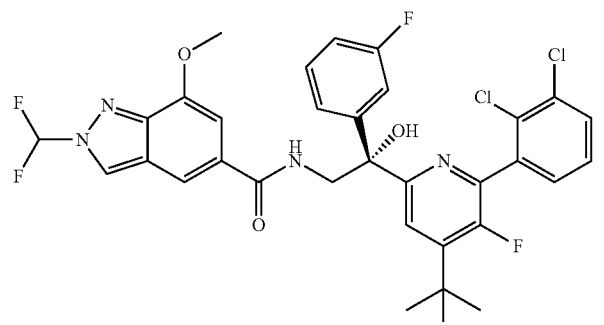 |

-continued

| Compound | Structure |
|---|---|
| 100 | 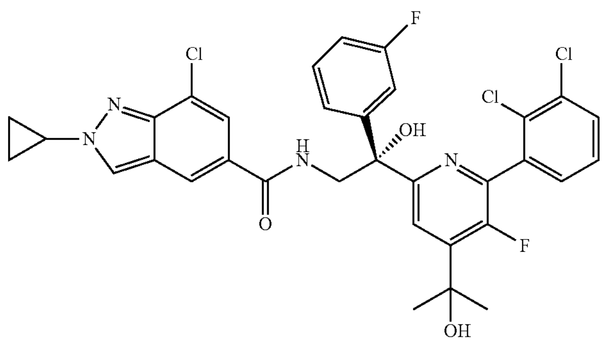 [SMILES: CC(C)(O)c1cc([C@@](O)(CNC(=O)c2cc(Cl)c3nn(C4CC4)cc3c2)c2cccc(F)c2)nc(-c2cccc(Cl)c2Cl)c1F] |
| 103 | 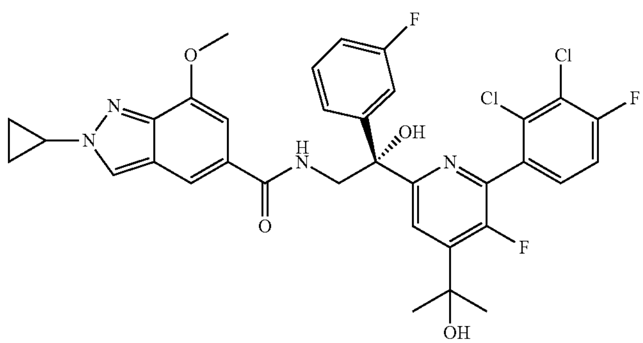 [SMILES: COc1cc(C(=O)NC[C@@](O)(c2cccc(F)c2)c2cc(C(C)(C)O)c(F)c(-c3ccc(F)c(Cl)c3Cl)n2)cc2cn(C3CC3)nc12] |
| 104 | 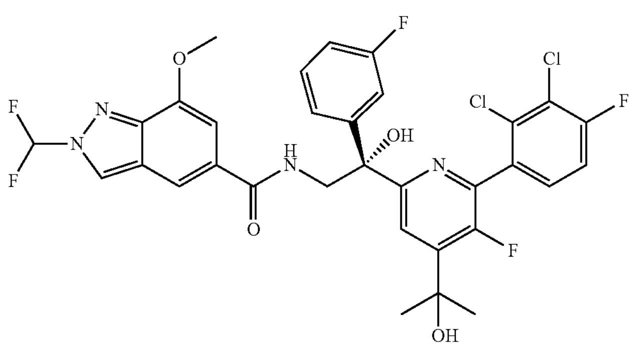 [SMILES: COc1cc(C(=O)NC[C@@](O)(c2cccc(F)c2)c2cc(C(C)(C)O)c(F)c(-c3ccc(F)c(Cl)c3Cl)n2)cc2cn(C(F)F)nc12] |
| 105 | 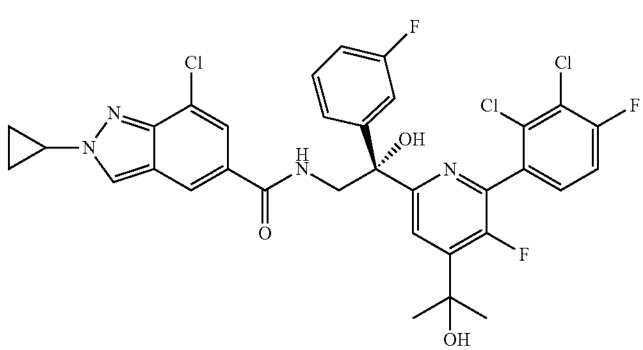 [SMILES: CC(C)(O)c1cc([C@@](O)(CNC(=O)c2cc(Cl)c3nn(C4CC4)cc3c2)c2cccc(F)c2)nc(-c2ccc(F)c(Cl)c2Cl)c1F] |

| Compound | Structure |
|---|---|
| 109 | 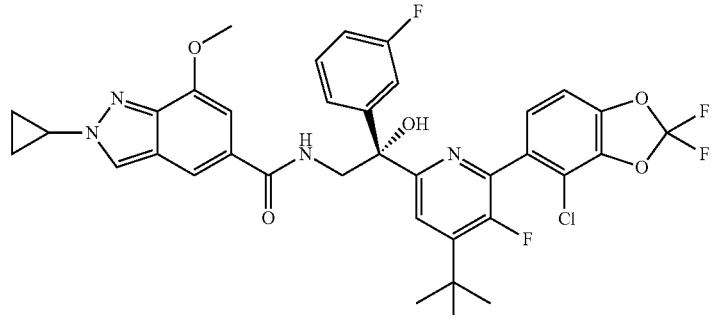 |
| 110 | 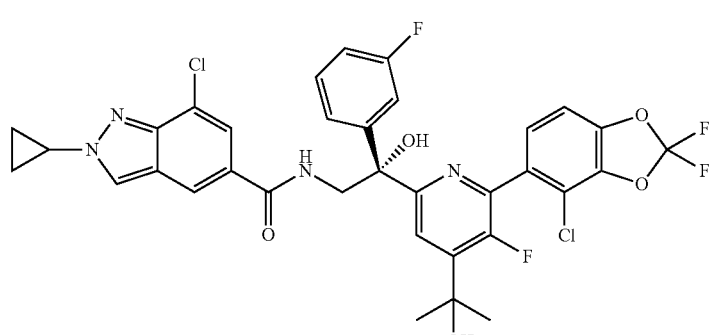 |
| 111 | 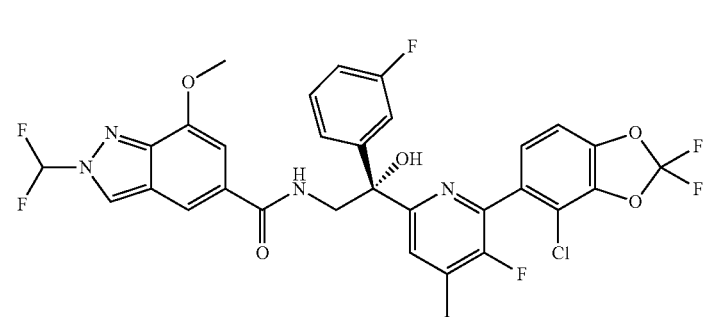 |
| 113 | 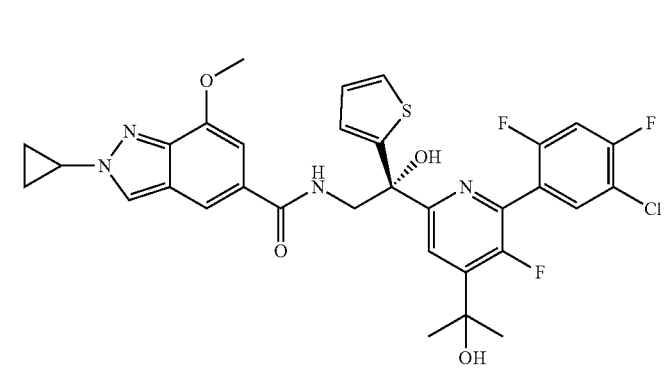 [SMILES: COc1cc(C(=O)NC[C@](O)(c2cc(C(C)(C)O)c(F)c(-c3cc(Cl)c(F)cc3F)n2)c2cccs2)cc2cn(C3CC3)nc12] |

| Compound | Structure |
|---|---|
| 114 | 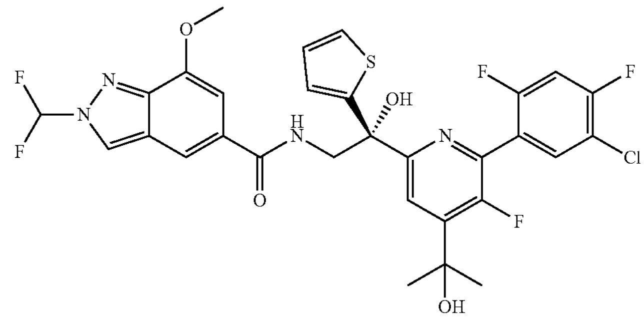 [SMILES: COc1cc(C(=O)NC[C@](O)(c2cc(C(C)(C)O)c(F)c(-c3cc(Cl)c(F)cc3F)n2)c2cccs2)cc2cn(C(F)F)nc12] |
| 116 | 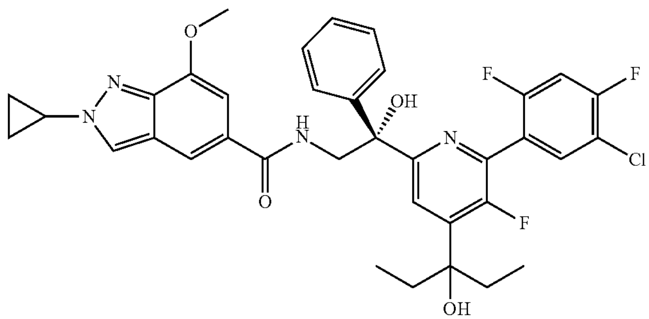 [SMILES: CCC(O)(CC)c1cc([C@@](O)(CNC(=O)c2cc(OC)c3nn(C4CC4)cc3c2)c2ccccc2)nc(-c2cc(Cl)c(F)cc2F)c1F] |
| 117 | 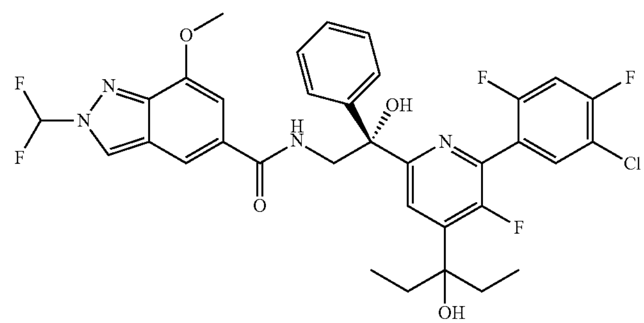 [SMILES: CCC(O)(CC)c1cc([C@@](O)(CNC(=O)c2cc(OC)c3nn(C(F)F)cc3c2)c2ccccc2)nc(-c2cc(Cl)c(F)cc2F)c1F] |
| 118 | 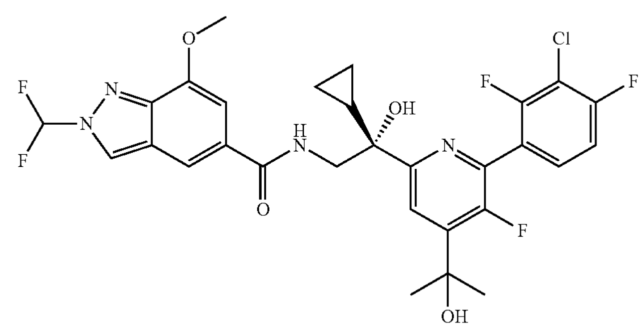 [SMILES: COc1cc(C(=O)NC[C@](O)(c2cc(C(C)(C)O)c(F)c(-c3ccc(F)c(Cl)c3F)n2)C2CC2)cc2cn(C(F)F)nc12] |
| 119 | 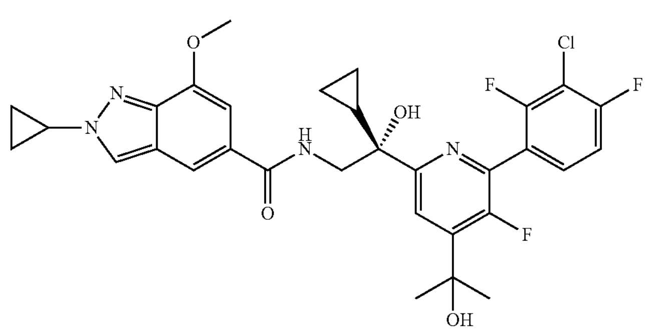 [SMILES: COc1cc(C(=O)NC[C@](O)(c2cc(C(C)(C)O)c(F)c(-c3ccc(F)c(Cl)c3F)n2)C2CC2)cc2cn(C3CC3)nc12] |

-continued
| Compound | Structure |
|---|---|
| 120 | 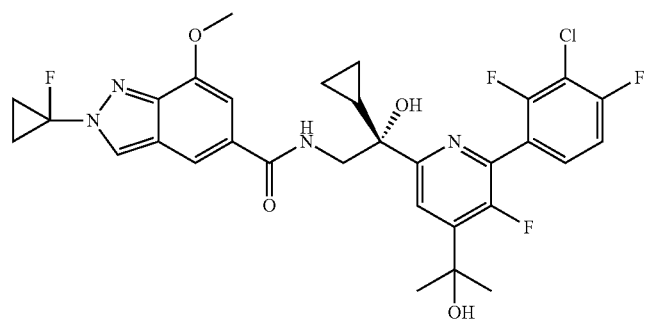 [SMILES: COc1cc(C(=O)NC[C@](O)(c2cc(C(C)(C)O)c(F)c(-c3ccc(F)c(Cl)c3F)n2)C2CC2)cc2cn(C3(F)CC3)nc12] |
| 121 | 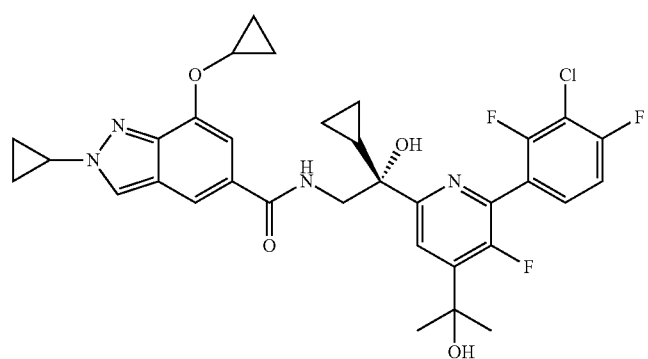 [SMILES: CC(C)(O)c1cc([C@@](O)(CNC(=O)c2cc(OC3CC3)c3nn(C4CC4)cc3c2)C2CC2)nc(-c2ccc(F)c(Cl)c2F)c1F] |
| 122 | 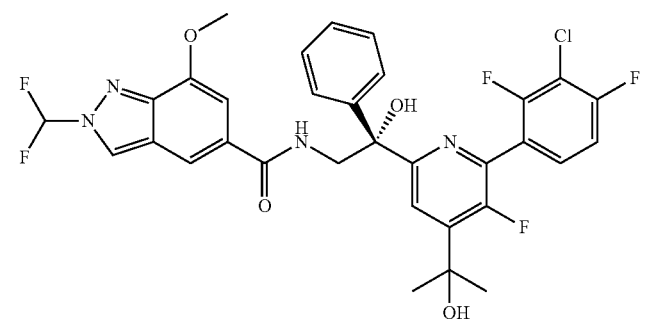 [SMILES: COc1cc(C(=O)NC[C@@](O)(c2ccccc2)c2cc(C(C)(C)O)c(F)c(-c3ccc(F)c(Cl)c3F)n2)cc2cn(C(F)F)nc12] |
| 123 | 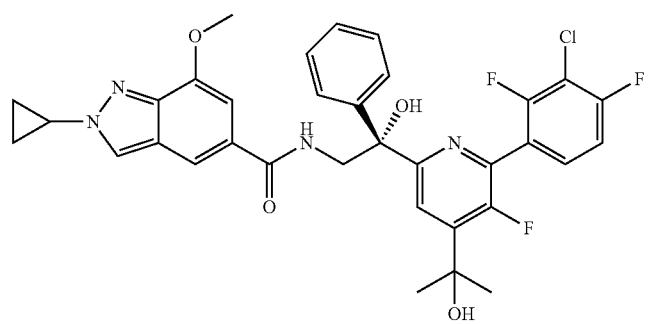 [SMILES: COc1cc(C(=O)NC[C@@](O)(c2ccccc2)c2cc(C(C)(C)O)c(F)c(-c3ccc(F)c(Cl)c3F)n2)cc2cn(C3CC3)nc12] |

| Compound | Structure |
|---|---|
| 124 | 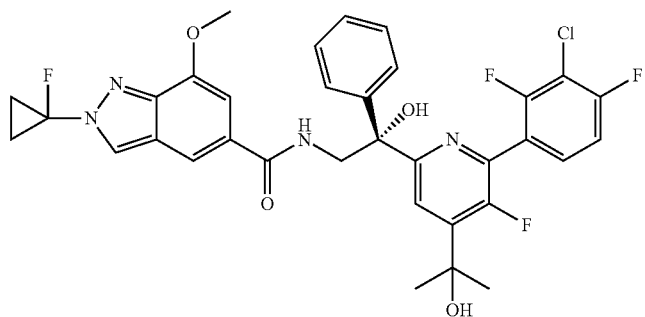 [SMILES: COc1cc(C(=O)NC[C@@](O)(c2ccccc2)c2cc(C(C)(C)O)c(F)c(-c3ccc(F)c(Cl)c3F)n2)cc2cn(C3(F)CC3)nc12] |
| 125 | 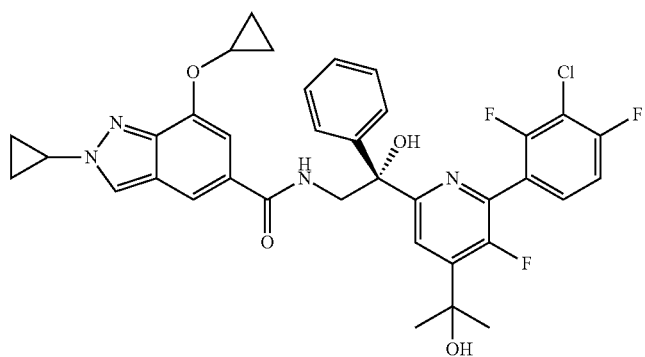 [SMILES: CC(C)(O)c1cc([C@@](O)(CNC(=O)c2cc(OC3CC3)c3nn(C4CC4)cc3c2)c2ccccc2)nc(-c2ccc(F)c(Cl)c2F)c1F] |
| 127 | 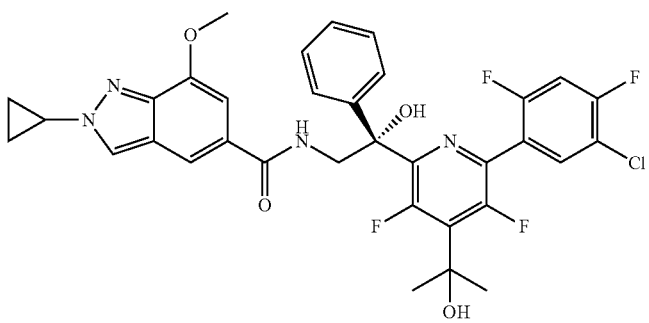 [SMILES: COc1cc(C(=O)NC[C@@](O)(c2ccccc2)c2nc(-c3cc(Cl)c(F)cc3F)c(F)c(C(C)(C)O)c2F)cc2cn(C3CC3)nc12] |
| 128 | 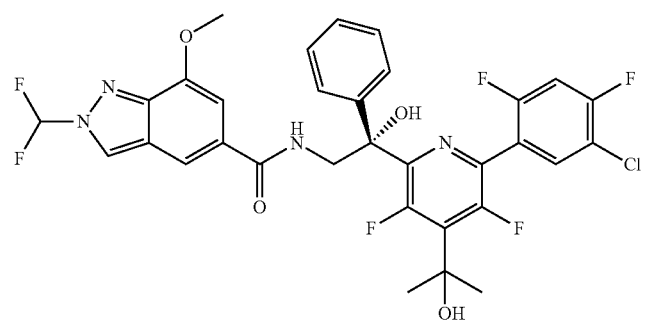 [SMILES: COc1cc(C(=O)NC[C@@](O)(c2ccccc2)c2nc(-c3cc(Cl)c(F)cc3F)c(F)c(C(C)(C)O)c2F)cc2cn(C(F)F)nc12] |

-continued
| Compound | Structure |
|---|---|
| 132 | 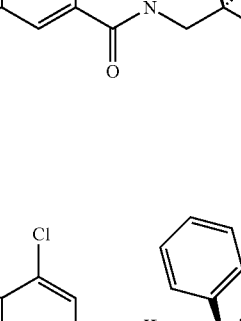 |
| 133 | 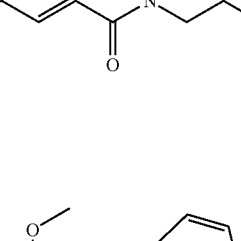 |
| 134 | 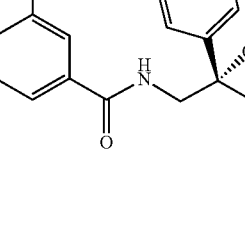 |
| 136 | 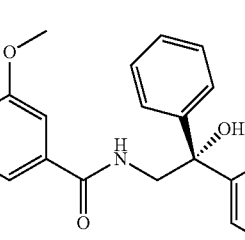 |
| 137 | 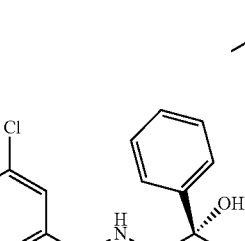 |

-continued
| Compound | Structure |
|---|---|
| 138 | 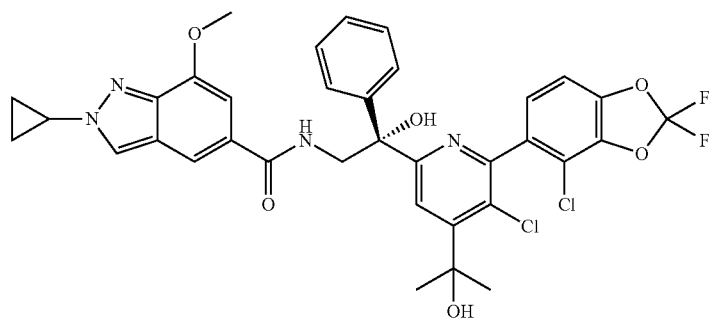 [SMILES: COc1cc(C(=O)NC[C@@](O)(c2ccccc2)c2cc(C(C)(C)O)c(Cl)c(-c3ccc4c(c3Cl)OC(F)(F)O4)n2)cc2cn(C3CC3)nc12] |
| 140 | 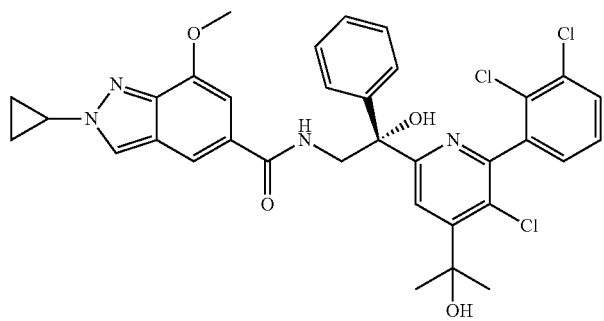 [SMILES: COc1cc(C(=O)NC[C@@](O)(c2ccccc2)c2cc(C(C)(C)O)c(Cl)c(-c3cccc(Cl)c3Cl)n2)cc2cn(C3CC3)nc12] |
| 141 | 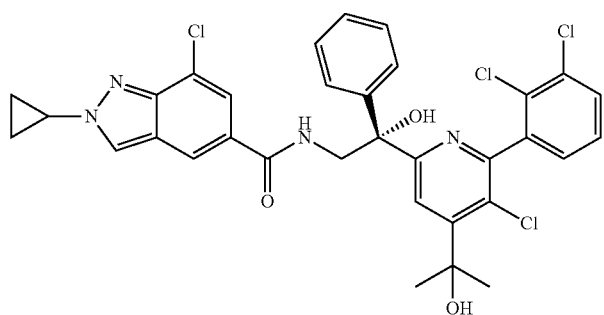 [SMILES: CC(C)(O)c1cc([C@@](O)(CNC(=O)c2cc(Cl)c3nn(C4CC4)cc3c2)c2ccccc2)nc(-c2cccc(Cl)c2Cl)c1Cl] |
| 142 | 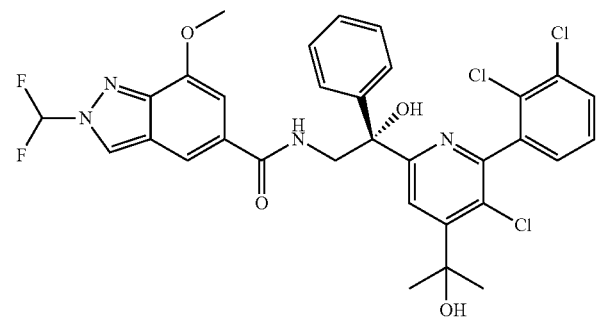 [SMILES: COc1cc(C(=O)NC[C@@](O)(c2ccccc2)c2cc(C(C)(C)O)c(Cl)c(-c3cccc(Cl)c3Cl)n2)cc2cn(C(F)F)nc12] |

-continued

| Compound | Structure |
|---|---|
| 144 | 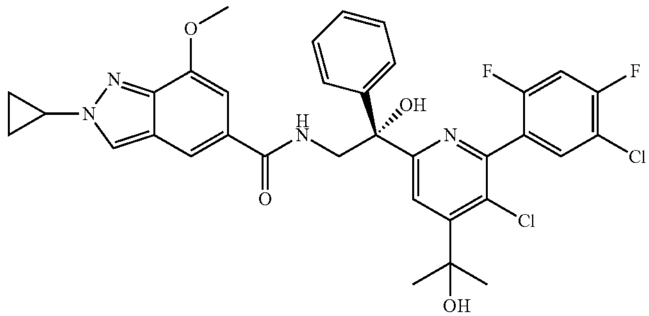 [SMILES: COc1cc(C(=O)NC[C@@](O)(c2ccccc2)c2cc(C(C)(C)O)c(Cl)c(-c3cc(Cl)c(F)cc3F)n2)cc2cn(C3CC3)nc12] |
| 145 | 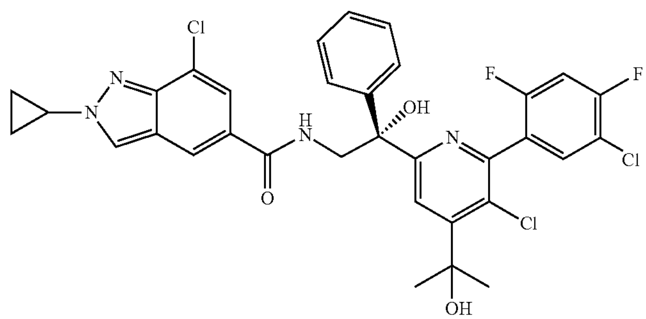 [SMILES: CC(C)(O)c1cc([C@@](O)(CNC(=O)c2cc(Cl)c3nn(C4CC4)cc3c2)c2ccccc2)nc(-c2cc(Cl)c(F)cc2F)c1Cl] |
| 146 | 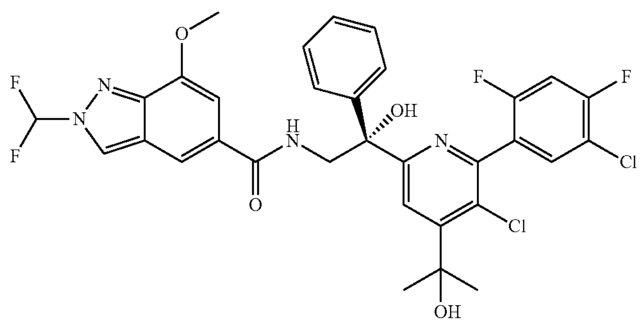 [SMILES: COc1cc(C(=O)NC[C@@](O)(c2ccccc2)c2cc(C(C)(C)O)c(Cl)c(-c3cc(Cl)c(F)cc3F)n2)cc2cn(C(F)F)nc12] |
| 148 | 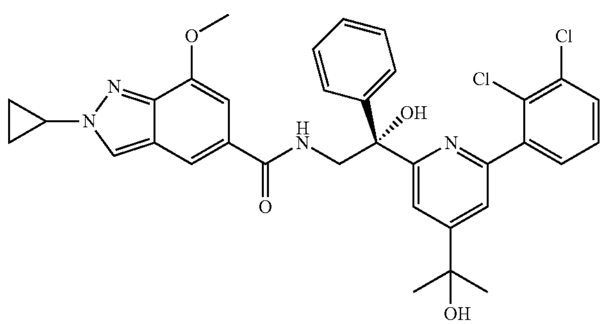 [SMILES: COc1cc(C(=O)NC[C@@](O)(c2ccccc2)c2cc(C(C)(C)O)cc(-c3cccc(Cl)c3Cl)n2)cc2cn(C3CC3)nc12] |
| 149 | 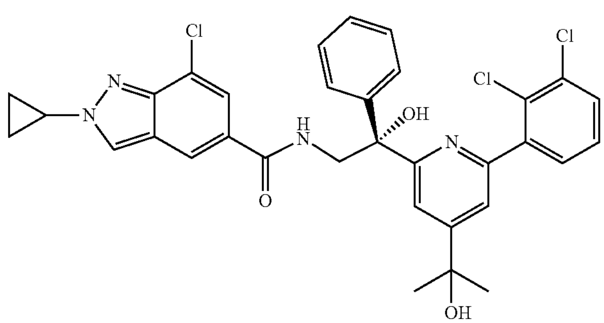 [SMILES: CC(C)(O)c1cc(-c2cccc(Cl)c2Cl)nc([C@@](O)(CNC(=O)c2cc(Cl)c3nn(C4CC4)cc3c2)c2ccccc2)c1] |

-continued
| Compound | Structure |
|---|---|
| 150 | 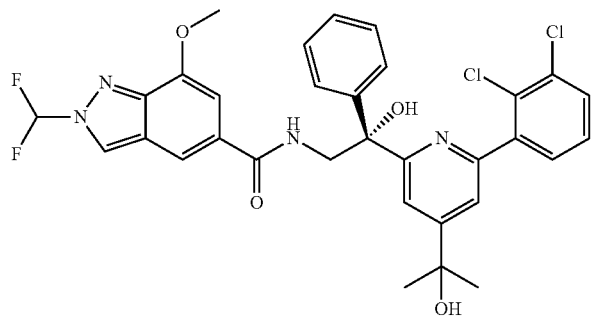 [SMILES: COc1cc(C(=O)NC[C@@](O)(c2ccccc2)c2cc(C(C)(C)O)cc(-c3cccc(Cl)c3Cl)n2)cc2cn(C(F)F)nc12] |
| 152 | 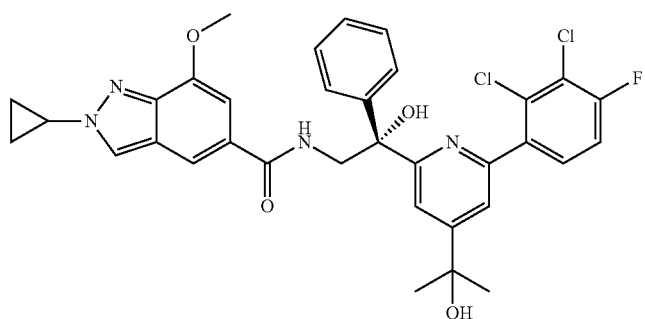 [SMILES: COc1cc(C(=O)NC[C@@](O)(c2ccccc2)c2cc(C(C)(C)O)cc(-c3ccc(F)c(Cl)c3Cl)n2)cc2cn(C3CC3)nc12] |
| 153 | 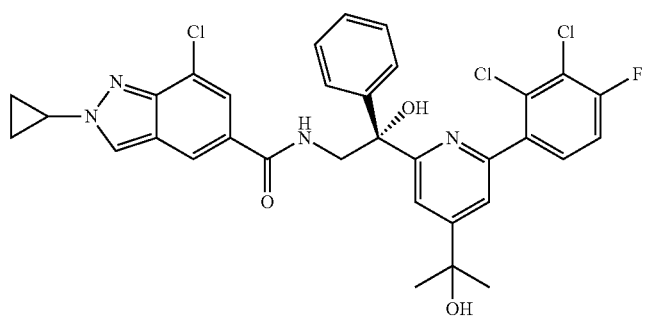 [SMILES: CC(C)(O)c1cc(-c2ccc(F)c(Cl)c2Cl)nc([C@@](O)(CNC(=O)c2cc(Cl)c3nn(C4CC4)cc3c2)c2ccccc2)c1] |
| 154 | 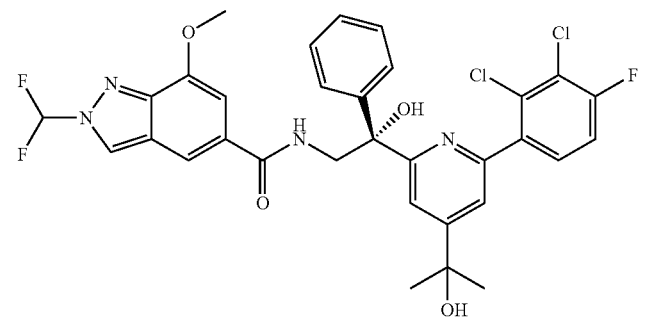 [SMILES: COc1cc(C(=O)NC[C@@](O)(c2ccccc2)c2cc(C(C)(C)O)cc(-c3ccc(F)c(Cl)c3Cl)n2)cc2cn(C(F)F)nc12] |

-continued

| Compound | Structure |
|---|---|
| 156 | 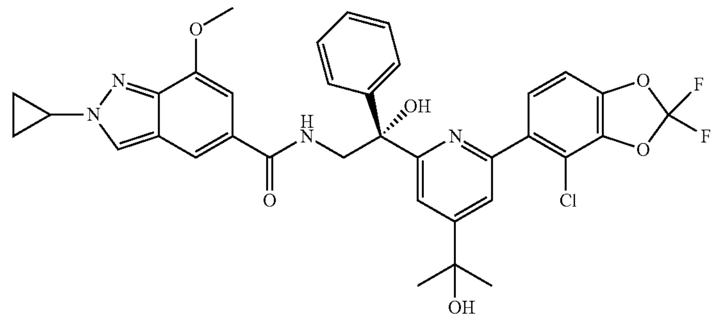 [SMILES: COc1cc(C(=O)NC[C@@](O)(c2ccccc2)c2cc(C(C)(C)O)cc(-c3ccc4c(c3Cl)OC(F)(F)O4)n2)cc2cn(C3CC3)nc12] |
| 158 | 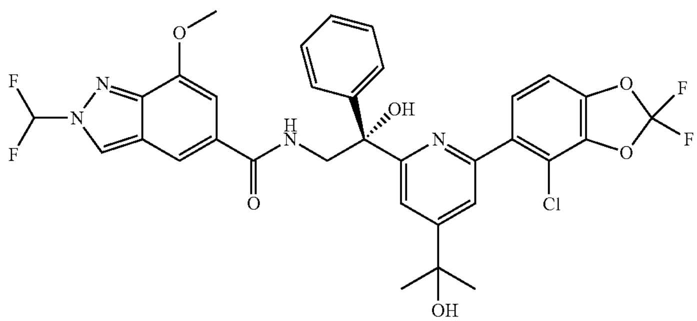 [SMILES: COc1cc(C(=O)NC[C@@](O)(c2ccccc2)c2cc(C(C)(C)O)cc(-c3ccc4c(c3Cl)OC(F)(F)O4)n2)cc2cn(C(F)F)nc12] |
| 159 | 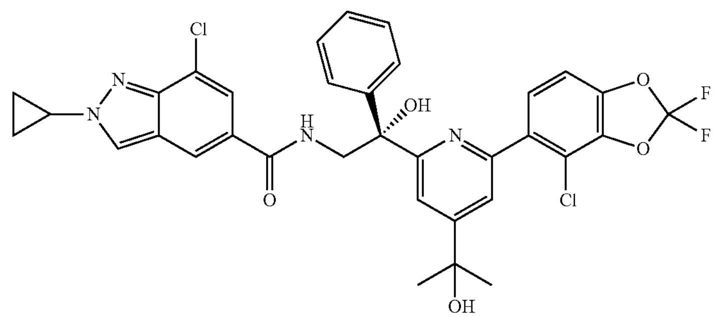 [SMILES: CC(C)(O)c1cc(-c2ccc3c(c2Cl)OC(F)(F)O3)nc([C@@](O)(CNC(=O)c2cc(Cl)c3nn(C4CC4)cc3c2)c2ccccc2)c1] |
| 160 | 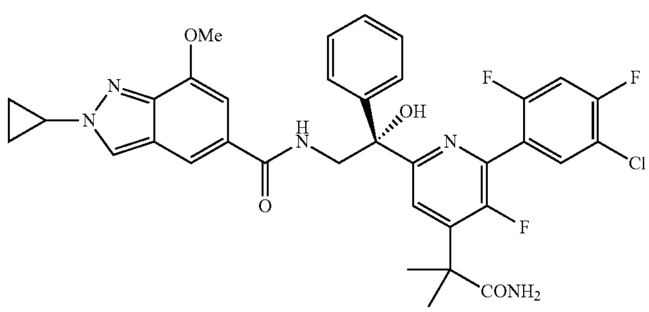 [SMILES: COc1cc(C(=O)NC[C@@](O)(c2ccccc2)c2cc(C(C)(C)C(N)=O)c(F)c(-c3cc(Cl)c(F)cc3F)n2)cc2cn(C3CC3)nc12] |
| 161 | 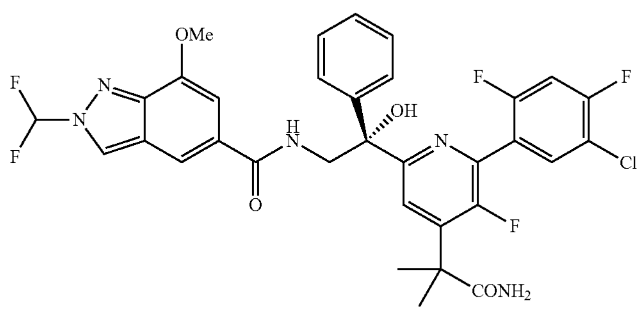 [SMILES: COc1cc(C(=O)NC[C@@](O)(c2ccccc2)c2cc(C(C)(C)C(N)=O)c(F)c(-c3cc(Cl)c(F)cc3F)n2)cc2cn(C(F)F)nc12] |

-continued
| Compound | Structure |
|---|---|
| 162 | 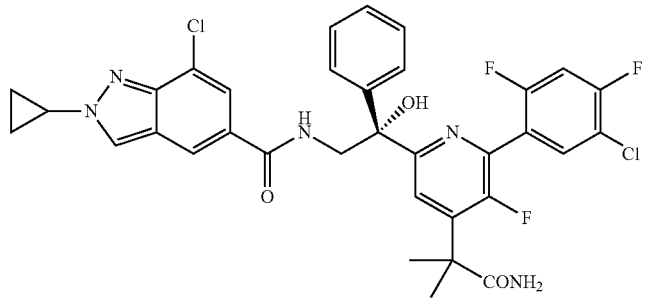 [SMILES: CC(C)(C(N)=O)c1cc([C@@](O)(CNC(=O)c2cc(Cl)c3nn(C4CC4)cc3c2)c2ccccc2)nc(-c2cc(Cl)c(F)cc2F)c1F] |
| 164 | 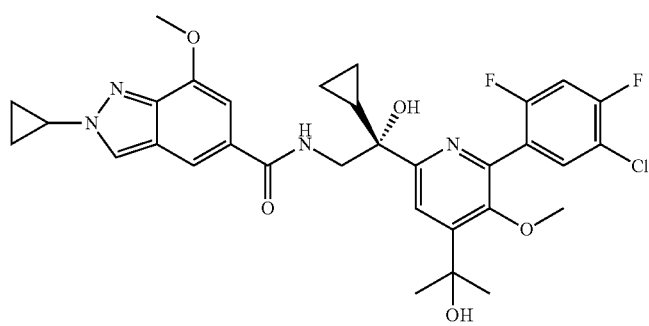 [SMILES: COc1c(C(C)(C)O)cc([C@@](O)(CNC(=O)c2cc(OC)c3nn(C4CC4)cc3c2)C2CC2)nc1-c1cc(Cl)c(F)cc1F] |
| 165 | 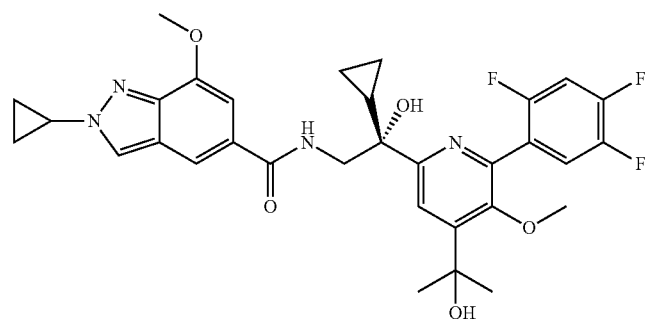 [SMILES: COc1c(C(C)(C)O)cc([C@@](O)(CNC(=O)c2cc(OC)c3nn(C4CC4)cc3c2)C2CC2)nc1-c1cc(F)c(F)cc1F] |
| 166 | 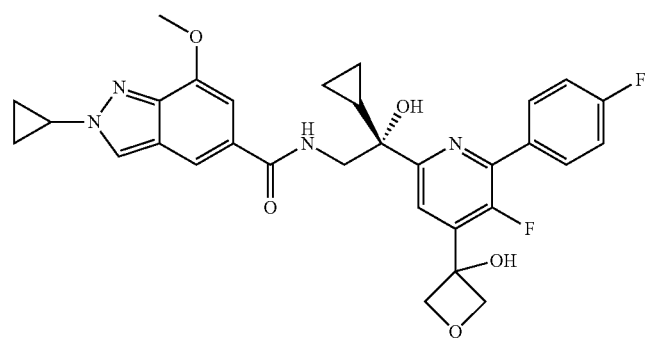 [SMILES: COc1cc(C(=O)NC[C@](O)(c2cc(C3(O)COC3)c(F)c(-c3ccc(F)cc3)n2)C2CC2)cc2cn(C3CC3)nc12] |

| Compound | Structure |
|---|---|
| 167 | 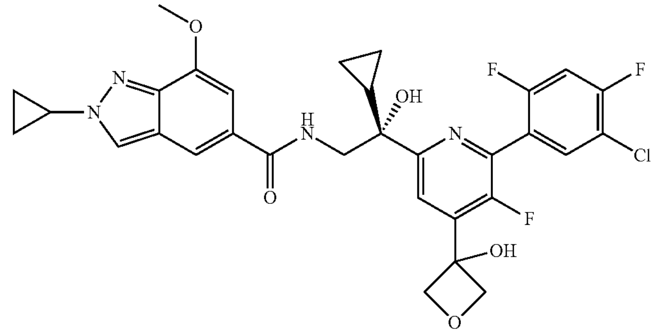 [SMILES: COc1cc(C(=O)NC[C@](O)(c2cc(C3(O)COC3)c(F)c(-c3cc(Cl)c(F)cc3F)n2)C2CC2)cc2cn(C3CC3)nc12] |
| 168 | 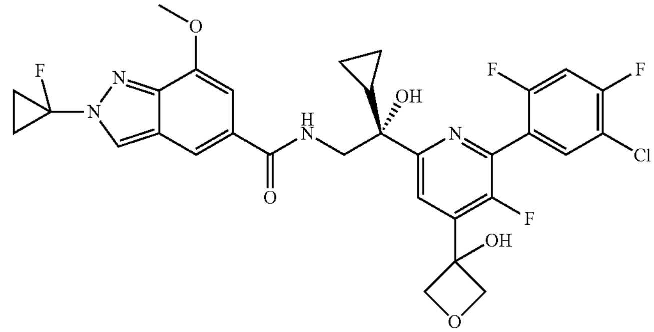 [SMILES: COc1cc(C(=O)NC[C@](O)(c2cc(C3(O)COC3)c(F)c(-c3cc(Cl)c(F)cc3F)n2)C2CC2)cc2cn(C3(F)CC3)nc12] |
| 169 | 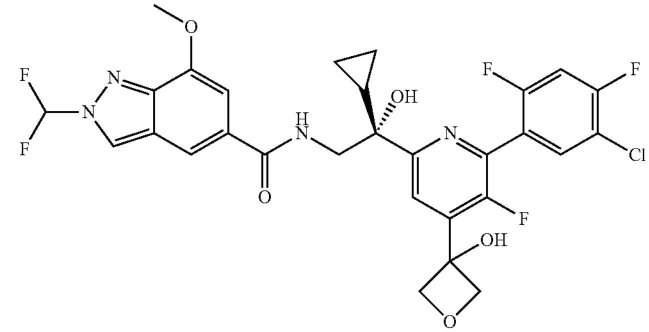 [SMILES: COc1cc(C(=O)NC[C@](O)(c2cc(C3(O)COC3)c(F)c(-c3cc(Cl)c(F)cc3F)n2)C2CC2)cc2cn(C(F)F)nc12] |
| 170 | 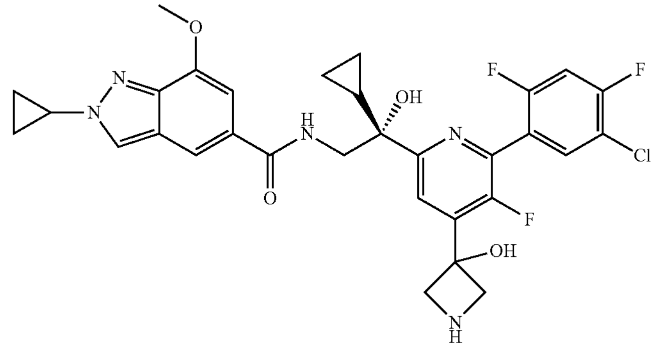 [SMILES: COc1cc(C(=O)NC[C@](O)(c2cc(C3(O)CNC3)c(F)c(-c3cc(Cl)c(F)cc3F)n2)C2CC2)cc2cn(C3CC3)nc12] |
| 171 | 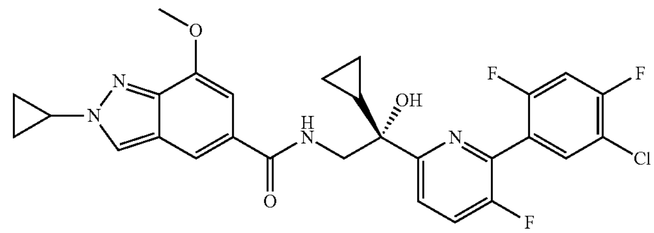 [SMILES: COc1cc(C(=O)NC[C@](O)(c2ccc(F)c(-c3cc(Cl)c(F)cc3F)n2)C2CC2)cc2cn(C3CC3)nc12] |

| Compound | Structure |
|---|---|
| 172 | 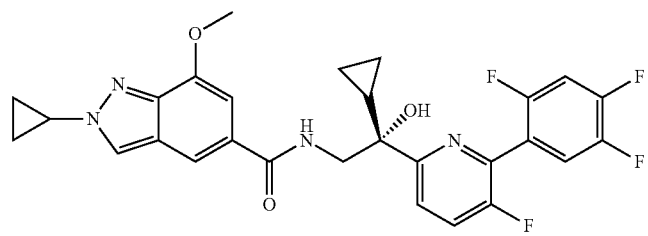 [SMILES: COc1cc(C(=O)NC[C@](O)(c2ccc(F)c(-c3cc(F)c(F)cc3F)n2)C2CC2)cc2cn(C3CC3)nc12] |
| 173 | 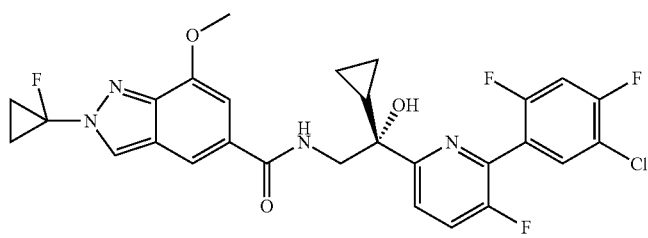 [SMILES: COc1cc(C(=O)NC[C@](O)(c2ccc(F)c(-c3cc(Cl)c(F)cc3F)n2)C2CC2)cc2cn(C3(F)CC3)nc12] |
| 174 | 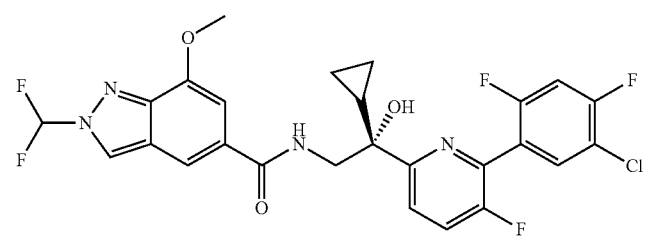 [SMILES: COc1cc(C(=O)NC[C@](O)(c2ccc(F)c(-c3cc(Cl)c(F)cc3F)n2)C2CC2)cc2cn(C(F)F)nc12] |
| 177 | 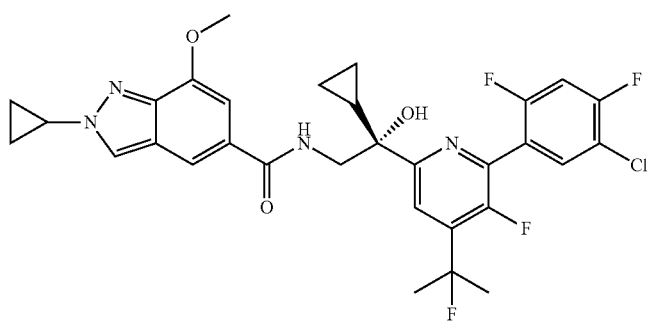 [SMILES: COc1cc(C(=O)NC[C@](O)(c2cc(C(C)(C)F)c(F)c(-c3cc(Cl)c(F)cc3F)n2)C2CC2)cc2cn(C3CC3)nc12] |
| 179 | 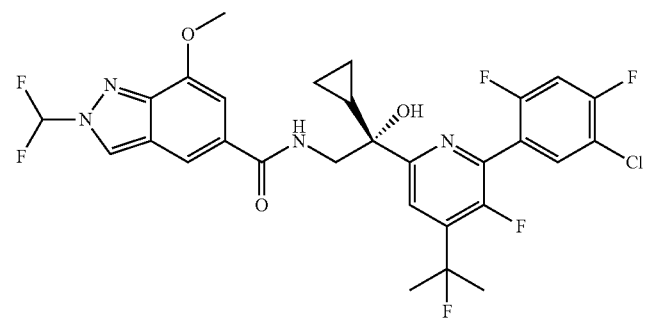 [SMILES: COc1cc(C(=O)NC[C@](O)(c2cc(C(C)(C)F)c(F)c(-c3cc(Cl)c(F)cc3F)n2)C2CC2)cc2cn(C(F)F)nc12] |

-continued
| Compound | Structure |
|---|---|
| 180 | 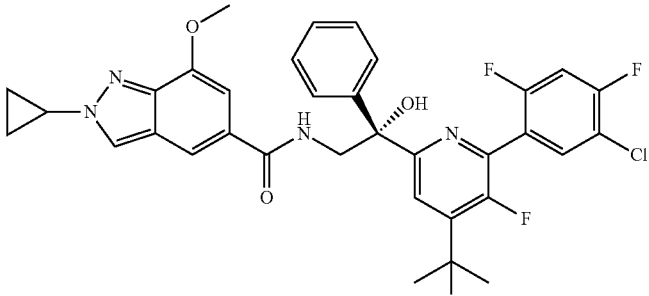 |
| 182 | 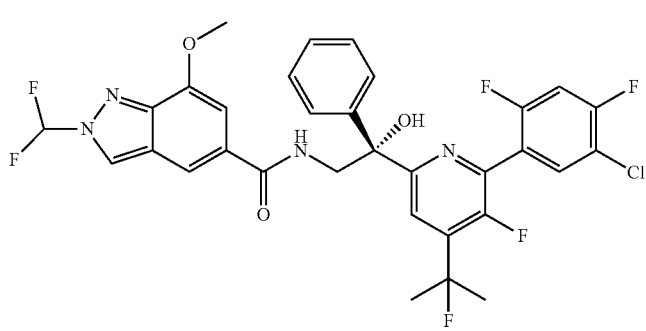 [SMILES: COc1cc(C(=O)NC[C@@](O)(c2ccccc2)c2cc(C(C)(C)F)c(F)c(-c3cc(Cl)c(F)cc3F)n2)cc2cn(C(F)F)nc12] |
| 183 | 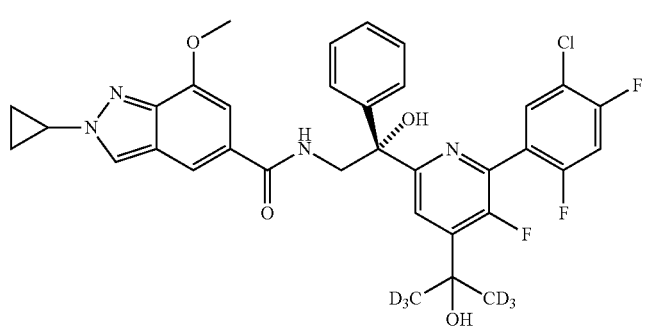 [SMILES: [2H]C([2H])([2H])C(O)(c1cc([C@@](O)(CNC(=O)c2cc(OC)c3nn(C4CC4)cc3c2)c2ccccc2)nc(-c2cc(Cl)c(F)cc2F)c1F)C([2H])([2H])[2H]] |
| 185 | 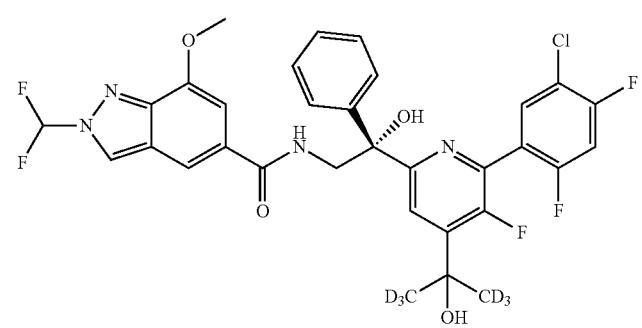 [SMILES: [2H]C([2H])([2H])C(O)(c1cc([C@@](O)(CNC(=O)c2cc(OC)c3nn(C(F)F)cc3c2)c2ccccc2)nc(-c2cc(Cl)c(F)cc2F)c1F)C([2H])([2H])[2H]] |
| 186 | 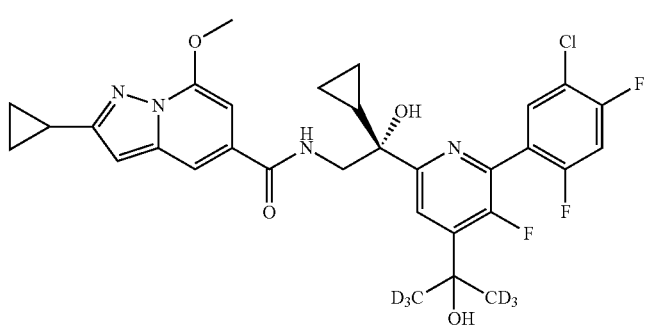 [SMILES: [2H]C([2H])([2H])C(O)(c1cc([C@@](O)(CNC(=O)c2cc(OC)n3nc(C4CC4)cc3c2)C2CC2)nc(-c2cc(Cl)c(F)cc2F)c1F)C([2H])([2H])[2H]] |

| Compound | Structure |
|---|---|
| 188 | 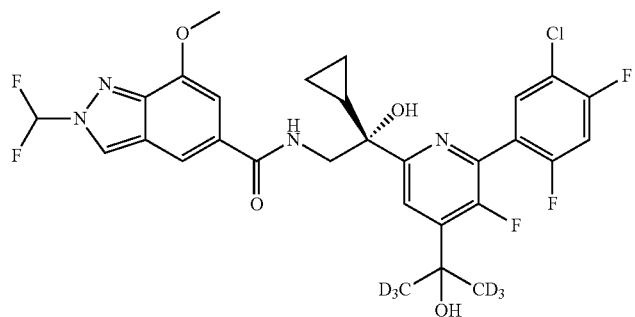 [SMILES: [2H]C([2H])([2H])C(O)(c1cc([C@@](O)(CNC(=O)c2cc(OC)c3nn(C(F)F)cc3c2)C2CC2)nc(-c2cc(Cl)c(F)cc2F)c1F)C([2H])([2H])[2H]] |
| 189 | 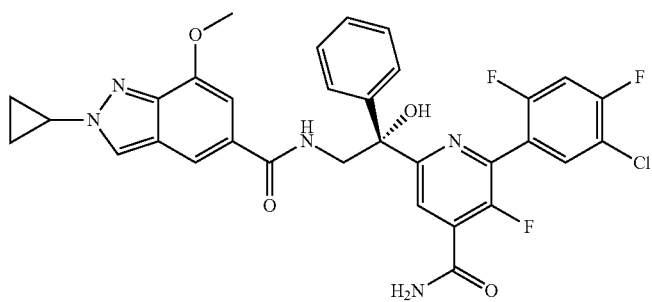 [SMILES: COc1cc(C(=O)NC[C@@](O)(c2ccccc2)c2cc(C(N)=O)c(F)c(-c3cc(Cl)c(F)cc3F)n2)cc2cn(C3CC3)nc12] |
| 190 | 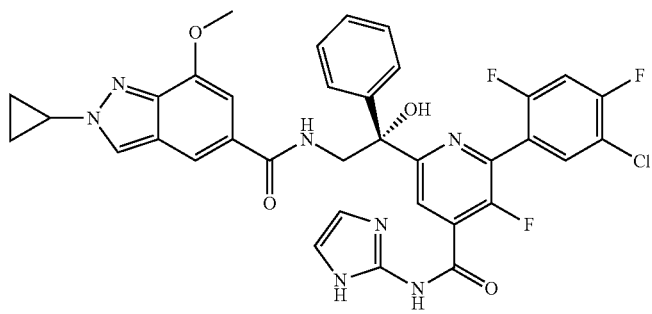 [SMILES: COc1cc(C(=O)NC[C@@](O)(c2ccccc2)c2cc(C(=O)Nc3ncc[nH]3)c(F)c(-c3cc(Cl)c(F)cc3F)n2)cc2cn(C3CC3)nc12] |
| 191 | 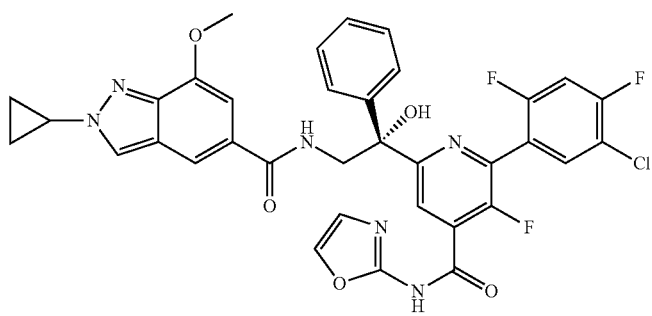 [SMILES: COc1cc(C(=O)NC[C@@](O)(c2ccccc2)c2cc(C(=O)Nc3ncco3)c(F)c(-c3cc(Cl)c(F)cc3F)n2)cc2cn(C3CC3)nc12] |
| 192 | 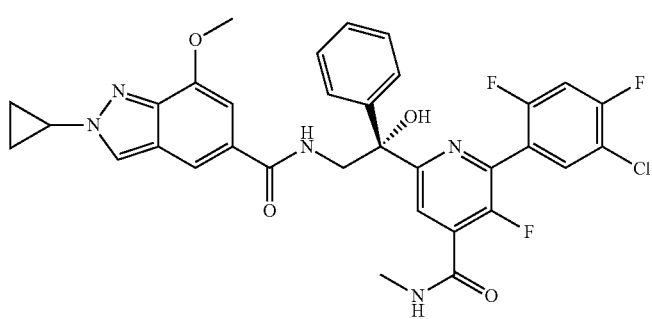 [SMILES: CNC(=O)c1cc([C@@](O)(CNC(=O)c2cc(OC)c3nn(C4CC4)cc3c2)c2ccccc2)nc(-c2cc(Cl)c(F)cc2F)c1F] |

-continued
| Compound | Structure |
|---|---|
| 193 | 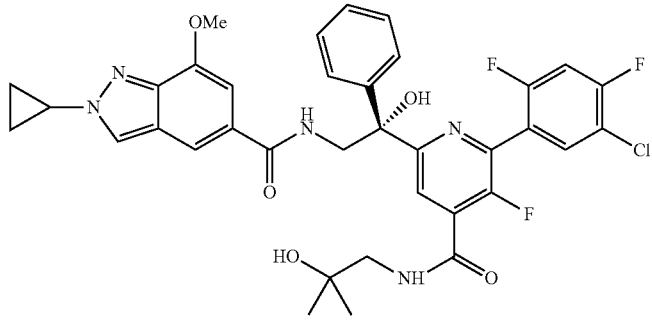 [SMILES: COc1cc(C(=O)NC[C@@](O)(c2ccccc2)c2cc(C(=O)NCC(C)(C)O)c(F)c(-c3cc(Cl)c(F)cc3F)n2)cc2cn(C3CC3)nc12] |
| 194 | 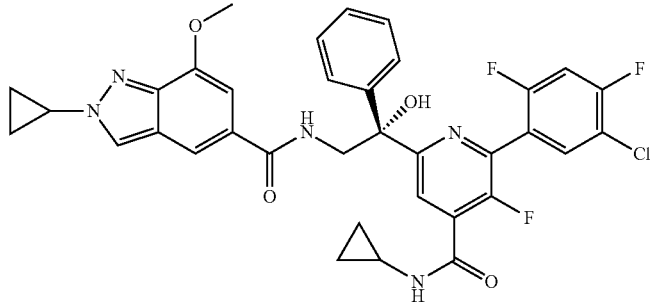 [SMILES: COc1cc(C(=O)NC[C@@](O)(c2ccccc2)c2cc(C(=O)NC3CC3)c(F)c(-c3cc(Cl)c(F)cc3F)n2)cc2cn(C3CC3)nc12] |
| 195 | 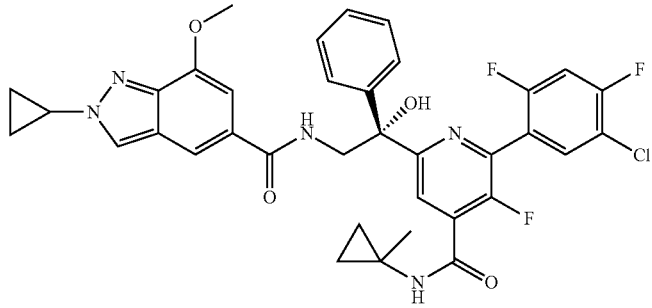 [SMILES: COc1cc(C(=O)NC[C@@](O)(c2ccccc2)c2cc(C(=O)NC3(C)CC3)c(F)c(-c3cc(Cl)c(F)cc3F)n2)cc2cn(C3CC3)nc12] |
| 196 | 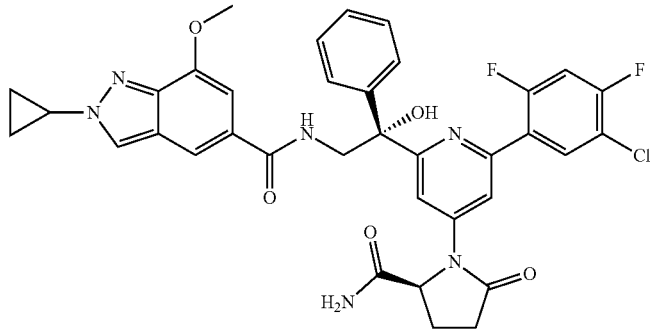 [SMILES: COc1cc(C(=O)NC[C@@](O)(c2ccccc2)c2cc(N3C(=O)CC[C@H]3C(N)=O)cc(-c3cc(Cl)c(F)cc3F)n2)cc2cn(C3CC3)nc12] |

| Compound | Structure |
|---|---|
| 197 | 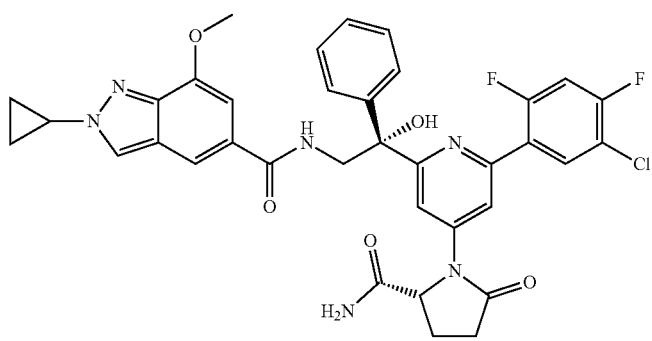 |
| 198 | 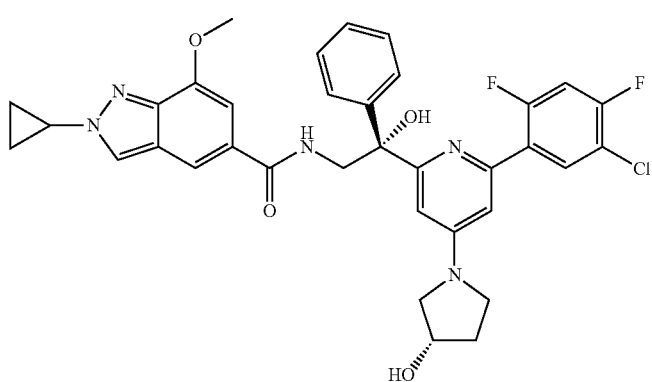 [SMILES: COc1cc(C(=O)NC[C@@](O)(c2ccccc2)c2cc(N3CC[C@H](O)C3)cc(-c3cc(Cl)c(F)cc3F)n2)cc2cn(C3CC3)nc12] |
| 199 | 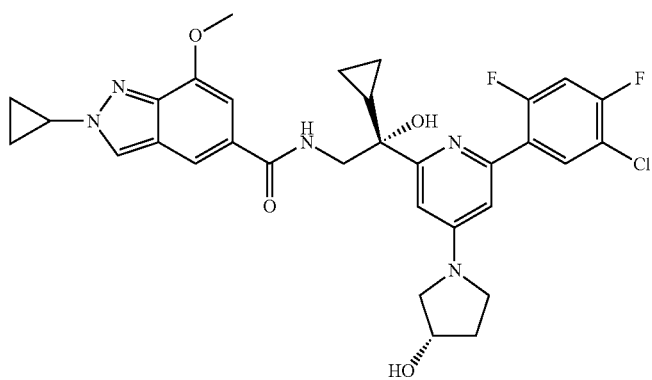 [SMILES: COc1cc(C(=O)NC[C@](O)(c2cc(N3CC[C@H](O)C3)cc(-c3cc(Cl)c(F)cc3F)n2)C2CC2)cc2cn(C3CC3)nc12] |
| 200 | 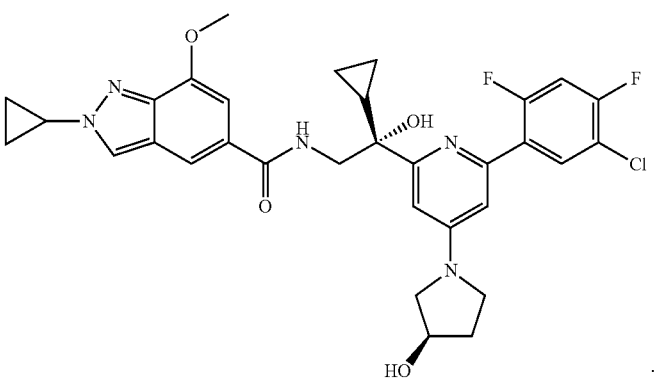 [SMILES: COc1cc(C(=O)NC[C@](O)(c2cc(N3CC[C@@H](O)C3)cc(-c3cc(Cl)c(F)cc3F)n2)C2CC2)cc2cn(C3CC3)nc12] |

5. A pharmaceutical composition comprising a compound according to claim 1, or a pharmaceutically acceptable salt thereof, and a pharmaceutically acceptable carrier, diluent or excipient.

6. A method of treating or preventing a respiratory syncytial virus (RSV) infection in a subject in need thereof, comprising administering to the subject a therapeutically effective amount of a compound of claim 1 or a pharmaceutically acceptable salt thereof.

7. The method of claim 6, further comprising the step of administering to the subject an additional anti-RSV agent.

8. The method of claim 6, further comprising administering to the subject a steroid anti-inflammatory compound.

9. A method of treating an RSV infection and influenza in a subject in need thereof, comprising administering to the subject a therapeutically effective amount of a compound of claim 1 and a therapeutically effective amount of an anti-influenza agent.

10. The method of claim 7, wherein the compound and the anti-RSV agent are co-formulated.

11. The method of claim 7, wherein the compound and the anti-RSV agent are co-administered.

12. A method of treating or preventing a human metapneumovirus (HMPV) infection in a subject in need thereof, comprising administering to the subject a therapeutically effective amount of a compound of claim 1.

13. The method of claim 12, further comprising the step of administering to the subject an anti-HMPV agent.

14. The method of claim 13, wherein the compound and the anti-HMPV agent are co-formulated.

15. The method of claim 13, wherein the compound and the anti-HMPV agent are co-administered.

\* \* \* \* \*

UNITED STATES PATENT AND TRADEMARK OFFICE
CERTIFICATE OF CORRECTION

| | | |
|---|---|---|
| PATENT NO. | : 12,162,857 B2 | Page 1 of 1 |
| APPLICATION NO. | : 18/139405 | |
| DATED | : December 10, 2024 | |
| INVENTOR(S) | : Jianming Yu et al. | |

It is certified that error appears in the above-identified patent and that said Letters Patent is hereby corrected as shown below:

In the Claims

<u>At Column 193</u>

In Claim 1, Line 45 should read: -- 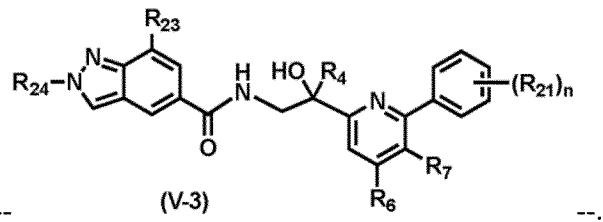 --.

<u>At Columns 241 and 242</u>

In Claim 4, Compound 138 should read: -- 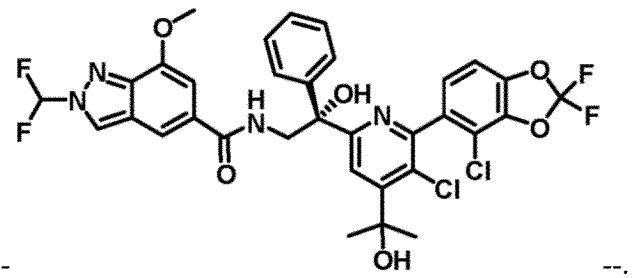 --.

Signed and Sealed this
Second Day of September, 2025

Coke Morgan Stewart
*Acting Director of the United States Patent and Trademark Office*